US012702466B2

(12) United States Patent
Wiener et al.

(10) Patent No.: US 12,702,466 B2
(45) **Date of Patent: *Aug. 11, 2026**

(54) TECHNIQUES FOR CIRCUIT TOPOLOGIES FOR COMBINED GENERATOR

(71) Applicant: Cilag GmbH International, Zug (CH)

(72) Inventors: Eitan T. Wiener, Cincinnati, OH (US); David C. Yates, Morrow, OH (US); Ryan M. Asher, Cincinnati, OH (US); John A. Hibner, Mason, OH (US); John E. Hein, Neenah, WI (US)

(73) Assignee: Cilag GmbH International, Zug (CH)

( * ) Notice: Subject to any disclaimer, the term of this patent is extended or adjusted under 35 U.S.C. 154(b) by 631 days.

This patent is subject to a terminal disclaimer.

(21) Appl. No.: 18/085,163

(22) Filed: Dec. 20, 2022

(65) Prior Publication Data

US 2023/0270486 A1 Aug. 31, 2023

Related U.S. Application Data

(63) Continuation of application No. 16/795,886, filed on Feb. 20, 2020, now Pat. No. 11,559,347, which is a (Continued)

(51) Int. Cl.
*A61B 18/12* (2006.01)
*A61B 17/00* (2006.01)
(Continued)

(52) U.S. Cl.
CPC ...... *A61B 18/1206* (2013.01); *A61B 18/1445* (2013.01); *A61B 18/1482* (2013.01); (Continued)

(58) Field of Classification Search
CPC .............. A61B 18/2106; A61B 18/128; A61B 2018/00994; A61B 2017/320069; A61B 2017/320095; A61B 17/320068
See application file for complete search history.

(56) References Cited

U.S. PATENT DOCUMENTS

| | | | |
|---|---|---|---|
| 969,528 | A | 9/1910 | Disbrow |
| 1,570,025 | A | 1/1926 | Young |

(Continued)

FOREIGN PATENT DOCUMENTS

| | | | |
|---|---|---|---|
| CA | 2535467 | A1 | 4/1993 |
| CN | 2460047 | Y | 11/2001 |

(Continued)

OTHER PUBLICATIONS

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

(Continued)

*Primary Examiner* — Ronald Hupczey, Jr.
(74) *Attorney, Agent, or Firm* — Vorys, Sater, Seymour and Pease LLP

(57) ABSTRACT

Provided is a method for managing radio frequency (RF) and ultrasonic signals output by a generator that includes a surgical instrument comprising an RF energy output and an ultrasonic energy output and a circuit configured to receive a combined RF and ultrasonic signal from the generator. The method includes receiving a combined radio frequency (RF) and ultrasonic signal from a generator, generating a RF filtered signal by filtering RF frequency content from the combined signal; filtering ultrasonic frequency content from the combined signal; generating an ultrasonic filtered signal; providing the RF filtered signal to the RF energy output; and providing the ultrasonic filtered signal to the ultrasonic energy output.

19 Claims, 60 Drawing Sheets

Related U.S. Application Data continuation of application No. 15/265,293, filed on Sep. 14, 2016, now Pat. No. 10,610,286.

(60) Provisional application No. 62/235,260, filed on Sep. 30, 2015, provisional application No. 62/235,466, filed on Sep. 30, 2015, provisional application No. 62/235,368, filed on Sep. 30, 2015.

(51) Int. Cl.

| | |
|---|---|
| ***A61B 17/32*** | (2006.01) |
| ***A61B 18/00*** | (2006.01) |
| ***A61B 18/14*** | (2006.01) |
| ***B06B 1/02*** | (2006.01) |
| ***G06F 1/02*** | (2006.01) |
| ***H03K 5/01*** | (2006.01) |

(52) U.S. Cl.

CPC ............... *G06F 1/022* (2013.01); *H03K 5/01* (2013.01); *A61B 2017/00017* (2013.01); *A61B 2017/00137* (2013.01); *A61B 2017/0015* (2013.01); *A61B 2017/320094* (2017.08); *A61B 2018/00642* (2013.01); *A61B 2018/00994* (2013.01); *A61B 2018/1273* (2013.01); *A61B 2018/128* (2013.01); *A61B 2018/1293* (2013.01); *B06B 1/0207* (2013.01)

(56) References Cited

U.S. PATENT DOCUMENTS 1,813,902 A 7/1931 Bovie
2,188,497 A 1/1940 Calva
2,366,274 A 1/1945 Luth et al.
2,425,245 A 8/1947 Johnson
2,442,966 A 6/1948 Wallace
2,458,152 A 1/1949 Eakins
2,510,693 A 6/1950 Green
2,597,564 A 5/1952 Bugg
2,704,333 A 3/1955 Calosi et al.
2,736,960 A 3/1956 Armstrong
2,748,967 A 6/1956 Roach
2,845,072 A 7/1958 Shafer
2,849,788 A 9/1958 Creek
2,867,039 A 1/1959 Zach
2,874,470 A 2/1959 Richards
2,990,616 A 7/1961 Balamuth et al.
RE25,033 E 8/1961 Balamuth et al.
3,015,961 A 1/1962 Roney
3,033,407 A 5/1962 Alfons
3,053,124 A 9/1962 Balamuth et al.
3,082,805 A 3/1963 Royce
3,166,971 A 1/1965 Stoecker
3,322,403 A 5/1967 Murphy
3,432,691 A 3/1969 Shoh
3,433,226 A 3/1969 Boyd
3,489,930 A 1/1970 Shoh
3,513,848 A 5/1970 Winston et al.
3,514,856 A 6/1970 Camp et al.
3,525,912 A 8/1970 Wallin
3,526,219 A 9/1970 Balamuth
3,554,198 A 1/1971 Tatoian et al.
3,580,841 A 5/1971 Cadotte et al.
3,606,682 A 9/1971 Camp et al.
3,614,484 A 10/1971 Shoh
3,616,375 A 10/1971 Inoue
3,629,726 A 12/1971 Popescu
3,636,943 A 1/1972 Balamuth
3,668,486 A 6/1972 Silver
3,702,948 A 11/1972 Balamuth
3,703,651 A 11/1972 Blowers
3,776,238 A 12/1973 Peyman et al.
3,777,760 A 12/1973 Essner
3,805,787 A 4/1974 Banko
3,809,977 A 5/1974 Balamuth et al.
3,830,098 A 8/1974 Antonevich
3,854,737 A 12/1974 Gilliam, Sr.
3,862,630 A 1/1975 Balamuth
3,875,945 A 4/1975 Friedman
3,885,438 A 5/1975 Harris, Sr. et al.
3,900,823 A 8/1975 Sokal et al.
3,918,442 A 11/1975 Nikolaev et al.
3,924,335 A 12/1975 Balamuth et al.
3,946,738 A 3/1976 Newton et al.
3,955,859 A 5/1976 Stella et al.
3,956,826 A 5/1976 Perdreaux, Jr.
3,989,952 A 11/1976 Hohmann
4,005,714 A 2/1977 Hiltebrandt
4,012,647 A 3/1977 Balamuth et al.
4,034,762 A 7/1977 Cosens et al.
4,058,126 A 11/1977 Leveen
4,074,719 A 2/1978 Semm
4,156,187 A 5/1979 Murry et al.
4,167,944 A 9/1979 Banko
4,188,927 A 2/1980 Harris
4,200,106 A 4/1980 Douvas et al.
4,203,430 A 5/1980 Takahashi
4,203,444 A 5/1980 Bonnell et al.
4,220,154 A 9/1980 Semm
4,237,441 A 12/1980 van Konynenburg et al.
4,244,371 A 1/1981 Farin
4,281,785 A 8/1981 Brooks
4,300,083 A 11/1981 Heiges
4,302,728 A 11/1981 Nakamura
4,304,987 A 12/1981 van Konynenburg
4,306,570 A 12/1981 Matthews
4,314,559 A 2/1982 Allen
4,353,371 A 10/1982 Cosman
4,409,981 A 10/1983 Lundberg
4,445,063 A 4/1984 Smith
4,461,304 A 7/1984 Kuperstein
4,463,759 A 8/1984 Garito et al.
4,491,132 A 1/1985 Aikins
4,492,231 A 1/1985 Auth
4,494,759 A 1/1985 Kieffer
4,504,264 A 3/1985 Kelman
4,512,344 A 4/1985 Barber
4,526,571 A 7/1985 Wuchinich
4,535,773 A 8/1985 Yoon
4,541,638 A 9/1985 Ogawa et al.
4,545,374 A 10/1985 Jacobson
4,545,926 A 10/1985 Fouts, Jr. et al.
4,549,147 A 10/1985 Kondo
4,550,870 A 11/1985 Krumme et al.
4,553,544 A 11/1985 Nomoto et al.
4,562,838 A 1/1986 Walker
4,574,615 A 3/1986 Bower et al.
4,582,236 A 4/1986 Hirose
4,593,691 A 6/1986 Lindstrom et al.
4,608,981 A 9/1986 Rothfuss et al.
4,617,927 A 10/1986 Manes
4,633,119 A 12/1986 Thompson
4,633,874 A 1/1987 Chow et al.
4,634,420 A 1/1987 Spinosa et al.
4,640,279 A 2/1987 Beard
4,641,053 A 2/1987 Takeda
4,646,738 A 3/1987 Trott
4,646,756 A 3/1987 Watmough et al.
4,649,919 A 3/1987 Thimsen et al.
4,662,068 A 5/1987 Polonsky
4,674,502 A 6/1987 Imonti
4,694,835 A 9/1987 Strand
4,708,127 A 11/1987 Abdelghani
4,712,722 A 12/1987 Hood et al.
4,735,603 A 4/1988 Goodson et al.
4,739,759 A 4/1988 Rexroth et al.
4,761,871 A 8/1988 O'Connor et al.
4,808,154 A 2/1989 Freeman
4,819,635 A 4/1989 Shapiro
4,827,911 A 5/1989 Broadwin et al.
4,830,462 A 5/1989 Karny et al.
4,832,683 A 5/1989 Idemoto et al.
4,836,186 A 6/1989 Scholz

(56) References Cited

U.S. PATENT DOCUMENTS 4,838,853 A 6/1989 Parisi
4,844,064 A 7/1989 Thimsen et al.
4,849,133 A 7/1989 Yoshida et al.
4,850,354 A 7/1989 McGurk-Burleson et al.
4,852,578 A 8/1989 Companion et al.
4,860,745 A 8/1989 Farin et al.
4,862,890 A 9/1989 Stasz et al.
4,865,159 A 9/1989 Jamison
4,867,157 A 9/1989 McGurk-Burleson et al.
4,878,493 A 11/1989 Pasternak et al.
4,880,015 A 11/1989 Nierman
4,881,550 A 11/1989 Kothe
4,896,009 A 1/1990 Pawlowski
4,903,696 A 2/1990 Stasz et al.
4,910,389 A 3/1990 Sherman et al.
4,915,643 A 4/1990 Samejima et al.
4,920,978 A 5/1990 Colvin
4,922,902 A 5/1990 Wuchinich et al.
4,926,860 A 5/1990 Stice et al.
4,936,842 A 6/1990 D'Amelio et al.
4,954,960 A 9/1990 Lo et al.
4,965,532 A 10/1990 Sakurai
4,979,952 A 12/1990 Kubota et al.
4,981,756 A 1/1991 Rhandhawa
5,001,649 A 3/1991 Lo et al.
5,003,693 A 4/1991 Atkinson et al.
5,009,661 A 4/1991 Michelson
5,013,956 A 5/1991 Kurozumi et al.
5,015,227 A 5/1991 Broadwin et al.
5,020,514 A 6/1991 Heckele
5,026,370 A 6/1991 Lottick
5,026,387 A 6/1991 Thomas
5,035,695 A 7/1991 Weber, Jr. et al.
5,042,461 A 8/1991 Inoue et al.
5,042,707 A 8/1991 Taheri
5,052,145 A 10/1991 Wang
5,061,269 A 10/1991 Muller
5,075,839 A 12/1991 Fisher et al.
5,084,052 A 1/1992 Jacobs
5,099,840 A 3/1992 Goble et al.
5,104,025 A 4/1992 Main et al.
5,105,117 A 4/1992 Yamaguchi
5,106,538 A 4/1992 Barma et al.
5,108,383 A 4/1992 White
5,109,819 A 5/1992 Custer et al.
5,112,300 A 5/1992 Ureche
5,113,139 A 5/1992 Furukawa
5,123,903 A 6/1992 Quaid et al.
5,126,618 A 6/1992 Takahashi et al.
D327,872 S 7/1992 McMills et al.
5,152,762 A 10/1992 McElhenney
5,156,633 A 10/1992 Smith
5,160,334 A 11/1992 Billings et al.
5,162,044 A 11/1992 Gahn et al.
5,163,421 A 11/1992 Bernstein et al.
5,163,537 A 11/1992 Radev
5,163,945 A 11/1992 Ortiz et al.
5,167,619 A 12/1992 Wuchinich
5,167,725 A 12/1992 Clark et al.
5,172,344 A 12/1992 Ehrlich
5,174,276 A 12/1992 Crockard
D332,660 S 1/1993 Rawson et al.
5,176,677 A 1/1993 Wuchinich
5,176,695 A 1/1993 Dulebohn
5,184,605 A 2/1993 Grzeszykowski
5,188,102 A 2/1993 Idemoto et al.
D334,173 S 3/1993 Liu et al.
5,190,517 A 3/1993 Zieve et al.
5,190,518 A 3/1993 Takasu
5,190,541 A 3/1993 Abele et al.
5,196,007 A 3/1993 Ellman et al.
5,203,380 A 4/1993 Chikama
5,205,459 A 4/1993 Brinkerhoff et al.
5,205,817 A 4/1993 Idemoto et al.
5,209,719 A 5/1993 Baruch et al.
5,213,569 A 5/1993 Davis
5,214,339 A 5/1993 Naito
5,217,460 A 6/1993 Knoepfler
5,218,529 A 6/1993 Meyer et al.
5,221,282 A 6/1993 Wuchinich
5,222,937 A 6/1993 Kagawa
5,226,909 A 7/1993 Evans et al.
5,226,910 A 7/1993 Kajiyama et al.
5,231,989 A 8/1993 Middleman et al.
5,234,428 A 8/1993 Kaufman
5,241,236 A 8/1993 Sasaki et al.
5,241,968 A 9/1993 Slater
5,242,339 A 9/1993 Thornton
5,242,460 A 9/1993 Klein et al.
5,246,003 A 9/1993 DeLonzor
5,254,129 A 10/1993 Alexander
5,257,988 A 11/1993 L'Esperance, Jr.
5,258,004 A 11/1993 Bales et al.
5,258,006 A 11/1993 Rydell et al.
5,261,922 A 11/1993 Hood
5,263,957 A 11/1993 Davison
5,264,925 A 11/1993 Shipp et al.
5,269,297 A 12/1993 Weng et al.
5,275,166 A 1/1994 Vaitekunas et al.
5,275,607 A 1/1994 Lo et al.
5,275,609 A 1/1994 Pingleton et al.
5,282,800 A 2/1994 Foshee et al.
5,282,817 A 2/1994 Hoogeboom et al.
5,285,795 A 2/1994 Ryan et al.
5,285,945 A 2/1994 Brinkerhoff et al.
5,290,286 A 3/1994 Parins
5,293,863 A 3/1994 Zhu et al.
5,300,068 A 4/1994 Rosar et al.
5,304,115 A 4/1994 Pflueger et al.
D347,474 S 5/1994 Olson
5,307,976 A 5/1994 Olson et al.
5,309,927 A 5/1994 Welch
5,312,023 A 5/1994 Green et al.
5,312,425 A 5/1994 Evans et al.
5,318,525 A 6/1994 West et al.
5,318,563 A 6/1994 Malis et al.
5,318,564 A 6/1994 Eggers
5,318,570 A 6/1994 Hood et al.
5,318,589 A 6/1994 Lichtman
5,322,055 A 6/1994 Davison et al.
5,324,299 A 6/1994 Davison et al.
5,326,013 A 7/1994 Green et al.
5,326,342 A 7/1994 Pflueger et al.
5,330,471 A 7/1994 Eggers
5,330,502 A 7/1994 Hassler et al.
5,334,183 A 8/1994 Wuchinich
5,339,723 A 8/1994 Huitema
5,342,356 A 8/1994 Ellman et al.
5,342,359 A 8/1994 Rydell
5,344,420 A 9/1994 Hilal et al.
5,345,937 A 9/1994 Middleman et al.
5,346,502 A 9/1994 Estabrook et al.
5,353,474 A 10/1994 Good et al.
5,357,164 A 10/1994 Imabayashi et al.
5,357,423 A 10/1994 Weaver et al.
5,359,994 A 11/1994 Krauter et al.
5,361,583 A 11/1994 Huitema
5,366,466 A 11/1994 Christian et al.
5,368,557 A 11/1994 Nita et al.
5,370,645 A 12/1994 Klicek et al.
5,371,429 A 12/1994 Manna
5,374,813 A 12/1994 Shipp
D354,564 S 1/1995 Medema
5,381,067 A 1/1995 Greenstein et al.
5,383,874 A 1/1995 Jackson et al.
5,383,917 A 1/1995 Desai et al.
5,387,207 A 2/1995 Dyer et al.
5,387,215 A 2/1995 Fisher
5,389,098 A 2/1995 Tsuruta et al.
5,394,187 A 2/1995 Shipp
5,395,033 A 3/1995 Byrne et al.
5,395,312 A 3/1995 Desai
5,395,363 A 3/1995 Billings et al.
5,395,364 A 3/1995 Anderhub et al.

(56) References Cited

U.S. PATENT DOCUMENTS 5,396,266 A 3/1995 Brimhall
5,396,900 A 3/1995 Slater et al.
5,400,267 A 3/1995 Denen et al.
5,403,312 A 4/1995 Yates et al.
5,403,334 A 4/1995 Evans et al.
5,406,503 A 4/1995 Williams, Jr. et al.
5,408,268 A 4/1995 Shipp
D358,887 S 5/1995 Feinberg
5,411,481 A 5/1995 Allen et al.
5,417,709 A 5/1995 Slater
5,419,761 A 5/1995 Narayanan et al.
5,421,829 A 6/1995 Olichney et al.
5,423,844 A 6/1995 Miller
5,428,504 A 6/1995 Bhatla
5,429,131 A 7/1995 Scheinman et al.
5,438,997 A 8/1995 Sieben et al.
5,441,499 A 8/1995 Fritzsch
5,443,463 A 8/1995 Stern et al.
5,445,638 A 8/1995 Rydell et al.
5,445,639 A 8/1995 Kuslich et al.
5,447,509 A 9/1995 Mills et al.
5,449,370 A 9/1995 Vaitekunas
5,451,053 A 9/1995 Garrido
5,451,161 A 9/1995 Sharp
5,451,220 A 9/1995 Ciervo
5,451,227 A 9/1995 Michaelson
5,456,684 A 10/1995 Schmidt et al.
5,458,598 A 10/1995 Feinberg et al.
5,462,604 A 10/1995 Shibano et al.
5,465,895 A 11/1995 Knodel et al.
5,471,988 A 12/1995 Fujio et al.
5,472,443 A 12/1995 Cordis et al.
5,476,479 A 12/1995 Green et al.
5,478,003 A 12/1995 Green et al.
5,480,409 A 1/1996 Riza
5,483,501 A 1/1996 Park et al.
5,484,436 A 1/1996 Eggers et al.
5,486,162 A 1/1996 Brumbach
5,486,189 A 1/1996 Mudry et al.
5,490,860 A 2/1996 Middle et al.
5,496,317 A 3/1996 Goble et al.
5,499,992 A 3/1996 Meade et al.
5,500,216 A 3/1996 Julian et al.
5,501,654 A 3/1996 Failla et al.
5,504,650 A 4/1996 Katsui et al.
5,505,693 A 4/1996 Mackool
5,507,297 A 4/1996 Slater et al.
5,507,738 A 4/1996 Ciervo
5,509,922 A 4/1996 Aranyi et al.
5,511,556 A 4/1996 DeSantis
5,520,704 A 5/1996 Castro et al.
5,522,832 A 6/1996 Kugo et al.
5,522,839 A 6/1996 Pilling
5,527,331 A 6/1996 Kresch et al.
5,531,744 A 7/1996 Nardella et al.
5,536,267 A 7/1996 Edwards et al.
5,540,681 A 7/1996 Strul et al.
5,540,684 A 7/1996 Hassler, Jr.
5,540,693 A 7/1996 Fisher
5,542,916 A 8/1996 Hirsch et al.
5,548,286 A 8/1996 Craven
5,549,637 A 8/1996 Crainich
5,553,675 A 9/1996 Pitzen et al.
5,558,671 A 9/1996 Yates
5,562,609 A 10/1996 Brumbach
5,562,610 A 10/1996 Brumbach
5,562,659 A 10/1996 Morris
5,562,703 A 10/1996 Desai
5,563,179 A 10/1996 Stone et al.
5,569,164 A 10/1996 Lurz
5,571,121 A 11/1996 Heifetz
5,573,424 A 11/1996 Poppe
5,573,533 A 11/1996 Strul
5,573,534 A 11/1996 Stone
5,577,654 A 11/1996 Bishop
5,584,830 A 12/1996 Ladd et al.
5,591,187 A 1/1997 Dekel
5,593,414 A 1/1997 Shipp et al.
5,599,350 A 2/1997 Schulze et al.
5,600,526 A 2/1997 Russell et al.
5,601,601 A 2/1997 Tal et al.
5,603,773 A 2/1997 Campbell
5,607,436 A 3/1997 Pratt et al.
5,607,450 A 3/1997 Zvenyatsky et al.
5,609,573 A 3/1997 Sandock
5,611,813 A 3/1997 Lichtman
5,618,304 A 4/1997 Hart et al.
5,618,307 A 4/1997 Donlon et al.
5,618,492 A 4/1997 Auten et al.
5,620,447 A 4/1997 Smith et al.
5,624,452 A 4/1997 Yates
5,626,587 A 5/1997 Bishop et al.
5,626,595 A 5/1997 Sklar et al.
5,626,608 A 5/1997 Cuny et al.
5,628,760 A 5/1997 Knopfler
5,630,420 A 5/1997 Vaitekunas
5,632,432 A 5/1997 Schulze et al.
5,632,717 A 5/1997 Yoon
5,638,827 A 6/1997 Palmer et al.
5,638,837 A 6/1997 Juhl et al.
5,640,741 A 6/1997 Yano
D381,077 S 7/1997 Hunt
5,647,871 A 7/1997 Levine et al.
5,649,937 A 7/1997 Bito et al.
5,649,955 A 7/1997 Hashimoto et al.
5,651,780 A 7/1997 Jackson et al.
5,653,713 A 8/1997 Michelson
5,655,100 A 8/1997 Ebrahim et al.
5,658,281 A 8/1997 Heard
5,662,662 A 9/1997 Bishop et al.
5,662,667 A 9/1997 Knodel
5,665,085 A 9/1997 Nardella
5,665,100 A 9/1997 Yoon
5,669,922 A 9/1997 Hood
5,674,219 A 10/1997 Monson et al.
5,674,220 A 10/1997 Fox et al.
5,674,235 A 10/1997 Parisi
5,678,568 A 10/1997 Uchikubo et al.
5,688,270 A 11/1997 Yates et al.
5,690,269 A 11/1997 Bolanos et al.
5,693,042 A 12/1997 Boiarski et al.
5,693,051 A 12/1997 Schulze et al.
5,694,936 A 12/1997 Fujimoto et al.
5,695,510 A 12/1997 Hood
5,700,261 A 12/1997 Brinkerhoff
5,704,534 A 1/1998 Huitema et al.
5,704,791 A 1/1998 Gillio
5,707,369 A 1/1998 Vaitekunas et al.
5,709,680 A 1/1998 Yates et al.
5,711,472 A 1/1998 Bryan
5,713,896 A 2/1998 Nardella
5,715,817 A 2/1998 Stevens-Wright et al.
5,716,366 A 2/1998 Yates
5,717,306 A 2/1998 Shipp
5,720,742 A 2/1998 Zacharias
5,720,744 A 2/1998 Eggleston et al.
5,722,980 A 3/1998 Schulz et al.
5,723,970 A 3/1998 Bell
5,728,130 A 3/1998 Ishikawa et al.
5,730,752 A 3/1998 Alden et al.
5,733,074 A 3/1998 Stock et al.
5,735,848 A 4/1998 Yates et al.
5,741,226 A 4/1998 Strukel et al.
5,743,906 A 4/1998 Parins et al.
5,752,973 A 5/1998 Kieturakis
5,755,717 A 5/1998 Yates et al.
5,759,183 A 6/1998 VanDusseldorp
5,762,255 A 6/1998 Chrisman et al.
5,766,164 A 6/1998 Mueller et al.
5,772,659 A 6/1998 Becker et al.
5,776,130 A 7/1998 Buysse et al.
5,776,155 A 7/1998 Beaupre et al.
5,779,130 A 7/1998 Alesi et al.
5,779,701 A 7/1998 McBrayer et al.

(56) References Cited

U.S. PATENT DOCUMENTS 5,782,834 A 7/1998 Lucey et al.
5,792,135 A 8/1998 Madhani et al.
5,792,138 A 8/1998 Shipp
5,792,165 A 8/1998 Klieman et al.
5,796,188 A 8/1998 Bays
5,797,941 A 8/1998 Schulze et al.
5,797,958 A 8/1998 Yoon
5,797,959 A 8/1998 Castro et al.
5,800,432 A 9/1998 Swanson
5,800,448 A 9/1998 Banko
5,800,449 A 9/1998 Wales
5,805,140 A 9/1998 Rosenberg et al.
5,807,393 A 9/1998 Williamson, IV et al.
5,808,396 A 9/1998 Boukhny
5,810,811 A 9/1998 Yates et al.
5,810,828 A 9/1998 Lightman et al.
5,810,859 A 9/1998 DiMatteo et al.
5,817,033 A 10/1998 DeSantis et al.
5,817,084 A 10/1998 Jensen
5,817,093 A 10/1998 Williamson, IV et al.
5,817,119 A 10/1998 Klieman et al.
5,823,197 A 10/1998 Edwards
5,827,271 A 10/1998 Buysse et al.
5,827,323 A 10/1998 Klieman et al.
5,828,160 A 10/1998 Sugishita
5,833,696 A 11/1998 Whitfield et al.
5,836,897 A 11/1998 Sakurai et al.
5,836,909 A 11/1998 Cosmescu
5,836,943 A 11/1998 Miller, III
5,836,957 A 11/1998 Schulz et al.
5,836,990 A 11/1998 Li
5,843,109 A 12/1998 Mehta et al.
5,851,212 A 12/1998 Zirps et al.
5,853,412 A 12/1998 Mayenberger
5,854,590 A 12/1998 Dalstein
5,858,018 A 1/1999 Shipp et al.
5,865,361 A 2/1999 Milliman et al.
5,873,873 A 2/1999 Smith et al.
5,873,882 A 2/1999 Straub et al.
5,876,401 A 3/1999 Schulze et al.
5,878,193 A 3/1999 Wang et al.
5,879,364 A 3/1999 Bromfield et al.
5,880,668 A 3/1999 Hall
5,883,615 A 3/1999 Fago et al.
5,891,142 A 4/1999 Eggers et al.
5,893,835 A 4/1999 Witt et al.
5,897,523 A 4/1999 Wright et al.
5,897,569 A 4/1999 Kellogg et al.
5,903,607 A 5/1999 Tailliet
5,904,681 A 5/1999 West, Jr.
5,906,625 A 5/1999 Bito et al.
5,906,627 A 5/1999 Spaulding
5,906,628 A 5/1999 Miyawaki et al.
5,910,129 A 6/1999 Koblish et al.
5,911,699 A 6/1999 Anis et al.
5,913,823 A 6/1999 Hedberg et al.
5,916,229 A 6/1999 Evans
5,921,956 A 7/1999 Grinberg et al.
5,929,846 A 7/1999 Rosenberg et al.
5,935,143 A 8/1999 Hood
5,935,144 A 8/1999 Estabrook
5,938,633 A 8/1999 Beaupre
5,944,718 A 8/1999 Austin et al.
5,944,737 A 8/1999 Tsonton et al.
5,947,984 A 9/1999 Whipple
5,954,717 A 9/1999 Behl et al.
5,954,736 A 9/1999 Bishop et al.
5,954,746 A 9/1999 Holthaus et al.
5,957,882 A 9/1999 Nita et al.
5,957,943 A 9/1999 Vaitekunas
5,968,007 A 10/1999 Simon et al.
5,968,060 A 10/1999 Kellogg
5,974,342 A 10/1999 Petrofsky
D416,089 S 11/1999 Barton et al.
5,980,510 A 11/1999 Tsonton et al.
5,980,546 A 11/1999 Hood
5,984,938 A 11/1999 Yoon
5,987,344 A 11/1999 West
5,989,274 A 11/1999 Davison et al.
5,989,275 A 11/1999 Estabrook et al.
5,993,465 A 11/1999 Shipp et al.
5,993,972 A 11/1999 Reich et al.
5,994,855 A 11/1999 Lundell et al.
6,003,517 A 12/1999 Sheffield et al.
6,004,335 A 12/1999 Vaitekunas et al.
6,011,416 A 1/2000 Mizuno et al.
6,013,052 A 1/2000 Durman et al.
6,024,741 A 2/2000 Williamson, IV et al.
6,024,744 A 2/2000 Kese et al.
6,024,750 A 2/2000 Mastri et al.
6,027,515 A 2/2000 Cimino
6,031,526 A 2/2000 Shipp
6,033,375 A 3/2000 Brumbach
6,033,399 A 3/2000 Gines
6,036,667 A 3/2000 Manna et al.
6,036,707 A 3/2000 Spaulding
6,039,734 A 3/2000 Goble
6,048,224 A 4/2000 Kay
6,050,943 A 4/2000 Slayton et al.
6,050,996 A 4/2000 Schmaltz et al.
6,051,010 A 4/2000 DiMatteo et al.
6,056,735 A 5/2000 Okada et al.
6,063,098 A 5/2000 Houser et al.
6,066,132 A 5/2000 Chen et al.
6,066,151 A 5/2000 Miyawaki et al.
6,068,627 A 5/2000 Orszulak et al.
6,068,629 A 5/2000 Haissaguerre et al.
6,068,647 A 5/2000 Witt et al.
6,074,389 A 6/2000 Levine et al.
6,077,285 A 6/2000 Boukhny
6,080,149 A 6/2000 Huang et al.
6,083,191 A 7/2000 Rose
6,086,584 A 7/2000 Miller
6,090,120 A 7/2000 Wright et al.
6,091,995 A 7/2000 Ingle et al.
6,096,033 A 8/2000 Tu et al.
6,099,483 A 8/2000 Palmer et al.
6,099,542 A 8/2000 Cohn et al.
6,099,550 A 8/2000 Yoon
6,102,909 A 8/2000 Chen et al.
6,109,500 A 8/2000 Alli et al.
6,110,127 A 8/2000 Suzuki
6,113,594 A 9/2000 Savage
6,113,598 A 9/2000 Baker
6,117,152 A 9/2000 Huitema
H1904 H 10/2000 Yates et al.
6,126,629 A 10/2000 Perkins
6,126,658 A 10/2000 Baker
6,129,735 A 10/2000 Okada et al.
6,129,740 A 10/2000 Michelson
6,132,368 A 10/2000 Cooper
6,132,427 A 10/2000 Jones et al.
6,132,429 A 10/2000 Baker
6,132,448 A 10/2000 Perez et al.
6,139,320 A 10/2000 Hahn
6,139,561 A 10/2000 Shibata et al.
6,142,615 A 11/2000 Qiu et al.
6,142,994 A 11/2000 Swanson et al.
6,144,402 A 11/2000 Norsworthy et al.
6,147,560 A 11/2000 Erhage et al.
6,152,902 A 11/2000 Christian et al.
6,152,923 A 11/2000 Ryan
6,154,198 A 11/2000 Rosenberg
6,156,029 A 12/2000 Mueller
6,159,160 A 12/2000 Hsei et al.
6,159,175 A 12/2000 Strukel et al.
6,162,194 A 12/2000 Shipp
6,162,208 A 12/2000 Hipps
6,165,150 A 12/2000 Banko
6,174,309 B1 1/2001 Wrublewski et al.
6,174,310 B1 1/2001 Kirwan, Jr.
6,176,857 B1 1/2001 Ashley
6,179,853 B1 1/2001 Sachse et al.
6,183,426 B1 2/2001 Akisada et al.

(56) References Cited

U.S. PATENT DOCUMENTS 6,187,003 B1 2/2001 Buysse et al.
6,190,386 B1 2/2001 Rydell
6,193,709 B1 2/2001 Miyawaki et al.
6,204,592 B1 3/2001 Hur
6,205,383 B1 3/2001 Hermann
6,205,855 B1 3/2001 Pfeiffer
6,206,844 B1 3/2001 Reichel et al.
6,206,876 B1 3/2001 Levine et al.
6,210,337 B1 4/2001 Dunham et al.
6,210,402 B1 4/2001 Olsen et al.
6,210,403 B1 4/2001 Klicek
6,214,023 B1 4/2001 Whipple et al.
6,228,080 B1 5/2001 Gines
6,231,565 B1 5/2001 Tovey et al.
6,232,899 B1 5/2001 Craven
6,233,476 B1 5/2001 Strommer et al.
6,238,366 B1 5/2001 Savage et al.
6,238,384 B1 5/2001 Peer
6,241,724 B1 6/2001 Fleischman et al.
6,245,065 B1 6/2001 Panescu et al.
6,251,110 B1 6/2001 Wampler
6,252,110 B1 6/2001 Uemura et al.
D444,365 S 7/2001 Bass et al.
D445,092 S 7/2001 Lee
D445,764 S 7/2001 Lee
6,254,623 B1 7/2001 Haibel, Jr. et al.
6,257,241 B1 7/2001 Wampler
6,258,034 B1 7/2001 Hanafy
6,259,230 B1 7/2001 Chou
6,261,286 B1 7/2001 Goble et al.
6,267,761 B1 7/2001 Ryan
6,270,831 B2 8/2001 Kumar et al.
6,273,852 B1 8/2001 Lehe et al.
6,274,963 B1 8/2001 Estabrook et al.
6,277,115 B1 8/2001 Saadat
6,277,117 B1 8/2001 Tetzlaff et al.
6,278,218 B1 8/2001 Madan et al.
6,280,407 B1 8/2001 Manna et al.
6,283,981 B1 9/2001 Beaupre
6,287,344 B1 9/2001 Wampler et al.
6,290,575 B1 9/2001 Shipp
6,292,700 B1 9/2001 Morrison et al.
6,299,591 B1 10/2001 Banko
6,306,131 B1 10/2001 Hareyama et al.
6,306,157 B1 10/2001 Shchervinsky
6,309,400 B2 10/2001 Beaupre
6,311,783 B1 11/2001 Harpell
6,319,221 B1 11/2001 Savage et al.
6,325,795 B1 12/2001 Lindemann et al.
6,325,799 B1 12/2001 Goble
6,325,811 B1 12/2001 Messerly
6,328,751 B1 12/2001 Beaupre
6,332,891 B1 12/2001 Himes
6,338,657 B1 1/2002 Harper et al.
6,340,352 B1 1/2002 Okada et al.
6,340,878 B1 1/2002 Oglesbee
6,350,269 B1 2/2002 Shipp et al.
6,352,532 B1 3/2002 Kramer et al.
6,356,224 B1 3/2002 Wohlfarth
6,358,246 B1 3/2002 Behl et al.
6,358,264 B2 3/2002 Banko
6,364,888 B1 4/2002 Niemeyer et al.
6,379,320 B1 4/2002 Lafon et al.
D457,958 S 5/2002 Dycus et al.
6,383,194 B1 5/2002 Pothula
6,384,690 B1 5/2002 Wilhelmsson et al.
6,387,094 B1 5/2002 Eitenmuller
6,387,109 B1 5/2002 Davison et al.
6,388,657 B1 5/2002 Natoli
6,390,973 B1 5/2002 Ouchi
6,391,026 B1 5/2002 Hung et al.
6,391,042 B1 5/2002 Cimino
6,398,779 B1 6/2002 Buysse et al.
6,402,743 B1 6/2002 Orszulak et al.
6,402,748 B1 6/2002 Schoenman et al.
6,405,184 B1 6/2002 Bohme et al.
6,405,733 B1 6/2002 Fogarty et al.
6,409,722 B1 6/2002 Hoey et al.
H2037 H 7/2002 Yates et al.
6,416,469 B1 7/2002 Phung et al.
6,416,486 B1 7/2002 Wampler
6,417,969 B1 7/2002 DeLuca et al.
6,419,675 B1 7/2002 Gallo, Sr.
6,423,073 B2 7/2002 Bowman
6,423,082 B1 7/2002 Houser et al.
6,425,906 B1 7/2002 Young et al.
6,428,538 B1 8/2002 Blewett et al.
6,428,539 B1 8/2002 Baxter et al.
6,430,446 B1 8/2002 Knowlton
6,432,118 B1 8/2002 Messerly
6,436,114 B1 8/2002 Novak et al.
6,436,115 B1 8/2002 Beaupre
6,436,129 B1 8/2002 Sharkey et al.
6,440,062 B1 8/2002 Ouchi
6,443,968 B1 9/2002 Holthaus et al.
6,443,969 B1 9/2002 Novak et al.
6,449,006 B1 9/2002 Shipp
6,454,781 B1 9/2002 Witt et al.
6,454,782 B1 9/2002 Schwemberger
6,458,128 B1 10/2002 Schulze
6,458,130 B1 10/2002 Frazier et al.
6,458,142 B1 10/2002 Faller et al.
6,459,363 B1 10/2002 Walker et al.
6,461,363 B1 10/2002 Gadberry et al.
6,464,689 B1 10/2002 Qin et al.
6,464,702 B2 10/2002 Schulze et al.
6,468,270 B1 10/2002 Hovda et al.
6,475,211 B2 11/2002 Chess et al.
6,475,215 B1 11/2002 Tanrisever
6,480,796 B2 11/2002 Wiener
6,485,490 B2 11/2002 Wampler et al.
6,491,690 B1 12/2002 Goble et al.
6,491,701 B2 12/2002 Tierney et al.
6,491,708 B2 12/2002 Madan et al.
6,497,715 B2 12/2002 Satou
6,500,112 B1 12/2002 Khouri
6,500,176 B1 12/2002 Truckai et al.
6,500,188 B2 12/2002 Harper et al.
6,500,312 B2 12/2002 Wedekamp
6,503,248 B1 1/2003 Levine
6,506,208 B2 1/2003 Hunt et al.
6,511,478 B1 1/2003 Burnside et al.
6,511,480 B1 1/2003 Tetzlaff et al.
6,511,493 B1 1/2003 Moutafis et al.
6,514,252 B2 2/2003 Nezhat et al.
6,514,267 B2 2/2003 Jewett
6,517,565 B1 2/2003 Whitman et al.
6,524,251 B2 2/2003 Rabiner et al.
6,524,316 B1 2/2003 Nicholson et al.
6,527,736 B1 3/2003 Attinger et al.
6,531,846 B1 3/2003 Smith
6,533,784 B2 3/2003 Truckai et al.
6,537,272 B2 3/2003 Christopherson et al.
6,537,291 B2 3/2003 Friedman et al.
6,543,452 B1 4/2003 Lavigne
6,543,456 B1 4/2003 Freeman
6,544,260 B1 4/2003 Markel et al.
6,551,309 B1 4/2003 LePivert
6,554,829 B2 4/2003 Schulze et al.
6,558,376 B2 5/2003 Bishop
6,558,380 B2 5/2003 Lingenfelder et al.
6,561,983 B2 5/2003 Cronin et al.
6,562,035 B1 5/2003 Levin
6,562,037 B2 5/2003 Paton et al.
6,565,558 B1 5/2003 Lindenmeier et al.
6,572,563 B2 6/2003 Ouchi
6,572,632 B2 6/2003 Zisterer et al.
6,572,639 B1 6/2003 Ingle et al.
6,575,969 B1 6/2003 Rittman, III et al.
6,582,427 B1 6/2003 Goble et al.
6,582,451 B1 6/2003 Marucci et al.
6,584,360 B2 6/2003 Francischelli et al.
D477,408 S 7/2003 Bromley
6,585,735 B1 7/2003 Frazier et al.

(56) References Cited

U.S. PATENT DOCUMENTS 6,588,277 B2 7/2003 Giordano et al.
6,589,200 B1 7/2003 Schwemberger et al.
6,589,239 B2 7/2003 Khandkar et al.
6,590,733 B1 7/2003 Wilson et al.
6,599,288 B2 7/2003 Maguire et al.
6,602,252 B2 8/2003 Mollenauer
6,602,262 B2 8/2003 Griego et al.
6,607,540 B1 8/2003 Shipp
6,610,059 B1 8/2003 West, Jr.
6,610,060 B2 8/2003 Mulier et al.
6,611,793 B1 8/2003 Burnside et al.
6,616,450 B2 9/2003 Mossle et al.
6,619,529 B2 9/2003 Green et al.
6,620,161 B2 9/2003 Schulze et al.
6,622,731 B2 9/2003 Daniel et al.
6,623,482 B2 9/2003 Pendekanti et al.
6,623,500 B1 9/2003 Cook et al.
6,623,501 B2 9/2003 Heller et al.
6,626,848 B2 9/2003 Neuenfeldt
6,626,926 B2 9/2003 Friedman et al.
6,629,974 B2 10/2003 Penny et al.
6,632,221 B1 10/2003 Edwards et al.
6,633,234 B2 10/2003 Wiener et al.
6,635,057 B2 10/2003 Harano et al.
6,644,532 B2 11/2003 Green et al.
6,651,669 B1 11/2003 Burnside
6,652,513 B2 11/2003 Panescu et al.
6,652,539 B2 11/2003 Shipp et al.
6,652,545 B2 11/2003 Shipp et al.
6,656,132 B1 12/2003 Ouchi
6,656,177 B2 12/2003 Truckai et al.
6,656,198 B2 12/2003 Tsonton et al.
6,660,017 B2 12/2003 Beaupre
6,662,127 B2 12/2003 Wiener et al.
6,663,941 B2 12/2003 Brown et al.
6,666,860 B1 12/2003 Takahashi
6,666,875 B1 12/2003 Sakurai et al.
6,669,690 B1 12/2003 Okada et al.
6,669,710 B2 12/2003 Moutafis et al.
6,673,248 B2 1/2004 Chowdhury
6,676,660 B2 1/2004 Wampler et al.
6,678,621 B2 1/2004 Wiener et al.
6,679,875 B2 1/2004 Honda et al.
6,679,882 B1 1/2004 Kornerup
6,679,899 B2 1/2004 Wiener et al.
6,682,501 B1 1/2004 Nelson et al.
6,682,544 B2 1/2004 Mastri et al.
6,685,700 B2 2/2004 Behl et al.
6,685,701 B2 2/2004 Orszulak et al.
6,685,703 B2 2/2004 Pearson et al.
6,689,145 B2 2/2004 Lee et al.
6,689,146 B1 2/2004 Himes
6,690,960 B2 2/2004 Chen et al.
6,695,840 B2 2/2004 Schulze
6,702,821 B2 3/2004 Bonutti
6,716,215 B1 4/2004 David et al.
6,719,692 B2 4/2004 Kleffner et al.
6,719,765 B2 4/2004 Bonutti
6,719,776 B2 4/2004 Baxter et al.
6,722,552 B2 4/2004 Fenton, Jr.
6,723,091 B2 4/2004 Goble et al.
D490,059 S 5/2004 Conway et al.
6,730,080 B2 5/2004 Harano et al.
6,731,047 B2 5/2004 Kauf et al.
6,733,498 B2 5/2004 Paton et al.
6,733,506 B1 5/2004 McDevitt et al.
6,736,813 B2 5/2004 Yamauchi et al.
6,739,872 B1 5/2004 Turri
6,740,079 B1 5/2004 Eggers et al.
D491,666 S 6/2004 Kimmell et al.
6,743,245 B2 6/2004 Lobdell
6,746,284 B1 6/2004 Spink, Jr.
6,746,443 B1 6/2004 Morley et al.
6,752,815 B2 6/2004 Beaupre
6,755,825 B2 6/2004 Shoenman et al.
6,761,698 B2 7/2004 Shibata et al.
6,762,535 B2 7/2004 Take et al.
6,766,202 B2 7/2004 Underwood et al.
6,770,072 B1 8/2004 Truckai et al.
6,773,409 B2 8/2004 Truckai et al.
6,773,434 B2 8/2004 Ciarrocca
6,773,435 B2 8/2004 Schulze et al.
6,773,443 B2 8/2004 Truwit et al.
6,773,444 B2 8/2004 Messerly
6,775,575 B2 8/2004 Bommannan et al.
6,778,023 B2 8/2004 Christensen
6,783,524 B2 8/2004 Anderson et al.
6,786,382 B1 9/2004 Hoffman
6,786,383 B2 9/2004 Stegelmann
6,789,939 B2 9/2004 Schrodinger et al.
6,790,173 B2 9/2004 Saadat et al.
6,790,216 B1 9/2004 Ishikawa
6,794,027 B1 9/2004 Araki et al.
6,796,981 B2 9/2004 Wham et al.
D496,997 S 10/2004 Dycus et al.
6,800,085 B2 10/2004 Selmon et al.
6,802,843 B2 10/2004 Truckai et al.
6,808,525 B2 10/2004 Latterell et al.
6,809,508 B2 10/2004 Donofrio
6,810,281 B2 10/2004 Brock et al.
6,811,842 B1 11/2004 Ehrnsperger et al.
6,814,731 B2 11/2004 Swanson
6,819,027 B2 11/2004 Saraf
6,821,273 B2 11/2004 Mollenauer
6,827,712 B2 12/2004 Tovey et al.
6,828,712 B2 12/2004 Battaglin et al.
6,835,082 B2 12/2004 Gonnering
6,835,199 B2 12/2004 McGuckin, Jr. et al.
6,840,938 B1 1/2005 Morley et al.
6,843,789 B2 1/2005 Goble
6,849,073 B2 2/2005 Hoey et al.
6,860,878 B2 3/2005 Brock
6,860,880 B2 3/2005 Treat et al.
6,863,676 B2 3/2005 Lee et al.
6,866,671 B2 3/2005 Tierney et al.
6,869,439 B2 3/2005 White et al.
6,875,220 B2 4/2005 Du et al.
6,877,647 B2 4/2005 Green et al.
6,882,439 B2 4/2005 Ishijima
6,887,209 B2 5/2005 Kadziauskas et al.
6,887,252 B1 5/2005 Okada et al.
6,893,435 B2 5/2005 Goble
6,898,536 B2 5/2005 Wiener et al.
6,899,685 B2 5/2005 Kermode et al.
6,905,497 B2 6/2005 Truckai et al.
6,908,463 B2 6/2005 Treat et al.
6,908,472 B2 6/2005 Wiener et al.
6,913,579 B2 7/2005 Truckai et al.
6,915,623 B2 7/2005 Dey et al.
6,923,804 B2 8/2005 Eggers et al.
6,923,806 B2 8/2005 Hooven et al.
6,926,712 B2 8/2005 Phan
6,926,716 B2 8/2005 Baker et al.
6,926,717 B1 8/2005 Garito et al.
6,929,602 B2 8/2005 Hirakui et al.
6,929,622 B2 8/2005 Chian
6,929,632 B2 8/2005 Nita et al.
6,929,644 B2 8/2005 Truckai et al.
6,933,656 B2 8/2005 Matsushita et al.
D509,589 S 9/2005 Wells
6,942,660 B2 9/2005 Pantera et al.
6,942,677 B2 9/2005 Nita et al.
6,945,981 B2 9/2005 Donofrio et al.
6,946,779 B2 9/2005 Birgel
6,948,503 B2 9/2005 Refior et al.
6,953,461 B2 10/2005 McClurken et al.
6,958,070 B2 10/2005 Witt et al.
D511,145 S 11/2005 Donofrio et al.
6,974,450 B2 12/2005 Weber et al.
6,976,844 B2 12/2005 Hickok et al.
6,976,969 B2 12/2005 Messerly
6,977,495 B2 12/2005 Donofrio
6,979,332 B2 12/2005 Adams
6,981,628 B2 1/2006 Wales

(56) References Cited

U.S. PATENT DOCUMENTS 6,984,220 B2 1/2006 Wuchinich
6,984,231 B2 1/2006 Goble et al.
6,988,295 B2 1/2006 Tillim
6,988,649 B2 1/2006 Shelton, IV et al.
6,994,708 B2 2/2006 Manzo
6,994,709 B2 2/2006 Iida
7,000,818 B2 2/2006 Shelton, IV et al.
7,001,335 B2 2/2006 Adachi et al.
7,001,379 B2 2/2006 Behl et al.
7,001,382 B2 2/2006 Gallo, Sr.
7,004,951 B2 2/2006 Gibbens, III
7,011,657 B2 3/2006 Truckai et al.
7,014,638 B2 3/2006 Michelson
7,018,389 B2 3/2006 Camerlengo
7,025,732 B2 4/2006 Thompson et al.
7,033,356 B2 4/2006 Latterell et al.
7,033,357 B2 4/2006 Baxter et al.
7,037,306 B2 5/2006 Podany et al.
7,041,083 B2 5/2006 Chu et al.
7,041,088 B2 5/2006 Nawrocki et al.
7,041,102 B2 5/2006 Truckai et al.
7,044,949 B2 5/2006 Orszulak et al.
7,052,494 B2 5/2006 Goble et al.
7,052,496 B2 5/2006 Yamauchi
7,055,731 B2 6/2006 Shelton, IV et al.
7,063,699 B2 6/2006 Hess et al.
7,066,893 B2 6/2006 Hibner et al.
7,066,895 B2 6/2006 Podany
7,066,936 B2 6/2006 Ryan
7,070,597 B2 7/2006 Truckai et al.
7,074,218 B2 7/2006 Washington et al.
7,074,219 B2 7/2006 Levine et al.
7,077,039 B2 7/2006 Gass et al.
7,077,845 B2 7/2006 Hacker et al.
7,077,853 B2 7/2006 Kramer et al.
7,083,075 B2 8/2006 Swayze et al.
7,083,613 B2 8/2006 Treat
7,083,618 B2 8/2006 Couture et al.
7,083,619 B2 8/2006 Truckai et al.
7,087,054 B2 8/2006 Truckai et al.
7,090,637 B2 8/2006 Danitz et al.
7,090,672 B2 8/2006 Underwood et al.
7,094,235 B2 8/2006 Francischelli
7,101,371 B2 9/2006 Dycus et al.
7,101,372 B2 9/2006 Dycus et al.
7,101,373 B2 9/2006 Dycus et al.
7,101,378 B2 9/2006 Salameh et al.
7,104,834 B2 9/2006 Robinson et al.
7,108,695 B2 9/2006 Witt et al.
7,111,769 B2 9/2006 Wales et al.
7,112,201 B2 9/2006 Truckai et al.
7,113,831 B2 9/2006 Hooven
D531,311 S 10/2006 Guerra et al.
7,117,034 B2 10/2006 Kronberg
7,118,564 B2 10/2006 Ritchie et al.
7,118,570 B2 10/2006 Tetzlaff et al.
7,118,587 B2 10/2006 Dycus et al.
7,119,516 B2 10/2006 Denning
7,124,932 B2 10/2006 Isaacson et al.
7,125,409 B2 10/2006 Truckai et al.
7,128,720 B2 10/2006 Podany
7,131,860 B2 11/2006 Sartor et al.
7,131,970 B2 11/2006 Moses et al.
7,135,018 B2 11/2006 Ryan et al.
7,135,030 B2 11/2006 Schwemberger et al.
7,137,980 B2 11/2006 Buysse et al.
7,143,925 B2 12/2006 Shelton, IV et al.
7,144,403 B2 12/2006 Booth
7,147,138 B2 12/2006 Shelton, IV
7,153,315 B2 12/2006 Miller
D536,093 S 1/2007 Nakajima et al.
7,156,189 B1 1/2007 Bar-Cohen et al.
7,156,846 B2 1/2007 Dycus et al.
7,156,853 B2 1/2007 Muratsu
7,157,058 B2 1/2007 Marhasin et al.
7,159,750 B2 1/2007 Racenet et al.
7,160,259 B2 1/2007 Tardy et al.
7,160,296 B2 1/2007 Pearson et al.
7,160,298 B2 1/2007 Lawes et al.
7,160,299 B2 1/2007 Baily
7,163,548 B2 1/2007 Stulen et al.
7,166,103 B2 1/2007 Carmel et al.
7,169,144 B2 1/2007 Hoey et al.
7,169,146 B2 1/2007 Truckai et al.
7,169,156 B2 1/2007 Hart
7,179,254 B2 2/2007 Pendekanti et al.
7,179,271 B2 2/2007 Friedman et al.
7,186,253 B2 3/2007 Truckai et al.
7,189,233 B2 3/2007 Truckai et al.
7,195,631 B2 3/2007 Dumbauld
D541,418 S 4/2007 Schechter et al.
7,198,635 B2 4/2007 Danek et al.
7,204,820 B2 4/2007 Akahoshi
7,207,471 B2 4/2007 Heinrich et al.
7,207,997 B2 4/2007 Shipp et al.
7,208,005 B2 4/2007 Frecker et al.
7,210,881 B2 5/2007 Greenberg
7,211,079 B2 5/2007 Treat
7,217,128 B2 5/2007 Atkin et al.
7,217,269 B2 5/2007 El-Galley et al.
7,220,951 B2 5/2007 Truckai et al.
7,223,229 B2 5/2007 Inman et al.
7,225,964 B2 6/2007 Mastri et al.
7,226,447 B2 6/2007 Uchida et al.
7,226,448 B2 6/2007 Bertolero et al.
7,229,455 B2 6/2007 Sakurai et al.
7,232,440 B2 6/2007 Dumbauld et al.
7,235,071 B2 6/2007 Gonnering
7,235,073 B2 6/2007 Levine et al.
7,241,294 B2 7/2007 Reschke
7,244,262 B2 7/2007 Wiener et al.
7,251,531 B2 7/2007 Mosher et al.
7,252,641 B2 8/2007 Thompson et al.
7,252,667 B2 8/2007 Moses et al.
7,258,688 B1 8/2007 Shah et al.
7,264,618 B2 9/2007 Murakami et al.
7,267,677 B2 9/2007 Johnson et al.
7,267,685 B2 9/2007 Butaric et al.
7,269,873 B2 9/2007 Brewer et al.
7,273,483 B2 9/2007 Wiener et al.
D552,241 S 10/2007 Bromley et al.
7,282,048 B2 10/2007 Goble et al.
7,285,895 B2 10/2007 Beaupre
7,287,682 B1 10/2007 Ezzat et al.
7,297,149 B2 11/2007 Vitali et al.
7,300,431 B2 11/2007 Dubrovsky
7,300,435 B2 11/2007 Wham et al.
7,300,446 B2 11/2007 Beaupre
7,300,450 B2 11/2007 Vleugels et al.
7,303,531 B2 12/2007 Lee et al.
7,303,557 B2 12/2007 Wham et al.
7,306,597 B2 12/2007 Manzo
7,307,313 B2 12/2007 Ohyanagi et al.
7,309,849 B2 12/2007 Truckai et al.
7,311,706 B2 12/2007 Schoenman et al.
7,311,709 B2 12/2007 Truckai et al.
7,317,955 B2 1/2008 McGreevy
7,318,831 B2 1/2008 Alvarez et al.
7,318,832 B2 1/2008 Young et al.
7,326,236 B2 2/2008 Andreas et al.
7,329,257 B2 2/2008 Kanehira et al.
7,331,410 B2 2/2008 Yong et al.
7,335,165 B2 2/2008 Truwit et al.
7,335,997 B2 2/2008 Wiener
7,337,010 B2 2/2008 Howard et al.
7,353,068 B2 4/2008 Tanaka et al.
7,354,440 B2 4/2008 Truckal et al.
7,357,287 B2 4/2008 Shelton, IV et al.
7,357,802 B2 4/2008 Palanker et al.
7,361,172 B2 4/2008 Cimino
7,364,577 B2 4/2008 Wham et al.
7,367,976 B2 5/2008 Lawes et al.
7,371,227 B2 5/2008 Zeiner
RE40,388 E 6/2008 Gines

(56) References Cited

U.S. PATENT DOCUMENTS 7,380,695 B2 6/2008 Doll et al.
7,380,696 B2 6/2008 Shelton, IV et al.
7,381,209 B2 6/2008 Truckai et al.
7,384,420 B2 6/2008 Dycus et al.
7,390,317 B2 6/2008 Taylor et al.
7,396,356 B2 7/2008 Mollenauer
7,403,224 B2 7/2008 Fuller et al.
7,404,508 B2 7/2008 Smith et al.
7,407,077 B2 8/2008 Ortiz et al.
7,408,288 B2 8/2008 Hara
7,412,008 B2 8/2008 Lliev
7,416,101 B2 8/2008 Shelton, IV et al.
7,416,437 B2 8/2008 Sartor et al.
D576,725 S 9/2008 Shumer et al.
7,419,490 B2 9/2008 Falkenstein et al.
7,422,139 B2 9/2008 Shelton, IV et al.
7,422,463 B2 9/2008 Kuo
7,422,582 B2 9/2008 Malackowski et al.
D578,643 S 10/2008 Shumer et al.
D578,644 S 10/2008 Shumer et al.
D578,645 S 10/2008 Shumer et al.
7,431,694 B2 10/2008 Stefanchik et al.
7,431,704 B2 10/2008 Babaev
7,431,720 B2 10/2008 Pendekanti et al.
7,435,582 B2 10/2008 Zimmermann et al.
7,441,684 B2 10/2008 Shelton, IV et al.
7,442,193 B2 10/2008 Shields et al.
7,445,621 B2 11/2008 Dumbauld et al.
7,449,004 B2 11/2008 Yamada et al.
7,451,904 B2 11/2008 Shelton, IV
7,455,208 B2 11/2008 Wales et al.
7,455,641 B2 11/2008 Yamada et al.
7,462,181 B2 12/2008 Kraft et al.
7,464,846 B2 12/2008 Shelton, IV et al.
7,464,849 B2 12/2008 Shelton, IV et al.
7,472,815 B2 1/2009 Shelton, IV et al.
7,473,145 B2 1/2009 Ehr et al.
7,473,253 B2 1/2009 Dycus et al.
7,473,263 B2 1/2009 Johnston et al.
7,479,148 B2 1/2009 Beaupre
7,479,160 B2 1/2009 Branch et al.
7,481,775 B2 1/2009 Weikel, Jr. et al.
7,488,285 B2 2/2009 Honda et al.
7,488,319 B2 2/2009 Yates
7,491,201 B2 2/2009 Shields et al.
7,491,202 B2 2/2009 Odom et al.
7,494,468 B2 2/2009 Rabiner et al.
7,494,501 B2 2/2009 Ahlberg et al.
7,498,080 B2 3/2009 Tung et al.
7,502,234 B2 3/2009 Goliszek et al.
7,503,893 B2 3/2009 Kucklick
7,503,895 B2 3/2009 Rabiner et al.
7,506,790 B2 3/2009 Shelton, IV
7,506,791 B2 3/2009 Omaits et al.
7,507,239 B2 3/2009 Shadduck
7,510,107 B2 3/2009 Timm et al.
7,510,556 B2 3/2009 Nguyen et al.
7,513,025 B2 4/2009 Fischer
7,517,349 B2 4/2009 Truckai et al.
7,520,865 B2 4/2009 Radley Young et al.
7,524,320 B2 4/2009 Tierney et al.
7,525,309 B2 4/2009 Sherman et al.
7,530,986 B2 5/2009 Beaupre et al.
7,534,243 B1 5/2009 Chin et al.
7,535,233 B2 5/2009 Kojovic et al.
D594,983 S 6/2009 Price et al.
7,540,871 B2 6/2009 Gonnering
7,540,872 B2 6/2009 Schechter et al.
7,543,730 B1 6/2009 Marczyk
7,544,200 B2 6/2009 Houser
7,549,564 B2 6/2009 Boudreaux
7,550,216 B2 6/2009 Ofer et al.
7,553,309 B2 6/2009 Buysse et al.
7,554,343 B2 6/2009 Bromfield
7,559,450 B2 7/2009 Wales et al.
7,559,452 B2 7/2009 Wales et al.
7,563,259 B2 7/2009 Takahashi
7,566,318 B2 7/2009 Haefner
7,567,012 B2 7/2009 Namikawa
7,568,603 B2 8/2009 Shelton, IV et al.
7,569,057 B2 8/2009 Liu et al.
7,572,266 B2 8/2009 Young et al.
7,572,268 B2 8/2009 Babaev
7,578,820 B2 8/2009 Moore et al.
7,582,084 B2 9/2009 Swanson et al.
7,582,086 B2 9/2009 Privitera et al.
7,582,087 B2 9/2009 Tetzlaff et al.
7,582,095 B2 9/2009 Shipp et al.
7,585,181 B2 9/2009 Olsen
7,586,289 B2 9/2009 Andruk et al.
7,587,536 B2 9/2009 McLeod
7,588,176 B2 9/2009 Timm et al.
7,588,177 B2 9/2009 Racenet
7,594,925 B2 9/2009 Danek et al.
7,597,693 B2 10/2009 Garrison
7,601,119 B2 10/2009 Shahinian
7,601,136 B2 10/2009 Akahoshi
7,604,150 B2 10/2009 Boudreaux
7,607,557 B2 10/2009 Shelton, IV et al.
7,617,961 B2 11/2009 Viola
7,621,910 B2 11/2009 Sugi
7,621,930 B2 11/2009 Houser
7,625,370 B2 12/2009 Hart et al.
7,628,791 B2 12/2009 Garrison et al.
7,628,792 B2 12/2009 Guerra
7,632,267 B2 12/2009 Dahla
7,632,269 B2 12/2009 Truckai et al.
7,637,410 B2 12/2009 Marczyk
7,641,653 B2 1/2010 Dalla Betta et al.
7,641,671 B2 1/2010 Crainich
7,644,848 B2 1/2010 Swayze et al.
7,645,240 B2 1/2010 Thompson et al.
7,645,277 B2 1/2010 McClurken et al.
7,645,278 B2 1/2010 Ichihashi et al.
7,648,499 B2 1/2010 Orszulak et al.
7,649,410 B2 1/2010 Andersen et al.
7,654,431 B2 2/2010 Hueil et al.
7,655,003 B2 2/2010 Lorang et al.
7,658,311 B2 2/2010 Boudreaux
7,659,833 B2 2/2010 Warner et al.
7,662,151 B2 2/2010 Crompton, Jr. et al.
7,665,647 B2 2/2010 Shelton, IV et al.
7,666,206 B2 2/2010 Taniguchi et al.
7,667,592 B2 2/2010 Ohyama et al.
7,670,334 B2 3/2010 Hueil et al.
7,670,338 B2 3/2010 Albrecht et al.
7,674,263 B2 3/2010 Ryan
7,678,069 B1 3/2010 Baker et al.
7,678,105 B2 3/2010 McGreevy et al.
7,678,125 B2 3/2010 Shipp
7,682,366 B2 3/2010 Sakurai et al.
7,686,770 B2 3/2010 Cohen
7,686,826 B2 3/2010 Lee et al.
7,688,028 B2 3/2010 Phillips et al.
7,691,095 B2 4/2010 Bednarek et al.
7,691,098 B2 4/2010 Wallace et al.
7,696,441 B2 4/2010 Kataoka
7,699,846 B2 4/2010 Ryan
7,703,459 B2 4/2010 Saadat et al.
7,703,653 B2 4/2010 Shah et al.
7,708,735 B2 5/2010 Chapman et al.
7,708,751 B2 5/2010 Hughes et al.
7,708,758 B2 5/2010 Lee et al.
7,708,768 B2 5/2010 Danek et al.
7,713,202 B2 5/2010 Boukhny et al.
7,713,267 B2 5/2010 Pozzato
7,714,481 B2 5/2010 Sakai
7,717,312 B2 5/2010 Beetel
7,717,914 B2 5/2010 Kimura
7,717,915 B2 5/2010 Miyazawa
7,721,935 B2 5/2010 Racenet et al.
7,722,527 B2 5/2010 Bouchier et al.
7,722,607 B2 5/2010 Dumbauld et al.
7,723,951 B2 5/2010 Poisner

(56) References Cited

U.S. PATENT DOCUMENTS

D618,797 S 6/2010 Price et al.
7,726,537 B2 6/2010 Olson et al.
7,727,177 B2 6/2010 Bayat
7,731,717 B2 6/2010 Odom et al.
7,738,969 B2 6/2010 Bleich
7,740,594 B2 6/2010 Hibner
7,744,615 B2 6/2010 Couture
7,749,240 B2 7/2010 Takahashi et al.
7,751,115 B2 7/2010 Song
7,753,245 B2 7/2010 Boudreaux et al.
7,753,904 B2 7/2010 Shelton, IV et al.
7,753,908 B2 7/2010 Swanson
7,762,445 B2 7/2010 Heinrich et al.
D621,503 S 8/2010 Otten et al.
7,766,210 B2 8/2010 Shelton, IV et al.
7,766,693 B2 8/2010 Sartor et al.
7,766,910 B2 8/2010 Hixson et al.
7,768,510 B2 8/2010 Tsai et al.
7,770,774 B2 8/2010 Mastri et al.
7,770,775 B2 8/2010 Shelton, IV et al.
7,771,425 B2 8/2010 Dycus et al.
7,771,444 B2 8/2010 Patel et al.
7,775,972 B2 8/2010 Brock et al.
7,776,036 B2 8/2010 Schechter et al.
7,776,037 B2 8/2010 Odom
7,778,733 B2 8/2010 Nowlin et al.
7,780,054 B2 8/2010 Wales
7,780,593 B2 8/2010 Ueno et al.
7,780,651 B2 8/2010 Madhani et al.
7,780,659 B2 8/2010 Okada et al.
7,780,663 B2 8/2010 Yates et al.
7,784,662 B2 8/2010 Wales et al.
7,784,663 B2 8/2010 Shelton, IV
7,789,883 B2 9/2010 Takashino et al.
7,793,814 B2 9/2010 Racenet et al.
7,794,475 B2 9/2010 Hess et al.
7,796,969 B2 9/2010 Kelly et al.
7,798,386 B2 9/2010 Schall et al.
7,799,020 B2 9/2010 Shores et al.
7,799,027 B2 9/2010 Hafner
7,799,045 B2 9/2010 Masuda
7,803,151 B2 9/2010 Whitman
7,803,152 B2 9/2010 Honda et al.
7,803,156 B2 9/2010 Eder et al.
7,803,168 B2 9/2010 Gifford et al.
7,806,891 B2 10/2010 Nowlin et al.
7,810,693 B2 10/2010 Broehl et al.
7,811,283 B2 10/2010 Moses et al.
7,815,238 B2 10/2010 Cao
7,815,641 B2 10/2010 Dodde et al.
7,819,298 B2 10/2010 Hall et al.
7,819,299 B2 10/2010 Shelton, IV et al.
7,819,819 B2 10/2010 Quick et al.
7,819,872 B2 10/2010 Johnson et al.
7,821,143 B2 10/2010 Wiener
D627,066 S 11/2010 Romero
7,824,401 B2 11/2010 Manzo et al.
7,832,408 B2 11/2010 Shelton, IV et al.
7,832,611 B2 11/2010 Boyden et al.
7,832,612 B2 11/2010 Baxter, III et al.
7,834,484 B2 11/2010 Sartor
7,837,699 B2 11/2010 Yamada et al.
7,845,537 B2 12/2010 Shelton, IV et al.
7,846,155 B2 12/2010 Houser et al.
7,846,159 B2 12/2010 Morrison et al.
7,846,160 B2 12/2010 Payne et al.
7,846,161 B2 12/2010 Dumbauld et al.
7,854,735 B2 12/2010 Houser et al.
D631,155 S 1/2011 Peine et al.
7,861,906 B2 1/2011 Doll et al.
7,862,560 B2 1/2011 Marion
7,862,561 B2 1/2011 Swanson et al.
7,867,228 B2 1/2011 Nobis et al.
7,871,392 B2 1/2011 Sartor
7,871,423 B2 1/2011 Livneh
7,876,030 B2 1/2011 Taki et al.
D631,965 S 2/2011 Price et al.
7,877,852 B2 2/2011 Unger et al.
7,878,991 B2 2/2011 Babaev
7,879,029 B2 2/2011 Jimenez
7,879,033 B2 2/2011 Sartor et al.
7,879,035 B2 2/2011 Garrison et al.
7,879,070 B2 2/2011 Ortiz et al.
7,883,475 B2 2/2011 Dupont et al.
7,892,606 B2 2/2011 Thies et al.
7,896,875 B2 3/2011 Heim et al.
7,897,792 B2 3/2011 Iikura et al.
7,901,400 B2 3/2011 Wham et al.
7,901,423 B2 3/2011 Stulen et al.
7,905,881 B2 3/2011 Masuda et al.
7,909,220 B2 3/2011 Viola
7,909,820 B2 3/2011 Lipson et al.
7,909,824 B2 3/2011 Masuda et al.
7,918,848 B2 4/2011 Lau et al.
7,919,184 B2 4/2011 Mohapatra et al.
7,922,061 B2 4/2011 Shelton, IV et al.
7,922,651 B2 4/2011 Yamada et al.
7,931,611 B2 4/2011 Novak et al.
7,931,649 B2 4/2011 Couture et al.
D637,288 S 5/2011 Houghton
D638,540 S 5/2011 Ijiri et al.
7,935,114 B2 5/2011 Takashino et al.
7,936,203 B2 5/2011 Zimlich
7,951,095 B2 5/2011 Makin et al.
7,951,165 B2 5/2011 Golden et al.
7,954,682 B2 6/2011 Giordano et al.
7,955,331 B2 6/2011 Truckai et al.
7,956,620 B2 6/2011 Gilbert
7,959,050 B2 6/2011 Smith et al.
7,959,626 B2 6/2011 Hong et al.
7,963,963 B2 6/2011 Francischelli et al.
7,967,602 B2 6/2011 Lindquist
7,972,328 B2 7/2011 Wham et al.
7,972,329 B2 7/2011 Refior et al.
7,975,895 B2 7/2011 Milliman
7,976,544 B2 7/2011 McClurken et al.
7,980,443 B2 7/2011 Scheib et al.
7,981,050 B2 7/2011 Ritchart et al.
7,981,113 B2 7/2011 Truckai et al.
7,997,278 B2 8/2011 Utley et al.
7,998,157 B2 8/2011 Culp et al.
8,002,732 B2 8/2011 Visconti
8,002,770 B2 8/2011 Swanson et al.
8,020,743 B2 9/2011 Shelton, IV
8,025,672 B2 9/2011 Novak et al.
8,028,885 B2 10/2011 Smith et al.
8,033,173 B2 10/2011 Ehlert et al.
8,034,049 B2 10/2011 Odom et al.
8,038,693 B2 10/2011 Allen
8,048,070 B2 11/2011 O'Brien et al.
8,048,074 B2 11/2011 Masuda
8,052,672 B2 11/2011 Laufer et al.
8,055,208 B2 11/2011 Lilla et al.
8,056,720 B2 11/2011 Hawkes
8,056,787 B2 11/2011 Boudreaux et al.
8,057,468 B2 11/2011 Konesky
8,057,498 B2 11/2011 Robertson
8,058,771 B2 11/2011 Giordano et al.
8,061,014 B2 11/2011 Smith et al.
8,066,167 B2 11/2011 Measamer et al.
8,070,036 B1 12/2011 Knodel
8,070,711 B2 12/2011 Bassinger et al.
8,070,762 B2 12/2011 Escudero et al.
8,075,555 B2 12/2011 Truckai et al.
8,075,558 B2 12/2011 Truckai et al.
8,089,197 B2 1/2012 Rinner et al.
8,092,475 B2 1/2012 Cotter et al.
8,096,459 B2 1/2012 Ortiz et al.
8,097,012 B2 1/2012 Kagarise
8,100,894 B2 1/2012 Mucko et al.
8,105,230 B2 1/2012 Honda et al.
8,105,323 B2 1/2012 Buysse et al.
8,105,324 B2 1/2012 Palanker et al.
8,114,104 B2 2/2012 Young et al.

(56) References Cited

U.S. PATENT DOCUMENTS 8,118,276 B2 2/2012 Sanders et al.
8,128,624 B2 3/2012 Couture et al.
8,133,218 B2 3/2012 Daw et al.
8,136,712 B2 3/2012 Zingman
8,141,762 B2 3/2012 Bedi et al.
8,142,421 B2 3/2012 Cooper et al.
8,142,461 B2 3/2012 Houser et al.
8,147,485 B2 4/2012 Wham et al.
8,147,488 B2 4/2012 Masuda
8,147,508 B2 4/2012 Madan et al.
8,152,801 B2 4/2012 Goldberg et al.
8,152,825 B2 4/2012 Madan et al.
8,157,145 B2 4/2012 Shelton, IV et al.
8,161,977 B2 4/2012 Shelton, IV et al.
8,162,966 B2 4/2012 Connor et al.
8,170,717 B2 5/2012 Sutherland et al.
8,172,846 B2 5/2012 Brunnett et al.
8,172,870 B2 5/2012 Shipp
8,177,800 B2 5/2012 Spitz et al.
8,182,502 B2 5/2012 Stulen et al.
8,186,560 B2 5/2012 Hess et al.
8,186,877 B2 5/2012 Klimovitch et al.
8,187,267 B2 5/2012 Pappone et al.
D661,801 S 6/2012 Price et al.
D661,802 S 6/2012 Price et al.
D661,803 S 6/2012 Price et al.
D661,804 S 6/2012 Price et al.
8,197,472 B2 6/2012 Lau et al.
8,197,479 B2 6/2012 Olson et al.
8,197,502 B2 6/2012 Smith et al.
8,207,651 B2 6/2012 Gilbert
8,210,411 B2 7/2012 Yates et al.
8,211,100 B2 7/2012 Podhajsky et al.
8,220,688 B2 7/2012 Laurent et al.
8,221,306 B2 7/2012 Okada et al.
8,221,415 B2 7/2012 Francischelli
8,221,418 B2 7/2012 Prakash et al.
8,226,580 B2 7/2012 Govari et al.
8,226,665 B2 7/2012 Cohen
8,226,675 B2 7/2012 Houser et al.
8,231,607 B2 7/2012 Takuma
8,235,917 B2 8/2012 Joseph et al.
8,236,018 B2 8/2012 Yoshimine et al.
8,236,019 B2 8/2012 Houser
8,236,020 B2 8/2012 Smith et al.
8,241,235 B2 8/2012 Kahler et al.
8,241,271 B2 8/2012 Millman et al.
8,241,282 B2 8/2012 Unger et al.
8,241,283 B2 8/2012 Guerra et al.
8,241,284 B2 8/2012 Dycus et al.
8,241,312 B2 8/2012 Messerly
8,246,575 B2 8/2012 Viola
8,246,615 B2 8/2012 Behnke
8,246,616 B2 8/2012 Amoah et al.
8,246,618 B2 8/2012 Bucciaglia et al.
8,246,642 B2 8/2012 Houser et al.
8,251,994 B2 8/2012 McKenna et al.
8,252,012 B2 8/2012 Stulen
8,253,303 B2 8/2012 Giordano et al.
8,257,377 B2 9/2012 Wiener et al.
8,257,387 B2 9/2012 Cunningham
8,262,563 B2 9/2012 Bakos et al.
8,267,300 B2 9/2012 Boudreaux
8,267,935 B2 9/2012 Couture et al.
8,273,087 B2 9/2012 Kimura et al.
D669,992 S 10/2012 Schafer et al.
D669,993 S 10/2012 Merchant et al.
8,277,446 B2 10/2012 Heard
8,277,447 B2 10/2012 Garrison et al.
8,277,471 B2 10/2012 Wiener et al.
8,282,581 B2 10/2012 Zhao et al.
8,282,669 B2 10/2012 Gerber et al.
8,286,846 B2 10/2012 Smith et al.
8,287,485 B2 10/2012 Kimura et al.
8,287,528 B2 10/2012 Wham et al.
8,287,532 B2 10/2012 Carroll et al.
8,292,886 B2 10/2012 Kerr et al.
8,292,888 B2 10/2012 Whitman
8,292,905 B2 10/2012 Taylor et al.
8,295,902 B2 10/2012 Salahieh et al.
8,298,223 B2 10/2012 Wham et al.
8,298,225 B2 10/2012 Gilbert
8,298,232 B2 10/2012 Unger
8,298,233 B2 10/2012 Mueller
8,303,576 B2 11/2012 Brock
8,303,579 B2 11/2012 Shibata
8,303,580 B2 11/2012 Wham et al.
8,303,583 B2 11/2012 Hosier et al.
8,303,613 B2 11/2012 Crandall et al.
8,306,629 B2 11/2012 Mioduski et al.
8,308,040 B2 11/2012 Huang et al.
8,308,721 B2 11/2012 Shibata et al.
8,319,400 B2 11/2012 Houser et al.
8,323,302 B2 12/2012 Robertson et al.
8,323,310 B2 12/2012 Kingsley
8,328,061 B2 12/2012 Kasvikis
8,328,761 B2 12/2012 Widenhouse et al.
8,328,802 B2 12/2012 Deville et al.
8,328,833 B2 12/2012 Cuny
8,328,834 B2 12/2012 Isaacs et al.
8,333,764 B2 12/2012 Francischelli et al.
8,333,778 B2 12/2012 Smith et al.
8,333,779 B2 12/2012 Smith et al.
8,334,468 B2 12/2012 Palmer et al.
8,334,635 B2 12/2012 Voegele et al.
8,337,407 B2 12/2012 Quistgaard et al.
8,338,726 B2 12/2012 Palmer et al.
8,343,146 B2 1/2013 Godara et al.
8,344,596 B2 1/2013 Nield et al.
8,348,880 B2 1/2013 Messerly et al.
8,348,947 B2 1/2013 Takashino et al.
8,348,967 B2 1/2013 Stulen
8,353,297 B2 1/2013 Dacquay et al.
8,357,103 B2 1/2013 Mark et al.
8,357,144 B2 1/2013 Whitman et al.
8,357,149 B2 1/2013 Govari et al.
8,357,158 B2 1/2013 McKenna et al.
8,360,299 B2 1/2013 Zemlok et al.
8,361,066 B2 1/2013 Long et al.
8,361,072 B2 1/2013 Dumbauld et al.
8,361,569 B2 1/2013 Saito et al.
8,366,727 B2 2/2013 Witt et al.
8,372,064 B2 2/2013 Douglass et al.
8,372,099 B2 2/2013 Deville et al.
8,372,101 B2 2/2013 Smith et al.
8,372,102 B2 2/2013 Stulen et al.
8,374,670 B2 2/2013 Selkee
8,377,044 B2 2/2013 Coe et al.
8,377,059 B2 2/2013 Deville et al.
8,377,085 B2 2/2013 Smith et al.
8,382,748 B2 2/2013 Geisel
8,382,775 B1 2/2013 Bender et al.
8,382,782 B2 2/2013 Robertson et al.
8,382,792 B2 2/2013 Chojin
8,388,646 B2 3/2013 Chojin
8,388,647 B2 3/2013 Nau, Jr. et al.
8,393,514 B2 3/2013 Shelton, IV et al.
8,394,115 B2 3/2013 Houser et al.
8,397,971 B2 3/2013 Yates et al.
8,398,394 B2 3/2013 Sauter et al.
8,398,674 B2 3/2013 Prestel
8,403,926 B2 3/2013 Nobis et al.
8,403,945 B2 3/2013 Whitfield et al.
8,403,948 B2 3/2013 Deville et al.
8,403,949 B2 3/2013 Palmer et al.
8,403,950 B2 3/2013 Palmer et al.
8,409,234 B2 4/2013 Stahler et al.
8,414,577 B2 4/2013 Boudreaux et al.
8,418,073 B2 4/2013 Mohr et al.
8,418,349 B2 4/2013 Smith et al.
8,419,757 B2 4/2013 Smith et al.
8,419,758 B2 4/2013 Smith et al.
8,419,759 B2 4/2013 Dietz
8,423,182 B2 4/2013 Robinson et al.

(56) References Cited

U.S. PATENT DOCUMENTS 8,425,410 B2 4/2013 Murray et al.
8,425,545 B2 4/2013 Smith et al.
8,430,811 B2 4/2013 Hess et al.
8,430,874 B2 4/2013 Newton et al.
8,430,876 B2 4/2013 Kappus et al.
8,430,897 B2 4/2013 Novak et al.
8,430,898 B2 4/2013 Wiener et al.
8,435,257 B2 5/2013 Smith et al.
8,437,832 B2 5/2013 Govari et al.
8,439,912 B2 5/2013 Cunningham et al.
8,439,939 B2 5/2013 Deville et al.
8,444,036 B2 5/2013 Shelton, IV
8,444,637 B2 5/2013 Podmore et al.
8,444,662 B2 5/2013 Palmer et al.
8,444,663 B2 5/2013 Houser et al.
8,444,664 B2 5/2013 Balanev et al.
8,453,906 B2 6/2013 Huang et al.
8,454,599 B2 6/2013 Inagaki et al.
8,454,639 B2 6/2013 Du et al.
8,459,525 B2 6/2013 Yates et al.
8,460,284 B2 6/2013 Aronow et al.
8,460,288 B2 6/2013 Tamai et al.
8,460,292 B2 6/2013 Truckai et al.
8,461,744 B2 6/2013 Wiener et al.
8,469,981 B2 6/2013 Robertson et al.
8,471,685 B2 6/2013 Shingai
8,479,969 B2 7/2013 Shelton, IV
8,480,703 B2 7/2013 Nicholas et al.
8,484,833 B2 7/2013 Cunningham et al.
8,485,413 B2 7/2013 Scheib et al.
8,485,970 B2 7/2013 Widenhouse et al.
8,486,057 B2 7/2013 Behnke, II
8,486,096 B2 7/2013 Robertson et al.
8,491,578 B2 7/2013 Manwaring et al.
8,491,625 B2 7/2013 Horner
8,496,682 B2 7/2013 Guerra et al.
D687,549 S 8/2013 Johnson et al.
8,506,555 B2 8/2013 Ruiz Morales
8,509,318 B2 8/2013 Tailliet
8,512,336 B2 8/2013 Couture
8,512,337 B2 8/2013 Francischelli et al.
8,512,359 B2 8/2013 Whitman et al.
8,512,364 B2 8/2013 Kowalski et al.
8,512,365 B2 8/2013 Wiener et al.
8,517,239 B2 8/2013 Scheib et al.
8,518,067 B2 8/2013 Masuda et al.
8,521,331 B2 8/2013 Itkowitz
8,523,043 B2 9/2013 Ullrich et al.
8,523,882 B2 9/2013 Huitema et al.
8,523,889 B2 9/2013 Stulen et al.
8,528,563 B2 9/2013 Gruber
8,529,437 B2 9/2013 Taylor et al.
8,529,565 B2 9/2013 Masuda et al.
8,531,064 B2 9/2013 Robertson et al.
8,535,308 B2 9/2013 Govari et al.
8,535,311 B2 9/2013 Schall
8,535,340 B2 9/2013 Allen
8,535,341 B2 9/2013 Allen
8,540,128 B2 9/2013 Shelton, IV et al.
8,546,996 B2 10/2013 Messerly et al.
8,546,999 B2 10/2013 Houser et al.
8,551,077 B2 10/2013 Main et al.
8,551,086 B2 10/2013 Kimura et al.
8,556,929 B2 10/2013 Harper et al.
8,561,870 B2 10/2013 Baxter, III et al.
8,562,592 B2 10/2013 Conlon et al.
8,562,598 B2 10/2013 Falkenstein et al.
8,562,600 B2 10/2013 Kirkpatrick et al.
8,562,604 B2 10/2013 Nishimura
8,568,390 B2 10/2013 Mueller
8,568,397 B2 10/2013 Horner et al.
8,568,400 B2 10/2013 Gilbert
8,568,412 B2 10/2013 Brandt et al.
8,569,997 B2 10/2013 Lee
8,573,461 B2 11/2013 Shelton, IV et al.
8,573,465 B2 11/2013 Shelton, IV
8,574,231 B2 11/2013 Boudreaux et al.
8,574,253 B2 11/2013 Gruber et al.
8,579,176 B2 11/2013 Smith et al.
8,579,897 B2 11/2013 Vakharia et al.
8,579,928 B2 11/2013 Robertson et al.
8,579,937 B2 11/2013 Gresham
8,585,727 B2 11/2013 Polo
8,588,371 B2 11/2013 Ogawa et al.
8,591,459 B2 11/2013 Clymer et al.
8,591,506 B2 11/2013 Wham et al.
8,591,536 B2 11/2013 Robertson
D695,407 S 12/2013 Price et al.
D696,631 S 12/2013 Price et al.
8,596,513 B2 12/2013 Olson et al.
8,597,193 B2 12/2013 Grunwald et al.
8,597,287 B2 12/2013 Benamou et al.
8,602,031 B2 12/2013 Reis et al.
8,602,288 B2 12/2013 Shelton, IV et al.
8,603,085 B2 12/2013 Jimenez
8,603,089 B2 12/2013 Viola
8,608,044 B2 12/2013 Hueil et al.
8,608,045 B2 12/2013 Smith et al.
8,608,745 B2 12/2013 Guzman et al.
8,613,383 B2 12/2013 Beckman et al.
8,616,431 B2 12/2013 Timm et al.
8,617,152 B2 12/2013 Werneth et al.
8,617,194 B2 12/2013 Beaupre
8,622,274 B2 1/2014 Yates et al.
8,623,011 B2 1/2014 Spivey
8,623,016 B2 1/2014 Fischer
8,623,027 B2 1/2014 Price et al.
8,623,040 B2 1/2014 Artsyukhovich et al.
8,623,044 B2 1/2014 Timm et al.
8,628,529 B2 1/2014 Aldridge et al.
8,628,534 B2 1/2014 Jones et al.
8,632,461 B2 1/2014 Glossop
8,636,736 B2 1/2014 Yates et al.
8,638,428 B2 1/2014 Brown
8,640,788 B2 2/2014 Dachs, II et al.
8,641,663 B2 2/2014 Kirschenman et al.
8,647,350 B2 2/2014 Mohan et al.
8,650,728 B2 2/2014 Wan et al.
8,652,120 B2 2/2014 Giordano et al.
8,652,132 B2 2/2014 Tsuchiya et al.
8,652,155 B2 2/2014 Houser et al.
8,657,489 B2 2/2014 Ladurner et al.
8,659,208 B1 2/2014 Rose et al.
8,663,214 B2 3/2014 Weinberg et al.
8,663,220 B2 3/2014 Wiener et al.
8,663,222 B2 3/2014 Anderson et al.
8,663,223 B2 3/2014 Masuda et al.
8,663,262 B2 3/2014 Smith et al.
8,668,691 B2 3/2014 Heard
8,668,710 B2 3/2014 Slipszenko et al.
8,684,253 B2 4/2014 Giordano et al.
8,685,016 B2 4/2014 Wham et al.
8,685,020 B2 4/2014 Weizman et al.
8,690,582 B2 4/2014 Rohrbach et al.
8,695,866 B2 4/2014 Leimbach et al.
8,696,366 B2 4/2014 Chen et al.
8,696,665 B2 4/2014 Hunt et al.
8,696,666 B2 4/2014 Sanai et al.
8,696,917 B2 4/2014 Petisce et al.
8,702,609 B2 4/2014 Hadjicostis
8,702,702 B1 4/2014 Edwards et al.
8,702,704 B2 4/2014 Shelton, IV et al.
8,704,425 B2 4/2014 Giordano et al.
8,708,213 B2 4/2014 Shelton, IV et al.
8,709,008 B2 4/2014 Willis et al.
8,709,031 B2 4/2014 Stulen
8,709,035 B2 4/2014 Johnson et al.
8,715,270 B2 5/2014 Weitzner et al.
8,715,277 B2 5/2014 Weizman
8,721,640 B2 5/2014 Taylor et al.
8,721,657 B2 5/2014 Kondoh et al.
8,733,613 B2 5/2014 Huitema et al.
8,733,614 B2 5/2014 Ross et al.
8,734,443 B2 5/2014 Hixson et al.

(56) References Cited

U.S. PATENT DOCUMENTS 8,738,110 B2 5/2014 Tabada et al.
8,747,238 B2 6/2014 Shelton, IV et al.
8,747,351 B2 6/2014 Schultz
8,747,404 B2 6/2014 Boudreaux et al.
8,749,116 B2 6/2014 Messerly et al.
8,752,264 B2 6/2014 Ackley et al.
8,752,749 B2 6/2014 Moore et al.
8,753,338 B2 6/2014 Widenhouse et al.
8,754,570 B2 6/2014 Voegele et al.
8,758,342 B2 6/2014 Bales et al.
8,758,352 B2 6/2014 Cooper et al.
8,758,391 B2 6/2014 Swayze et al.
8,764,735 B2 7/2014 Coe et al.
8,764,747 B2 7/2014 Cummings et al.
8,767,970 B2 7/2014 Eppolito
8,770,459 B2 7/2014 Racenet et al.
8,771,269 B2 7/2014 Sherman et al.
8,771,270 B2 7/2014 Burbank
8,771,293 B2 7/2014 Surti et al.
8,773,001 B2 7/2014 Wiener et al.
8,777,944 B2 7/2014 Frankhouser et al.
8,777,945 B2 7/2014 Floume et al.
8,779,648 B2 7/2014 Giordano et al.
8,783,541 B2 7/2014 Shelton, IV et al.
8,784,415 B2 7/2014 Malackowski et al.
8,784,418 B2 7/2014 Romero
8,790,342 B2 7/2014 Stulen et al.
8,795,274 B2 8/2014 Hanna
8,795,275 B2 8/2014 Hafner
8,795,276 B2 8/2014 Dietz et al.
8,795,327 B2 8/2014 Dietz et al.
8,800,838 B2 8/2014 Shelton, IV
8,801,710 B2 8/2014 Ullrich et al.
8,801,752 B2 8/2014 Fortier et al.
8,807,414 B2 8/2014 Ross et al.
8,808,204 B2 8/2014 Irisawa et al.
8,808,319 B2 8/2014 Houser et al.
8,814,856 B2 8/2014 Elmouelhi et al.
8,814,870 B2 8/2014 Paraschiv et al.
8,820,605 B2 9/2014 Shelton, IV
8,821,388 B2 9/2014 Naito et al.
8,827,992 B2 9/2014 Koss et al.
8,827,995 B2 9/2014 Schaller et al.
8,831,779 B2 9/2014 Ortmaier et al.
8,834,466 B2 9/2014 Cummings et al.
8,834,518 B2 9/2014 Faller et al.
8,844,789 B2 9/2014 Shelton, IV et al.
8,845,537 B2 9/2014 Tanaka et al.
8,845,630 B2 9/2014 Mehta et al.
8,848,808 B2 9/2014 Dress
8,851,354 B2 10/2014 Swensgard et al.
8,852,184 B2 10/2014 Kucklick
8,858,547 B2 10/2014 Brogna
8,862,955 B2 10/2014 Cesari
8,864,749 B2 10/2014 Okada
8,864,757 B2 10/2014 Klimovitch et al.
8,864,761 B2 10/2014 Johnson et al.
8,870,865 B2 10/2014 Frankhouser et al.
8,874,220 B2 10/2014 Draghici et al.
8,876,726 B2 11/2014 Amit et al.
8,876,858 B2 11/2014 Braun
8,882,766 B2 11/2014 Couture et al.
8,882,791 B2 11/2014 Stulen
8,888,776 B2 11/2014 Dietz et al.
8,888,783 B2 11/2014 Young
8,888,809 B2 11/2014 Davison et al.
8,899,462 B2 12/2014 Kostrzewski et al.
8,900,259 B2 12/2014 Houser et al.
8,906,016 B2 12/2014 Boudreaux et al.
8,906,017 B2 12/2014 Rioux et al.
8,911,438 B2 12/2014 Swoyer et al.
8,911,460 B2 12/2014 Neurohr et al.
8,920,412 B2 12/2014 Fritz et al.
8,920,414 B2 12/2014 Stone et al.
8,920,421 B2 12/2014 Rupp
8,926,607 B2 1/2015 Norvell et al.
8,926,608 B2 1/2015 Bacher et al.
8,926,620 B2 1/2015 Chasmawala et al.
8,931,682 B2 1/2015 Timm et al.
8,932,282 B2 1/2015 Gilbert
8,932,299 B2 1/2015 Bono et al.
8,936,614 B2 1/2015 Allen, IV
8,939,974 B2 1/2015 Boudreaux et al.
8,945,126 B2 2/2015 Garrison et al.
8,951,248 B2 2/2015 Messerly et al.
8,951,272 B2 2/2015 Robertson et al.
8,956,349 B2 2/2015 Aldridge et al.
8,960,520 B2 2/2015 McCuen
8,961,515 B2 2/2015 Twomey et al.
8,961,547 B2 2/2015 Dietz et al.
8,967,443 B2 3/2015 McCuen
8,968,283 B2 3/2015 Kharin
8,968,294 B2 3/2015 Maass et al.
8,968,296 B2 3/2015 McPherson
8,968,355 B2 3/2015 Malkowski et al.
8,974,447 B2 3/2015 Kimball et al.
8,974,477 B2 3/2015 Yamada
8,974,479 B2 3/2015 Ross et al.
8,974,932 B2 3/2015 McGahan et al.
8,979,843 B2 3/2015 Timm et al.
8,979,844 B2 3/2015 White et al.
8,979,890 B2 3/2015 Boudreaux
8,986,287 B2 3/2015 Park et al.
8,986,297 B2 3/2015 Daniel et al.
8,986,302 B2 3/2015 Aldridge et al.
8,989,855 B2 3/2015 Murphy et al.
8,989,903 B2 3/2015 Weir et al.
8,991,678 B2 3/2015 Wellman et al.
8,992,422 B2 3/2015 Spivey et al.
8,992,526 B2 3/2015 Brodbeck et al.
8,998,891 B2 4/2015 Garito et al.
9,005,199 B2 4/2015 Beckman et al.
9,011,437 B2 4/2015 Woodruff et al.
9,011,471 B2 4/2015 Timm et al.
9,017,326 B2 4/2015 DiNardo et al.
9,017,355 B2 4/2015 Smith et al.
9,017,370 B2 4/2015 Reschke et al.
9,017,372 B2 4/2015 Artale et al.
9,023,035 B2 5/2015 Allen, IV et al.
9,023,070 B2 5/2015 Levine et al.
9,023,071 B2 5/2015 Miller et al.
9,028,397 B2 5/2015 Naito
9,028,476 B2 5/2015 Bonn
9,028,478 B2 5/2015 Mueller
9,028,481 B2 5/2015 Behnke, II
9,028,494 B2 5/2015 Shelton, IV et al.
9,028,519 B2 5/2015 Yates et al.
9,031,667 B2 5/2015 Williams
9,033,973 B2 5/2015 Krapohl et al.
9,035,741 B2 5/2015 Hamel et al.
9,037,259 B2 5/2015 Mathur
9,039,690 B2 5/2015 Kersten et al.
9,039,691 B2 5/2015 Moua et al.
9,039,692 B2 5/2015 Behnke, II et al.
9,039,695 B2 5/2015 Giordano et al.
9,039,696 B2 5/2015 Assmus et al.
9,039,705 B2 5/2015 Takashino
9,039,731 B2 5/2015 Joseph
9,043,018 B2 5/2015 Mohr
9,044,227 B2 6/2015 Shelton, IV et al.
9,044,230 B2 6/2015 Morgan et al.
9,044,238 B2 6/2015 Orszulak
9,044,243 B2 6/2015 Johnson et al.
9,044,245 B2 6/2015 Condie et al.
9,044,256 B2 6/2015 Cadeddu et al.
9,044,261 B2 6/2015 Houser
9,050,083 B2 6/2015 Yates et al.
9,050,093 B2 6/2015 Aldridge et al.
9,050,098 B2 6/2015 Deville et al.
9,050,123 B2 6/2015 Krause et al.
9,050,124 B2 6/2015 Houser
9,055,961 B2 6/2015 Manzo et al.
9,059,547 B2 6/2015 McLawhorn
9,060,770 B2 6/2015 Shelton, IV et al.

(56) References Cited

U.S. PATENT DOCUMENTS 9,060,775 B2 6/2015 Wiener et al.
9,060,776 B2 6/2015 Yates et al.
9,060,778 B2 6/2015 Condie et al.
9,066,720 B2 6/2015 Ballakur et al.
9,066,723 B2 6/2015 Beller et al.
9,066,747 B2 6/2015 Robertson
9,072,523 B2 7/2015 Houser et al.
9,072,535 B2 7/2015 Shelton, IV et al.
9,072,536 B2 7/2015 Shelton, IV et al.
9,072,538 B2 7/2015 Suzuki et al.
9,072,539 B2 7/2015 Messerly et al.
9,084,624 B2 7/2015 Larkin et al.
9,089,327 B2 7/2015 Worrell et al.
9,089,337 B2 7/2015 Batchelor et al.
9,089,360 B2 7/2015 Messerly et al.
9,095,333 B2 8/2015 Konesky et al.
9,095,362 B2 8/2015 Dachs, II et al.
9,095,367 B2 8/2015 Olson et al.
9,099,863 B2 8/2015 Smith et al.
9,101,358 B2 8/2015 Kerr et al.
9,101,385 B2 8/2015 Shelton, IV et al.
9,107,684 B2 8/2015 Ma
9,107,689 B2 8/2015 Robertson et al.
9,107,690 B2 8/2015 Bales, Jr. et al.
9,113,900 B2 8/2015 Buysse et al.
9,113,907 B2 8/2015 Allen, IV et al.
9,113,940 B2 8/2015 Twomey
9,119,657 B2 9/2015 Shelton, IV et al.
9,119,957 B2 9/2015 Gantz et al.
9,125,662 B2 9/2015 Shelton, IV
9,125,667 B2 9/2015 Stone et al.
9,144,453 B2 9/2015 Rencher et al.
9,147,965 B2 9/2015 Lee
9,149,324 B2 10/2015 Huang et al.
9,149,325 B2 10/2015 Worrell et al.
9,161,803 B2 10/2015 Yates et al.
9,165,114 B2 10/2015 Jain et al.
9,168,054 B2 10/2015 Turner et al.
9,168,085 B2 10/2015 Juzkiw et al.
9,168,089 B2 10/2015 Buysse et al.
9,173,656 B2 11/2015 Schurr et al.
9,179,912 B2 11/2015 Yates et al.
9,186,199 B2 11/2015 Strauss et al.
9,186,204 B2 11/2015 Nishimura et al.
9,186,796 B2 11/2015 Ogawa
9,192,380 B2 11/2015 (Tarinelli) Racenet et al.
9,192,421 B2 11/2015 Garrison
9,192,428 B2 11/2015 Houser et al.
9,192,431 B2 11/2015 Woodruff et al.
9,198,714 B2 12/2015 Worrell et al.
9,198,715 B2 12/2015 Livneh
9,198,718 B2 12/2015 Marczyk et al.
9,198,776 B2 12/2015 Young
9,204,879 B2 12/2015 Shelton, IV
9,204,891 B2 12/2015 Weitzman
9,204,918 B2 12/2015 Germain et al.
9,204,923 B2 12/2015 Manzo et al.
9,216,050 B2 12/2015 Condie et al.
9,216,051 B2 12/2015 Fischer et al.
9,216,062 B2 12/2015 Duque et al.
9,220,483 B2 12/2015 Frankhouser et al.
9,220,527 B2 12/2015 Houser et al.
9,220,559 B2 12/2015 Worrell et al.
9,226,750 B2 1/2016 Weir et al.
9,226,751 B2 1/2016 Shelton, IV et al.
9,226,766 B2 1/2016 Aldridge et al.
9,226,767 B2 1/2016 Stulen et al.
9,232,979 B2 1/2016 Parihar et al.
9,237,891 B2 1/2016 Shelton, IV
9,237,921 B2 1/2016 Messerly et al.
9,241,060 B1 1/2016 Fujisaki
9,241,692 B2 1/2016 Gunday et al.
9,241,728 B2 1/2016 Price et al.
9,241,730 B2 1/2016 Babaev
9,241,731 B2 1/2016 Boudreaux et al.
9,241,768 B2 1/2016 Sandhu et al.
9,247,953 B2 2/2016 Palmer et al.
9,254,165 B2 2/2016 Aronow et al.
9,259,234 B2 2/2016 Robertson et al.
9,259,265 B2 2/2016 Harris et al.
9,265,567 B2 2/2016 Orban, III et al.
9,265,926 B2 2/2016 Strobl et al.
9,265,973 B2 2/2016 Akagane
9,266,310 B2 2/2016 Krogdahl et al.
9,277,962 B2 3/2016 Koss et al.
9,282,974 B2 3/2016 Shelton, IV
9,283,027 B2 3/2016 Monson et al.
9,283,045 B2 3/2016 Rhee et al.
9,283,054 B2 3/2016 Morgan et al.
9,289,256 B2 3/2016 Shelton, IV et al.
9,295,514 B2 3/2016 Shelton, IV et al.
9,301,759 B2 4/2016 Spivey et al.
9,305,497 B2 4/2016 Seo et al.
9,307,388 B2 4/2016 Liang et al.
9,307,986 B2 4/2016 Hall et al.
9,308,009 B2 4/2016 Madan et al.
9,308,014 B2 4/2016 Fischer
9,314,261 B2 4/2016 Bales, Jr. et al.
9,314,292 B2 4/2016 Trees et al.
9,314,301 B2 4/2016 Ben-Haim et al.
9,326,754 B2 5/2016 Polster
9,326,767 B2 5/2016 Koch, Jr. et al.
9,326,787 B2 5/2016 Sanai et al.
9,326,788 B2 5/2016 Batross et al.
9,332,987 B2 5/2016 Leimbach et al.
9,333,025 B2 5/2016 Monson et al.
9,333,034 B2 5/2016 Hancock
9,339,289 B2 5/2016 Robertson
9,339,323 B2 5/2016 Eder et al.
9,339,326 B2 5/2016 McCullagh et al.
9,345,481 B2 5/2016 Hall et al.
9,345,534 B2 5/2016 Artale et al.
9,345,900 B2 5/2016 Wu et al.
9,351,642 B2 5/2016 Nadkarni et al.
9,351,726 B2 5/2016 Leimbach et al.
9,351,727 B2 5/2016 Leimbach et al.
9,351,754 B2 5/2016 Vakharia et al.
9,352,173 B2 5/2016 Yamada et al.
9,358,003 B2 6/2016 Hall et al.
9,358,065 B2 6/2016 Ladtkow et al.
9,364,171 B2 6/2016 Harris et al.
9,364,230 B2 6/2016 Shelton, IV et al.
9,364,279 B2 6/2016 Houser et al.
9,370,364 B2 6/2016 Smith et al.
9,370,400 B2 6/2016 Parihar
9,370,611 B2 6/2016 Ross et al.
9,375,206 B2 6/2016 Vidal et al.
9,375,230 B2 6/2016 Ross et al.
9,375,232 B2 6/2016 Hunt et al.
9,375,256 B2 6/2016 Cunningham et al.
9,375,264 B2 6/2016 Horner et al.
9,375,267 B2 6/2016 Kerr et al.
9,385,831 B2 7/2016 Marr et al.
9,386,983 B2 7/2016 Swensgard et al.
9,393,037 B2 7/2016 Olson et al.
9,393,070 B2 7/2016 Gelfand et al.
9,398,911 B2 7/2016 Auld
9,402,680 B2 8/2016 Ginnebaugh et al.
9,402,682 B2 8/2016 Worrell et al.
9,408,606 B2 8/2016 Shelton, IV
9,408,622 B2 8/2016 Stulen et al.
9,408,660 B2 8/2016 Strobl et al.
9,414,853 B2 8/2016 Stulen et al.
9,414,880 B2 8/2016 Monson et al.
9,421,014 B2 8/2016 Ingmanson et al.
9,421,060 B2 8/2016 Monson et al.
9,427,249 B2 8/2016 Robertson et al.
9,427,279 B2 8/2016 Muniz-Medina et al.
9,439,668 B2 9/2016 Timm et al.
9,439,669 B2 9/2016 Wiener et al.
9,439,671 B2 9/2016 Akagane
9,442,288 B2 9/2016 Tanimura
9,445,784 B2 9/2016 O'Keeffe
9,445,832 B2 9/2016 Wiener et al.

(56) References Cited

U.S. PATENT DOCUMENTS 9,451,967 B2 9/2016 Jordan et al.
9,456,863 B2 10/2016 Moua
9,456,864 B2 10/2016 Witt et al.
9,468,438 B2 10/2016 Baber et al.
9,468,498 B2 10/2016 Sigmon, Jr.
9,474,542 B2 10/2016 Slipszenko et al.
9,474,568 B2 10/2016 Akagane
9,486,236 B2 11/2016 Price et al.
9,492,146 B2 11/2016 Kostrzewski et al.
9,492,224 B2 11/2016 Boudreaux et al.
9,498,245 B2 11/2016 Voegele et al.
9,498,275 B2 11/2016 Wham et al.
9,504,483 B2 11/2016 Houser et al.
9,504,520 B2 11/2016 Worrell et al.
9,504,524 B2 11/2016 Behnke, II
9,504,855 B2 11/2016 Messerly et al.
9,510,850 B2 12/2016 Robertson et al.
9,510,906 B2 12/2016 Boudreaux et al.
9,522,029 B2 12/2016 Yates et al.
9,522,032 B2 12/2016 Behnke
9,526,564 B2 12/2016 Rusin
9,526,565 B2 12/2016 Strobl
9,545,253 B2 1/2017 Worrell et al.
9,545,497 B2 1/2017 Wenderow et al.
9,554,465 B1 1/2017 Liu et al.
9,554,794 B2 1/2017 Baber et al.
9,554,846 B2 1/2017 Boudreaux
9,554,854 B2 1/2017 Yates et al.
9,560,995 B2 2/2017 Addison et al.
9,561,038 B2 2/2017 Shelton, IV et al.
9,572,592 B2 2/2017 Price et al.
9,574,644 B2 2/2017 Parihar
9,585,714 B2 3/2017 Livneh
9,592,056 B2 3/2017 Mozdzierz et al.
9,592,072 B2 3/2017 Akagane
9,597,143 B2 3/2017 Madan et al.
9,603,669 B2 3/2017 Govari et al.
9,610,091 B2 4/2017 Johnson et al.
9,610,114 B2 4/2017 Baxter, III et al.
9,615,877 B2 4/2017 Tyrrell et al.
9,623,237 B2 4/2017 Turner et al.
9,629,623 B2 4/2017 Lytle, IV et al.
9,629,629 B2 4/2017 Leimbach et al.
9,632,573 B2 4/2017 Ogawa et al.
9,636,135 B2 5/2017 Stulen
9,636,165 B2 5/2017 Larson et al.
9,636,167 B2 5/2017 Gregg
9,638,770 B2 5/2017 Dietz et al.
9,642,644 B2 5/2017 Houser et al.
9,642,669 B2 5/2017 Takashino et al.
9,643,052 B2 5/2017 Tchao et al.
9,649,110 B2 5/2017 Parihar et al.
9,649,111 B2 5/2017 Shelton, IV et al.
9,649,126 B2 5/2017 Robertson et al.
9,649,173 B2 5/2017 Choi et al.
9,655,670 B2 5/2017 Larson et al.
9,662,131 B2 5/2017 Omori et al.
9,668,806 B2 6/2017 Unger et al.
9,671,860 B2 6/2017 Ogawa et al.
9,674,949 B1 6/2017 Liu et al.
9,675,374 B2 6/2017 Stulen et al.
9,675,375 B2 6/2017 Houser et al.
9,681,884 B2 6/2017 Clem et al.
9,687,230 B2 6/2017 Leimbach et al.
9,687,290 B2 6/2017 Keller
9,690,362 B2 6/2017 Leimbach et al.
9,693,817 B2 7/2017 Mehta et al.
9,700,309 B2 7/2017 Jaworek et al.
9,700,339 B2 7/2017 Nield
9,700,343 B2 7/2017 Messerly et al.
9,705,456 B2 7/2017 Gilbert
9,707,004 B2 7/2017 Houser et al.
9,707,027 B2 7/2017 Ruddenklau et al.
9,707,030 B2 7/2017 Davison et al.
9,713,507 B2 7/2017 Stulen et al.
9,717,548 B2 8/2017 Couture
9,717,552 B2 8/2017 Cosman et al.
9,724,094 B2 8/2017 Baber et al.
9,724,118 B2 8/2017 Schulte et al.
9,724,120 B2 8/2017 Faller et al.
9,724,152 B2 8/2017 Horlle et al.
9,730,695 B2 8/2017 Leimbach et al.
9,733,663 B2 8/2017 Leimbach et al.
9,737,301 B2 8/2017 Baber et al.
9,737,326 B2 8/2017 Worrell et al.
9,737,355 B2 8/2017 Yates et al.
9,737,358 B2 8/2017 Beckman et al.
9,743,929 B2 8/2017 Leimbach et al.
9,743,946 B2 8/2017 Faller et al.
9,743,947 B2 8/2017 Price et al.
9,750,499 B2 9/2017 Leimbach et al.
9,757,128 B2 9/2017 Baber et al.
9,757,142 B2 9/2017 Shimizu
9,757,150 B2 9/2017 Alexander et al.
9,757,186 B2 9/2017 Boudreaux et al.
9,764,164 B2 9/2017 Wiener et al.
9,770,285 B2 9/2017 Zoran et al.
9,782,169 B2 10/2017 Kimsey et al.
9,782,214 B2 10/2017 Houser et al.
9,788,836 B2 10/2017 Overmyer et al.
9,788,851 B2 10/2017 Dannaher et al.
9,795,405 B2 10/2017 Price et al.
9,795,436 B2 10/2017 Yates et al.
9,795,808 B2 10/2017 Messerly et al.
9,801,626 B2 10/2017 Parihar et al.
9,801,648 B2 10/2017 Houser et al.
9,802,033 B2 10/2017 Hibner et al.
9,804,618 B2 10/2017 Leimbach et al.
9,808,244 B2 11/2017 Leimbach et al.
9,808,246 B2 11/2017 Shelton, IV et al.
9,808,308 B2 11/2017 Faller et al.
9,814,460 B2 11/2017 Kimsey et al.
9,814,514 B2 11/2017 Shelton, IV et al.
9,815,211 B2 11/2017 Cao et al.
9,820,738 B2 11/2017 Lytle, IV et al.
9,820,768 B2 11/2017 Gee et al.
9,820,771 B2 11/2017 Norton et al.
9,820,806 B2 11/2017 Lee et al.
9,826,976 B2 11/2017 Parihar et al.
9,826,977 B2 11/2017 Leimbach et al.
9,839,443 B2 12/2017 Brockman et al.
9,844,368 B2 12/2017 Boudreaux et al.
9,844,374 B2 12/2017 Lytle, IV et al.
9,844,375 B2 12/2017 Overmyer et al.
9,848,901 B2 12/2017 Robertson et al.
9,848,902 B2 12/2017 Price et al.
9,848,937 B2 12/2017 Trees et al.
9,861,381 B2 1/2018 Johnson
9,861,428 B2 1/2018 Trees et al.
9,867,612 B2 1/2018 Parihar et al.
9,867,651 B2 1/2018 Wham
9,867,670 B2 1/2018 Brannan et al.
9,872,722 B2 1/2018 Lech
9,872,725 B2 1/2018 Worrell et al.
9,872,726 B2 1/2018 Morisaki
9,877,720 B2 1/2018 Worrell et al.
9,877,776 B2 1/2018 Boudreaux
9,877,782 B2 1/2018 Voegele et al.
9,878,184 B2 1/2018 Beaupre
9,883,860 B2 2/2018 Leimbach et al.
9,883,884 B2 2/2018 Neurohr et al.
9,888,919 B2 2/2018 Leimbach et al.
9,888,958 B2 2/2018 Evans et al.
9,895,148 B2 2/2018 Shelton, IV et al.
9,895,160 B2 2/2018 Fan et al.
9,901,321 B2 2/2018 Harks et al.
9,901,342 B2 2/2018 Shelton, IV et al.
9,901,383 B2 2/2018 Hassler, Jr.
9,901,385 B2 2/2018 Wham et al.
9,901,754 B2 2/2018 Yamada
9,907,563 B2 3/2018 Germain et al.
9,913,642 B2 3/2018 Leimbach et al.
9,913,656 B2 3/2018 Stulen
9,913,680 B2 3/2018 Voegele et al.

(56) References Cited

U.S. PATENT DOCUMENTS 9,918,730 B2 3/2018 Trees et al.
9,924,961 B2 3/2018 Shelton, IV et al.
9,925,003 B2 3/2018 Parihar et al.
9,931,118 B2 4/2018 Shelton, IV et al.
9,937,001 B2 4/2018 Nakamura
9,943,309 B2 4/2018 Shelton, IV et al.
9,949,785 B2 4/2018 Price et al.
9,949,788 B2 4/2018 Boudreaux
9,962,182 B2 5/2018 Dietz et al.
9,968,355 B2 5/2018 Shelton, IV et al.
9,974,539 B2 5/2018 Yates et al.
9,987,000 B2 6/2018 Shelton, IV et al.
9,987,033 B2 6/2018 Neurohr et al.
9,993,248 B2 6/2018 Shelton, IV et al.
9,993,258 B2 6/2018 Shelton, IV et al.
9,993,289 B2 6/2018 Sobajima et al.
10,004,497 B2 6/2018 Overmyer et al.
10,004,501 B2 6/2018 Shelton, IV et al.
10,004,526 B2 6/2018 Dycus et al.
10,004,527 B2 6/2018 Gee et al.
D822,206 S 7/2018 Shelton, IV et al.
10,010,339 B2 7/2018 Witt et al.
10,010,341 B2 7/2018 Houser et al.
10,013,049 B2 7/2018 Leimbach et al.
10,016,199 B2 7/2018 Baber et al.
10,016,207 B2 7/2018 Suzuki et al.
10,022,142 B2 7/2018 Aranyi et al.
10,022,567 B2 7/2018 Messerly et al.
10,022,568 B2 7/2018 Messerly et al.
10,028,761 B2 7/2018 Leimbach et al.
10,028,786 B2 7/2018 Mucilli et al.
10,034,684 B2 7/2018 Weisenburgh, II et al.
10,034,704 B2 7/2018 Asher et al.
D826,405 S 8/2018 Shelton, IV et al.
10,039,588 B2 8/2018 Harper et al.
10,041,822 B2 8/2018 Zemlok
10,045,776 B2 8/2018 Shelton, IV et al.
10,045,779 B2 8/2018 Savage et al.
10,045,794 B2 8/2018 Witt et al.
10,045,810 B2 8/2018 Schall et al.
10,045,819 B2 8/2018 Jensen et al.
10,052,044 B2 8/2018 Shelton, IV et al.
10,052,102 B2 8/2018 Baxter, III et al.
10,070,916 B2 9/2018 Artale
10,080,609 B2 9/2018 Hancock et al.
10,085,748 B2 10/2018 Morgan et al.
10,085,762 B2 10/2018 Timm et al.
10,085,792 B2 10/2018 Johnson et al.
10,092,310 B2 10/2018 Boudreaux et al.
10,092,344 B2 10/2018 Mohr et al.
10,092,347 B2 10/2018 Weisshaupt et al.
10,092,348 B2 10/2018 Boudreaux
10,092,350 B2 10/2018 Rothweiler et al.
10,105,140 B2 10/2018 Malinouskas et al.
10,111,679 B2 10/2018 Baber et al.
10,111,699 B2 10/2018 Boudreaux
10,111,703 B2 10/2018 Cosman, Jr. et al.
10,117,649 B2 11/2018 Baxter, III et al.
10,117,667 B2 11/2018 Robertson et al.
10,117,702 B2 11/2018 Danziger et al.
10,123,835 B2 11/2018 Keller et al.
10,130,367 B2 11/2018 Cappola et al.
10,130,410 B2 11/2018 Strobl et al.
10,130,412 B2 11/2018 Wham
10,135,242 B2 11/2018 Baber et al.
10,136,887 B2 11/2018 Shelton, IV et al.
10,149,680 B2 12/2018 Parihar et al.
10,154,848 B2 12/2018 Chernov et al.
10,154,852 B2 12/2018 Conlon et al.
10,159,483 B2 12/2018 Beckman et al.
10,159,524 B2 12/2018 Yates et al.
10,166,060 B2 1/2019 Johnson et al.
10,172,665 B2 1/2019 Heckel et al.
10,172,669 B2 1/2019 Felder et al.
10,178,992 B2 1/2019 Wise et al.
10,179,022 B2 1/2019 Yates et al.
10,180,463 B2 1/2019 Beckman et al.
10,182,816 B2 1/2019 Shelton, IV et al.
10,182,818 B2 1/2019 Hensel et al.
10,188,385 B2 1/2019 Kerr et al.
10,188,455 B2 1/2019 Hancock et al.
10,194,907 B2 2/2019 Marczyk et al.
10,194,972 B2 2/2019 Yates et al.
10,194,973 B2 2/2019 Wiener et al.
10,194,976 B2 2/2019 Boudreaux
10,194,977 B2 2/2019 Yang
10,194,999 B2 2/2019 Bacher et al.
10,201,364 B2 2/2019 Leimbach et al.
10,201,365 B2 2/2019 Boudreaux et al.
10,201,382 B2 2/2019 Wiener et al.
10,226,250 B2 3/2019 Beckman et al.
10,226,273 B2 3/2019 Messerly et al.
10,231,747 B2 3/2019 Stulen et al.
10,238,385 B2 3/2019 Yates et al.
10,238,391 B2 3/2019 Leimbach et al.
10,245,027 B2 4/2019 Shelton, IV et al.
10,245,028 B2 4/2019 Shelton, IV et al.
10,245,029 B2 4/2019 Hunter et al.
10,245,030 B2 4/2019 Hunter et al.
10,245,033 B2 4/2019 Overmyer et al.
10,245,095 B2 4/2019 Boudreaux
10,245,097 B2 4/2019 Honda et al.
10,245,104 B2 4/2019 McKenna et al.
10,251,664 B2 4/2019 Shelton, IV et al.
10,258,331 B2 4/2019 Shelton, IV et al.
10,258,505 B2 4/2019 Ovchinnikov
10,263,171 B2 4/2019 Wiener et al.
10,265,068 B2 4/2019 Harris et al.
10,265,117 B2 4/2019 Wiener et al.
10,265,118 B2 4/2019 Gerhardt
10,271,840 B2 4/2019 Sapre
10,271,851 B2 4/2019 Shelton, IV et al.
D847,989 S 5/2019 Shelton, IV et al.
10,278,721 B2 5/2019 Dietz et al.
10,285,705 B2 5/2019 Shelton, IV et al.
10,285,724 B2 5/2019 Faller et al.
10,285,750 B2 5/2019 Coulson et al.
10,292,704 B2 5/2019 Harris et al.
10,299,810 B2 5/2019 Robertson et al.
10,299,821 B2 5/2019 Shelton, IV et al.
D850,617 S 6/2019 Shelton, IV et al.
D851,762 S 6/2019 Shelton, IV et al.
10,307,159 B2 6/2019 Harris et al.
10,314,579 B2 6/2019 Chowaniec et al.
10,314,582 B2 6/2019 Shelton, IV et al.
10,314,638 B2 6/2019 Gee et al.
10,321,907 B2 6/2019 Shelton, IV et al.
10,321,950 B2 6/2019 Yates et al.
D854,151 S 7/2019 Shelton, IV et al.
10,335,149 B2 7/2019 Baxter, III et al.
10,335,182 B2 7/2019 Stulen et al.
10,335,183 B2 7/2019 Worrell et al.
10,335,614 B2 7/2019 Messerly et al.
10,342,543 B2 7/2019 Shelton, IV et al.
10,342,602 B2 7/2019 Strobl et al.
10,342,606 B2 7/2019 Cosman et al.
10,342,623 B2 7/2019 Huelman et al.
10,348,941 B2 7/2019 Elliot, Jr. et al.
10,349,999 B2 7/2019 Yates et al.
10,350,016 B2 7/2019 Burbank et al.
10,350,025 B1 7/2019 Loyd et al.
10,357,246 B2 7/2019 Shelton, IV et al.
10,357,247 B2 7/2019 Shelton, IV et al.
10,357,303 B2 7/2019 Conlon et al.
10,363,084 B2 7/2019 Friedrichs
10,368,861 B2 8/2019 Baxter, III et al.
10,368,865 B2 8/2019 Harris et al.
10,376,263 B2 8/2019 Morgan et al.
10,376,305 B2 8/2019 Yates et al.
10,390,841 B2 8/2019 Shelton, IV et al.
10,398,439 B2 9/2019 Cabrera et al.
10,398,466 B2 9/2019 Stulen et al.
10,398,497 B2 9/2019 Batross et al.
10,405,857 B2 9/2019 Shelton, IV et al.

(56) References Cited

U.S. PATENT DOCUMENTS 10,405,863 B2 9/2019 Wise et al.
10,413,291 B2 9/2019 Worthington et al.
10,413,293 B2 9/2019 Shelton, IV et al.
10,413,297 B2 9/2019 Harris et al.
10,413,352 B2 9/2019 Thomas et al.
10,413,353 B2 9/2019 Kerr et al.
10,420,552 B2 9/2019 Shelton, IV et al.
10,420,579 B2 9/2019 Wiener et al.
10,420,607 B2 9/2019 Woloszko et al.
D865,175 S 10/2019 Widenhouse et al.
10,426,471 B2 10/2019 Shelton, IV et al.
10,426,507 B2 10/2019 Wiener et al.
10,426,546 B2 10/2019 Graham et al.
10,426,978 B2 10/2019 Akagane
10,433,837 B2 10/2019 Worthington et al.
10,433,849 B2 10/2019 Shelton, IV et al.
10,433,865 B2 10/2019 Witt et al.
10,433,866 B2 10/2019 Witt et al.
10,433,900 B2 10/2019 Harris et al.
10,441,279 B2 10/2019 Shelton, IV et al.
10,441,308 B2 10/2019 Robertson
10,441,310 B2 10/2019 Olson et al.
10,441,345 B2 10/2019 Aldridge et al.
10,448,948 B2 10/2019 Shelton, IV et al.
10,448,950 B2 10/2019 Shelton, IV et al.
10,448,986 B2 10/2019 Zikorus et al.
10,456,140 B2 10/2019 Shelton, IV et al.
10,456,193 B2 10/2019 Yates et al.
10,463,421 B2 11/2019 Boudreaux et al.
10,463,887 B2 11/2019 Witt et al.
10,470,762 B2 11/2019 Leimbach et al.
10,470,764 B2 11/2019 Baxter, III et al.
10,478,182 B2 11/2019 Taylor
10,478,190 B2 11/2019 Miller et al.
10,485,542 B2 11/2019 Shelton, IV et al.
10,485,543 B2 11/2019 Shelton, IV et al.
10,485,607 B2 11/2019 Strobl et al.
D869,655 S 12/2019 Shelton, IV et al.
10,492,785 B2 12/2019 Overmyer et al.
10,492,849 B2 12/2019 Juergens et al.
10,499,914 B2 12/2019 Huang et al.
10,507,033 B2 12/2019 Dickerson et al.
10,512,795 B2 12/2019 Voegele et al.
10,517,595 B2 12/2019 Hunter et al.
10,517,596 B2 12/2019 Hunter et al.
10,517,627 B2 12/2019 Timm et al.
10,524,787 B2 1/2020 Shelton, IV et al.
10,524,789 B2 1/2020 Swayze et al.
10,524,854 B2 1/2020 Woodruff et al.
10,524,872 B2 1/2020 Stewart et al.
10,531,874 B2 1/2020 Morgan et al.
10,537,324 B2 1/2020 Shelton, IV et al.
10,537,325 B2 1/2020 Bakos et al.
10,537,351 B2 1/2020 Shelton, IV et al.
10,542,979 B2 1/2020 Shelton, IV et al.
10,542,982 B2 1/2020 Beckman et al.
10,542,991 B2 1/2020 Shelton, IV et al.
10,543,008 B2 1/2020 Vakharia et al.
10,548,504 B2 2/2020 Shelton, IV et al.
10,548,655 B2 2/2020 Scheib et al.
10,555,769 B2 2/2020 Worrell et al.
10,561,560 B2 2/2020 Boutoussov et al.
10,568,624 B2 2/2020 Shelton, IV et al.
10,568,625 B2 2/2020 Harris et al.
10,568,626 B2 2/2020 Shelton, IV et al.
10,568,632 B2 2/2020 Miller et al.
10,575,892 B2 3/2020 Danziger et al.
10,582,928 B2 3/2020 Hunter et al.
10,588,625 B2 3/2020 Weaner et al.
10,588,630 B2 3/2020 Shelton, IV et al.
10,588,631 B2 3/2020 Shelton, IV et al.
10,588,632 B2 3/2020 Shelton, IV et al.
10,588,633 B2 3/2020 Shelton, IV et al.
10,595,929 B2 3/2020 Boudreaux et al.
10,595,930 B2 3/2020 Scheib et al.
10,603,036 B2 3/2020 Hunter et al.
10,610,224 B2 4/2020 Shelton, IV et al.
10,610,286 B2 * 4/2020 Wiener .................... H03K 5/01
10,610,313 B2 4/2020 Bailey et al.
10,617,412 B2 4/2020 Shelton, IV et al.
10,617,420 B2 4/2020 Shelton, IV et al.
10,617,464 B2 4/2020 Duppuis
10,624,635 B2 4/2020 Harris et al.
10,624,691 B2 4/2020 Wiener et al.
10,631,858 B2 4/2020 Burbank
10,631,859 B2 4/2020 Shelton, IV et al.
10,631,928 B2 4/2020 Basu et al.
10,632,630 B2 4/2020 Cao et al.
RE47,996 E 5/2020 Turner et al.
10,639,034 B2 5/2020 Harris et al.
10,639,035 B2 5/2020 Shelton, IV et al.
10,639,037 B2 5/2020 Shelton, IV et al.
10,639,092 B2 5/2020 Corbett et al.
10,639,098 B2 5/2020 Cosman et al.
10,646,269 B2 5/2020 Worrell et al.
10,646,292 B2 5/2020 Solomon et al.
10,653,413 B2 5/2020 Worthington et al.
10,660,692 B2 5/2020 Lesko et al.
10,667,809 B2 6/2020 Bakos et al.
10,667,810 B2 6/2020 Shelton, IV et al.
10,667,811 B2 6/2020 Harris et al.
10,675,021 B2 6/2020 Harris et al.
10,675,024 B2 6/2020 Shelton, IV et al.
10,675,025 B2 6/2020 Swayze et al.
10,675,026 B2 6/2020 Harris et al.
10,677,764 B2 6/2020 Ross et al.
10,682,136 B2 6/2020 Harris et al.
10,682,138 B2 6/2020 Shelton, IV et al.
10,687,806 B2 6/2020 Shelton, IV et al.
10,687,809 B2 6/2020 Shelton, IV et al.
10,687,810 B2 6/2020 Shelton, IV et al.
10,687,884 B2 6/2020 Wiener et al.
10,688,321 B2 6/2020 Wiener et al.
10,695,055 B2 6/2020 Shelton, IV et al.
10,695,057 B2 6/2020 Shelton, IV et al.
10,695,058 B2 6/2020 Lytle, IV et al.
10,695,119 B2 6/2020 Smith
10,702,270 B2 7/2020 Shelton, IV et al.
10,702,329 B2 7/2020 Strobl et al.
10,709,446 B2 7/2020 Harris et al.
10,709,469 B2 7/2020 Shelton, IV et al.
10,709,906 B2 7/2020 Nield
10,716,615 B2 7/2020 Shelton, IV et al.
10,722,233 B2 7/2020 Wellman
D893,717 S 8/2020 Messerly et al.
10,729,458 B2 8/2020 Stoddard et al.
10,729,494 B2 8/2020 Parihar et al.
10,736,629 B2 8/2020 Shelton, IV et al.
10,736,685 B2 8/2020 Wiener et al.
10,751,108 B2 8/2020 Yates et al.
10,751,138 B2 8/2020 Giordano et al.
10,758,229 B2 9/2020 Shelton, IV et al.
10,758,230 B2 9/2020 Shelton, IV et al.
10,758,232 B2 9/2020 Shelton, IV et al.
10,758,294 B2 9/2020 Jones
10,765,427 B2 9/2020 Shelton, IV et al.
10,765,470 B2 9/2020 Yates et al.
10,772,629 B2 9/2020 Shelton, IV et al.
10,772,630 B2 9/2020 Wixey
10,779,821 B2 9/2020 Harris et al.
10,779,823 B2 9/2020 Shelton, IV et al.
10,779,824 B2 9/2020 Shelton, IV et al.
10,779,825 B2 9/2020 Shelton, IV et al.
10,779,845 B2 9/2020 Timm et al.
10,779,849 B2 9/2020 Shelton, IV et al.
10,779,879 B2 9/2020 Yates et al.
10,786,253 B2 9/2020 Shelton, IV et al.
10,786,276 B2 9/2020 Hirai et al.
10,806,454 B2 10/2020 Kopp
10,813,638 B2 10/2020 Shelton, IV et al.
10,820,938 B2 11/2020 Fischer et al.
10,828,058 B2 11/2020 Shelton, IV et al.
10,835,245 B2 11/2020 Swayze et al.
10,835,246 B2 11/2020 Shelton, IV et al.

(56) References Cited

U.S. PATENT DOCUMENTS

| | | | |
|---|---|---|---|
| 10,835,247 | B2 | 11/2020 | Shelton, IV et al. |
| 10,835,307 | B2 | 11/2020 | Shelton, IV et al. |
| 10,842,492 | B2 | 11/2020 | Shelton, IV et al. |
| 10,842,523 | B2 | 11/2020 | Shelton, IV et al. |
| 10,842,563 | B2 | 11/2020 | Gilbert et al. |
| D906,355 | S | 12/2020 | Messerly et al. |
| 10,856,867 | B2 | 12/2020 | Shelton, IV et al. |
| 10,856,868 | B2 | 12/2020 | Shelton, IV et al. |
| 10,856,869 | B2 | 12/2020 | Shelton, IV et al. |
| 10,856,870 | B2 | 12/2020 | Harris et al. |
| 10,856,896 | B2 | 12/2020 | Eichmann et al. |
| 10,856,929 | B2 | 12/2020 | Yates et al. |
| 10,856,934 | B2 | 12/2020 | Trees et al. |
| 10,874,465 | B2 | 12/2020 | Weir et al. |
| D908,216 | S | 1/2021 | Messerly et al. |
| 10,881,399 | B2 | 1/2021 | Shelton, IV et al. |
| 10,881,401 | B2 | 1/2021 | Baber et al. |
| 10,881,409 | B2 | 1/2021 | Cabrera |
| 10,881,449 | B2 | 1/2021 | Boudreaux et al. |
| 10,888,322 | B2 | 1/2021 | Morgan et al. |
| 10,888,347 | B2 | 1/2021 | Witt et al. |
| 10,893,863 | B2 | 1/2021 | Shelton, IV et al. |
| 10,893,864 | B2 | 1/2021 | Harris et al. |
| 10,893,883 | B2 | 1/2021 | Dannaher |
| 10,898,186 | B2 | 1/2021 | Bakos et al. |
| 10,898,256 | B2 | 1/2021 | Yates et al. |
| 10,912,559 | B2 | 2/2021 | Harris et al. |
| 10,912,580 | B2 | 2/2021 | Green et al. |
| 10,912,603 | B2 | 2/2021 | Boudreaux et al. |
| 10,918,385 | B2 | 2/2021 | Overmyer et al. |
| 10,925,659 | B2 | 2/2021 | Shelton, IV et al. |
| 10,926,022 | B2 | 2/2021 | Hickey et al. |
| D914,878 | S | 3/2021 | Shelton, IV et al. |
| 10,932,766 | B2 | 3/2021 | Tesar et al. |
| 10,932,847 | B2 | 3/2021 | Yates et al. |
| 10,945,727 | B2 | 3/2021 | Shelton, IV et al. |
| 10,952,788 | B2 | 3/2021 | Asher et al. |
| 10,959,727 | B2 | 3/2021 | Hunter et al. |
| 10,966,741 | B2 | 4/2021 | Illizaliturri-Sanchez et al. |
| 10,966,747 | B2 | 4/2021 | Worrell et al. |
| 10,973,516 | B2 | 4/2021 | Shelton, IV et al. |
| 10,973,517 | B2 | 4/2021 | Wixey |
| 10,973,520 | B2 | 4/2021 | Shelton, IV et al. |
| 10,980,536 | B2 | 4/2021 | Weaner et al. |
| 10,987,105 | B2 | 4/2021 | Cappola et al. |
| 10,987,123 | B2 | 4/2021 | Weir et al. |
| 10,987,156 | B2 | 4/2021 | Trees et al. |
| 10,993,715 | B2 | 5/2021 | Shelton, IV et al. |
| 10,993,716 | B2 | 5/2021 | Shelton, IV et al. |
| 10,993,763 | B2 | 5/2021 | Batross et al. |
| 11,000,278 | B2 | 5/2021 | Shelton, IV et al. |
| 11,000,279 | B2 | 5/2021 | Shelton, IV et al. |
| 11,020,114 | B2 | 6/2021 | Shelton, IV et al. |
| 11,020,140 | B2 | 6/2021 | Gee et al. |
| 11,020,166 | B2 | 6/2021 | Batchelor et al. |
| 11,033,322 | B2 | 6/2021 | Wiener et al. |
| 11,039,834 | B2 | 6/2021 | Harris et al. |
| 11,045,191 | B2 | 6/2021 | Shelton, IV et al. |
| 11,045,192 | B2 | 6/2021 | Harris et al. |
| 11,045,275 | B2 | 6/2021 | Boudreaux et al. |
| 11,051,840 | B2 | 7/2021 | Shelton, IV et al. |
| 11,051,873 | B2 | 7/2021 | Wiener et al. |
| 11,058,424 | B2 | 7/2021 | Shelton, IV et al. |
| 11,058,447 | B2 | 7/2021 | Houser |
| 11,058,448 | B2 | 7/2021 | Shelton, IV et al. |
| 11,058,475 | B2 | 7/2021 | Wiener et al. |
| 11,064,997 | B2 | 7/2021 | Shelton, IV et al. |
| 11,065,048 | B2 | 7/2021 | Messerly et al. |
| 11,083,455 | B2 | 8/2021 | Shelton, IV et al. |
| 11,083,458 | B2 | 8/2021 | Harris et al. |
| 11,090,048 | B2 | 8/2021 | Fanelli et al. |
| 11,090,049 | B2 | 8/2021 | Bakos et al. |
| 11,090,104 | B2 | 8/2021 | Wiener et al. |
| 11,096,688 | B2 | 8/2021 | Shelton, IV et al. |
| 11,096,752 | B2 | 8/2021 | Stulen et al. |
| 11,109,866 | B2 | 9/2021 | Shelton, IV et al. |
| 11,129,611 | B2 | 9/2021 | Shelton, IV et al. |
| 11,129,666 | B2 | 9/2021 | Messerly et al. |
| 11,129,669 | B2 | 9/2021 | Stulen et al. |
| 11,129,670 | B2 | 9/2021 | Shelton, IV et al. |
| 11,134,942 | B2 | 10/2021 | Harris et al. |
| 11,134,978 | B2 | 10/2021 | Shelton, IV et al. |
| 11,141,154 | B2 | 10/2021 | Shelton, IV et al. |
| 11,141,213 | B2 | 10/2021 | Yates et al. |
| 11,147,551 | B2 | 10/2021 | Shelton, IV |
| 11,147,553 | B2 | 10/2021 | Shelton, IV |
| 11,160,551 | B2 | 11/2021 | Shelton, IV et al. |
| 11,166,716 | B2 | 11/2021 | Shelton, IV et al. |
| 11,172,929 | B2 | 11/2021 | Shelton, IV |
| 11,179,155 | B2 | 11/2021 | Shelton, IV et al. |
| 11,179,173 | B2 | 11/2021 | Price et al. |
| 11,191,539 | B2 | 12/2021 | Overmyer et al. |
| 11,191,540 | B2 | 12/2021 | Aronhalt et al. |
| 11,197,668 | B2 | 12/2021 | Shelton, IV et al. |
| 11,202,670 | B2 | 12/2021 | Worrell et al. |
| 11,207,065 | B2 | 12/2021 | Harris et al. |
| 11,207,067 | B2 | 12/2021 | Shelton, IV et al. |
| 11,213,293 | B2 | 1/2022 | Worthington et al. |
| 11,213,294 | B2 | 1/2022 | Shelton, IV et al. |
| 11,219,453 | B2 | 1/2022 | Shelton, IV et al. |
| 11,224,426 | B2 | 1/2022 | Shelton, IV et al. |
| 11,224,497 | B2 | 1/2022 | Shelton, IV et al. |
| 11,229,437 | B2 | 1/2022 | Shelton, IV et al. |
| 11,229,450 | B2 | 1/2022 | Shelton, IV et al. |
| 11,229,471 | B2 | 1/2022 | Shelton, IV et al. |
| 11,229,472 | B2 | 1/2022 | Shelton, IV et al. |
| 11,234,698 | B2 | 2/2022 | Shelton, IV et al. |
| 11,241,235 | B2 | 2/2022 | Shelton, IV et al. |
| 11,246,592 | B2 | 2/2022 | Shelton, IV et al. |
| 11,246,625 | B2 | 2/2022 | Kane et al. |
| 11,246,678 | B2 | 2/2022 | Shelton, IV et al. |
| 11,253,256 | B2 | 2/2022 | Harris et al. |
| 11,259,803 | B2 | 3/2022 | Shelton, IV et al. |
| 11,259,805 | B2 | 3/2022 | Shelton, IV et al. |
| 11,259,806 | B2 | 3/2022 | Shelton, IV et al. |
| 11,259,807 | B2 | 3/2022 | Shelton, IV et al. |
| 11,266,405 | B2 | 3/2022 | Shelton, IV et al. |
| 11,266,430 | B2 | 3/2022 | Clauda et al. |
| 11,272,931 | B2 | 3/2022 | Boudreaux et al. |
| 11,278,280 | B2 | 3/2022 | Shelton, IV et al. |
| 11,284,890 | B2 | 3/2022 | Nalagatla et al. |
| 11,291,440 | B2 | 4/2022 | Harris et al. |
| 11,291,444 | B2 | 4/2022 | Boudreaux et al. |
| 11,291,445 | B2 | 4/2022 | Shelton, IV et al. |
| 11,291,447 | B2 | 4/2022 | Shelton, IV et al. |
| 11,291,451 | B2 | 4/2022 | Shelton, IV |
| 11,298,127 | B2 | 4/2022 | Shelton, IV |
| 11,298,129 | B2 | 4/2022 | Bakos et al. |
| 11,298,130 | B2 | 4/2022 | Bakos et al. |
| 11,304,695 | B2 | 4/2022 | Shelton, IV et al. |
| 11,304,696 | B2 | 4/2022 | Shelton, IV et al. |
| 11,304,699 | B2 | 4/2022 | Shelton, IV et al. |
| 11,311,306 | B2 | 4/2022 | Shelton, IV et al. |
| 11,311,326 | B2 | 4/2022 | Boudreaux |
| 11,311,342 | B2 | 4/2022 | Parihar et al. |
| D950,728 | S | 5/2022 | Bakos et al. |
| D952,144 | S | 5/2022 | Boudreaux |
| 11,317,915 | B2 | 5/2022 | Boudreaux et al. |
| 11,324,503 | B2 | 5/2022 | Shelton, IV et al. |
| 11,324,527 | B2 | 5/2022 | Aldridge et al. |
| 11,324,557 | B2 | 5/2022 | Shelton, IV et al. |
| 11,331,100 | B2 | 5/2022 | Boudreaux et al. |
| 11,331,101 | B2 | 5/2022 | Harris et al. |
| 11,337,747 | B2 | 5/2022 | Voegele et al. |
| 11,344,362 | B2 | 5/2022 | Yates et al. |
| 11,350,938 | B2 | 6/2022 | Shelton, IV et al. |
| 11,357,503 | B2 | 6/2022 | Bakos et al. |
| 11,361,176 | B2 | 6/2022 | Shelton, IV et al. |
| 11,369,377 | B2 | 6/2022 | Boudreaux et al. |
| 11,376,098 | B2 | 7/2022 | Shelton, IV et al. |
| 11,382,642 | B2 | 7/2022 | Robertson et al. |
| 11,389,161 | B2 | 7/2022 | Shelton, IV et al. |
| 11,389,164 | B2 | 7/2022 | Yates et al. |
| 11,399,837 | B2 | 8/2022 | Shelton, IV et al. |

(56) References Cited

U.S. PATENT DOCUMENTS 11,399,855 B2 8/2022 Boudreaux et al.
11,406,382 B2 8/2022 Shelton, IV et al.
11,413,060 B2 8/2022 Faller et al.
11,419,606 B2 8/2022 Overmyer et al.
11,419,626 B2 8/2022 Timm et al.
11,424,027 B2 8/2022 Shelton, IV
11,426,167 B2 8/2022 Shelton, IV et al.
11,426,191 B2 8/2022 Vakharia et al.
D964,564 S 9/2022 Boudreaux
11,446,029 B2 9/2022 Shelton, IV et al.
11,452,525 B2 9/2022 Shelton, IV et al.
11,452,560 B2 9/2022 Kase
11,464,511 B2 10/2022 Timm et al.
11,464,512 B2 10/2022 Shelton, IV et al.
11,464,601 B2 10/2022 Shelton, IV et al.
11,471,155 B2 10/2022 Shelton, IV et al.
11,471,156 B2 10/2022 Shelton, IV et al.
11,471,206 B2 10/2022 Henderson et al.
11,471,209 B2 10/2022 Yates et al.
11,478,242 B2 10/2022 Shelton, IV et al.
11,484,310 B2 11/2022 Shelton, IV et al.
11,504,122 B2 11/2022 Shelton, IV et al.
11,517,309 B2 12/2022 Bakos et al.
11,529,137 B2 12/2022 Shelton, IV et al.
11,529,139 B2 12/2022 Shelton, IV et al.
11,553,971 B2 1/2023 Shelton, IV et al.
11,559,304 B2 1/2023 Boudreaux et al.
11,559,307 B2 1/2023 Shelton, IV et al.
11,559,308 B2 1/2023 Yates et al.
11,559,347 B2 * 1/2023 Wiener .............. A61B 18/1445
11,571,210 B2 2/2023 Shelton, IV et al.
11,576,672 B2 2/2023 Shelton, IV et al.
11,576,677 B2 2/2023 Shelton, IV et al.
11,583,306 B2 2/2023 Olson et al.
11,589,865 B2 2/2023 Shelton, IV et al.
11,589,888 B2 2/2023 Shelton, IV et al.
11,589,916 B2 2/2023 Shelton, IV et al.
11,607,219 B2 3/2023 Shelton, IV et al.
11,638,587 B2 5/2023 Shelton, IV et al.
11,653,920 B2 5/2023 Shelton, IV et al.
11,659,023 B2 5/2023 Shelton, IV et al.
11,660,089 B2 5/2023 Shelton, IV et al.
11,660,163 B2 5/2023 Shelton, IV et al.
11,666,368 B2 6/2023 Henderson et al.
11,666,375 B2 6/2023 Scheib et al.
11,678,880 B2 6/2023 Shelton, IV et al.
11,678,925 B2 6/2023 Henderson et al.
11,684,402 B2 6/2023 Shelton, IV et al.
11,684,412 B2 6/2023 Shelton, IV et al.
11,684,434 B2 6/2023 Shelton, IV
11,696,759 B2 7/2023 Shelton, IV et al.
11,696,761 B2 7/2023 Shelton, IV
11,696,776 B2 7/2023 Shelton, IV et al.
11,701,111 B2 7/2023 Shelton, IV et al.
11,707,318 B2 7/2023 Shelton, IV et al.
11,717,311 B2 8/2023 Weir et al.
11,717,706 B2 8/2023 Wiener et al.
11,723,716 B2 8/2023 Fiebig et al.
11,744,636 B2 9/2023 Shelton, IV et al.
11,751,872 B2 9/2023 Zeiner et al.
11,751,929 B2 9/2023 Shelton, IV et al.
11,759,251 B2 9/2023 Shelton, IV et al.
2001/0025173 A1 9/2001 Ritchie et al.
2001/0025183 A1 9/2001 Shahidi
2001/0025184 A1 9/2001 Messerly
2001/0031950 A1 10/2001 Ryan
2001/0039419 A1 11/2001 Francischelli et al.
2002/0002377 A1 1/2002 Cimino
2002/0002380 A1 1/2002 Bishop
2002/0019649 A1 2/2002 Sikora et al.
2002/0022836 A1 2/2002 Goble et al.
2002/0029036 A1 3/2002 Goble et al.
2002/0029055 A1 3/2002 Bonutti
2002/0032452 A1 3/2002 Tierney et al.
2002/0049551 A1 4/2002 Friedman et al.
2002/0052617 A1 5/2002 Anis et al.
2002/0077550 A1 6/2002 Rabiner et al.
2002/0107517 A1 8/2002 Witt et al.
2002/0123749 A1 9/2002 Jain
2002/0133152 A1 9/2002 Strul
2002/0151884 A1 10/2002 Hoey et al.
2002/0156466 A1 10/2002 Sakurai et al.
2002/0156493 A1 10/2002 Houser et al.
2002/0165577 A1 11/2002 Witt et al.
2002/0177373 A1 11/2002 Shibata et al.
2002/0177862 A1 11/2002 Aranyi et al.
2003/0009164 A1 1/2003 Woloszko et al.
2003/0014053 A1 1/2003 Nguyen et al.
2003/0014087 A1 1/2003 Fang et al.
2003/0036705 A1 2/2003 Hare et al.
2003/0040758 A1 2/2003 Wang et al.
2003/0050572 A1 3/2003 Brautigam et al.
2003/0055443 A1 3/2003 Spotnitz
2003/0073981 A1 4/2003 Whitman et al.
2003/0109778 A1 6/2003 Rashidi
2003/0109875 A1 6/2003 Tetzlaff et al.
2003/0114851 A1 6/2003 Truckai et al.
2003/0130693 A1 7/2003 Levin et al.
2003/0139741 A1 7/2003 Goble et al.
2003/0144680 A1 7/2003 Kellogg et al.
2003/0158548 A1 8/2003 Phan et al.
2003/0171747 A1 9/2003 Kanehira et al.
2003/0176778 A1 9/2003 Messing et al.
2003/0181898 A1 9/2003 Bowers
2003/0199794 A1 10/2003 Sakurai et al.
2003/0204199 A1 10/2003 Novak et al.
2003/0208186 A1 11/2003 Moreyra
2003/0212332 A1 11/2003 Fenton et al.
2003/0212363 A1 11/2003 Shipp
2003/0212392 A1 11/2003 Fenton et al.
2003/0212422 A1 11/2003 Fenton et al.
2003/0225332 A1 12/2003 Okada et al.
2003/0229344 A1 12/2003 Dycus et al.
2004/0030254 A1 2/2004 Babaev
2004/0030330 A1 2/2004 Brassell et al.
2004/0047485 A1 3/2004 Sherrit et al.
2004/0054364 A1 3/2004 Aranyi et al.
2004/0064151 A1 4/2004 Mollenauer
2004/0087943 A1 5/2004 Dycus et al.
2004/0092921 A1 5/2004 Kadziauskas et al.
2004/0092992 A1 5/2004 Adams et al.
2004/0094597 A1 5/2004 Whitman et al.
2004/0097911 A1 5/2004 Murakami et al.
2004/0097912 A1 5/2004 Gonnering
2004/0097919 A1 5/2004 Wellman et al.
2004/0097996 A1 5/2004 Rabiner et al.
2004/0116952 A1 6/2004 Sakurai et al.
2004/0122423 A1 6/2004 Dycus et al.
2004/0132383 A1 7/2004 Langford et al.
2004/0138621 A1 7/2004 Jahns et al.
2004/0142667 A1 7/2004 Lochhead et al.
2004/0143263 A1 7/2004 Schechter et al.
2004/0147934 A1 7/2004 Kiester
2004/0147945 A1 7/2004 Fritzsch
2004/0158237 A1 8/2004 Abboud et al.
2004/0167508 A1 8/2004 Wham et al.
2004/0176686 A1 9/2004 Hare et al.
2004/0176751 A1 9/2004 Weitzner et al.
2004/0181242 A1 9/2004 Stack et al.
2004/0193150 A1 9/2004 Sharkey et al.
2004/0193153 A1 9/2004 Sartor et al.
2004/0193212 A1 9/2004 Taniguchi et al.
2004/0199193 A1 10/2004 Hayashi et al.
2004/0215132 A1 10/2004 Yoon
2004/0243147 A1 12/2004 Lipow
2004/0249374 A1 12/2004 Tetzlaff et al.
2004/0260273 A1 12/2004 Wan
2004/0260300 A1 12/2004 Gorensek et al.
2004/0267311 A1 12/2004 Viola et al.
2005/0015125 A1 1/2005 Mioduski et al.
2005/0020967 A1 1/2005 Ono
2005/0021018 A1 1/2005 Anderson et al.
2005/0021065 A1 1/2005 Yamada et al.
2005/0021078 A1 1/2005 Vleugels et al.

(56) References Cited

U.S. PATENT DOCUMENTS

2005/0033278 A1 2/2005 McClurken et al.
2005/0033337 A1 2/2005 Muir et al.
2005/0070800 A1 3/2005 Takahashi
2005/0080427 A1 4/2005 Govari et al.
2005/0088285 A1 4/2005 Jei
2005/0090817 A1 4/2005 Phan
2005/0096683 A1 5/2005 Ellins et al.
2005/0099824 A1 5/2005 Dowling et al.
2005/0107777 A1 5/2005 West et al.
2005/0131390 A1 6/2005 Heinrich et al.
2005/0143769 A1 6/2005 White et al.
2005/0149108 A1 7/2005 Cox
2005/0165429 A1 7/2005 Douglas et al.
2005/0171522 A1 8/2005 Christopherson
2005/0171533 A1 8/2005 Latterell et al.
2005/0177184 A1 8/2005 Easley
2005/0182339 A1 8/2005 Lee et al.
2005/0187576 A1 8/2005 Whitman et al.
2005/0188743 A1 9/2005 Land
2005/0192610 A1 9/2005 Houser et al.
2005/0192611 A1 9/2005 Houser
2005/0206583 A1 9/2005 Lemelson et al.
2005/0222598 A1 10/2005 Ho et al.
2005/0234484 A1 10/2005 Houser et al.
2005/0249667 A1 11/2005 Tuszynski et al.
2005/0256405 A1 11/2005 Makin et al.
2005/0261588 A1 11/2005 Makin et al.
2005/0262175 A1 11/2005 Iino et al.
2005/0267464 A1 12/2005 Truckai et al.
2005/0271807 A1 12/2005 Iljima et al.
2005/0273090 A1 12/2005 Nieman et al.
2005/0288659 A1 12/2005 Kimura et al.
2006/0025757 A1 2/2006 Heim
2006/0030797 A1 2/2006 Zhou et al.
2006/0030848 A1 2/2006 Craig et al.
2006/0058825 A1 3/2006 Ogura et al.
2006/0063130 A1 3/2006 Hayman et al.
2006/0064086 A1 3/2006 Odom
2006/0066181 A1 3/2006 Bromfield et al.
2006/0074442 A1 4/2006 Noriega et al.
2006/0079874 A1 4/2006 Faller et al.
2006/0079879 A1 4/2006 Faller et al.
2006/0095046 A1 5/2006 Trieu et al.
2006/0109061 A1 5/2006 Dobson et al.
2006/0142656 A1 6/2006 Malackowski et al.
2006/0159731 A1 7/2006 Shoshan
2006/0190034 A1 8/2006 Nishizawa et al.
2006/0206100 A1 9/2006 Eskridge et al.
2006/0206115 A1 9/2006 Schomer et al.
2006/0211943 A1 9/2006 Beaupre
2006/0217700 A1 9/2006 Garito et al.
2006/0217729 A1 9/2006 Eskridge et al.
2006/0224160 A1 10/2006 Trieu et al.
2006/0247558 A1 11/2006 Yamada
2006/0253050 A1 11/2006 Yoshimine et al.
2006/0259026 A1 11/2006 Godara et al.
2006/0259102 A1 11/2006 Slatkine
2006/0264809 A1 11/2006 Hansmann et al.
2006/0264995 A1 11/2006 Fanton et al.
2006/0265035 A1 11/2006 Yachi et al.
2006/0270916 A1 11/2006 Skwarek et al.
2006/0271030 A1 11/2006 Francis et al.
2006/0293656 A1 12/2006 Shadduck et al.
2007/0016235 A1 1/2007 Tanaka et al.
2007/0016236 A1 1/2007 Beaupre
2007/0021738 A1 1/2007 Hasser et al.
2007/0027468 A1 2/2007 Wales et al.
2007/0032704 A1 2/2007 Gandini et al.
2007/0055228 A1 3/2007 Berg et al.
2007/0056596 A1 3/2007 Fanney et al.
2007/0060935 A1 3/2007 Schwardt et al.
2007/0063618 A1 3/2007 Bromfield
2007/0066971 A1 3/2007 Podhajsky
2007/0067123 A1 3/2007 Jungerman
2007/0073185 A1 3/2007 Nakao
2007/0073341 A1 3/2007 Smith et al.
2007/0074584 A1 4/2007 Talarico et al.
2007/0106317 A1 5/2007 Shelton et al.
2007/0118115 A1 5/2007 Artale et al.
2007/0129726 A1 6/2007 Eder et al.
2007/0130771 A1 6/2007 Ehlert et al.
2007/0135803 A1 6/2007 Belson
2007/0149881 A1 6/2007 Rabin
2007/0156163 A1 7/2007 Davison et al.
2007/0166663 A1 7/2007 Telles et al.
2007/0173803 A1 7/2007 Wham et al.
2007/0173813 A1 7/2007 Odom
2007/0173872 A1 7/2007 Neuenfeldt
2007/0175955 A1 8/2007 Shelton et al.
2007/0185474 A1 8/2007 Nahen
2007/0187444 A1 8/2007 Hajari
2007/0191712 A1 8/2007 Messerly et al.
2007/0191713 A1 8/2007 Eichmann et al.
2007/0203483 A1 8/2007 Kim et al.
2007/0208336 A1 9/2007 Kim et al.
2007/0208340 A1 9/2007 Ganz et al.
2007/0219481 A1 9/2007 Babaev
2007/0232926 A1 10/2007 Stulen et al.
2007/0232928 A1 10/2007 Wiener et al.
2007/0236213 A1 10/2007 Paden et al.
2007/0239101 A1 10/2007 Kellogg
2007/0249941 A1 10/2007 Salehi et al.
2007/0260242 A1 11/2007 Dycus et al.
2007/0265560 A1 11/2007 Soltani et al.
2007/0265613 A1 11/2007 Edelstein et al.
2007/0265616 A1 11/2007 Couture et al.
2007/0265620 A1 11/2007 Kraas et al.
2007/0275348 A1 11/2007 Lemon
2007/0287933 A1 12/2007 Phan et al.
2007/0288055 A1 12/2007 Lee
2007/0299895 A1 12/2007 Johnson et al.
2008/0005213 A1 1/2008 Holtzman
2008/0013809 A1 1/2008 Zhu et al.
2008/0015473 A1 1/2008 Shimizu
2008/0015575 A1 1/2008 Odom et al.
2008/0033465 A1 2/2008 Schmitz et al.
2008/0039746 A1 2/2008 Hissong et al.
2008/0046122 A1 2/2008 Manzo et al.
2008/0051812 A1 2/2008 Schmitz et al.
2008/0058775 A1 3/2008 Darian et al.
2008/0058845 A1 3/2008 Shimizu et al.
2008/0071269 A1 3/2008 Hilario et al.
2008/0077145 A1 3/2008 Boyden et al.
2008/0082039 A1 4/2008 Babaev
2008/0082098 A1 4/2008 Tanaka et al.
2008/0097501 A1 4/2008 Blier
2008/0114355 A1 5/2008 Whayne et al.
2008/0114364 A1 5/2008 Goldin et al.
2008/0122496 A1 5/2008 Wagner
2008/0125768 A1 5/2008 Tahara et al.
2008/0147058 A1 6/2008 Horrell et al.
2008/0147062 A1 6/2008 Truckai et al.
2008/0147092 A1 6/2008 Rogge et al.
2008/0167670 A1 7/2008 Shelton et al.
2008/0171938 A1 7/2008 Masuda et al.
2008/0177268 A1 7/2008 Daum et al.
2008/0188755 A1 8/2008 Hart
2008/0200940 A1 8/2008 Eichmann et al.
2008/0208108 A1 8/2008 Kimura
2008/0208231 A1 8/2008 Ota et al.
2008/0214967 A1 9/2008 Aranyi et al.
2008/0234709 A1 9/2008 Houser
2008/0243162 A1 10/2008 Shibata et al.
2008/0255413 A1 10/2008 Zemlok et al.
2008/0275440 A1 11/2008 Kratoska et al.
2008/0281200 A1 11/2008 Voic et al.
2008/0281315 A1 11/2008 Gines
2008/0287944 A1 11/2008 Pearson et al.
2008/0287948 A1 11/2008 Newton et al.
2008/0296346 A1 12/2008 Shelton, IV et al.
2008/0300588 A1 12/2008 Groth et al.
2009/0012516 A1 1/2009 Curtis et al.
2009/0023985 A1 1/2009 Ewers
2009/0036913 A1 2/2009 Wiener et al.

(56) References Cited

U.S. PATENT DOCUMENTS

2009/0043293 A1 2/2009 Pankratov et al.
2009/0048537 A1 2/2009 Lydon et al.
2009/0048589 A1 2/2009 Takashino et al.
2009/0054886 A1 2/2009 Yachi et al.
2009/0054889 A1 2/2009 Newton et al.
2009/0054894 A1 2/2009 Yachi
2009/0065565 A1 3/2009 Cao
2009/0076506 A1 3/2009 Baker
2009/0082716 A1 3/2009 Akahoshi
2009/0082766 A1 3/2009 Unger et al.
2009/0088745 A1 4/2009 Hushka et al.
2009/0088785 A1 4/2009 Masuda
2009/0090763 A1 4/2009 Zemlok et al.
2009/0101692 A1 4/2009 Whitman et al.
2009/0105750 A1 4/2009 Price et al.
2009/0112206 A1 4/2009 Dumbauld et al.
2009/0118751 A1 5/2009 Wiener et al.
2009/0131885 A1 5/2009 Akahoshi
2009/0131934 A1 5/2009 Odom et al.
2009/0138025 A1 5/2009 Stahler et al.
2009/0143678 A1 6/2009 Keast et al.
2009/0143799 A1 6/2009 Smith et al.
2009/0143800 A1 6/2009 Deville et al.
2009/0157064 A1 6/2009 Hodel
2009/0163807 A1 6/2009 Sliwa
2009/0177119 A1 7/2009 Heidner et al.
2009/0179923 A1 7/2009 Amundson et al.
2009/0182322 A1 7/2009 D'Amelio et al.
2009/0182331 A1 7/2009 D'Amelio et al.
2009/0182332 A1 7/2009 Long et al.
2009/0182333 A1 7/2009 Eder et al.
2009/0192441 A1 7/2009 Gelbart et al.
2009/0198272 A1 8/2009 Kerver et al.
2009/0204114 A1 8/2009 Odom
2009/0216157 A1 8/2009 Yamada
2009/0223033 A1 9/2009 Houser
2009/0240244 A1 9/2009 Malis et al.
2009/0248021 A1 10/2009 McKenna
2009/0248022 A1 10/2009 Falkenstein et al.
2009/0254077 A1 10/2009 Craig
2009/0254080 A1 10/2009 Honda
2009/0259149 A1 10/2009 Tahara et al.
2009/0264909 A1 10/2009 Beaupre
2009/0270771 A1 10/2009 Takahashi
2009/0270812 A1 10/2009 Litscher et al.
2009/0270853 A1 10/2009 Yachi et al.
2009/0270891 A1 10/2009 Beaupre
2009/0270899 A1 10/2009 Carusillo et al.
2009/0287205 A1 11/2009 Ingle
2009/0292283 A1 11/2009 Odom
2009/0299141 A1 12/2009 Downey et al.
2009/0306639 A1 12/2009 Nevo et al.
2009/0327715 A1 12/2009 Smith et al.
2010/0004508 A1 1/2010 Naito et al.
2010/0022825 A1 1/2010 Yoshie
2010/0030233 A1 2/2010 Whitman et al.
2010/0034605 A1 2/2010 Huckins et al.
2010/0036370 A1 2/2010 Mirel et al.
2010/0036373 A1 2/2010 Ward
2010/0042093 A9 2/2010 Wham et al.
2010/0049180 A1 2/2010 Wells et al.
2010/0057081 A1 3/2010 Hanna
2010/0057118 A1 3/2010 Dietz et al.
2010/0063437 A1 3/2010 Nelson et al.
2010/0063525 A1 3/2010 Beaupre et al.
2010/0063528 A1 3/2010 Beaupre
2010/0081863 A1 4/2010 Hess et al.
2010/0081864 A1 4/2010 Hess et al.
2010/0081883 A1 4/2010 Murray et al.
2010/0094323 A1 4/2010 Isaacs et al.
2010/0106173 A1 4/2010 Yoshimine
2010/0109480 A1 5/2010 Forslund et al.
2010/0145335 A1 6/2010 Johnson et al.
2010/0158307 A1 6/2010 Kubota et al.
2010/0168741 A1 7/2010 Sanai et al.
2010/0181966 A1 7/2010 Sakakibara
2010/0187283 A1 7/2010 Crainich et al.
2010/0193566 A1 8/2010 Scheib et al.
2010/0204721 A1 8/2010 Young et al.
2010/0222714 A1 9/2010 Muir et al.
2010/0222752 A1 9/2010 Collins, Jr. et al.
2010/0225209 A1 9/2010 Goldberg et al.
2010/0228249 A1 9/2010 Mohr et al.
2010/0228250 A1 9/2010 Brogna
2010/0234906 A1 9/2010 Koh
2010/0256635 A1 10/2010 McKenna et al.
2010/0274160 A1 10/2010 Yachi et al.
2010/0274278 A1 10/2010 Fleenor et al.
2010/0280368 A1 11/2010 Can et al.
2010/0298743 A1 11/2010 Nield et al.
2010/0305564 A1 12/2010 Livneh
2010/0331742 A1 12/2010 Masuda
2010/0331871 A1 12/2010 Nield et al.
2011/0004233 A1 1/2011 Muir et al.
2011/0015632 A1 1/2011 Artale
2011/0015650 A1 1/2011 Choi et al.
2011/0022032 A1 1/2011 Zemlok et al.
2011/0028964 A1 2/2011 Edwards
2011/0071523 A1 3/2011 Dickhans
2011/0082494 A1 4/2011 Kerr et al.
2011/0106141 A1 5/2011 Nakamura
2011/0112400 A1 5/2011 Emery et al.
2011/0125149 A1 5/2011 El-Galley et al.
2011/0125151 A1 5/2011 Strauss et al.
2011/0144640 A1 6/2011 Heinrich et al.
2011/0160725 A1 6/2011 Kabaya et al.
2011/0238010 A1 9/2011 Kirschenman et al.
2011/0238079 A1 9/2011 Hannaford et al.
2011/0273465 A1 11/2011 Konishi et al.
2011/0278343 A1 11/2011 Knodel et al.
2011/0279268 A1 11/2011 Konishi et al.
2011/0284014 A1 11/2011 Cadeddu et al.
2011/0290856 A1 12/2011 Shelton, IV et al.
2011/0295295 A1 12/2011 Shelton, IV et al.
2011/0306967 A1 12/2011 Payne et al.
2011/0313415 A1 12/2011 Fernandez et al.
2012/0004655 A1 1/2012 Kim et al.
2012/0016413 A1 1/2012 Timm et al.
2012/0022519 A1 1/2012 Huang et al.
2012/0022526 A1 1/2012 Aldridge et al.
2012/0022583 A1 1/2012 Sugalski et al.
2012/0041358 A1 2/2012 Mann et al.
2012/0053597 A1 3/2012 Anvari et al.
2012/0059286 A1 3/2012 Hastings et al.
2012/0059289 A1 3/2012 Nield et al.
2012/0071863 A1 3/2012 Lee et al.
2012/0078244 A1 3/2012 Worrell et al.
2012/0080344 A1 4/2012 Shelton, IV
2012/0101493 A1 4/2012 Masuda et al.
2012/0101495 A1 4/2012 Young et al.
2012/0109186 A1 5/2012 Parrott et al.
2012/0116222 A1 5/2012 Sawada et al.
2012/0116265 A1 5/2012 Houser et al.
2012/0116266 A1* 5/2012 Houser .................... A61N 7/00
606/1
2012/0116381 A1 5/2012 Houser et al.
2012/0136279 A1 5/2012 Tanaka et al.
2012/0136347 A1 5/2012 Brustad et al.
2012/0136386 A1 5/2012 Kishida et al.
2012/0143182 A1 6/2012 Ullrich et al.
2012/0143211 A1 6/2012 Kishi
2012/0150049 A1 6/2012 Zielinski et al.
2012/0150169 A1 6/2012 Zielinksi et al.
2012/0172904 A1 7/2012 Muir et al.
2012/0191091 A1 7/2012 Allen
2012/0193396 A1 8/2012 Zemlok et al.
2012/0211542 A1 8/2012 Racenet
2012/0226266 A1 9/2012 Ghosal et al.
2012/0234893 A1 9/2012 Schuckmann et al.
2012/0253328 A1 10/2012 Cunningham et al.
2012/0253329 A1 10/2012 Zemlok et al.
2012/0265196 A1* 10/2012 Turner .................... H01H 1/00
606/34
2012/0265241 A1 10/2012 Hart et al.

(56) References Cited

U.S. PATENT DOCUMENTS

2012/0296239 A1 11/2012 Chernov et al.
2012/0296325 A1 11/2012 Takashino
2012/0296371 A1 11/2012 Kappus et al.
2013/0023925 A1 1/2013 Mueller
2013/0041363 A1 2/2013 Van Wyek et al.
2013/0071282 A1 3/2013 Fry
2013/0085510 A1 4/2013 Stefanchik et al.
2013/0103031 A1 4/2013 Garrison
2013/0123776 A1 5/2013 Monson et al.
2013/0158659 A1 6/2013 Bergs et al.
2013/0158660 A1 6/2013 Bergs et al.
2013/0165929 A1 6/2013 Muir et al.
2013/0190760 A1 7/2013 Allen, IV et al.
2013/0214025 A1 8/2013 Zemlok et al.
2013/0253256 A1 9/2013 Griffith et al.
2013/0253480 A1 9/2013 Kimball et al.
2013/0264369 A1 10/2013 Whitman
2013/0267874 A1 10/2013 Marcotte et al.
2013/0277410 A1 10/2013 Fernandez et al.
2013/0296843 A1 11/2013 Boudreaux et al.
2013/0321425 A1 12/2013 Greene et al.
2013/0334989 A1 12/2013 Kataoka
2013/0345701 A1 12/2013 Allen, IV et al.
2014/0001231 A1 1/2014 Shelton, IV et al.
2014/0001234 A1 1/2014 Shelton, IV et al.
2014/0005640 A1 1/2014 Shelton, IV et al.
2014/0005663 A1 1/2014 Heard et al.
2014/0005678 A1 1/2014 Shelton, IV et al.
2014/0005702 A1 1/2014 Timm et al.
2014/0005705 A1 1/2014 Weir et al.
2014/0005718 A1 1/2014 Shelton, IV et al.
2014/0014544 A1 1/2014 Bugnard et al.
2014/0077426 A1 3/2014 Park
2014/0121569 A1 5/2014 Schafer et al.
2014/0135804 A1 5/2014 Weisenburgh, II et al.
2014/0163541 A1 6/2014 Shelton, IV et al.
2014/0163549 A1 6/2014 Yates et al.
2014/0180274 A1 6/2014 Kabaya et al.
2014/0194868 A1 7/2014 Sanai et al.
2014/0194874 A1 7/2014 Dietz et al.
2014/0194875 A1 7/2014 Reschke et al.
2014/0207124 A1 7/2014 Aldridge et al.
2014/0207135 A1 7/2014 Winter
2014/0221994 A1 8/2014 Reschke
2014/0236152 A1 8/2014 Walberg et al.
2014/0246475 A1 9/2014 Hall et al.
2014/0249557 A1 9/2014 Koch, Jr. et al.
2014/0263541 A1 9/2014 Leimbach et al.
2014/0263552 A1 9/2014 Hall et al.
2014/0276768 A1 9/2014 Juergens et al.
2014/0276777 A1 9/2014 Trees et al.
2014/0276794 A1 9/2014 Batchelor et al.
2014/0276797 A1 9/2014 Batchelor et al.
2014/0276798 A1 9/2014 Batchelor et al.
2014/0303605 A1 10/2014 Boyden et al.
2014/0303612 A1 10/2014 Williams
2014/0357984 A1 12/2014 Wallace et al.
2014/0373003 A1 12/2014 Grez et al.
2015/0014392 A1 1/2015 Williams et al.
2015/0025528 A1 1/2015 Arts
2015/0032150 A1 1/2015 Ishida et al.
2015/0048140 A1 2/2015 Penna et al.
2015/0066027 A1 3/2015 Garrison et al.
2015/0080876 A1 3/2015 Worrell et al.
2015/0080887 A1 3/2015 Sobajima et al.
2015/0080889 A1 3/2015 Cunningham et al.
2015/0088122 A1 3/2015 Jensen
2015/0100056 A1 4/2015 Nakamura
2015/0112335 A1 4/2015 Boudreaux et al.
2015/0119901 A1 4/2015 Steege
2015/0157356 A1 6/2015 Gee
2015/0164533 A1 6/2015 Felder et al.
2015/0164534 A1 6/2015 Felder et al.
2015/0164535 A1 6/2015 Felder et al.
2015/0164536 A1 6/2015 Czarnecki et al.
2015/0164537 A1 6/2015 Cagle et al.
2015/0230796 A1 8/2015 Calderoni
2015/0238260 A1 8/2015 Nau, Jr.
2015/0272557 A1 10/2015 Overmyer et al.
2015/0272571 A1 10/2015 Leimbach et al.
2015/0272580 A1 10/2015 Leimbach et al.
2015/0272582 A1 10/2015 Leimbach et al.
2015/0272657 A1 10/2015 Yates et al.
2015/0272659 A1 10/2015 Boudreaux et al.
2015/0282879 A1 10/2015 Ruelas
2015/0289364 A1 10/2015 Ilkko et al.
2015/0313667 A1 11/2015 Allen, IV
2015/0317899 A1 11/2015 Dumbauld et al.
2015/0351765 A1 12/2015 Valentine et al.
2015/0351857 A1 12/2015 Vander Poorten et al.
2015/0374430 A1 12/2015 Weiler et al.
2015/0374457 A1 12/2015 Colby
2016/0000437 A1 1/2016 Giordano et al.
2016/0038228 A1 2/2016 Daniel et al.
2016/0044841 A1 2/2016 Chamberlain
2016/0045248 A1 2/2016 Unger et al.
2016/0051314 A1 2/2016 Batchelor et al.
2016/0051316 A1 2/2016 Boudreaux
2016/0066913 A1 3/2016 Swayze et al.
2016/0120601 A1 5/2016 Boudreaux et al.
2016/0175025 A1 6/2016 Strobl
2016/0175029 A1 6/2016 Witt et al.
2016/0206342 A1 7/2016 Robertson et al.
2016/0228171 A1 8/2016 Boudreaux
2016/0249910 A1 9/2016 Shelton, IV et al.
2016/0262786 A1 9/2016 Madan et al.
2016/0270842 A1 9/2016 Strobl et al.
2016/0296251 A1 10/2016 Olson et al.
2016/0296252 A1 10/2016 Olson et al.
2016/0296270 A1 10/2016 Strobl et al.
2016/0317216 A1 11/2016 Hermes et al.
2016/0331455 A1 11/2016 Hancock et al.
2016/0358849 A1 12/2016 Jur et al.
2017/0020614 A1 1/2017 Jackson et al.
2017/0065331 A1 3/2017 Mayer et al.
2017/0086909 A1 3/2017 Yates et al.
2017/0119426 A1 5/2017 Akagane
2017/0135751 A1 5/2017 Rothweiler et al.
2017/0164972 A1 6/2017 Johnson et al.
2017/0164997 A1 6/2017 Johnson et al.
2017/0189095 A1 7/2017 Danziger et al.
2017/0202595 A1 7/2017 Shelton, IV
2017/0209145 A1 7/2017 Swayze et al.
2017/0224332 A1 8/2017 Hunter et al.
2017/0224405 A1 8/2017 Takashino et al.
2017/0231628 A1 8/2017 Shelton, IV et al.
2017/0281186 A1 10/2017 Shelton, IV et al.
2017/0296169 A1 10/2017 Yates et al.
2017/0296177 A1 10/2017 Harris et al.
2017/0296180 A1 10/2017 Harris et al.
2017/0303954 A1 10/2017 Ishii
2017/0312018 A1 11/2017 Trees et al.
2017/0325874 A1 11/2017 Noack et al.
2017/0333073 A1 11/2017 Faller et al.
2017/0348043 A1 12/2017 Wang et al.
2017/0348044 A1 12/2017 Wang et al.
2017/0367772 A1 12/2017 Gunn et al.
2018/0008312 A1 1/2018 Batchelor et al.
2018/0014872 A1 1/2018 Dickerson
2018/0085157 A1 3/2018 Batchelor et al.
2018/0132850 A1 5/2018 Leimbach et al.
2018/0168575 A1 6/2018 Simms et al.
2018/0168577 A1 6/2018 Aronhalt et al.
2018/0168579 A1 6/2018 Aronhalt et al.
2018/0168598 A1 6/2018 Shelton, IV et al.
2018/0168608 A1 6/2018 Shelton, IV et al.
2018/0168609 A1 6/2018 Fanelli et al.
2018/0168615 A1 6/2018 Shelton, IV et al.
2018/0168618 A1 6/2018 Scott et al.
2018/0168619 A1 6/2018 Scott et al.
2018/0168623 A1 6/2018 Simms et al.
2018/0168625 A1 6/2018 Posada et al.
2018/0168633 A1 6/2018 Shelton, IV et al.
2018/0168647 A1 6/2018 Shelton, IV et al.

(56) References Cited

U.S. PATENT DOCUMENTS

| | | | |
|---|---|---|---|
| 2018/0168648 | A1 | 6/2018 | Shelton, IV et al. |
| 2018/0168650 | A1 | 6/2018 | Shelton, IV et al. |
| 2018/0188125 | A1 | 7/2018 | Park et al. |
| 2018/0206904 | A1 | 7/2018 | Felder et al. |
| 2018/0221045 | A1 | 8/2018 | Zimmerman et al. |
| 2018/0250066 | A1 | 9/2018 | Ding et al. |
| 2018/0271578 | A1 | 9/2018 | Coulombe |
| 2018/0289432 | A1 | 10/2018 | Kostrzewski et al. |
| 2018/0303493 | A1 | 10/2018 | Chapolini |
| 2018/0325517 | A1 | 11/2018 | Wingardner et al. |
| 2018/0333179 | A1 | 11/2018 | Weisenburgh, II et al. |
| 2018/0353245 | A1 | 12/2018 | Mccloud et al. |
| 2018/0368844 | A1 | 12/2018 | Bakos et al. |
| 2019/0000459 | A1 | 1/2019 | Shelton, IV et al. |
| 2019/0000461 | A1 | 1/2019 | Shelton, IV et al. |
| 2019/0029746 | A1 | 1/2019 | Dudhedia et al. |
| 2019/0038283 | A1 | 2/2019 | Shelton, IV et al. |
| 2019/0053818 | A1 | 2/2019 | Nelson et al. |
| 2019/0104919 | A1 | 4/2019 | Shelton, IV et al. |
| 2019/0117293 | A1 | 4/2019 | Kano et al. |
| 2019/0125361 | A1 | 5/2019 | Shelton, IV et al. |
| 2019/0125384 | A1 | 5/2019 | Scheib et al. |
| 2019/0125390 | A1 | 5/2019 | Shelton, IV et al. |
| 2019/0175258 | A1 | 6/2019 | Tsuruta |
| 2019/0183504 | A1 | 6/2019 | Shelton, IV et al. |
| 2019/0200844 | A1 | 7/2019 | Shelton, IV et al. |
| 2019/0200977 | A1 | 7/2019 | Shelton, IV et al. |
| 2019/0200981 | A1 | 7/2019 | Harris et al. |
| 2019/0200987 | A1 | 7/2019 | Shelton, IV et al. |
| 2019/0201029 | A1 | 7/2019 | Shelton, IV et al. |
| 2019/0201030 | A1 | 7/2019 | Shelton, IV et al. |
| 2019/0201045 | A1 | 7/2019 | Yates et al. |
| 2019/0201048 | A1 | 7/2019 | Stulen et al. |
| 2019/0201104 | A1 | 7/2019 | Shelton, IV et al. |
| 2019/0201594 | A1 | 7/2019 | Shelton, IV et al. |
| 2019/0206564 | A1 | 7/2019 | Shelton, IV et al. |
| 2019/0206569 | A1 | 7/2019 | Shelton, IV et al. |
| 2019/0209201 | A1 | 7/2019 | Boudreaux et al. |
| 2019/0223941 | A1 | 7/2019 | Kitamura et al. |
| 2019/0269455 | A1 | 9/2019 | Mensch et al. |
| 2019/0290265 | A1 | 9/2019 | Shelton, IV et al. |
| 2019/0298353 | A1 | 10/2019 | Shelton, IV et al. |
| 2019/0366562 | A1 | 12/2019 | Zhang et al. |
| 2019/0388091 | A1 | 12/2019 | Eschbach et al. |
| 2020/0054321 | A1 | 2/2020 | Harris et al. |
| 2020/0078085 | A1 | 3/2020 | Yates et al. |
| 2020/0078609 | A1 | 3/2020 | Messerly et al. |
| 2020/0100825 | A1 | 4/2020 | Henderson et al. |
| 2020/0113622 | A1 | 4/2020 | Honegger |
| 2020/0129261 | A1 | 4/2020 | Eschbach |
| 2020/0138473 | A1 | 5/2020 | Shelton, IV et al. |
| 2020/0188047 | A1 | 6/2020 | Itkowitz et al. |
| 2020/0222111 | A1 | 7/2020 | Yates et al. |
| 2020/0222112 | A1 | 7/2020 | Hancock et al. |
| 2020/0268430 | A1 | 8/2020 | Takei et al. |
| 2020/0268433 | A1 | 8/2020 | Wiener et al. |
| 2020/0315623 | A1 | 10/2020 | Eisinger et al. |
| 2020/0315712 | A1 | 10/2020 | Jasperson et al. |
| 2020/0405296 | A1 | 12/2020 | Shelton, IV et al. |
| 2020/0405302 | A1 | 12/2020 | Shelton, IV et al. |
| 2020/0410177 | A1 | 12/2020 | Shelton, IV |
| 2021/0100579 | A1 | 4/2021 | Shelton, IV et al. |
| 2021/0128226 | A1 | 5/2021 | Akagane |
| 2021/0153927 | A1 | 5/2021 | Ross et al. |
| 2021/0177481 | A1 | 6/2021 | Shelton, IV et al. |
| 2021/0177494 | A1 | 6/2021 | Houser et al. |
| 2021/0177496 | A1 | 6/2021 | Shelton, IV et al. |
| 2021/0186492 | A1 | 6/2021 | Shelton, IV et al. |
| 2021/0186497 | A1 | 6/2021 | Shelton, IV et al. |
| 2021/0186499 | A1 | 6/2021 | Shelton, IV et al. |
| 2021/0186501 | A1 | 6/2021 | Shelton, IV et al. |
| 2021/0186553 | A1 | 6/2021 | Green et al. |
| 2021/0186554 | A1 | 6/2021 | Green et al. |
| 2021/0196266 | A1 | 7/2021 | Shelton, IV et al. |
| 2021/0196267 | A1 | 7/2021 | Shelton, IV et al. |
| 2021/0196268 | A1 | 7/2021 | Shelton, IV et al. |
| 2021/0196269 | A1 | 7/2021 | Shelton, IV et al. |
| 2021/0196270 | A1 | 7/2021 | Shelton, IV et al. |
| 2021/0196271 | A1 | 7/2021 | Shelton, IV et al. |
| 2021/0196302 | A1 | 7/2021 | Shelton, IV et al. |
| 2021/0196305 | A1 | 7/2021 | Strobl |
| 2021/0196306 | A1 | 7/2021 | Estera et al. |
| 2021/0196307 | A1 | 7/2021 | Shelton, IV |
| 2021/0196334 | A1 | 7/2021 | Sarley et al. |
| 2021/0196335 | A1 | 7/2021 | Messerly et al. |
| 2021/0196336 | A1 | 7/2021 | Faller et al. |
| 2021/0196344 | A1 | 7/2021 | Shelton, IV et al. |
| 2021/0196345 | A1 | 7/2021 | Messerly et al. |
| 2021/0196346 | A1 | 7/2021 | Leuck et al. |
| 2021/0196349 | A1 | 7/2021 | Fiebig et al. |
| 2021/0196351 | A1 | 7/2021 | Sarley et al. |
| 2021/0196352 | A1 | 7/2021 | Messerly et al. |
| 2021/0196353 | A1 | 7/2021 | Gee et al. |
| 2021/0196354 | A1 | 7/2021 | Shelton, IV et al. |
| 2021/0196357 | A1 | 7/2021 | Shelton, IV et al. |
| 2021/0196358 | A1 | 7/2021 | Shelton, IV et al. |
| 2021/0196359 | A1 | 7/2021 | Shelton, IV et al. |
| 2021/0196361 | A1 | 7/2021 | Shelton, IV et al. |
| 2021/0196362 | A1 | 7/2021 | Shelton, IV et al. |
| 2021/0196363 | A1 | 7/2021 | Shelton, IV et al. |
| 2021/0196364 | A1 | 7/2021 | Shelton, IV et al. |
| 2021/0196366 | A1 | 7/2021 | Shelton, IV et al. |
| 2021/0196367 | A1 | 7/2021 | Salguero et al. |
| 2021/0212754 | A1 | 7/2021 | Olson |
| 2021/0220036 | A1 | 7/2021 | Shelton, IV et al. |
| 2021/0236195 | A1 | 8/2021 | Asher et al. |
| 2021/0282804 | A1 | 9/2021 | Worrell et al. |
| 2021/0393288 | A1 | 12/2021 | Shelton, IV et al. |
| 2021/0393314 | A1 | 12/2021 | Wiener et al. |
| 2021/0393319 | A1 | 12/2021 | Shelton, IV et al. |
| 2022/0039891 | A1 | 2/2022 | Stulen et al. |
| 2022/0071655 | A1 | 3/2022 | Price et al. |
| 2022/0167982 | A1 | 6/2022 | Shelton, IV et al. |
| 2022/0168005 | A1 | 6/2022 | Aldridge et al. |
| 2022/0168039 | A1 | 6/2022 | Worrell et al. |
| 2022/0226014 | A1 | 7/2022 | Clauda, IV et al. |
| 2022/0304736 | A1 | 9/2022 | Boudreaux |
| 2022/0313297 | A1 | 10/2022 | Aldridge et al. |
| 2022/0346863 | A1 | 11/2022 | Yates et al. |
| 2022/0387067 | A1 | 12/2022 | Faller et al. |
| 2022/0406452 | A1 | 12/2022 | Shelton, IV |
| 2023/0038162 | A1 | 2/2023 | Timm et al. |
| 2023/0048996 | A1 | 2/2023 | Vakharia et al. |
| 2023/0277205 | A1 | 9/2023 | Olson et al. |

FOREIGN PATENT DOCUMENTS

| | | | |
|---|---|---|---|
| CN | 1634601 | A | 7/2005 |
| CN | 1775323 | A | 5/2006 |
| CN | 1922563 | A | 2/2007 |
| CN | 2868227 | Y | 2/2007 |
| CN | 201029899 | Y | 3/2008 |
| CN | 101474081 | A | 7/2009 |
| CN | 101516285 | A | 8/2009 |
| CN | 101522112 | A | 9/2009 |
| CN | 102100582 | A | 6/2011 |
| CN | 102149312 | A | 8/2011 |
| CN | 202027624 | U | 11/2011 |
| CN | 102792181 | A | 11/2012 |
| CN | 103281982 | A | 9/2013 |
| CN | 103379853 | A | 10/2013 |
| CN | 203468630 | U | 3/2014 |
| CN | 104001276 | A | 8/2014 |
| CN | 104013444 | A | 9/2014 |
| CN | 104434298 | A | 3/2015 |
| CN | 107374752 | A | 11/2017 |
| DE | 3904558 | A1 | 8/1990 |
| DE | 9210327 | U1 | 11/1992 |
| DE | 4300307 | A1 | 7/1994 |
| DE | 29623113 | U1 | 10/1997 |
| DE | 20004812 | U1 | 9/2000 |
| DE | 20021619 | U1 | 3/2001 |
| DE | 10042606 | A1 | 8/2001 |
| DE | 10201569 | A1 | 7/2003 |

(56) References Cited

FOREIGN PATENT DOCUMENTS

| | | | |
|---|---|---|---|
| DE | 102012109037 | A1 | 4/2014 |
| EP | 0171967 | A2 | 2/1986 |
| EP | 0336742 | A2 | 10/1989 |
| EP | 0136855 | B1 | 11/1989 |
| EP | 0468194 | A2 | 1/1992 |
| EP | 0705571 | A1 | 4/1996 |
| EP | 1698289 | A2 | 9/2006 |
| EP | 1862133 | A1 | 12/2007 |
| EP | 1972264 | A1 | 9/2008 |
| EP | 2060238 | A1 | 5/2009 |
| EP | 1747761 | B1 | 10/2009 |
| EP | 2131760 | A1 | 12/2009 |
| EP | 1214913 | B1 | 7/2010 |
| EP | 1946708 | B1 | 6/2011 |
| EP | 1767164 | B1 | 1/2013 |
| EP | 2578172 | A2 | 4/2013 |
| EP | 2668922 | A1 | 12/2013 |
| EP | 2076195 | B1 | 12/2015 |
| EP | 2510891 | B1 | 6/2016 |
| EP | 3476302 | A2 | 5/2019 |
| EP | 3476331 | A1 | 5/2019 |
| EP | 3694298 | A1 | 8/2020 |
| GB | 2032221 | A | 4/1980 |
| GB | 2317566 | A | 4/1998 |
| JP | S50100891 | A | 8/1975 |
| JP | S5968511 | A | 4/1984 |
| JP | S5968511 | U | 5/1984 |
| JP | S5968513 | U | 5/1984 |
| JP | S59141938 | A | 8/1984 |
| JP | S62221343 | A | 9/1987 |
| JP | S62227343 | A | 10/1987 |
| JP | S62292153 | A | 12/1987 |
| JP | S62292154 | A | 12/1987 |
| JP | S63109386 | A | 5/1988 |
| JP | S63315049 | A | 12/1988 |
| JP | H01151452 | A | 6/1989 |
| JP | H01198540 | A | 8/1989 |
| JP | H0271510 | U | 5/1990 |
| JP | H02286149 | A | 11/1990 |
| JP | H02292193 | A | 12/1990 |
| JP | H0337061 | A | 2/1991 |
| JP | H03126447 | A | 5/1991 |
| JP | H0425707 | U | 2/1992 |
| JP | H0464351 | A | 2/1992 |
| JP | H0430508 | U | 3/1992 |
| JP | H04152942 | A | 5/1992 |
| JP | H 0541716 | A | 2/1993 |
| JP | H0576482 | A | 3/1993 |
| JP | H0595955 | A | 4/1993 |
| JP | H05115490 | A | 5/1993 |
| JP | H0670938 | A | 3/1994 |
| JP | H06104503 | A | 4/1994 |
| JP | H07171161 | A | 7/1995 |
| JP | H0824266 | A | 1/1996 |
| JP | H08117242 | A | 5/1996 |
| JP | H08229050 | A | 9/1996 |
| JP | H08275951 | A | 10/1996 |
| JP | H08299351 | A | 11/1996 |
| JP | H08336545 | A | 12/1996 |
| JP | H0917660 | A | 1/1997 |
| JP | H0956726 | A | 3/1997 |
| JP | H09130655 | A | 5/1997 |
| JP | H09135553 | A | 5/1997 |
| JP | H09140722 | A | 6/1997 |
| JP | H105237 | A | 1/1998 |
| JP | H1033551 | A | 2/1998 |
| JP | 10127654 | A | 5/1998 |
| JP | H10295700 | A | 11/1998 |
| JP | H11128238 | A | 5/1999 |
| JP | H11169381 | A | 6/1999 |
| JP | H11226026 | A | 8/1999 |
| JP | 2000210299 | A | 8/2000 |
| JP | 2000271142 | A | 10/2000 |
| JP | 2000271145 | A | 10/2000 |
| JP | 2000287987 | A | 10/2000 |
| JP | 2001029353 | A | 2/2001 |
| JP | 2001120564 | A | 5/2001 |
| JP | 2001144595 | A | 5/2001 |
| JP | 2002059380 | A | 2/2002 |
| JP | 2002177287 | A | 6/2002 |
| JP | 2002186901 | A | 7/2002 |
| JP | 2002263579 | A | 9/2002 |
| JP | 2002330977 | A | 11/2002 |
| JP | 2003000612 | A | 1/2003 |
| JP | 2003010201 | A | 1/2003 |
| JP | 2003116870 | A | 4/2003 |
| JP | 2003126104 | A | 5/2003 |
| JP | 2003126110 | A | 5/2003 |
| JP | 2003153919 | A | 5/2003 |
| JP | 2003339730 | A | 12/2003 |
| JP | 2004129871 | A | 4/2004 |
| JP | 2004147701 | A | 5/2004 |
| JP | 2005003496 | A | 1/2005 |
| JP | 2005027026 | A | 1/2005 |
| JP | 2005074088 | A | 3/2005 |
| JP | 2005337119 | A | 12/2005 |
| JP | 2006068396 | A | 3/2006 |
| JP | 2006081664 | A | 3/2006 |
| JP | 2006114072 | A | 4/2006 |
| JP | 2006217716 | A | 8/2006 |
| JP | 2006288431 | A | 10/2006 |
| JP | 2007037568 | A | 2/2007 |
| JP | 200801876 | A | 1/2008 |
| JP | 2008017876 | A | 1/2008 |
| JP | 200833644 | A | 2/2008 |
| JP | 2008188160 | A | 8/2008 |
| JP | D1339835 | S | 8/2008 |
| JP | 2009236177 | A | 10/2009 |
| JP | 2010009686 | A | 1/2010 |
| JP | 2010121865 | A | 6/2010 |
| JP | 2012071186 | A | 4/2012 |
| JP | 2012223582 | A | 11/2012 |
| JP | 2012235658 | A | 11/2012 |
| JP | 2013126430 | A | 6/2013 |
| KR | 100789356 | B1 | 12/2007 |
| KR | 101298237 | B1 | 8/2013 |
| RU | 2154437 | C1 | 8/2000 |
| RU | 22035 | U1 | 3/2002 |
| RU | 2201169 | C2 | 3/2003 |
| RU | 2405603 | C1 | 12/2010 |
| RU | 2013119977 | A | 11/2014 |
| SU | 850068 | A1 | 7/1981 |
| WO | WO-8103272 | A1 | 11/1981 |
| WO | WO-9308757 | A1 | 5/1993 |
| WO | WO-9314708 | A1 | 8/1993 |
| WO | WO-9421183 | A1 | 9/1994 |
| WO | WO-9424949 | A1 | 11/1994 |
| WO | WO-9639086 | A1 | 12/1996 |
| WO | WO-9712557 | A1 | 4/1997 |
| WO | WO-9800069 | A1 | 1/1998 |
| WO | WO-9840015 | A2 | 9/1998 |
| WO | WO-9920213 | A1 | 4/1999 |
| WO | WO-9923960 | A1 | 5/1999 |
| WO | WO-0024330 | A1 | 5/2000 |
| WO | WO-0064358 | A2 | 11/2000 |
| WO | WO-0128444 | A1 | 4/2001 |
| WO | WO-0167970 | A1 | 9/2001 |
| WO | WO-0172251 | A1 | 10/2001 |
| WO | WO-0195810 | A2 | 12/2001 |
| WO | WO-02080793 | A1 | 10/2002 |
| WO | WO-03095028 | A1 | 11/2003 |
| WO | WO-2004037095 | A2 | 5/2004 |
| WO | WO-2004078051 | A2 | 9/2004 |
| WO | WO-2004098426 | A1 | 11/2004 |
| WO | WO-2006091494 | A1 | 8/2006 |
| WO | WO-2007008710 | A2 | 1/2007 |
| WO | WO-2008118709 | A1 | 10/2008 |
| WO | WO-2008130793 | A1 | 10/2008 |
| WO | WO-2010027109 | A1 | 3/2010 |
| WO | WO-2010104755 | A1 | 9/2010 |
| WO | WO-2011008672 | A2 | 1/2011 |
| WO | WO-2011044343 | A2 | 4/2011 |
| WO | WO-2011052939 | A2 | 5/2011 |
| WO | WO-2011060031 | A1 | 5/2011 |

(56) References Cited

FOREIGN PATENT DOCUMENTS

| | | | |
|---|---|---|---|
| WO | 2011092464 | A1 | 8/2011 |
| WO | WO-2012044606 | A2 | 4/2012 |
| WO | WO-2012061722 | A2 | 5/2012 |
| WO | WO-2012088535 | A1 | 6/2012 |
| WO | WO-2012150567 | A1 | 11/2012 |
| WO | WO-2016130844 | A1 | 8/2016 |
| WO | WO-2019130090 | A1 | 7/2019 |
| WO | WO-2019130113 | A1 | 7/2019 |

OTHER PUBLICATIONS

Hörmann et al., "Reversible and irreversible denaturation of collagen fibers." Biochemistry, 10, pp. 932-937 (1971).
Technology Overview, printed from www.harmonicscalpel.com, Internet site, website accessed on Jun. 13, 2007, (3 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
Lim et al., "A Review of Mechanism Used in Laparoscopic Surgical Instruments," Mechanism and Machine Theory, vol. 38, pp. 1133-1147, (2003).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.
Covidien Brochure, The LigaSure Precise™ Instrument, dated Mar. 2011 (2 pages).
AST Products, Inc., "Principles of Video Contact Angle Analysis," 20 pages, (2006).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Heat-induced changes in the mechanics of a collagenous tissue: pseudoelastic behavior at 37° C.," Journal of Biomechanics, 31, pp. 211-216 (1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Moraleda et al., A Temperature Sensor Based on a Polymer Optical Fiber Macro-Bend, Sensors 2013, 13, 13076-13089, doi: 10.3390/s131013076, ISSN 1424-8220.
Leonard I. Malis, M.D., "The Value of Irrigation During Bipolar Coagulation," 1989.
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Incropera et al., Fundamentals of Heat and Mass Transfer, Wiley, New York (1990). (Book—not attached).
F. A. Duck, "Optical Properties of Tissue Including Ultraviolet and Infrared Radiation," pp. 43-71 in Physical Properties of Tissue (1990).
Campbell et al, "Thermal Imaging in Surgery," p. 19-3, in Medical Infrared Imaging, N. A. Diakides and J. D. Bronzino, Eds. (2008).
Gerhard, Glen C., "Surgical Electrotechnology: Quo Vadis?," IEEE Transactions on Biomedical Engineering, vol. BME-31, No. 12, pp. 787-792, Dec. 1984.
Fowler, K.R., "A Programmable, Arbitrary Waveform Electrosurgical Device," IEEE Engineering in Medicine and Biology Society 10th Annual International Conference, pp. 1324, 1325 (1988).
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Graff, K.F., "Elastic Wave Propagation in a Curved Sonic Transmission Line," IEEE Transactions on Sonics and Ultrasonics, SU-17(1), 1-6 (1970).
Makarov, S. N., Ochmann, M., Desinger, K., "The longitudinal vibration response of a curved fiber used for laser ultrasound surgical therapy," Journal of the Acoustical Society of America 102, 1191-1199 (1997).
Morley, L. S. D., "Elastic Waves in a Naturally Curved Rod," Quarterly Journal of Mechanics and Applied Mathematics, 14: 155-172 (1961).
Walsh, S. J., White, R. G., "Vibrational Power Transmission in Curved Beams," Journal of Sound and Vibration, 233(3), 455-488 (2000).
Covidien Brochure, [Value Analysis Brief], LigaSure Advance™ Pistol Grip, dated Rev. Apr. 2010 (7 pages).
Wright, et al., "Time-Temperature Equivalence of Heat-Induced Changes in Cells and Proteins," Feb. 1998. ASME Journal of Biomechanical Engineering, vol. 120, pp. 22-26.
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Erbe Electrosurgery VIO® 200 S, (2012), p. 7, 12 pages, accessed Mar. 31, 2014 at http://www.erbe-med. com/erbe/media/Marketing materialien/85140170 ERBE EN VIO 200 S D027541.
Jang, J. et al. "Neuro-fuzzy and Soft Computing." Prentice Hall, 1997, pp. 13-89, 199-293, 335-393, 453-496, 535-549.
Sullivan, "Optimal Choice for Number of Strands in a Litz-Wire Transformer Winding," IEEE Transactions on Power Electronics, vol. 14, No. 2, Mar. 1999, pp. 283-291.
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Henriques. F.C., "Studies in thermal injury V. The predictability and the significance of thermally induced rate processes leading to irreversible epidermal injury." Archives of Pathology, 434, pp. 489-502 (1947).
Wall et al., "Thermal modification of collagen," J Shoulder Elbow Surg, No. 8, pp. 339-344 (Jul./Aug. 1999).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).

(56) References Cited

OTHER PUBLICATIONS

National Semiconductors Temperature Sensor Handbook—http://www.national.com/appinfo/tempsensors/files/temphb.pdf; accessed online: Apr. 1, 2011.
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Douglas, S.C. "Introduction to Adaptive Filter". Digital Signal Processing Handbook. Ed. Vijay K. Madisetti and Douglas B. Williams. Boca Raton: CRC Press LLC, 1999.
Kurt Gieck & Reiner Gieck, *Engineering Formulas* § Z.7 (7th ed. 1997).
Glaser and Subak-Sharpe,Integrated Circuit Engineering, Addison-Wesley Publishing, Reading, MA (1979). (book—not attached).
Covidien 501 (k) Summary Sonicision, dated Feb. 24, 2011 (7 pages).
LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
IEEE Std 802.3-2012 (Revision of IEEE Std 802.3-2008, published Dec. 28, 2012.
"ATM-MPLS Network Interworking Version 2.0, af-aic-0178.001" ATM Standard, the ATM Forum Technical Committee, published Aug. 2003.
Missinne, et al. "Stretchable Optical Waveguides," vol. 22, No. 4, Feb. 18, 2014, pp. 4168-4179 (12 pages).
"Ethicon Energy Devices", Retrieved from: http://www.ethicon.com/gb-en/healthcare-professionals/products/energy-devices/capital/ge, 1 page, May 30, 2013.
"Ethicon Ultracision G110 Electrosurgical Unit for Sale", Retrieved from: http://www.medicalexpo.com/medical-manufacturer/electrosurgical-generator-6951.html, 1 page, Jan. 15, 2013.
"Johnson & Johnson: Ethicon Endo-surgery Highlights Commitment to Nurse Education, Patient Safety and Key Product Innovations at the Association for Perioperative Registered Nurses (Aorn) Conference", http://www.4-traders.com/JOHNSON-JOHNSON-4832/news/John, 1 page, Mar. 23, 2012.
Andy Guarin International Medical Equipment, "Ethicon Ultracision G110 Electrosurgical Unit", Retrieved from internet: http://www.dotmed.com/listing/electrosurical-unit/ethicon/ultracision-g110-/1466724, 1 page, May 30, 2013.
Apical Instruments Inc., "RF/Electro-Surgical Generators", Retrieved from internet: http://www.apicalinstr.com/generators.htm, 1 page, Jan. 15, 2013.
Extended European Search Report received for European Application No. 24178531.0, 7 pages, mailed on Sep. 19, 2024.
International Search Report and Written Opinion received for PCT Application No. PCT/US2016/052979, 20 pages, mailed on Mar. 29, 2017.
International Search Report and Written Opinion received for PCT Application No. PCT/US2016/052981, 10 pages, mailed on Jan. 9, 2017.
International Search Report and Written Opinion received for PCT Application No. PCT/US2016/052982, 13 pages, mailed on Nov. 25, 2016.
International Search Report and Written Opinion received for PCT Application No. PCT/US2016/052984, 12 pages, mailed on Dec. 22, 2016.
EN 60601-2-2:2009/A11:2011, "Medical electrical equipment—Part 2-2: Particular requirements for basic safety and essential performance of high frequency surgical equipment and high frequency surgical accessories", IEC (International Electrotechnical Commission), 87 pages, Dec. 16, 2011.
Japan Lublight Ltd., "Introduction to Tribology", Retrieved from internet: http://www.lublight.co.jp/tribo.htm, 6 pages, Feb. 13, 2026.
Japanese Manufacturing, "Surface Temperature and Boundary Friction", 5 pages, Oct. 18, 2018.
Megadyne, "Mega Power Electrosurgical Generator (Diathermy)", Retrieved from internet: http://www.megadyne.com/es_generator.php, 1 page, Jan. 15, 2013.
U.S. Appl. No. 12/031,573, 43 pages, filed on Feb. 14, 2008.
Valleylab, "Force FXTM-C Electrosurgical Generator with Instant Response TM Technology", Retrieved from internet: http://www.valleylab.com/product/es/generators/index.html), 118 pages, Sep. 2009.

* cited by examiner 5601
300
200
100
0
-100
-200
-300
VOLTAGE (V)
15
10
5
0
VOLTAGE (V)
5603
2.90 2.92 2.94 2.96 2.98 3.00 3.02 3.04 3.06 3.08 3.10
TIME (ms)

TECHNIQUES FOR CIRCUIT TOPOLOGIES FOR COMBINED GENERATOR

PRIORITY

This application is a continuation application claiming priority under 35 U.S.C. § 120 to U.S. patent application Ser. No. 16/795,886, titled TECHNIQUES FOR CIRCUIT TOPOLOGIES FOR COMBINED GENERATOR, which issued on Jan. 24, 2023 as U.S. Pat. No. 11,559,347, which is a continuation application claiming priority under 35 U.S.C. § 120 to U.S. patent application Ser. No. 15/265,293, titled TECHNIQUES FOR CIRCUIT TOPOLOGIES FOR COMBINED GENERATOR, filed Sep. 14, 2016, which issued on Apr. 7, 2020 as U.S. Pat. No. 10,610,286, which claims the benefit of U.S. Provisional Application Ser. No. 62/235,260, titled GENERATOR FOR PROVIDING COMBINED RADIO FREQUENCY AND ULTRASONIC ENERGIES, filed Sep. 30, 2015, U.S. Provisional Application Ser. No. 62/235,368, titled CIRCUIT TOPOLOGIES FOR GENERATOR, filed Sep. 30, 2015, and U.S. Provisional Application Ser. No. 62/235,466, titled SURGICAL INSTRUMENT WITH USER ADAPTABLE ALGORITHMS, filed Sep. 30, 2015, the contents of each of which are incorporated herein by reference in their entirety.

TECHNICAL FIELD

The present disclosure generally relates to ultrasonic surgical systems, electrosurgical systems, and combination electrosurgical/ultrasonic systems for performing surgical procedures such as coagulating, sealing, and/or cutting tissue. In particular, the present disclosure relates to circuit topologies for a combined generator configured to deliver a combined signal for radio frequency (RF) and ultrasonic outputs to a medical instrument. The present disclosure also generally relates to ultrasonic surgical systems, electrosurgical systems, and combination electrosurgical/ultrasonic systems for performing surgical procedures such as coagulating, sealing, and/or cutting tissue. In particular, the present disclosure relates to method and apparatus for selecting operations of a surgical instrument based on user intention.

BACKGROUND

The present disclosure is related generally to surgical instruments and associated surgical techniques. More particularly, the present disclosure is related to ultrasonic and electrosurgical systems that allow surgeons to perform cutting and coagulation and to adapt and customize such procedures based on the type of tissue being treated.

Ultrasonic surgical instruments are finding increasingly widespread applications in surgical procedures by virtue of the unique performance characteristics of such instruments. Depending upon specific instrument configurations and operational parameters, ultrasonic surgical instruments can provide substantially simultaneous cutting of tissue and hemostasis by coagulation, desirably minimizing patient trauma. The cutting action is typically realized by an-end effector, or blade tip, at the distal end of the instrument, which transmits ultrasonic energy to tissue brought into contact with the end effector. Ultrasonic instruments of this nature can be configured for open surgical use, laparoscopic, or endoscopic surgical procedures including robotic-assisted procedures.

Some surgical instruments utilize ultrasonic energy for both precise cutting and controlled coagulation. Ultrasonic energy cuts and coagulates by vibrating a blade in contact with tissue. Vibrating at high frequencies (e.g., 55,500 times per second), the ultrasonic blade denatures protein in the tissue to form a sticky coagulum. Pressure exerted on tissue with the blade surface collapses blood vessels and allows the coagulum to form a hemostatic seal. The precision of cutting and coagulation is controlled by the surgeon's technique and adjusting the power level, blade edge, tissue traction, and blade pressure.

Electrosurgical devices for applying electrical energy to tissue in order to treat and/or destroy the tissue are also finding increasingly widespread applications in surgical procedures. An electrosurgical device typically includes a hand piece, an instrument having a distally-mounted end effector (e.g., one or more electrodes). The end effector can be positioned against the tissue such that electrical current is introduced into the tissue. Electrosurgical devices can be configured for bipolar or monopolar operation. During bipolar operation, current is introduced into and returned from the tissue by active and return electrodes, respectively, of the end effector. During monopolar operation, current is introduced into the tissue by an active electrode of the end effector and returned through a return electrode (e.g., a grounding pad) separately located on a patient's body. Heat generated by the current flowing through the tissue may form hemostatic seals within the tissue and/or between tissues and thus may be particularly useful for sealing blood vessels, for example. The end effector of an electrosurgical device may also include a cutting member that is movable relative to the tissue and the electrodes to transect the tissue.

Electrical energy applied by an electrosurgical device can be transmitted to the instrument by a generator in communication with the hand piece. The electrical energy may be in the form of radio frequency ("RF") energy. RF energy is a form of electrical energy that may be in the frequency range of 200 kilohertz (kHz) to 1 megahertz (MHz). In application, an electrosurgical device can transmit low frequency RF energy through tissue, which causes ionic agitation, or friction, in effect resistive heating, thereby increasing the temperature of the tissue. Because a sharp boundary is created between the affected tissue and the surrounding tissue, surgeons can operate with a high level of precision and control, without sacrificing un-targeted adjacent tissue. The low operating temperatures of RF energy are useful for removing, shrinking, or sculpting soft tissue while simultaneously sealing blood vessels. RF energy works particularly well on connective tissue, which is primarily comprised of collagen and shrinks when contacted by heat.

A challenge of using these medical devices is the inability to fully control and customize the functions of the surgical instruments. It would be desirable to provide a surgical instrument that overcomes some of the deficiencies of current instruments.

While several medical devices have been made and used, it is believed that no one prior to the inventors has made or used the subject matter described in the appended claims.

SUMMARY

In one aspect, the present disclosure is directed to a mixed energy surgical instrument that utilizes both Ultrasonic and RF energy modalities. Multiple circuit topologies are disclosed which when one (or more) of these circuit topologies are included in a mixed energy surgical instrument, the circuit topology enables a generator to drive both RF and Ultrasonic energy into tissue either simultaneously or by switching between RF and Ultrasonic.

In some aspects, the circuit topology may include high frequency filters configured to filter a combined ultrasonic and RF frequency signal into signals having only ultrasonic frequency content and separately, RF frequency content. In some cases, one or more band-stop filters are used. In some cases, one or more resonators are used to accentuate the desired frequencies. In other cases, one or more pass-based filters are used. In some aspects, the circuit topology allows for simultaneous application of both RF energy and ultrasonic energy, both derived from the single combined signal.

In some aspects, the circuit topology may include more or more switches configured to switch between the RF frequency and the ultrasonic frequency within the same combined signal. In some cases, one or more pairs of solid state switches provide the switching functionality. In one aspect, metal oxide semiconductor (MOSFET) switches may be employed to provide the switching functionality. In some cases, a control circuit, which may be implemented as n application specific integrated circuit (ASIC), is also used to control the switching. One or more pulse transformers may be coupled to the control circuit and the pairs of MOSFET switches, in some cases. In other cases, switching may occur through inclusion of one or more electromechanical relays coupled to the control circuit.

In one aspect, a method for operating a surgical instrument is provided, the surgical instrument comprising a radio frequency (RF) energy output, an ultrasonic energy output, and a first jaw and a second jaw configured for pivotal movement between a closed position and an open position, the method comprising: receiving a first input indicating a user selection of one of a first option and a second option; receiving a second input indicating whether the first jaw and the second jaw are in the closed position or in the open position; receiving a third input indicating electrical impedance at the RF energy output; and selecting a mode of operation for treating a tissue from a plurality of modes of operation based at least in part on the first input, the second input and the third input, wherein the plurality of modes of operation comprises: a first mode wherein the RF energy output applies RF energy to the tissue; and a second mode wherein the ultrasonic energy output applies ultrasonic energy to the tissue.

In another aspect, a generator for delivering radio frequency (RF) energy and ultrasonic energy to a surgical instrument is provided, the surgical instrument comprising a first jaw and a second jaw configured for pivotal movement between a closed position and an open position, the generator being configured to: receive a first input indicating a user selection of one of a first option and a second option; receive a second input indicating whether the first jaw and the second jaw are in the closed position or in the open position; receive a third input indicating electrical impedance at a RF energy output of the surgical instrument; and select a mode of operation for treating a tissue from a plurality of modes of operation based at least in part on the first input, the second input and the third input, wherein the plurality of modes of operation comprises: a first mode wherein the generator delivers RF energy to the surgical instrument; and a second mode wherein the generator delivers ultrasonic energy to the surgical instrument.

In yet another aspect, a surgical instrument is provided comprising: a first jaw and a second jaw configured for pivotal movement between a closed position and an open position; a radio frequency (RF) energy output configured to apply RF energy to a tissue at least when a first mode of operation is selected; and an ultrasonic energy output configured to apply ultrasonic energy to the tissue at least when a second mode of operation is selected, wherein a mode of operation is selected from a plurality of modes of operation comprising the first mode and the second mode based at least in part on a first input, a second input and a third input, wherein: the first input indicates a user selection of one of a first option and a second option; the second input indicates whether the first jaw and the second jaw are in the closed position or in the open position; and the third input indicates electrical impedance at the RF energy output.

In addition to the foregoing, various other method and/or system and/or program product aspects are set forth and described in the teachings such as text (e.g., claims and/or detailed description) and/or drawings of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

In one or more various aspects, related systems include but are not limited to circuitry and/or programming for effecting herein-referenced method aspects; the circuitry and/or programming can be virtually any combination of hardware, software, and/or firmware configured to affect the herein-referenced method aspects depending upon the design choices of the system. In addition to the foregoing, various other method and/or system aspects are set forth and described in the teachings such as text (e.g., claims and/or detailed description) and/or drawings of the present disclosure.

Further, it is understood that any one or more of the following-described forms, expressions of forms, examples, can be combined with any one or more of the other following-described forms, expressions of forms, and examples.

Various forms are directed to improved ultrasonic surgical instruments configured for effecting tissue dissecting, cutting, and/or coagulation during surgical procedures. In one form, an ultrasonic surgical instrument apparatus is configured for use in open surgical procedures, but has applications in other types of surgery, such as laparoscopic, endoscopic, and robotic-assisted procedures. Versatile use is facilitated by selective use of ultrasonic energy.

The various forms will be described in combination with an ultrasonic instrument as described herein. Such description is provided by way of example, and not limitation, and is not intended to limit the scope and applications thereof. For example, any one of the described forms is useful in combination with a multitude of ultrasonic instruments including those described in, for example, U.S. Pat. Nos. 5,938,633; 5,935,144; 5,944,737; 5,322,055; 5,630,420; and 5,449,370, each of which is herein incorporated by reference.

As will become apparent from the following description, it is contemplated that forms of the surgical instrument described herein may be used in association with an oscillator unit of a surgical system, whereby ultrasonic energy from the oscillator unit provides the desired ultrasonic actuation for the present surgical instrument. It is also contemplated that forms of the surgical instrument described herein may be used in association with a signal generator unit of a surgical system, whereby electrical energy in the form of radio frequencies (RF), for example, is used to provide feedback to the user regarding the surgical instrument. The ultrasonic oscillator and/or the signal generator unit may be non-detachably integrated with the surgical instrument or may be provided as separate components, which can be electrically attachable to the surgical instrument.

One form of the present surgical apparatus is particularly configured for disposable use by virtue of its straightforward construction. However, it is also contemplated that other forms of the present surgical instrument can be configured for non-disposable or multiple uses. Detachable connection of the present surgical instrument with an associated oscillator and signal generator unit is presently disclosed for single-patient use for illustrative purposes only. However, non-detachable integrated connection of the present surgical instrument with an associated oscillator and/or signal generator unit is also contemplated. Accordingly, various forms of the presently described surgical instruments may be configured for single use and/or multiple uses with either detachable and/or non-detachable integral oscillator and/or signal generator unit, without limitation, and all combinations of such configurations are contemplated to be within the scope of the present disclosure.

The foregoing summary is illustrative only and is not intended to be in any way limiting. In addition to the illustrative aspects and features described above, further aspects and features will become apparent by reference to the drawings and the following detailed description.

FIGURES

The novel features described herein are set forth with particularity in the appended claims. Various aspects, however, both as to organization and methods of operation may be better understood by reference to the following description, taken in conjunction with the accompanying drawings as follows:

Figure 14:
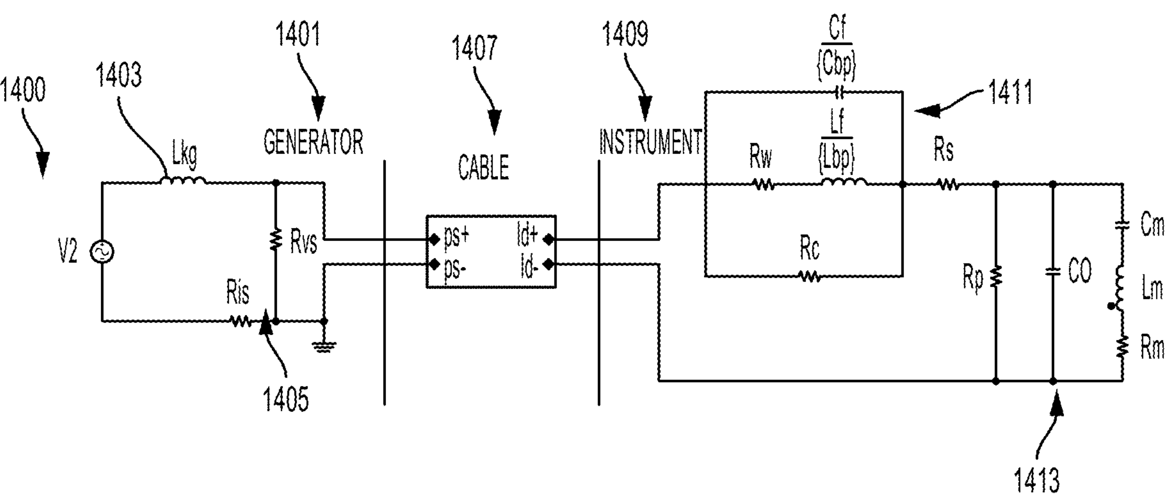
FIG. 14 is a circuit diagram for a system that is configured to manage RF and ultrasonic currents output by a generator according to one aspect of the present disclosure.
Figure 15:
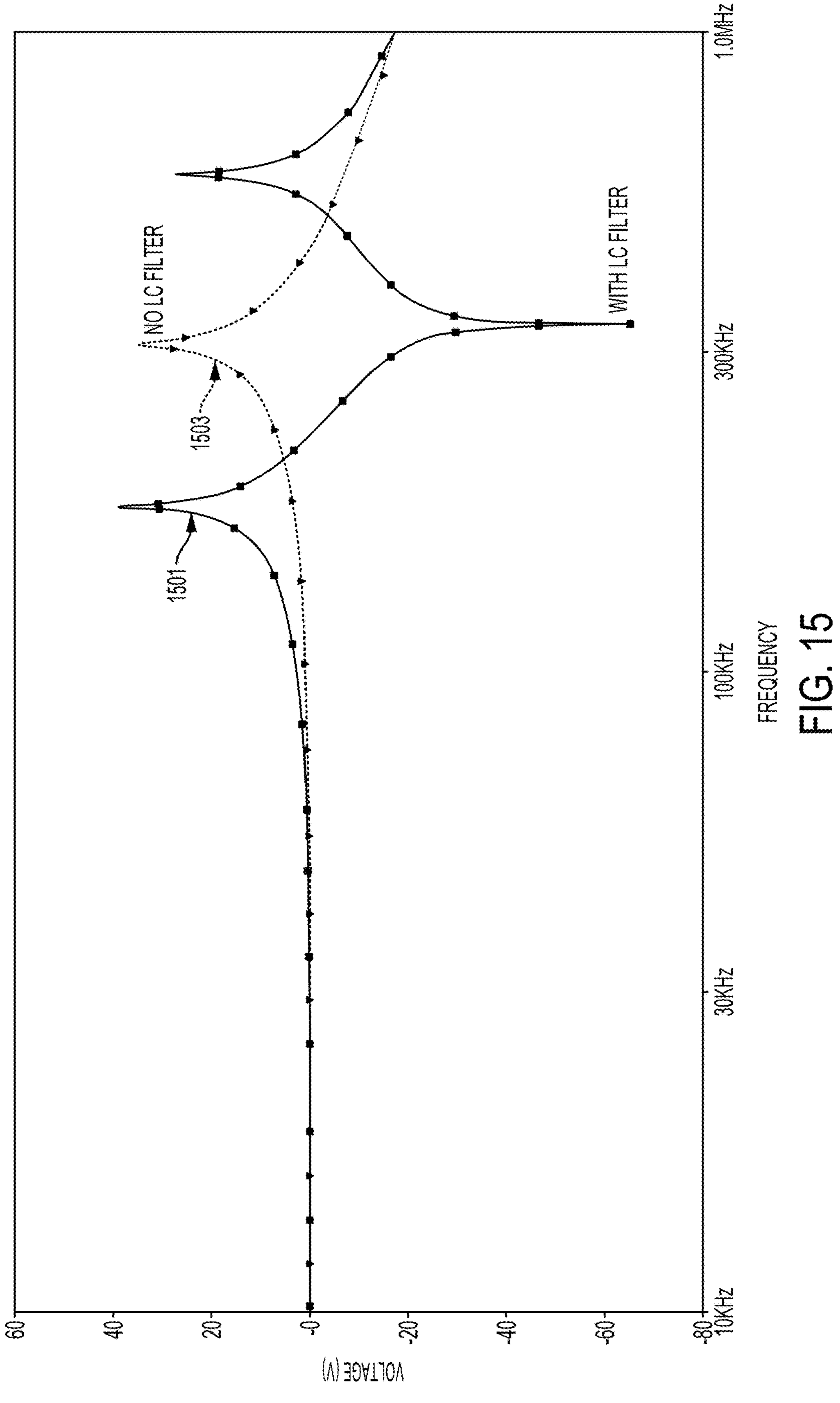
Figure 16:
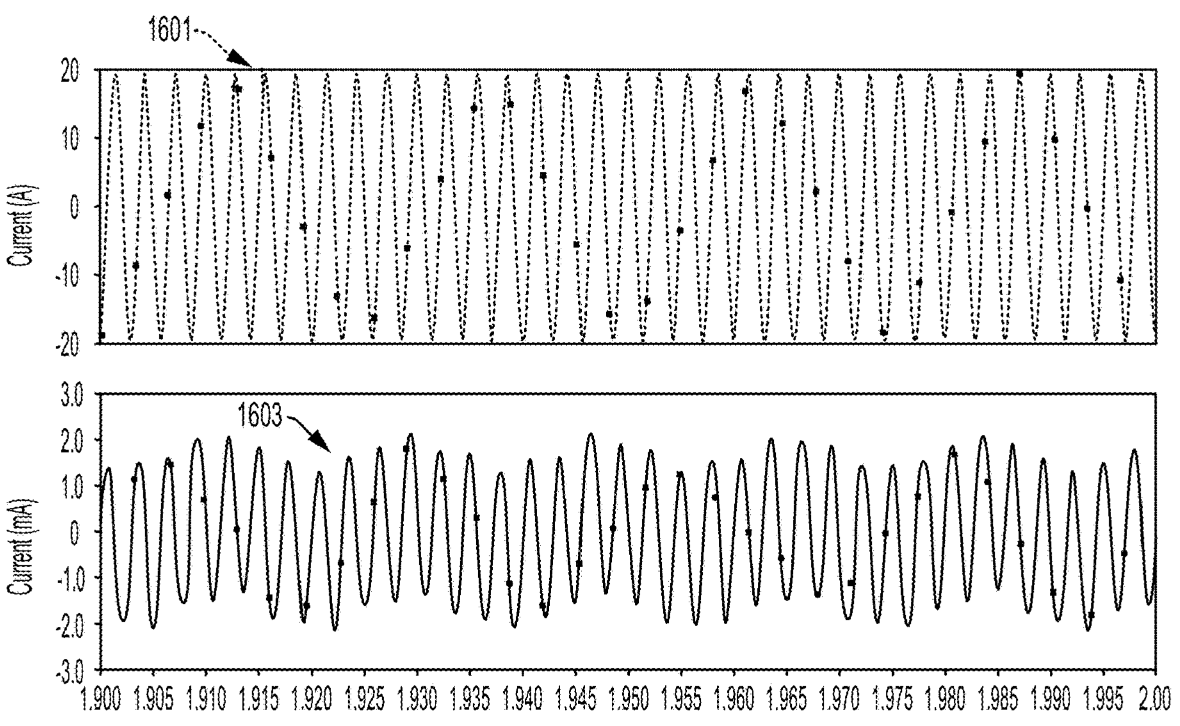
Figure 17:
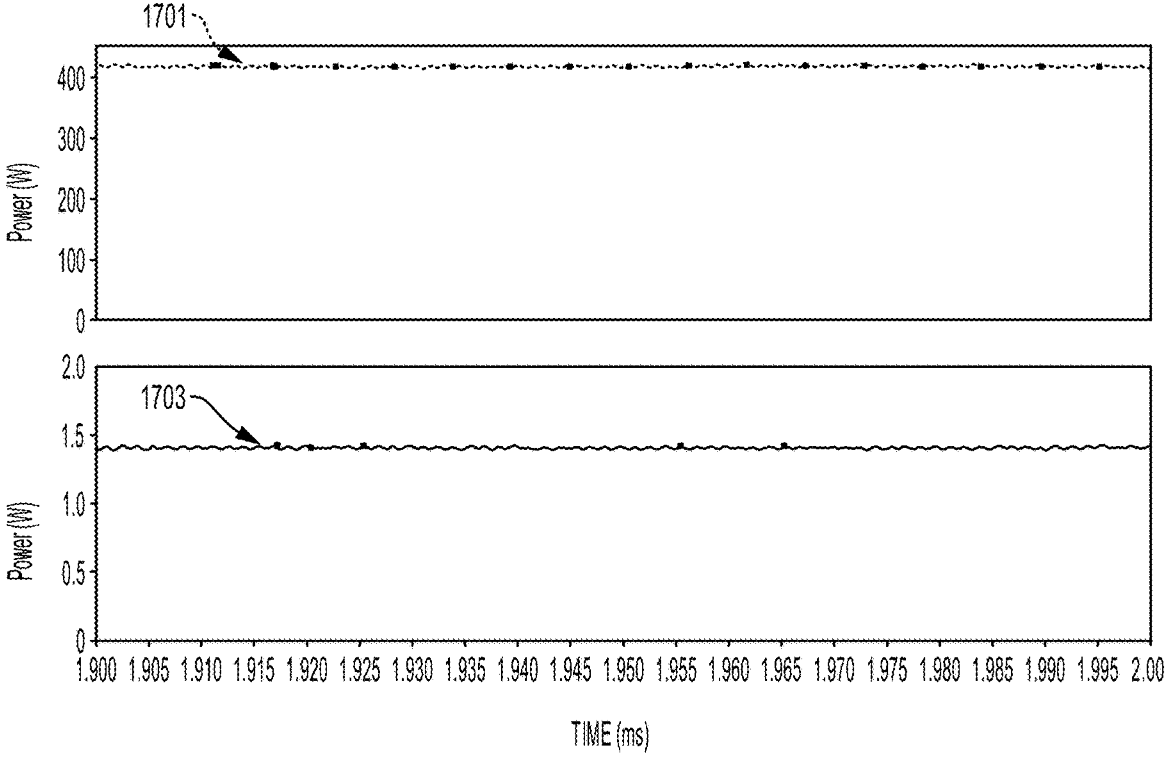
Figure 18:
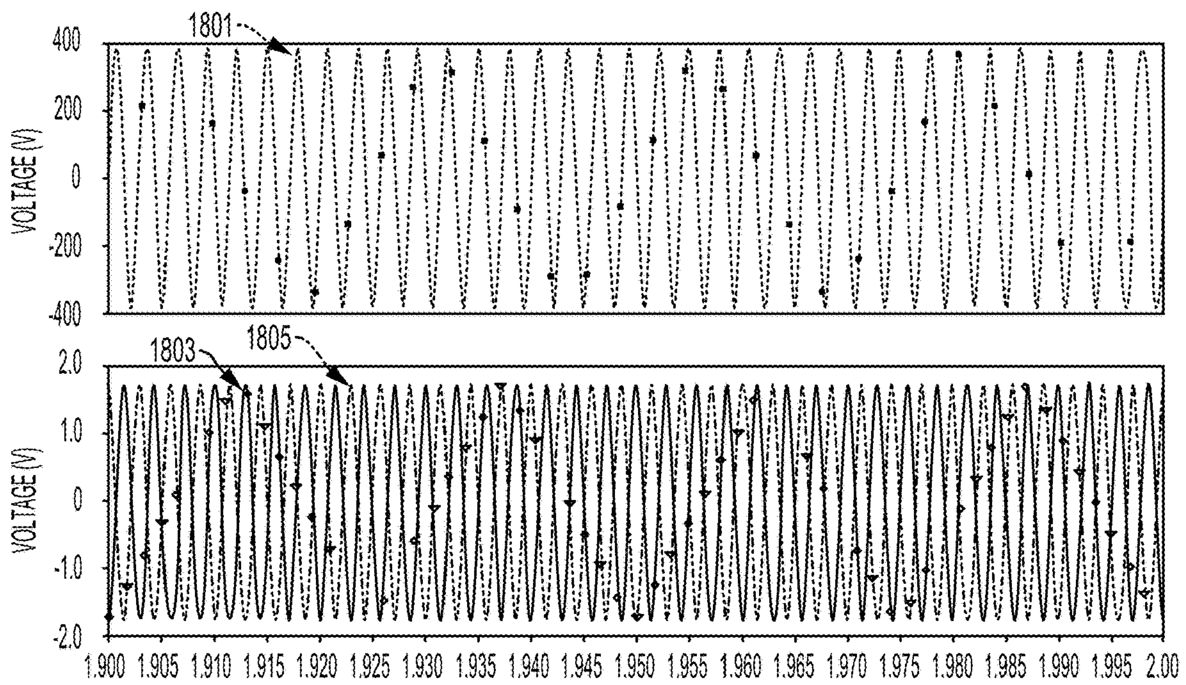
Figure 19:
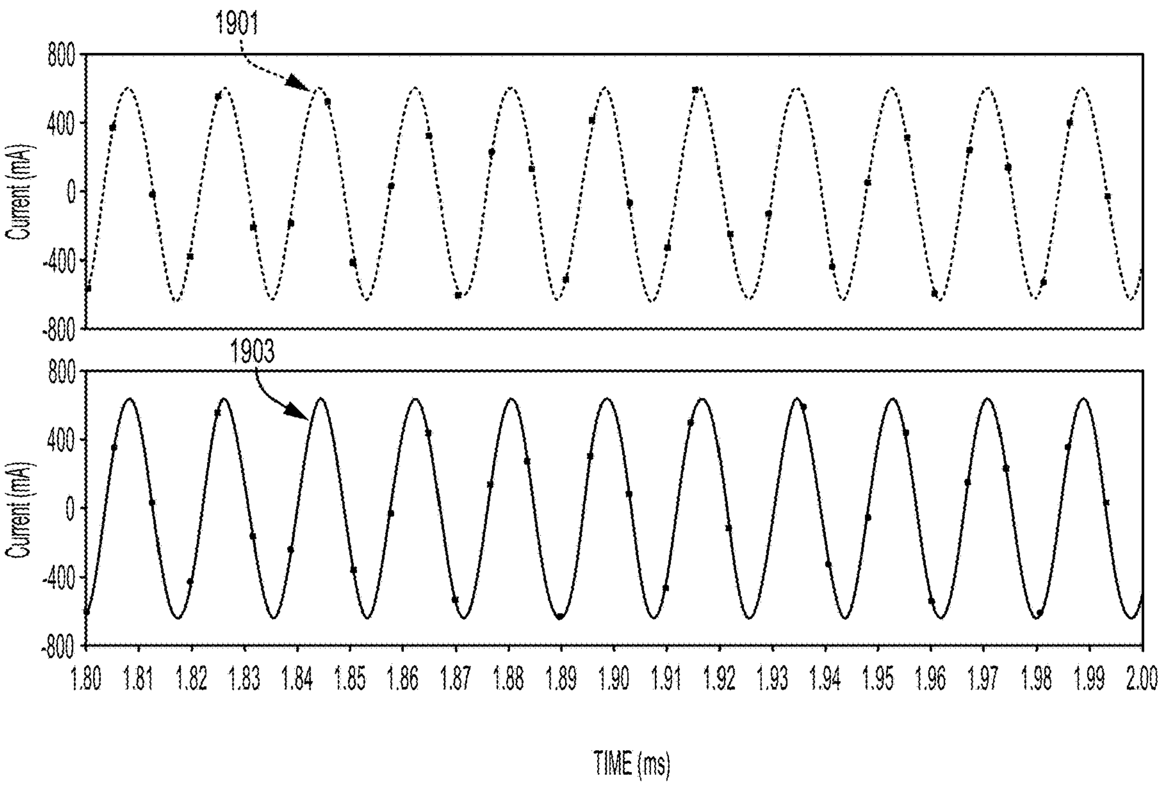
Figure 20:
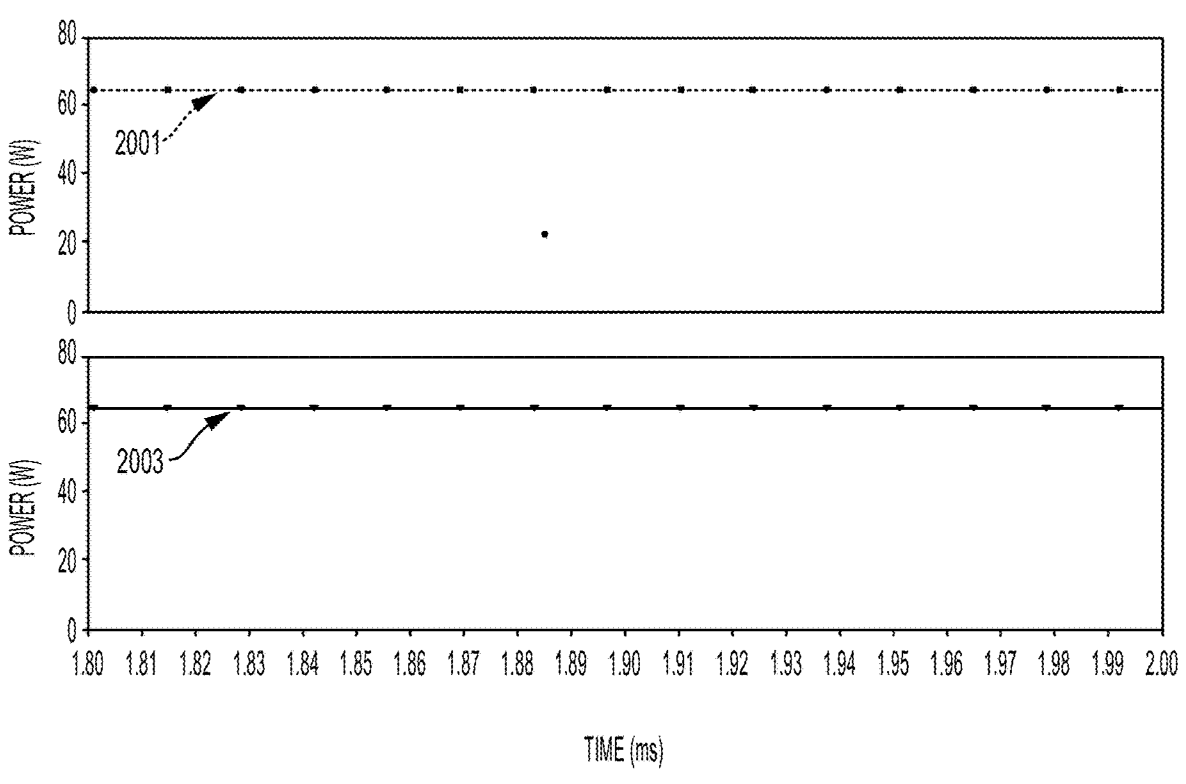
Figure 21:
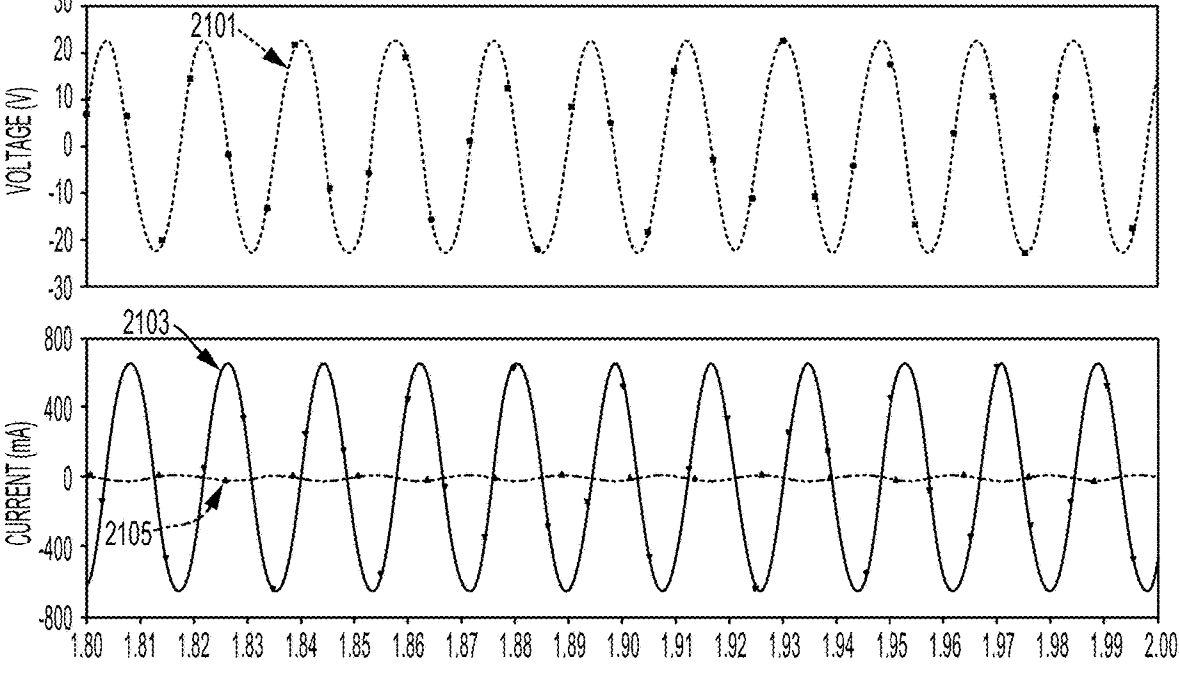
Figure 22:
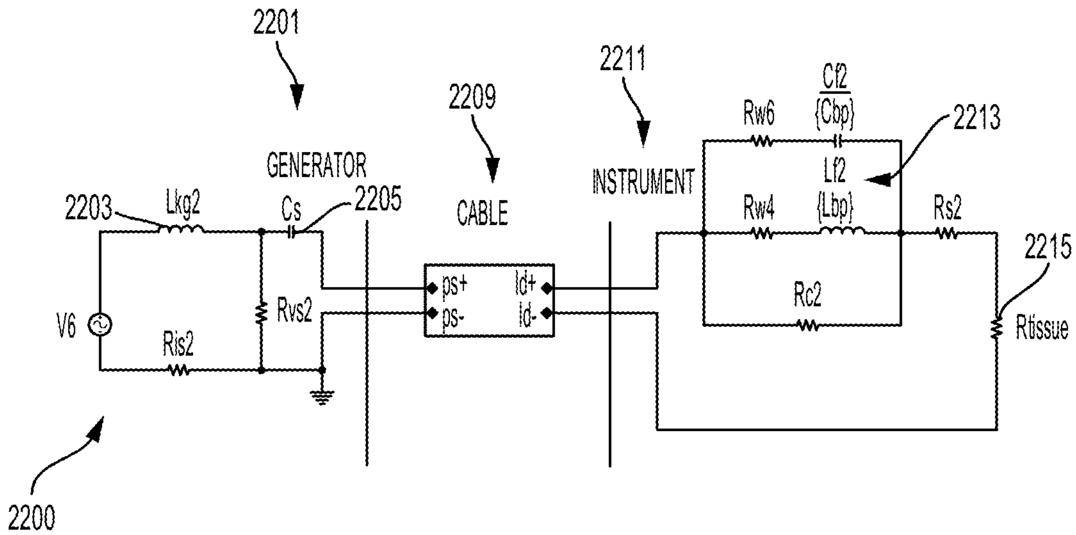
Figure 23:
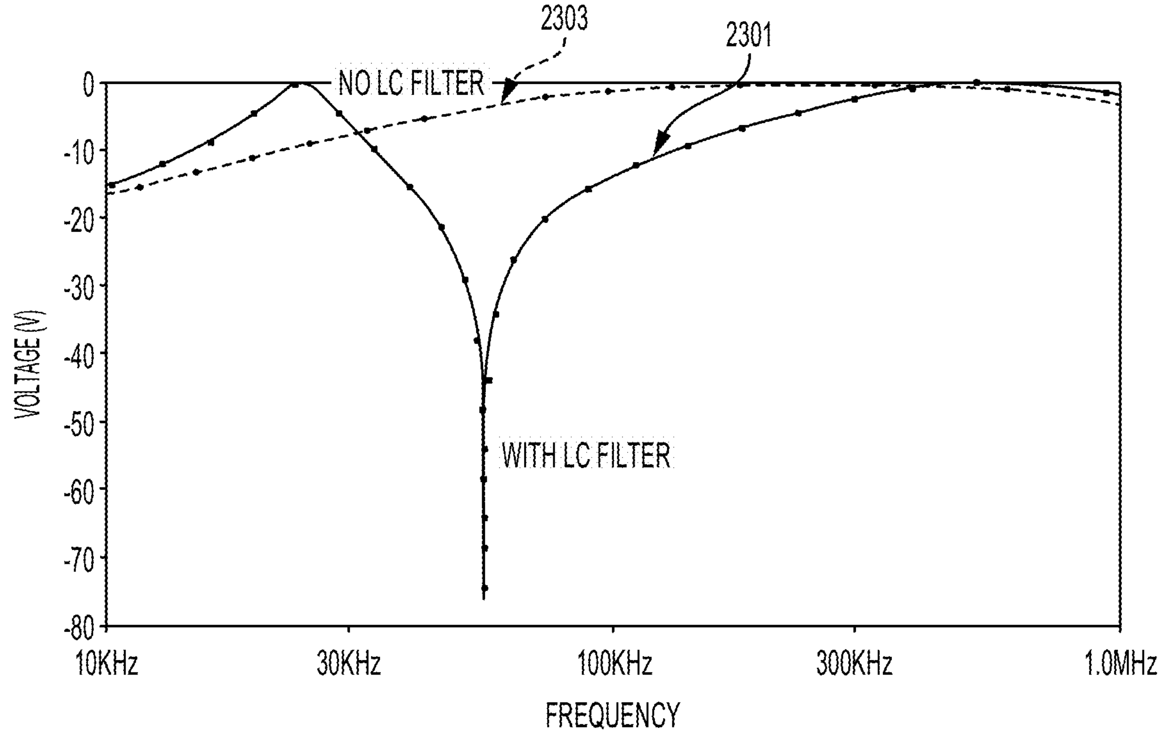
Figure 24:
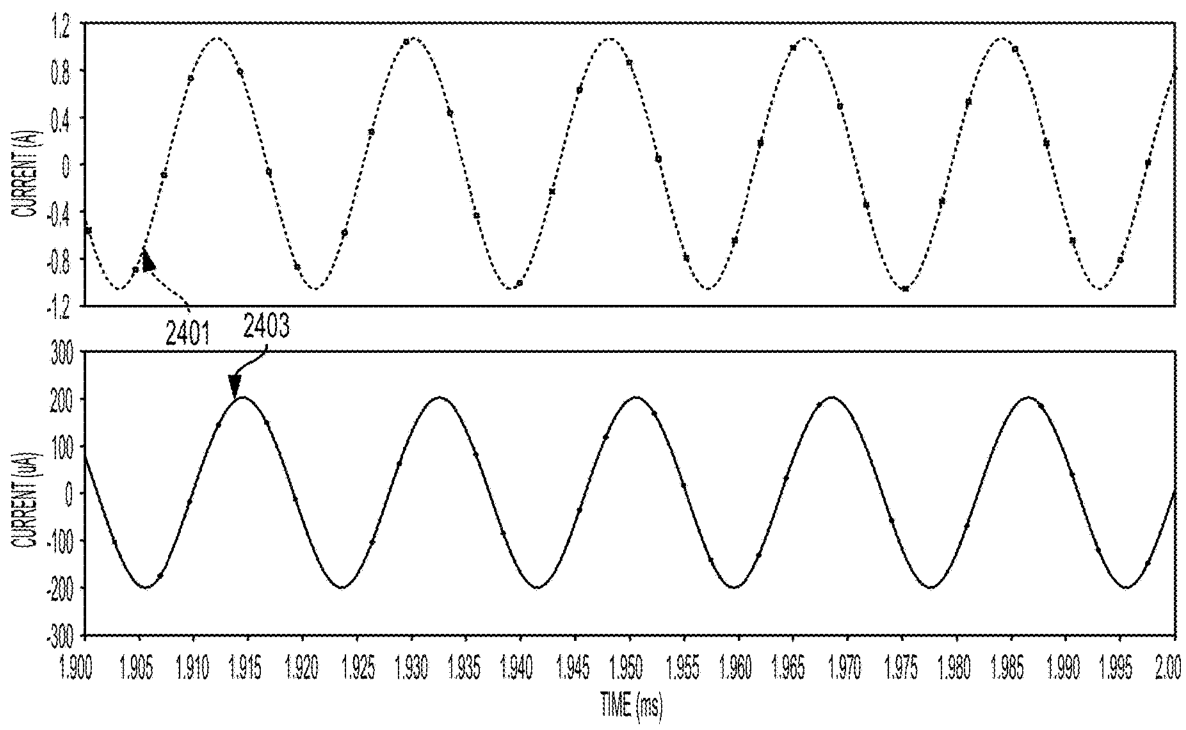
Figure 25:
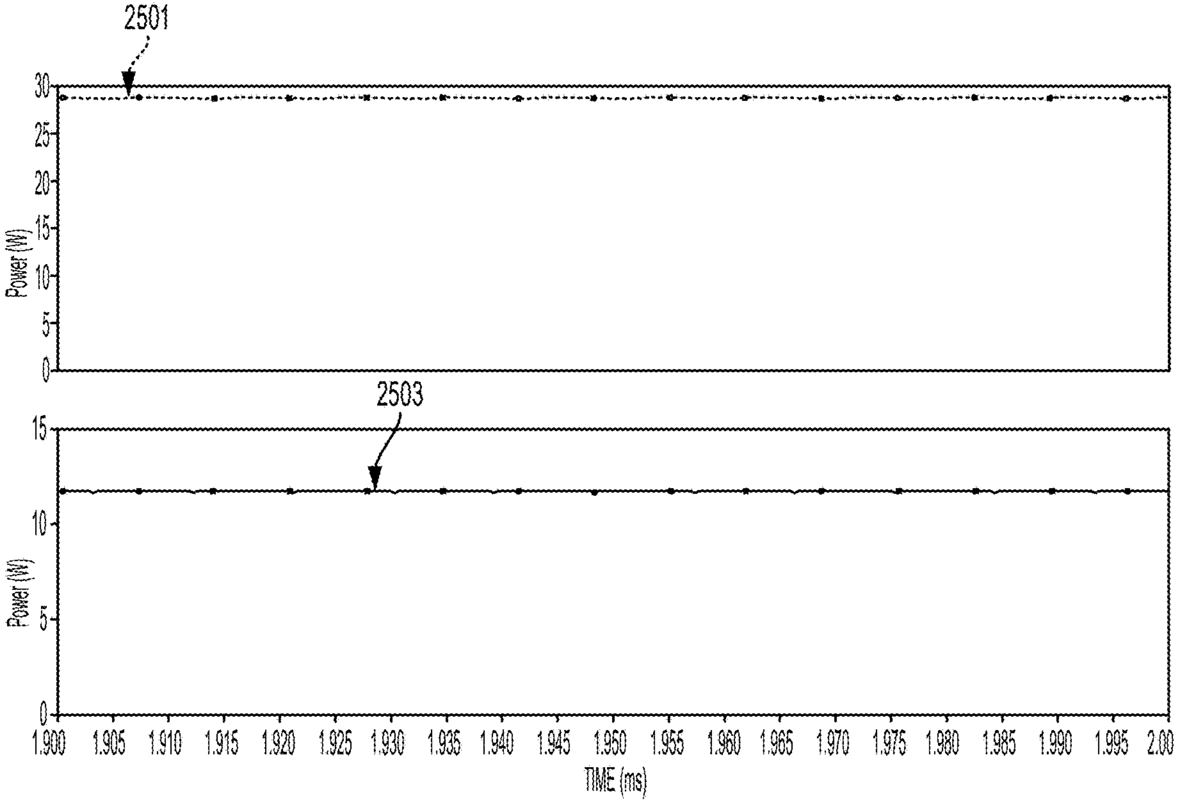
Figure 26:
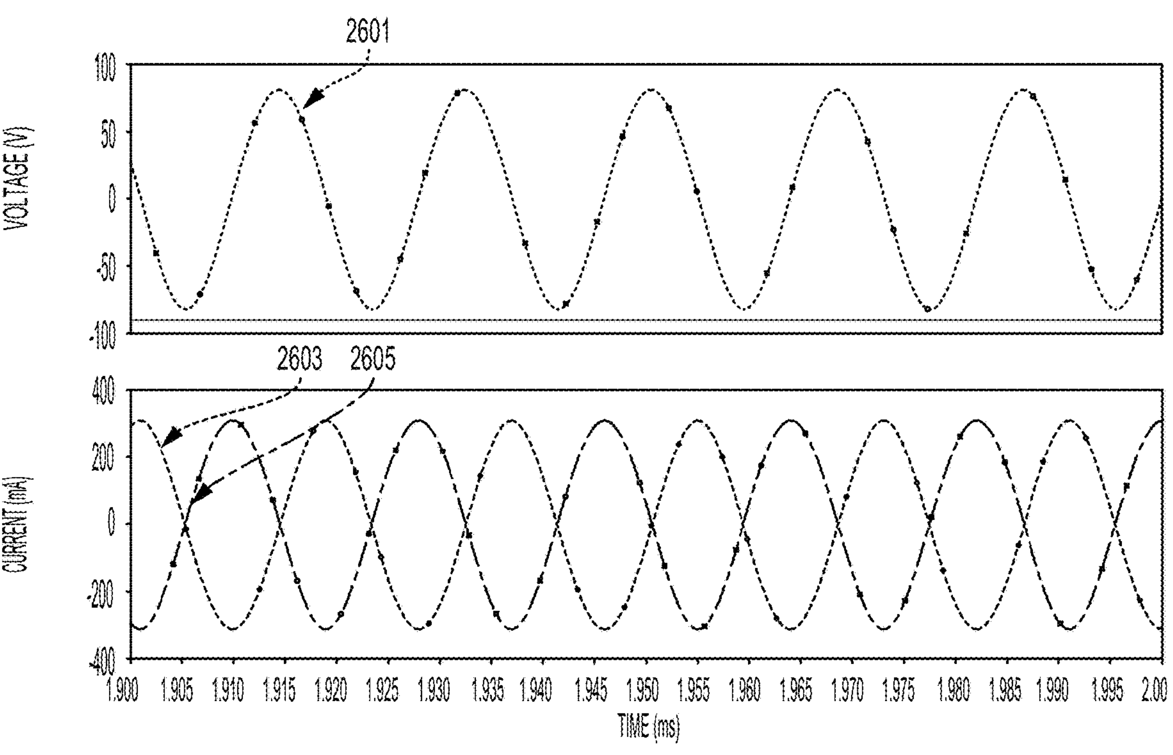
Figure 27:
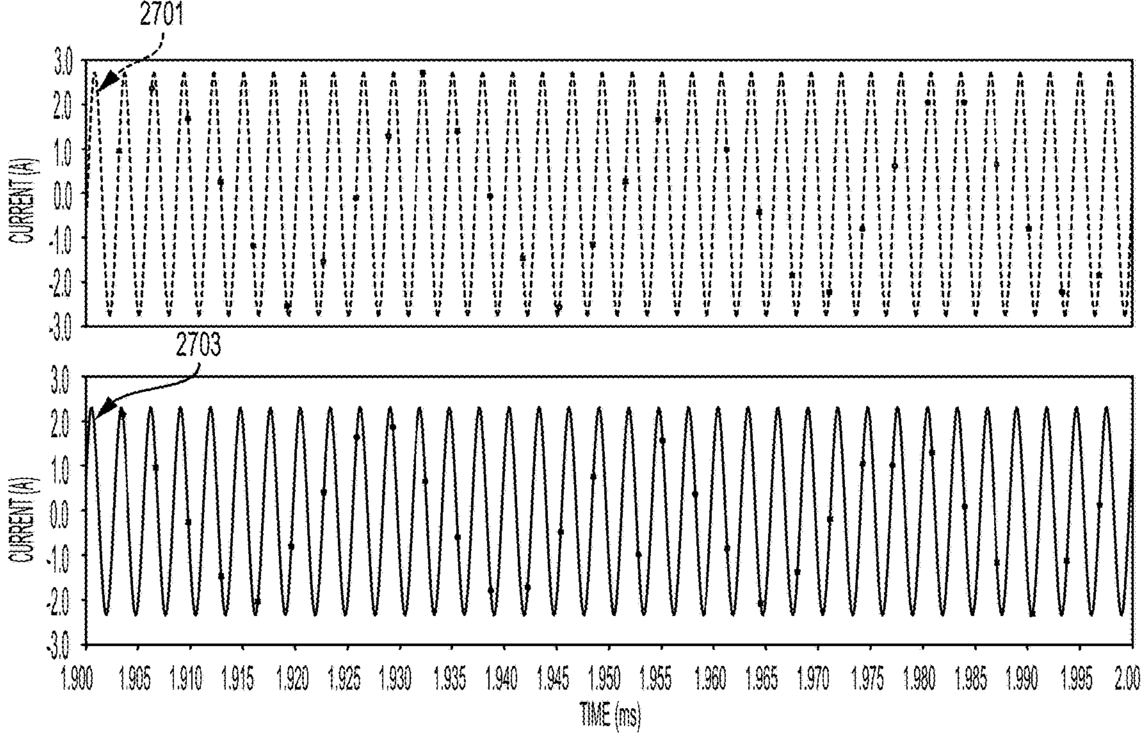
Figure 28:
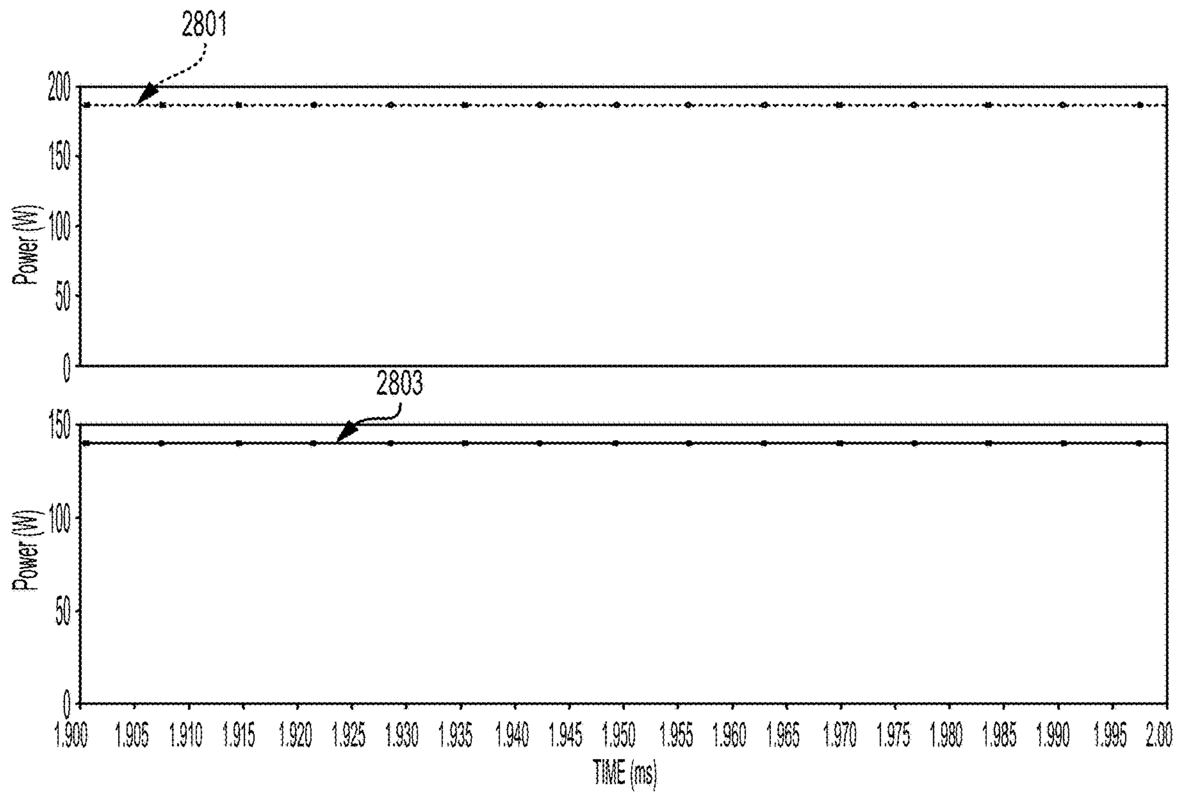
Figure 29:
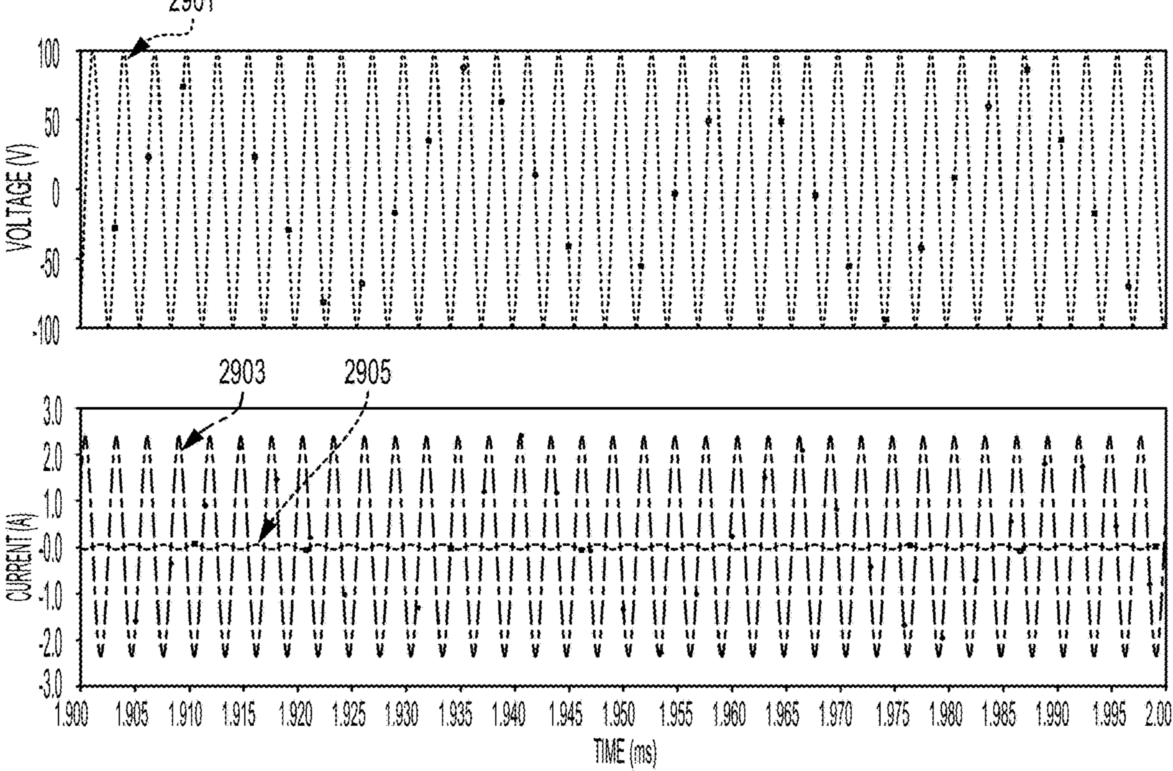
Figure 30:
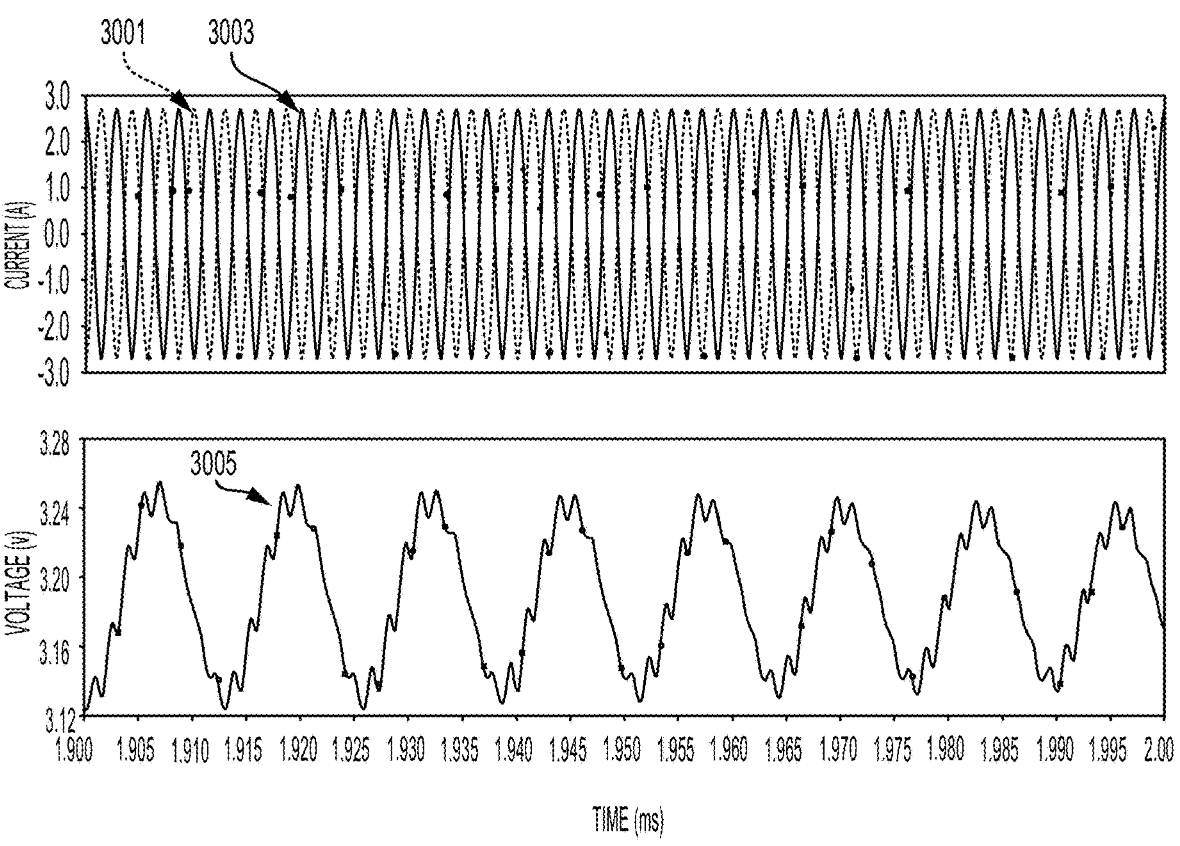
Figure 31:
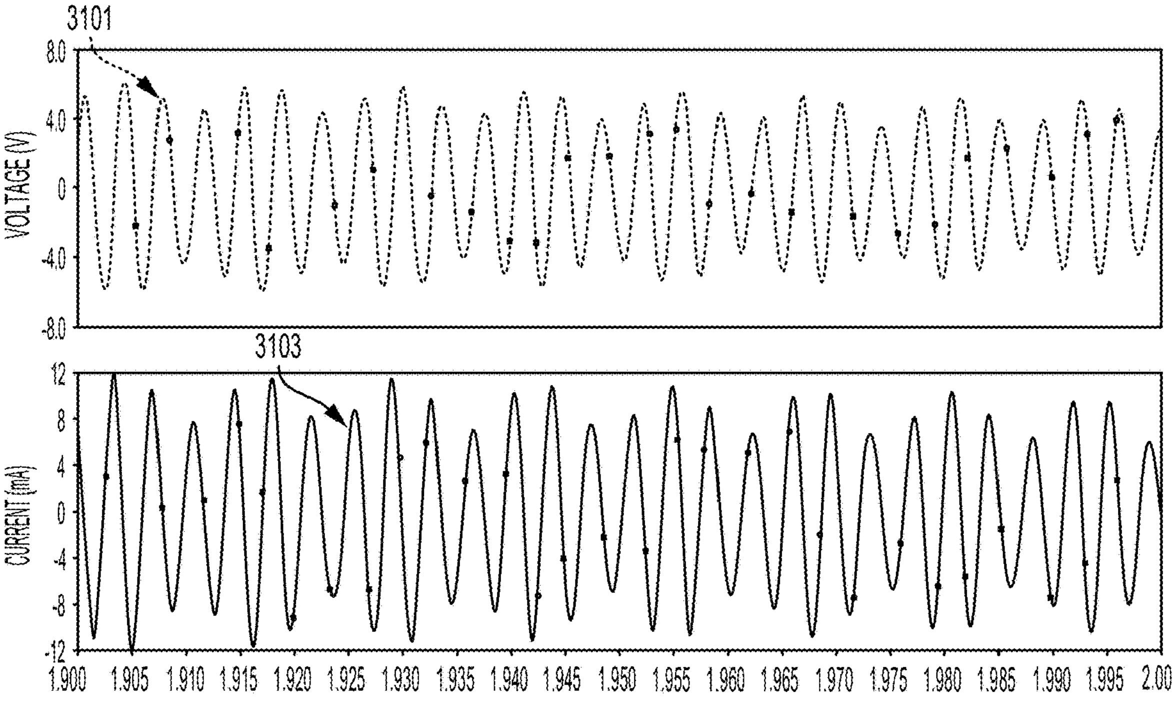
Figure 32:
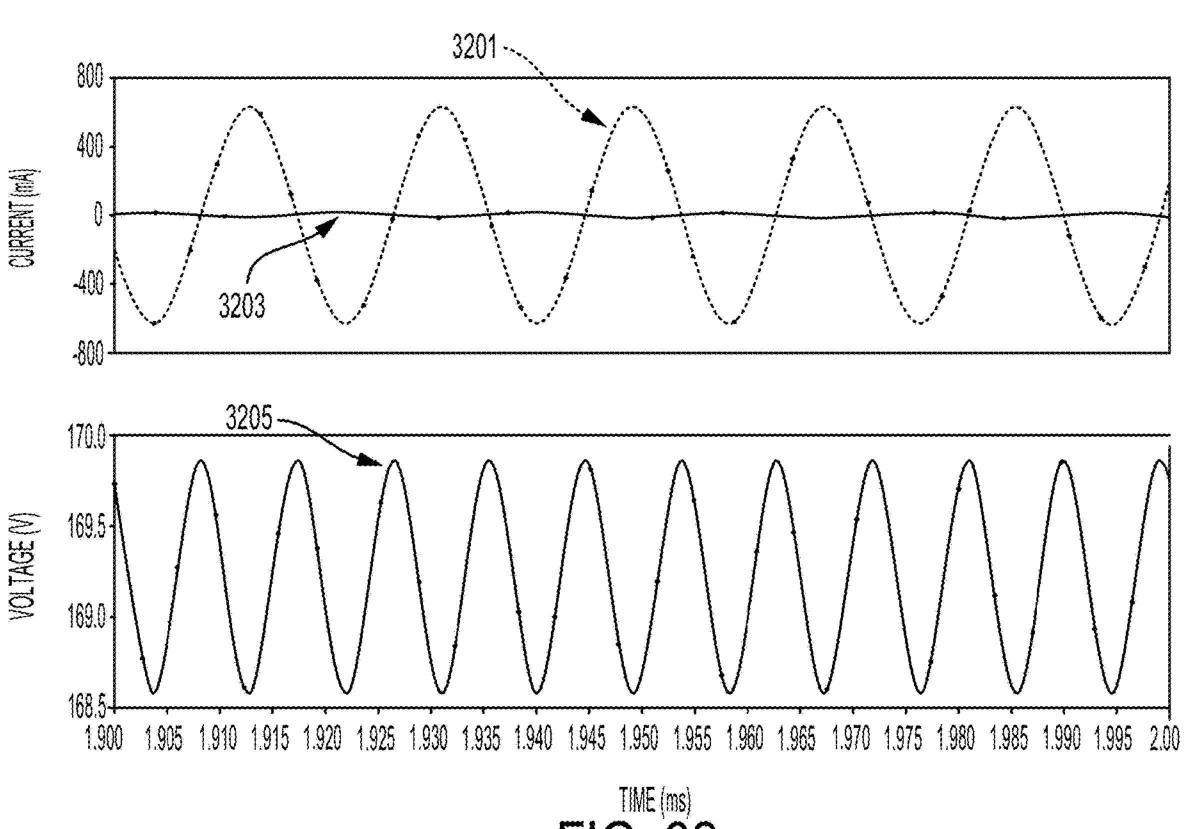
Figure 33:
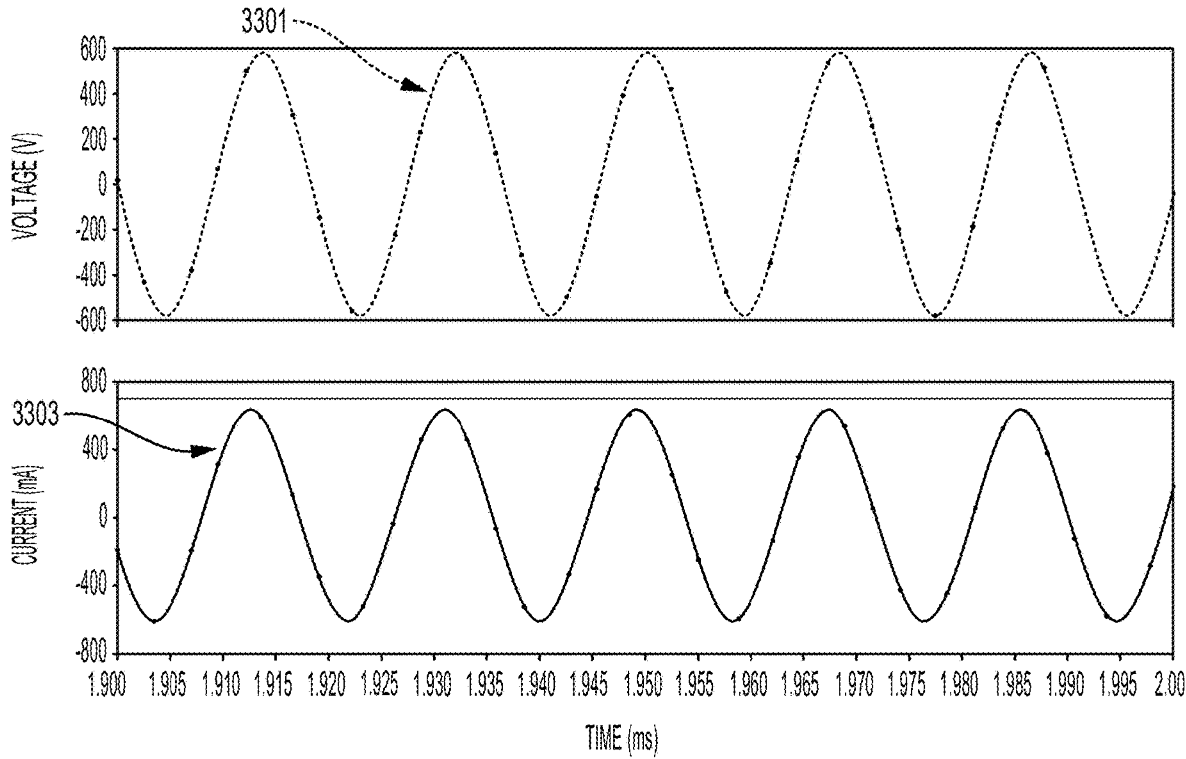
Figure 34:
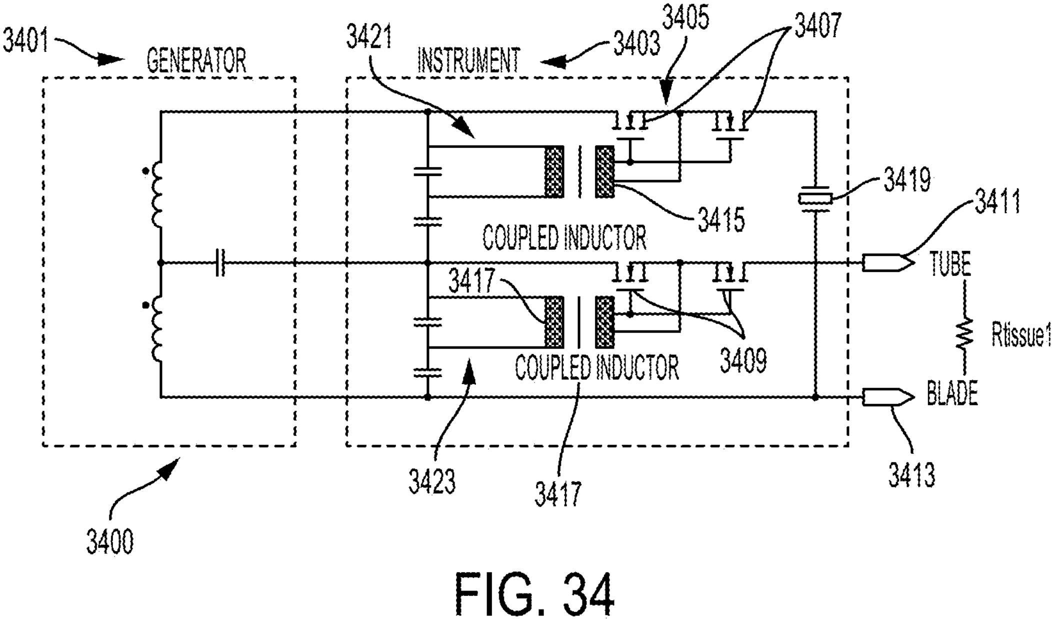
Figure 35:
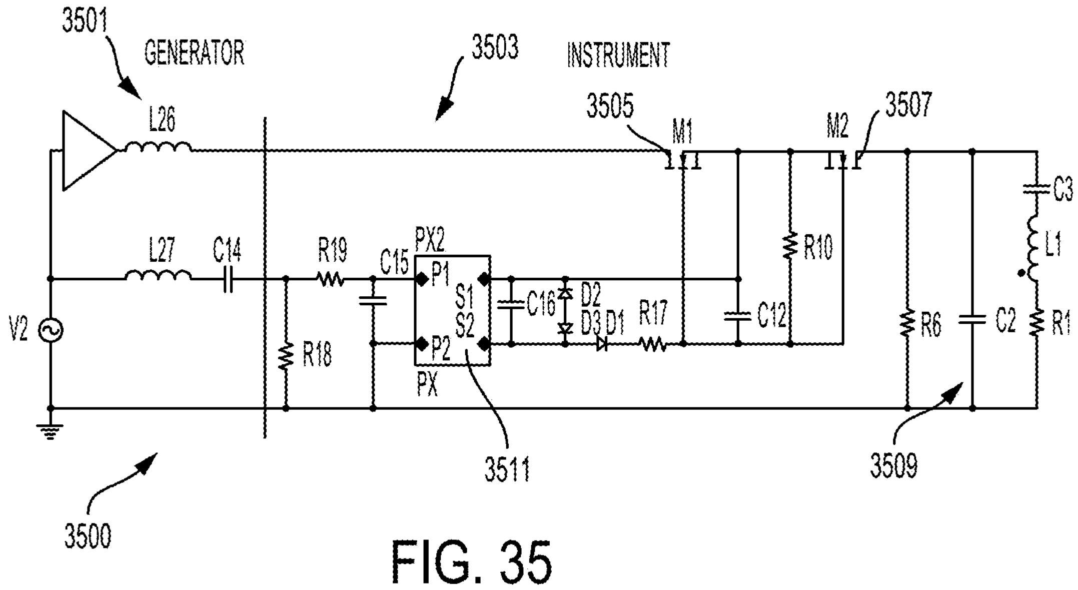
Figure 36:
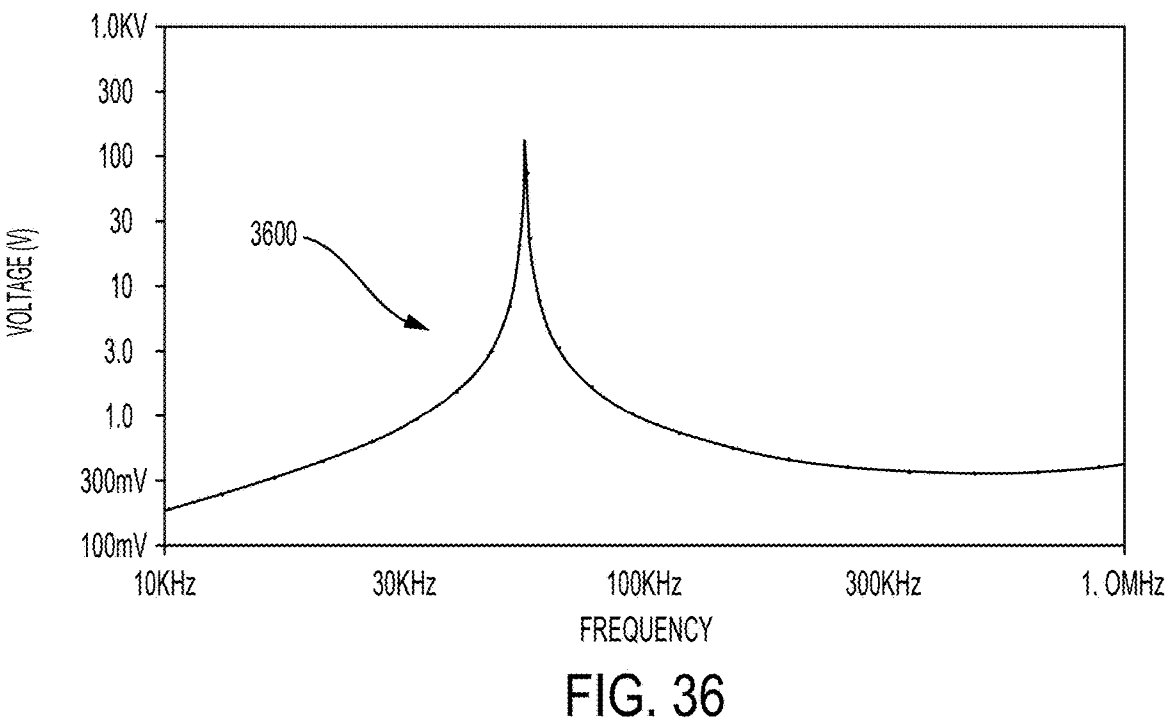
Figure 37:
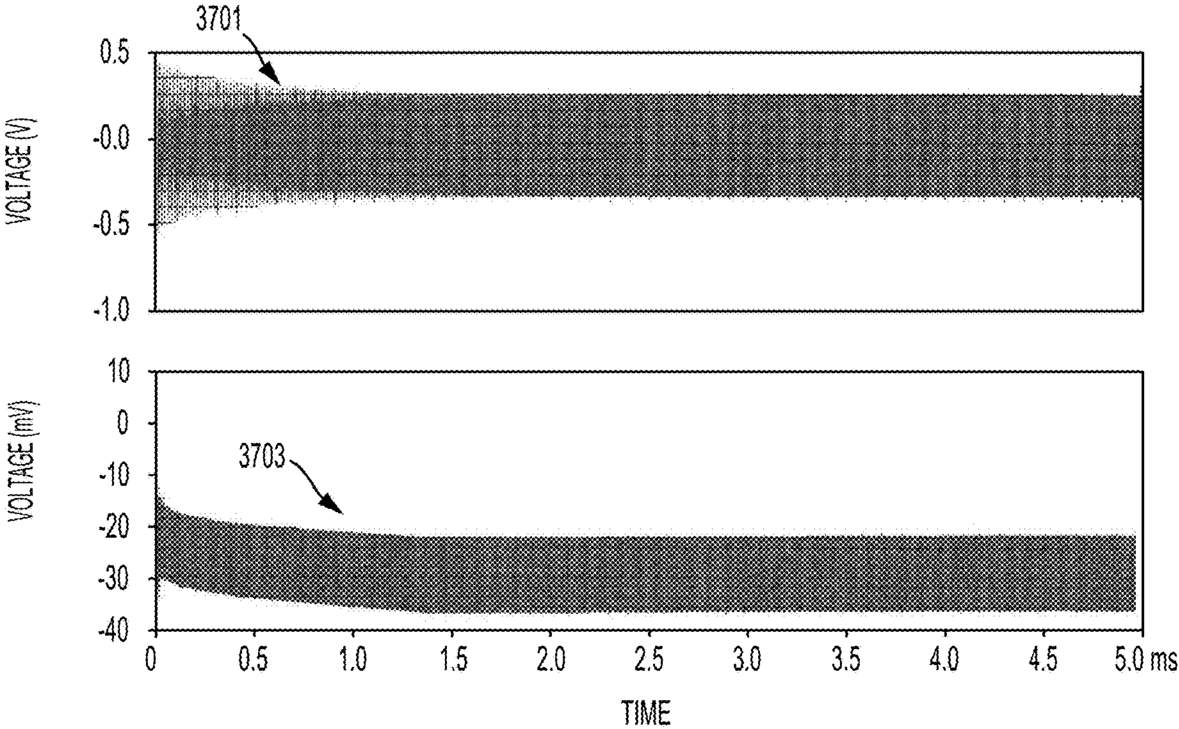
Figure 38:
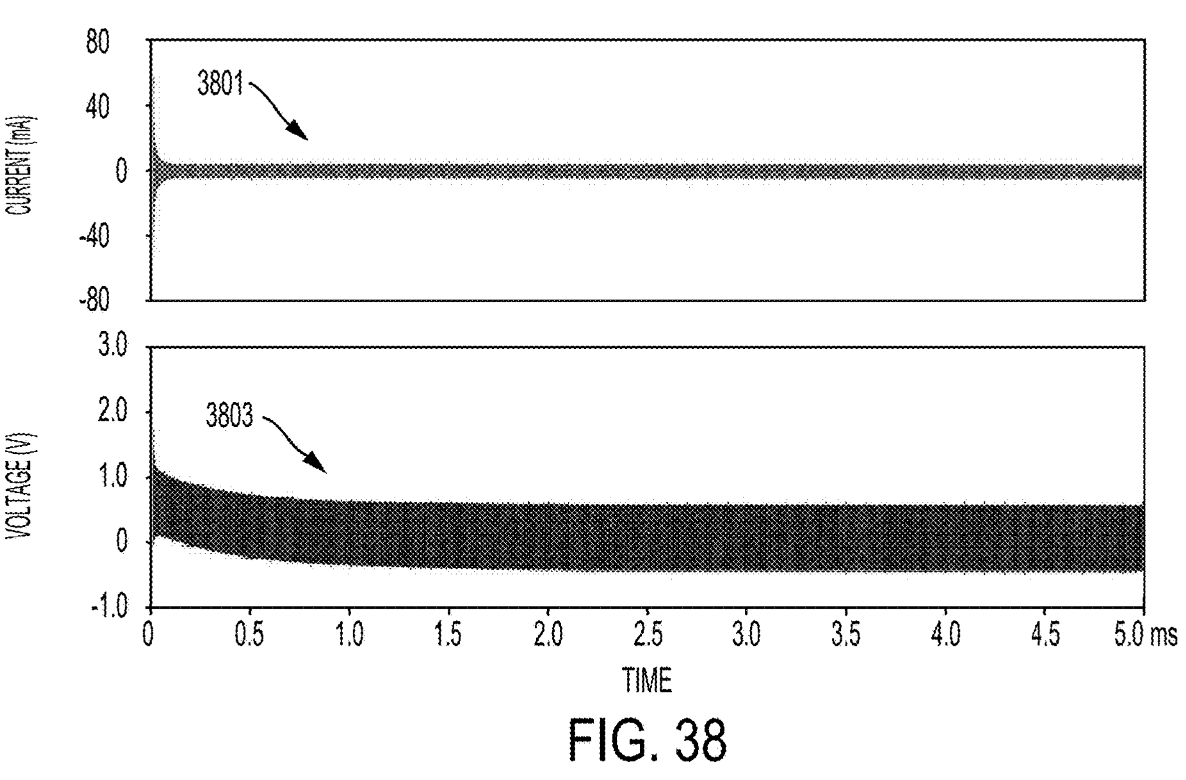
Figure 39:
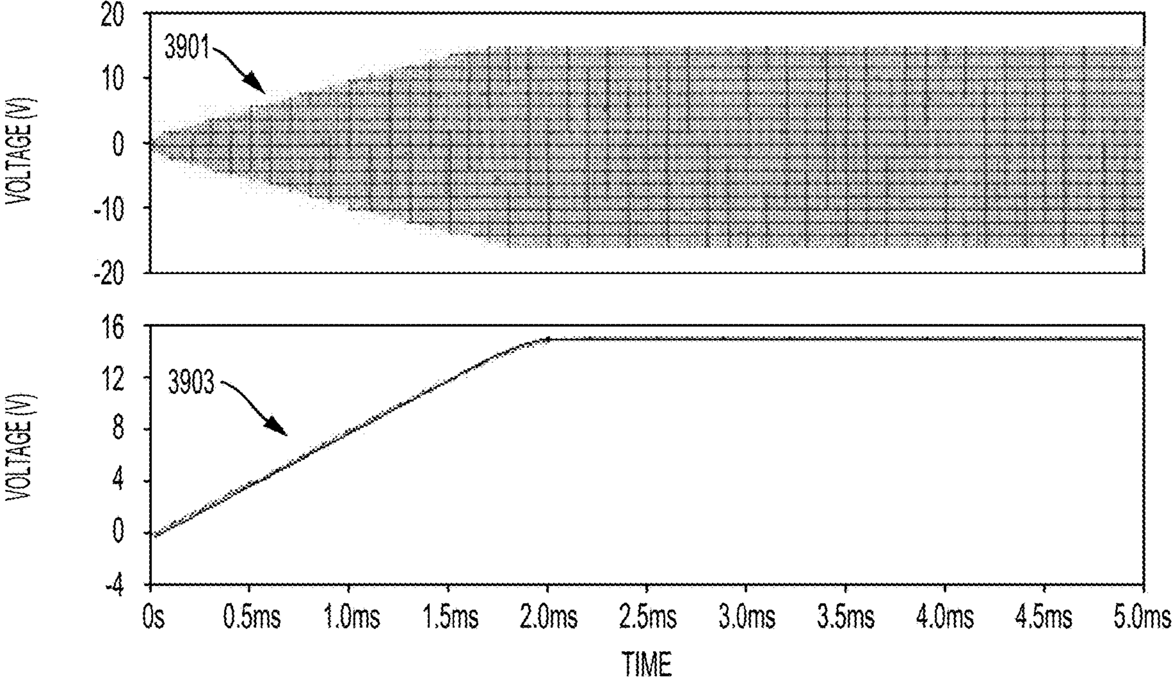
Figures 40, 41:
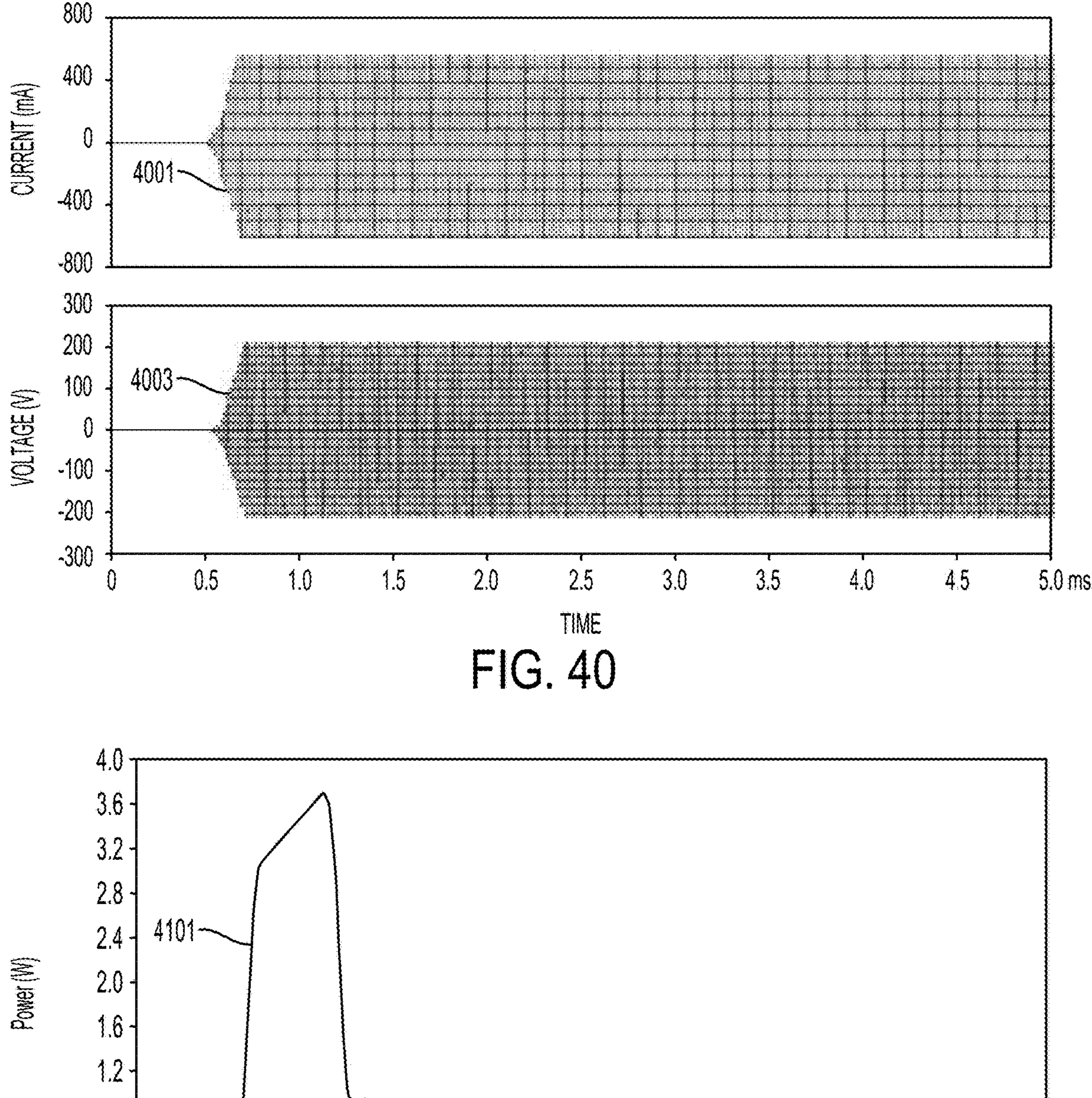
Figure 42:
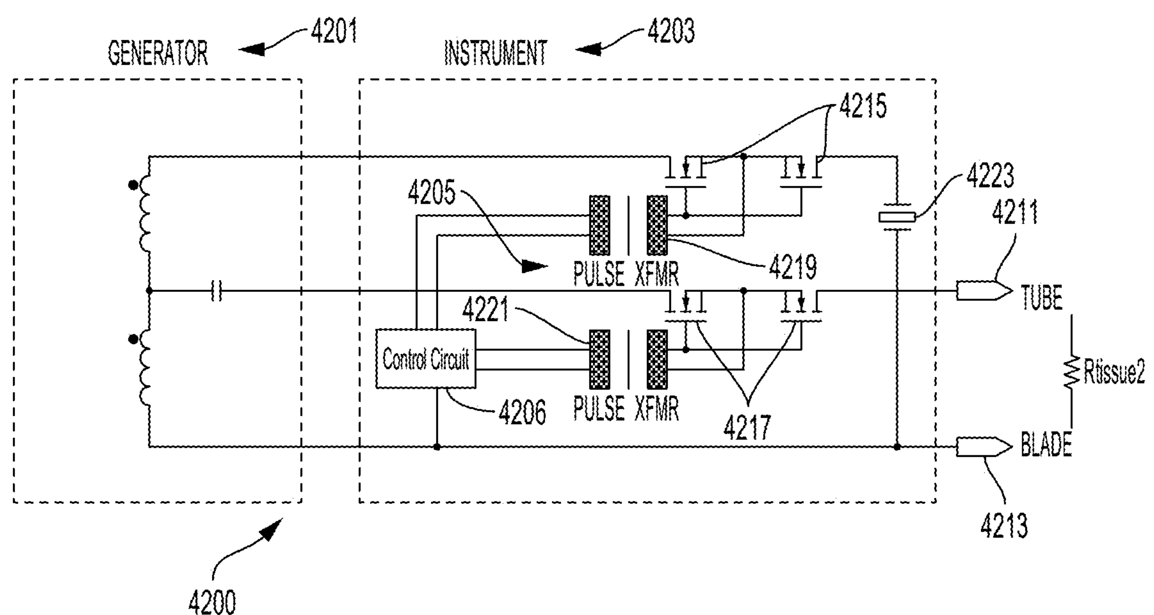
Figure 43:
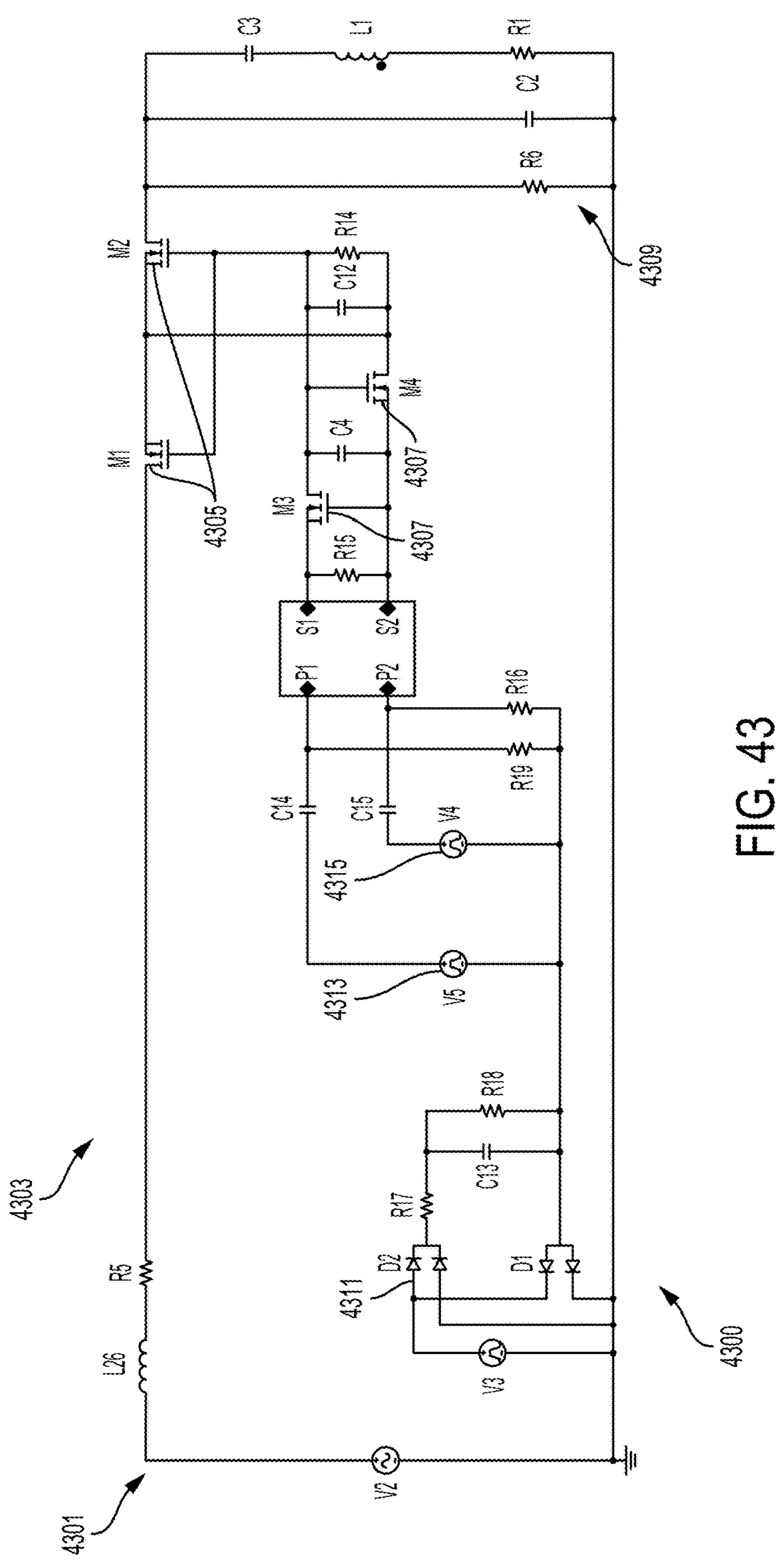
Figure 44:
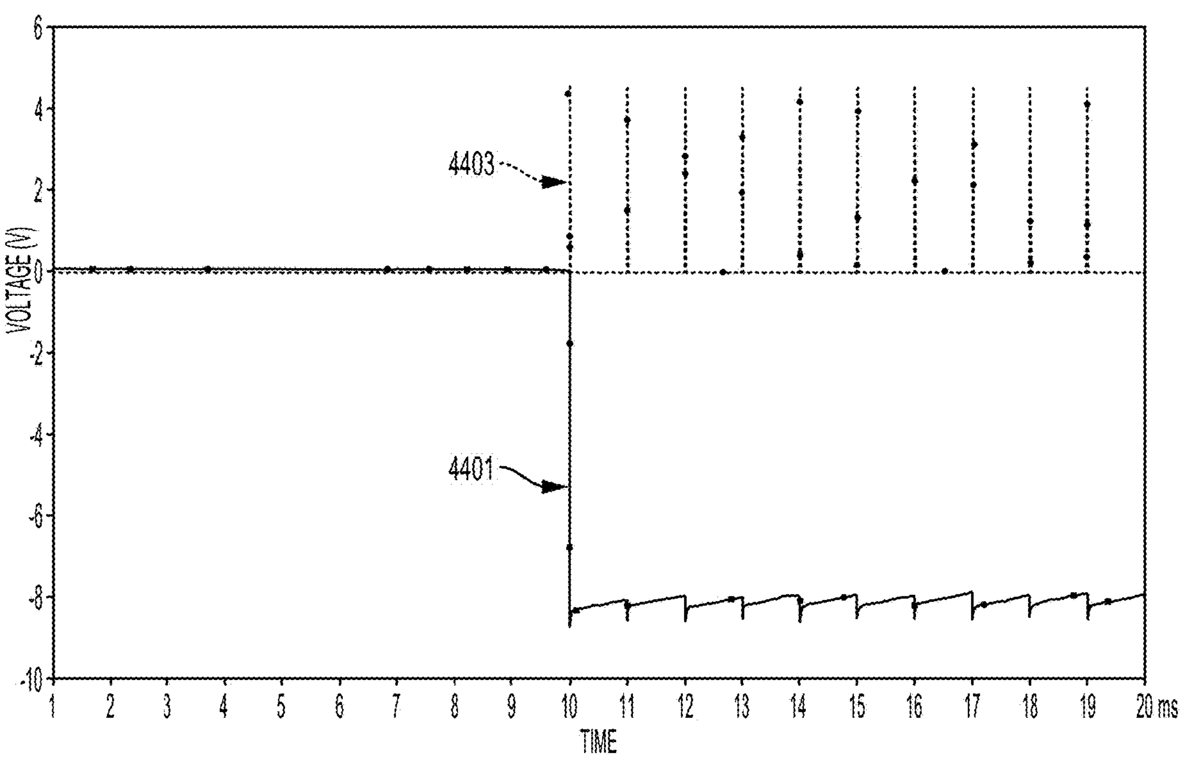
Figure 45:
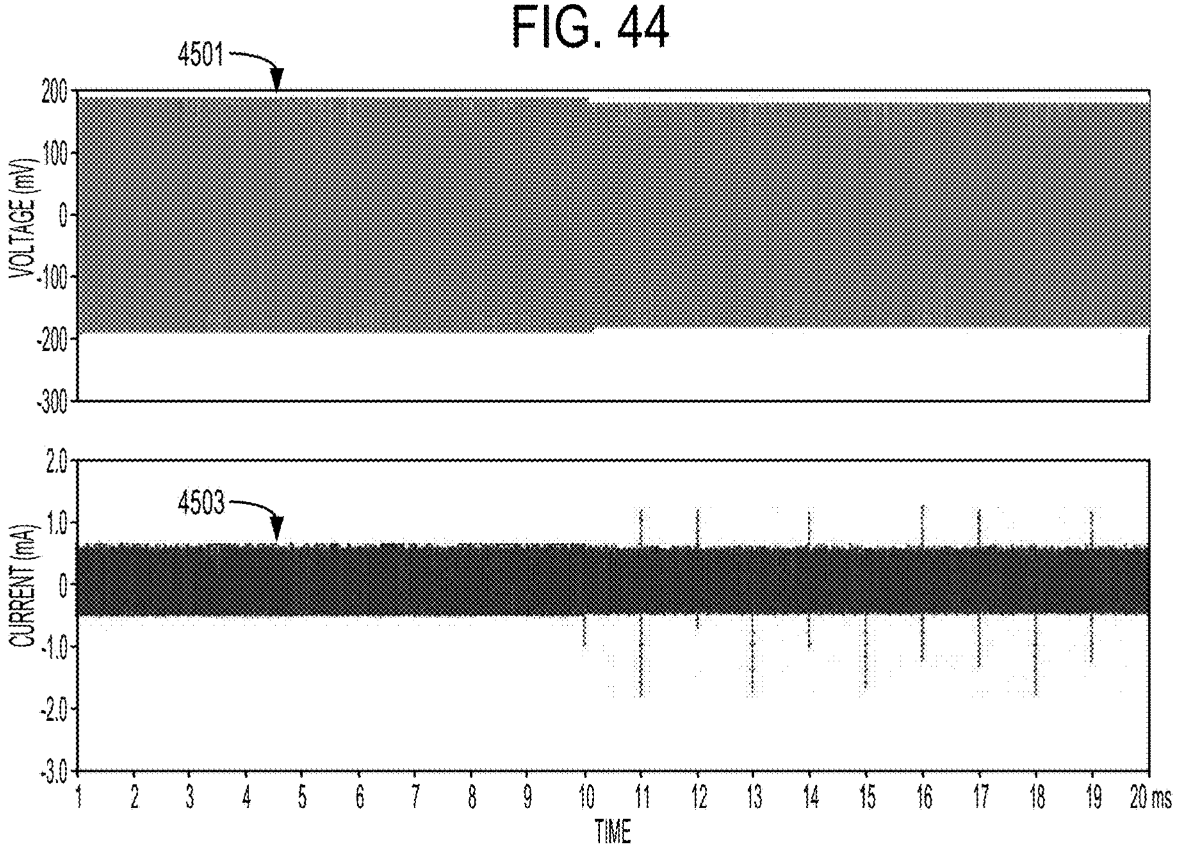
Figure 46:
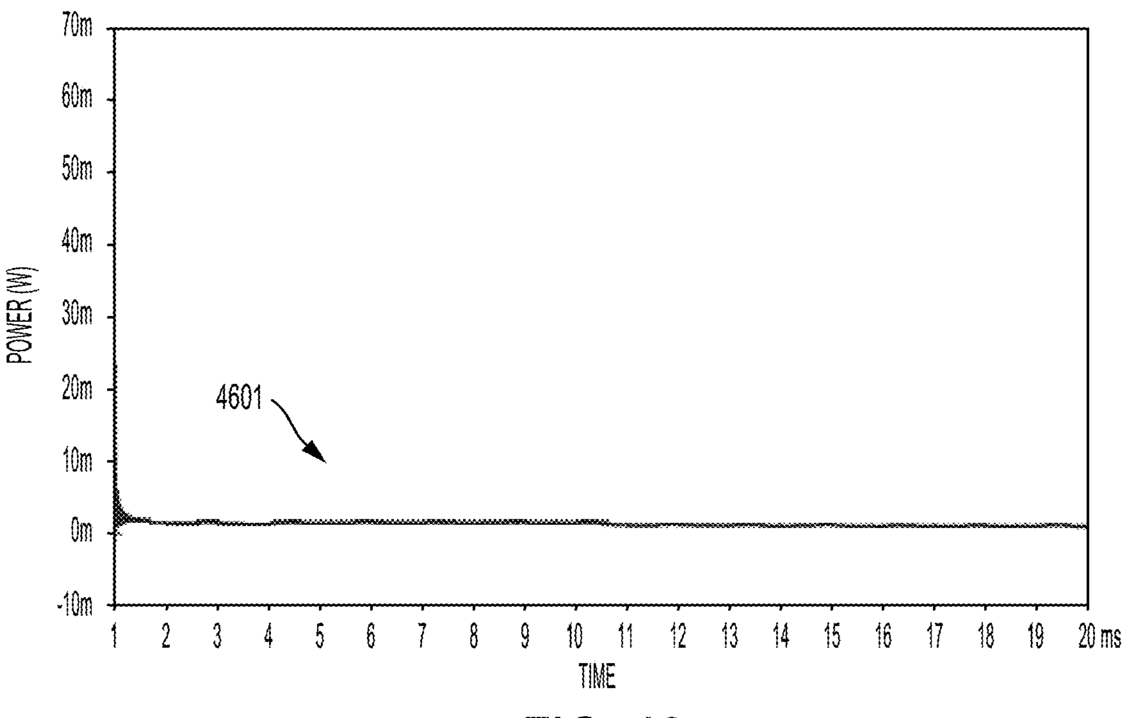
Figure 47:
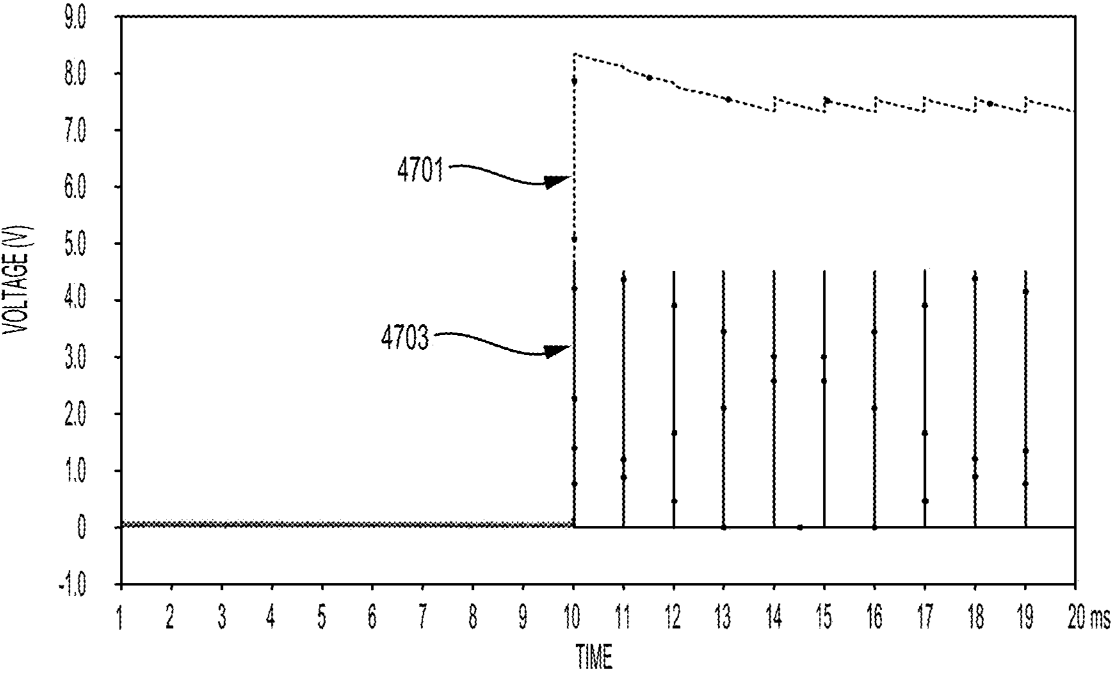
Figure 48:
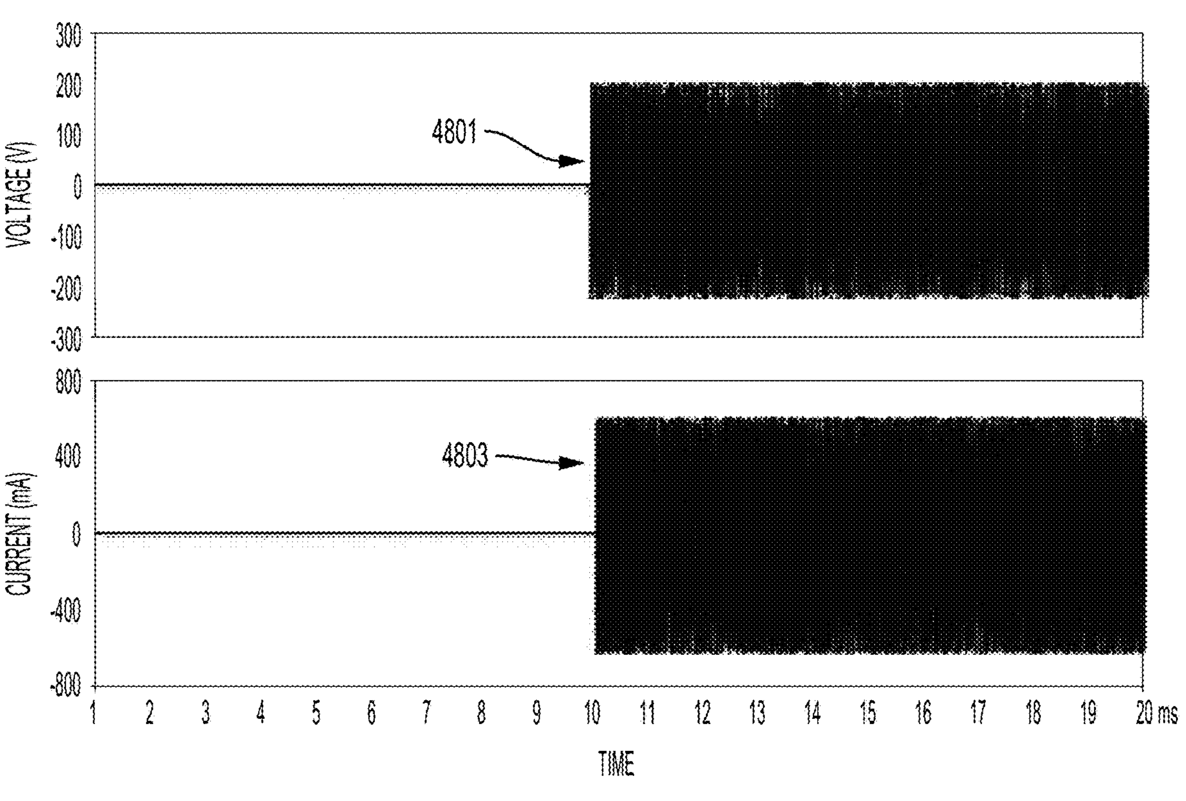
Figure 49:
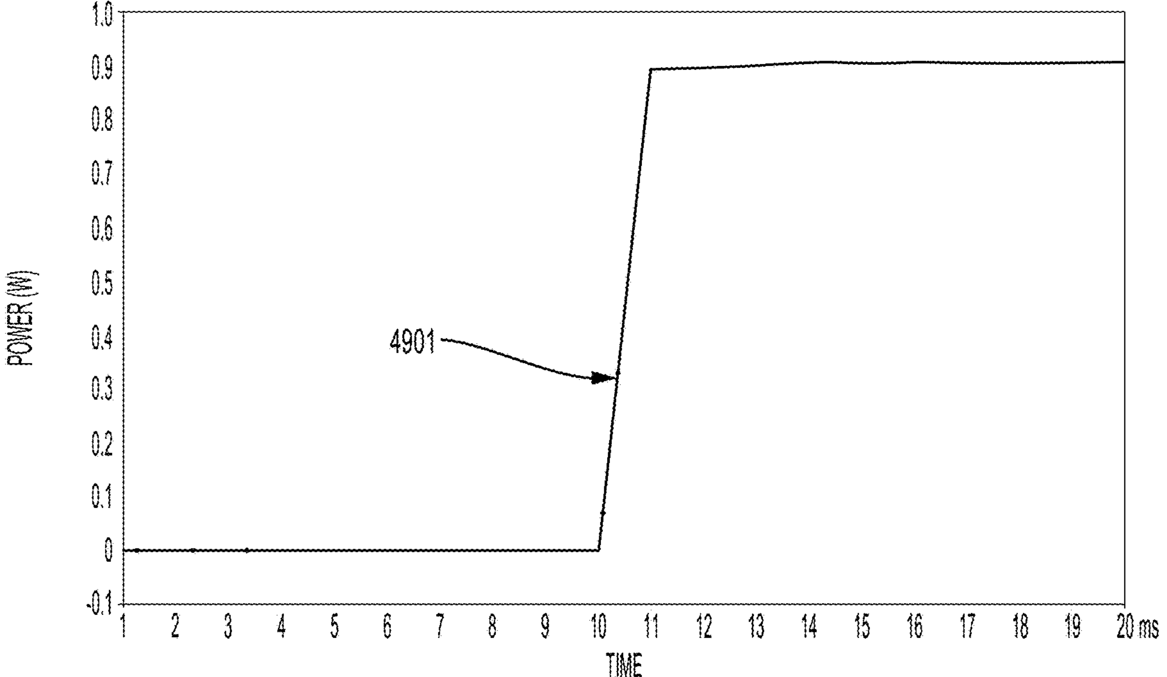
Figure 50:
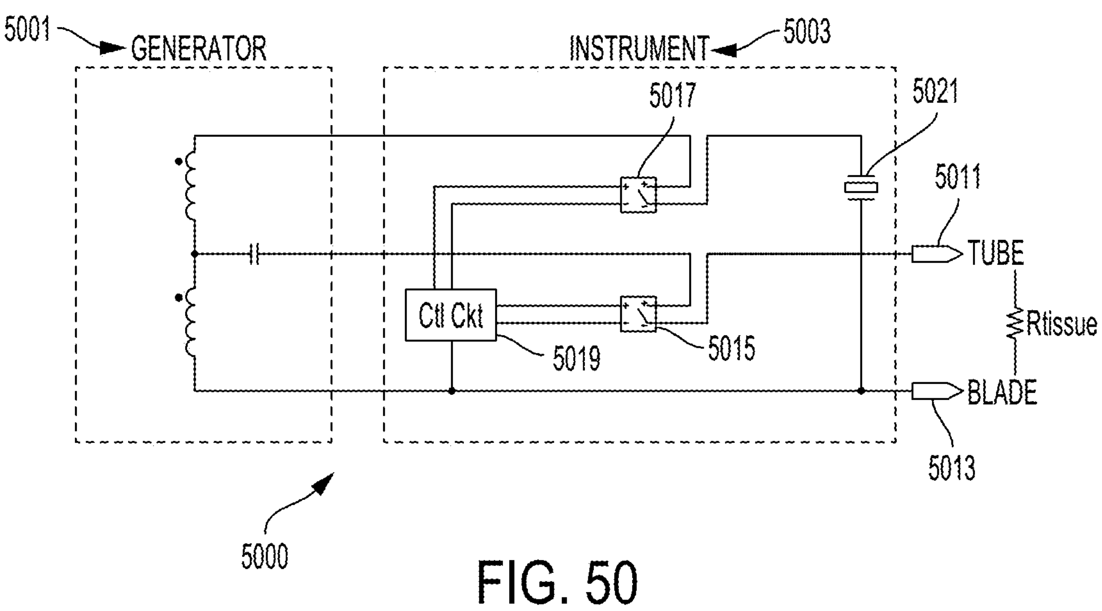
Figure 51:
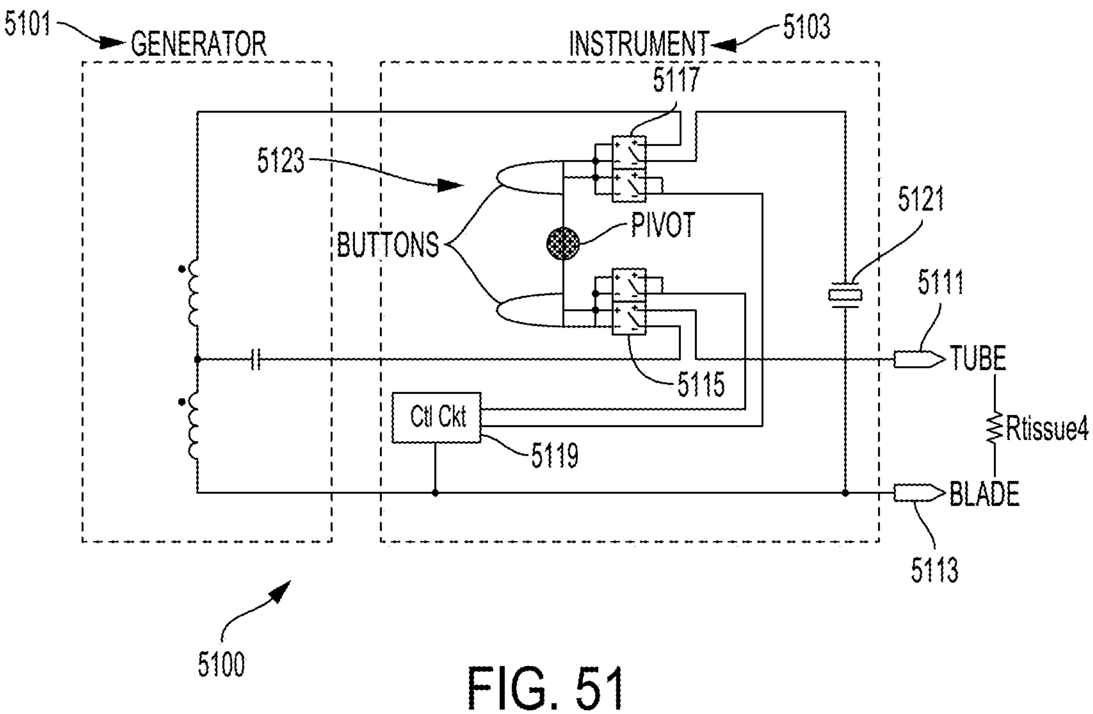
Figure 52:
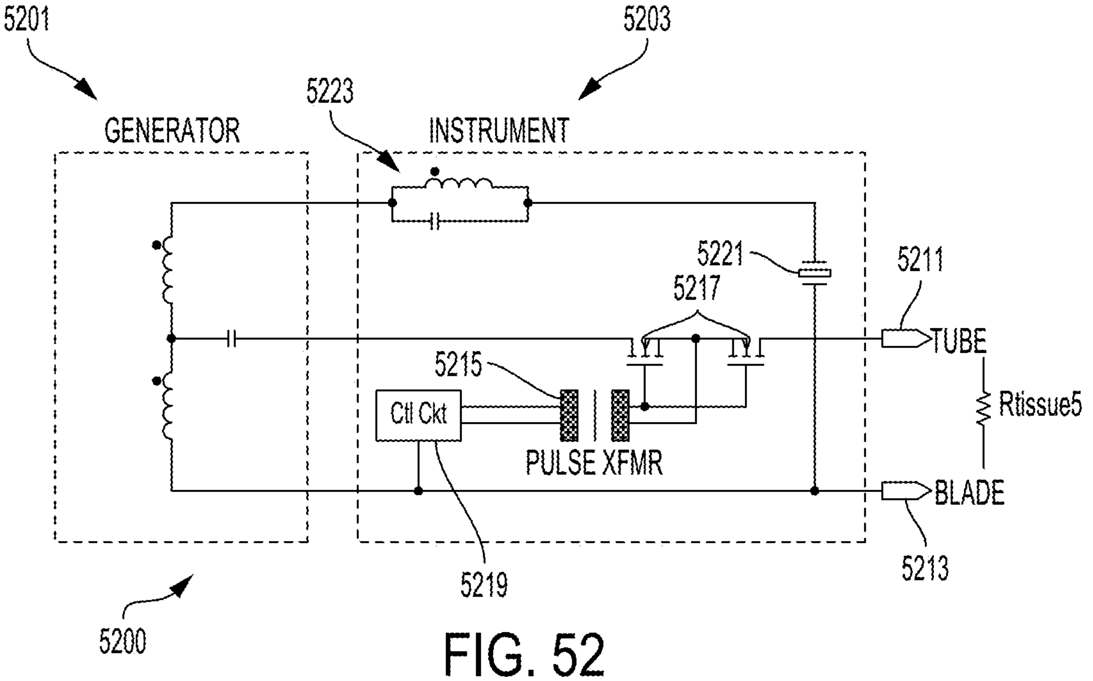
Figure 53:
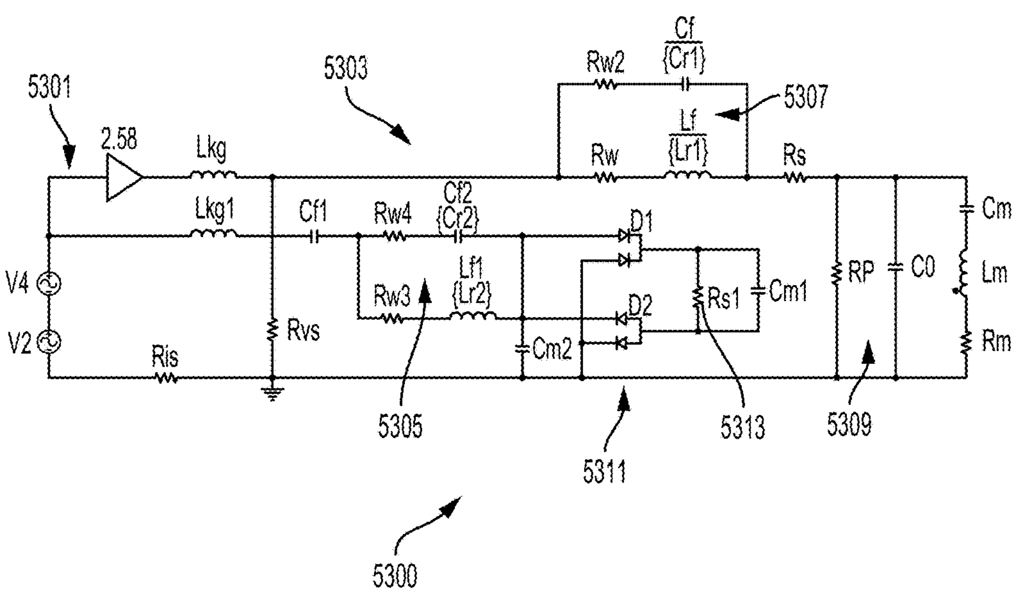
Figure 54:
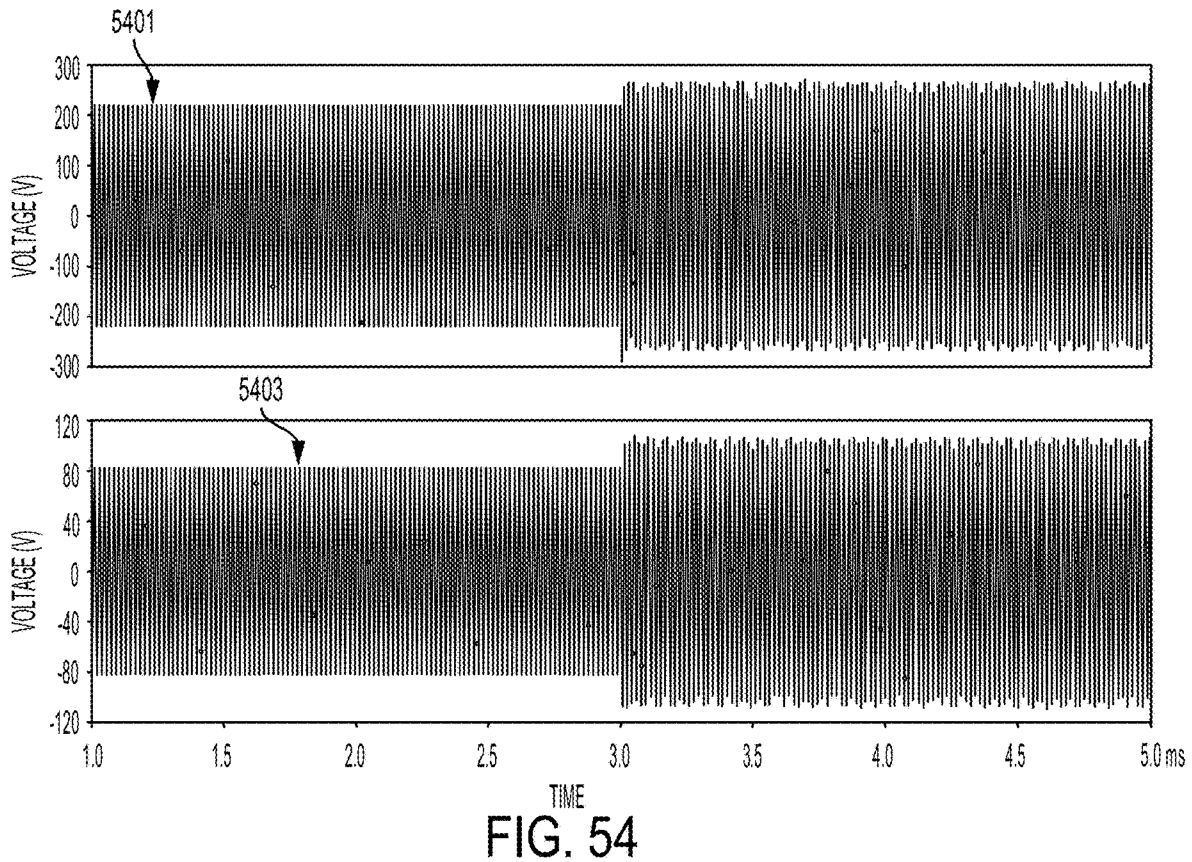
Figures 55, 56:
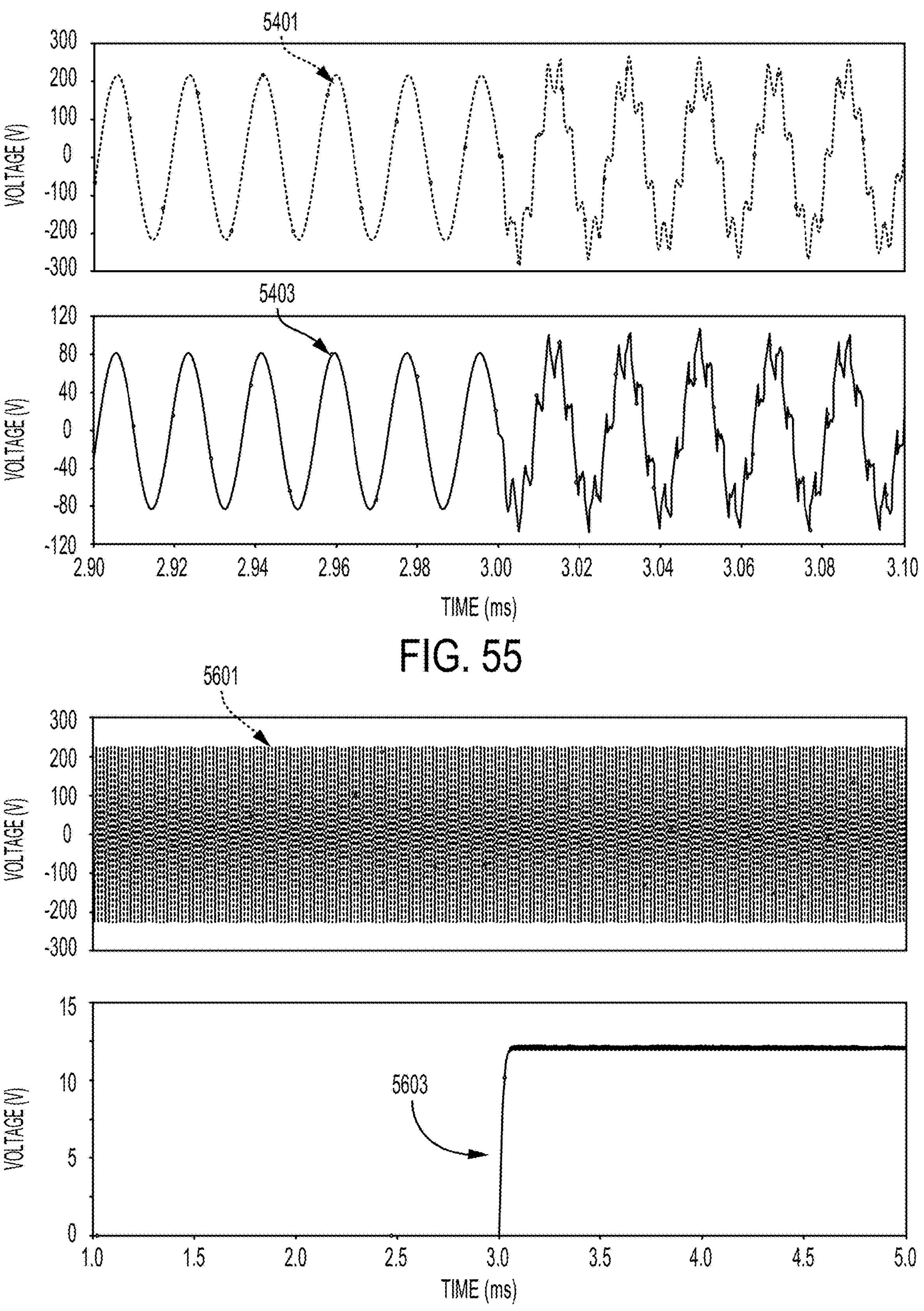
Figures 57, 58:
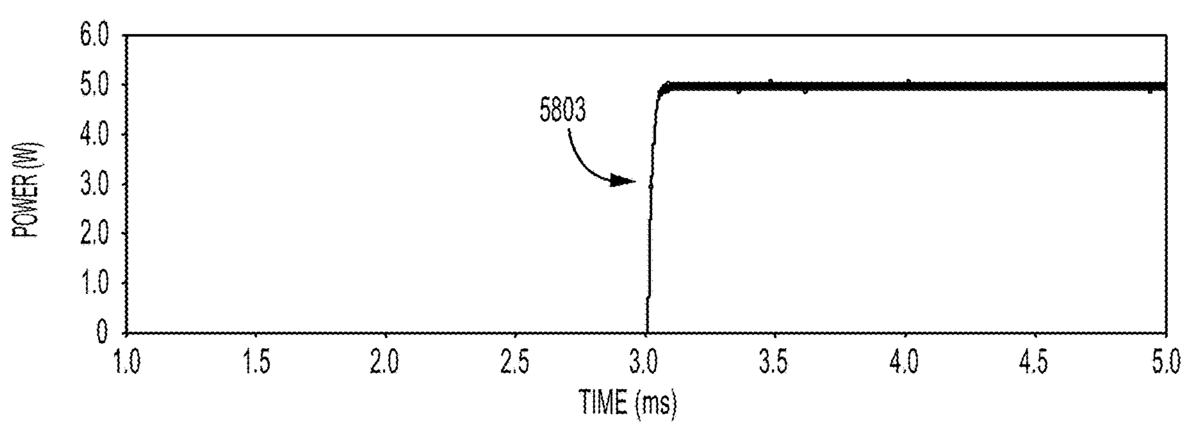
Figure 59:
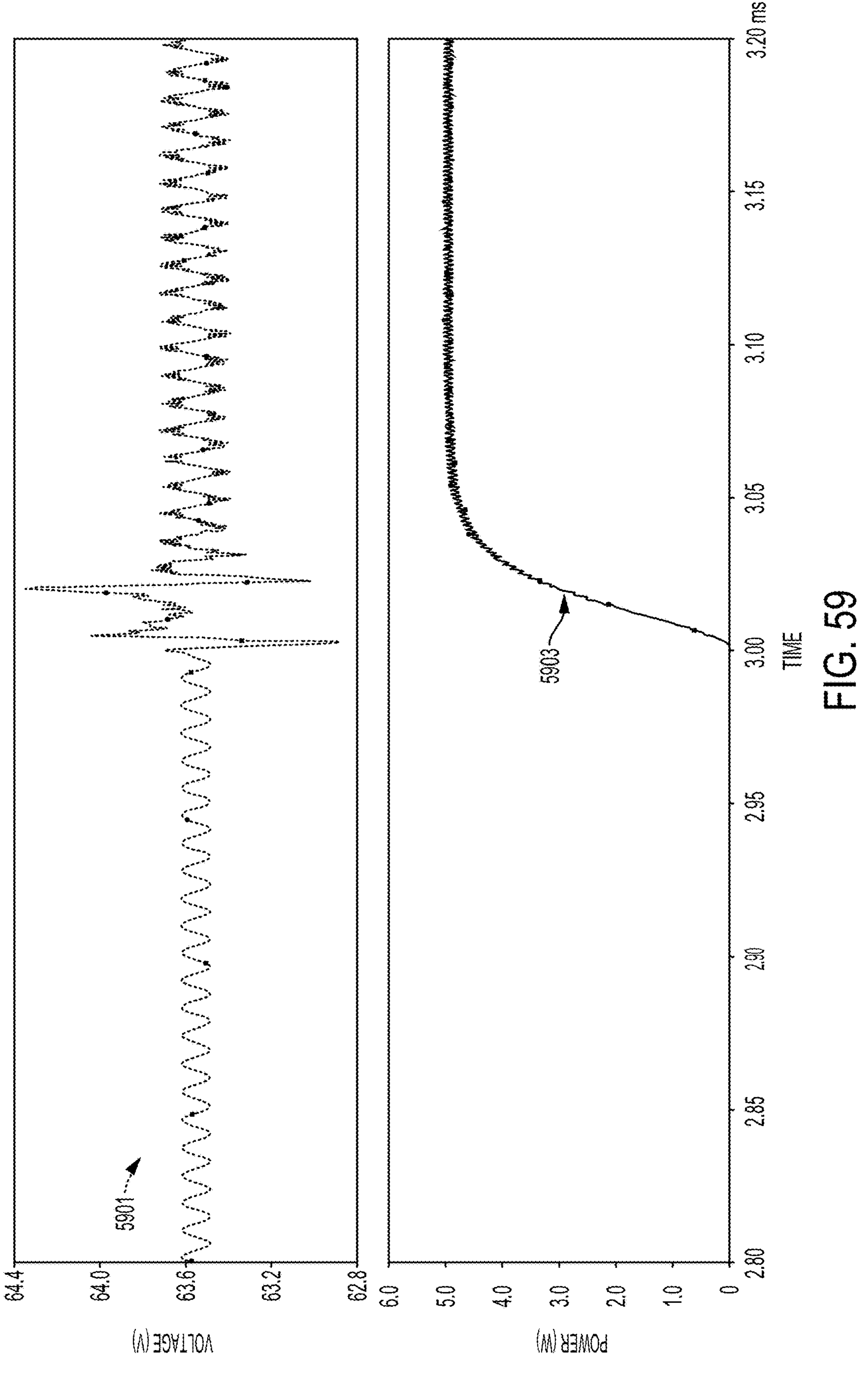
Figure 60:
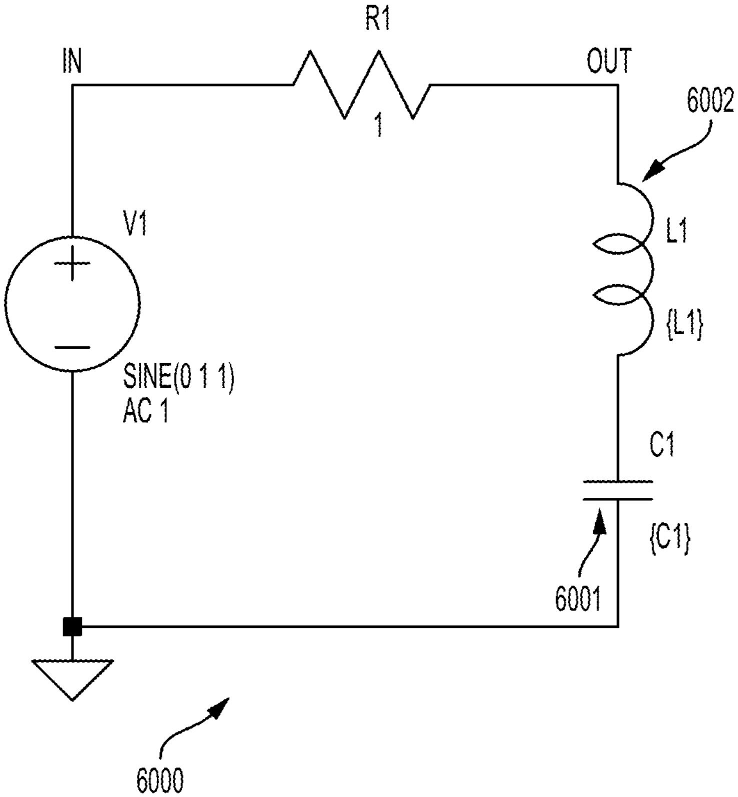
Figure 61:
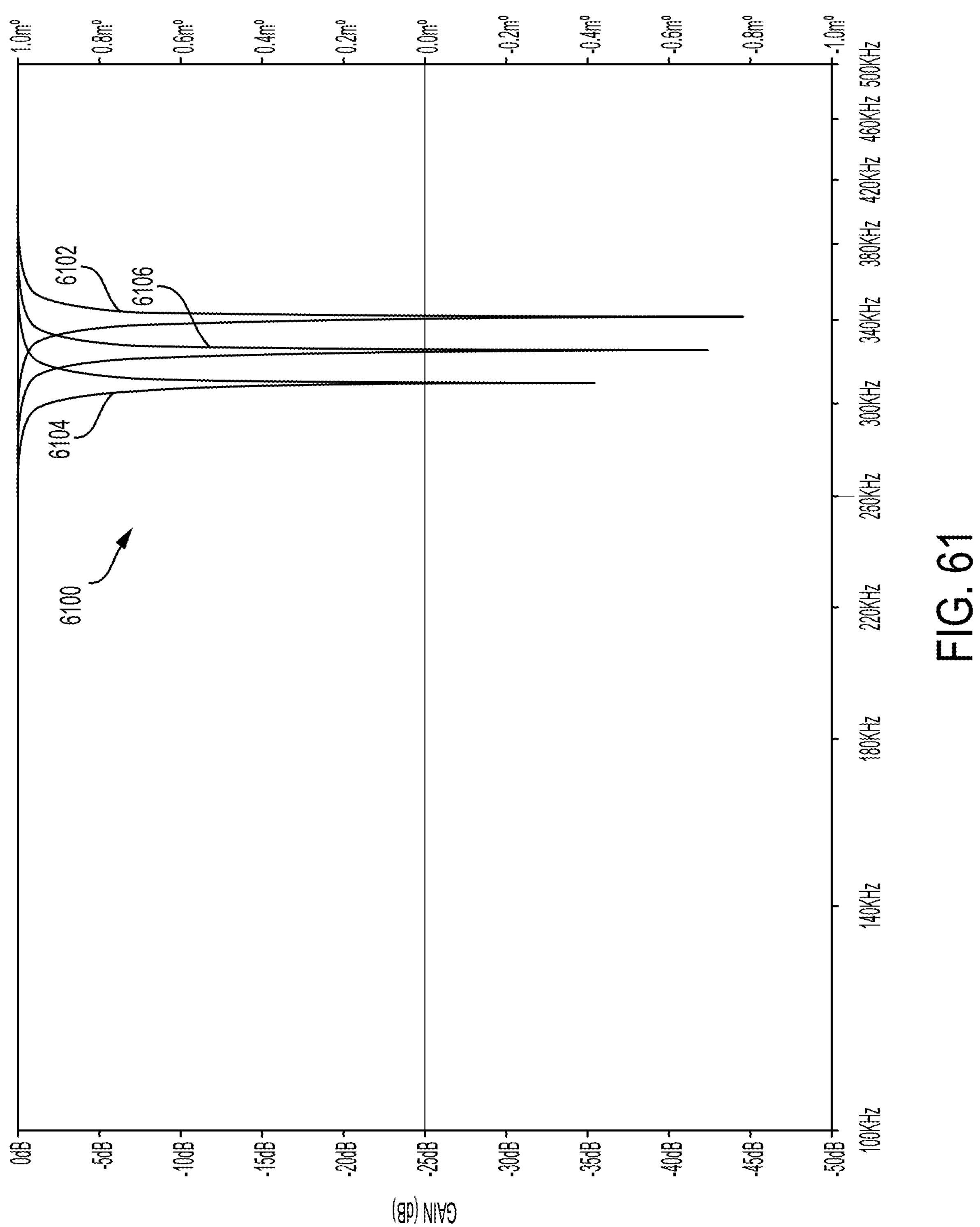
Figure 62:
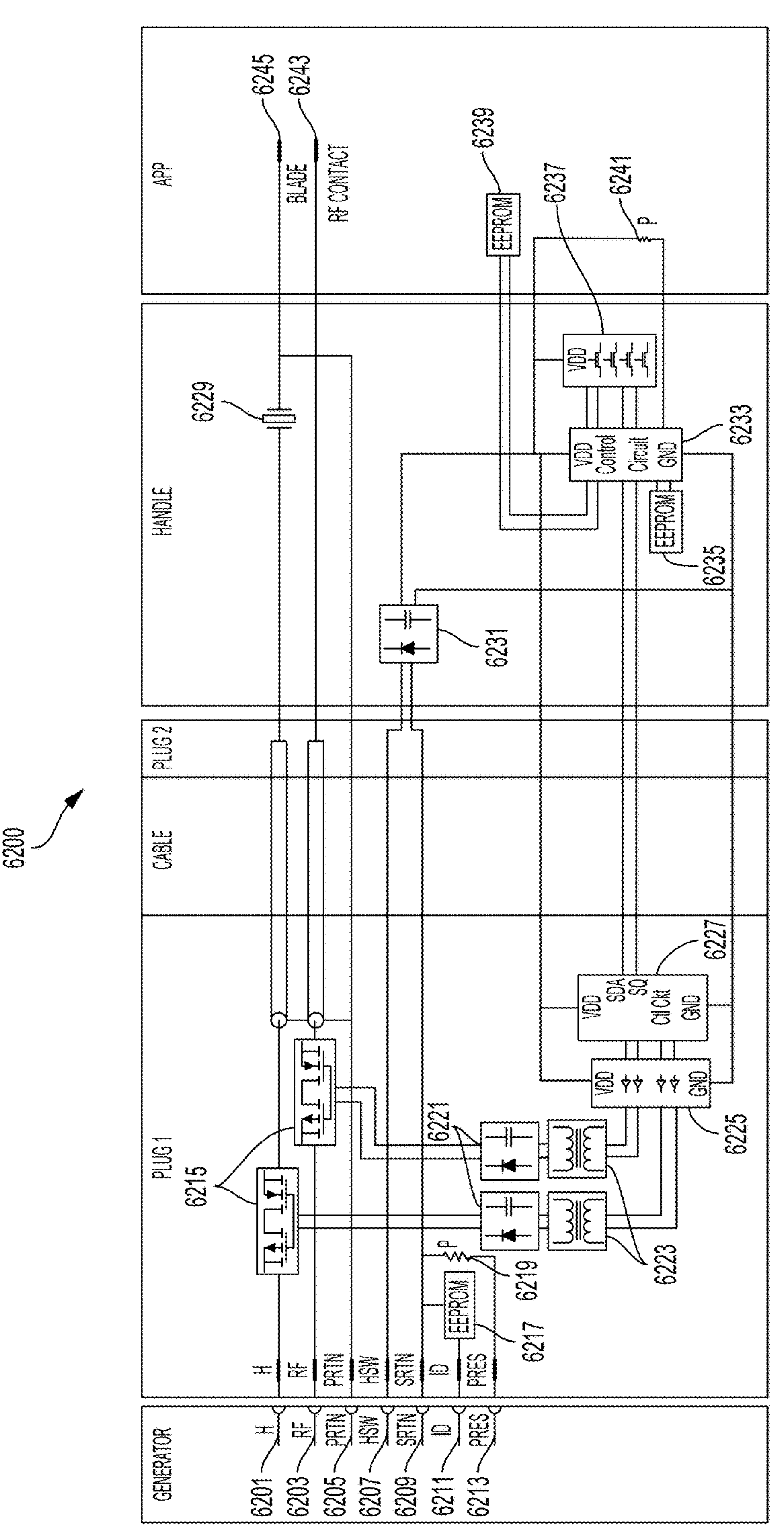
Figure 63:
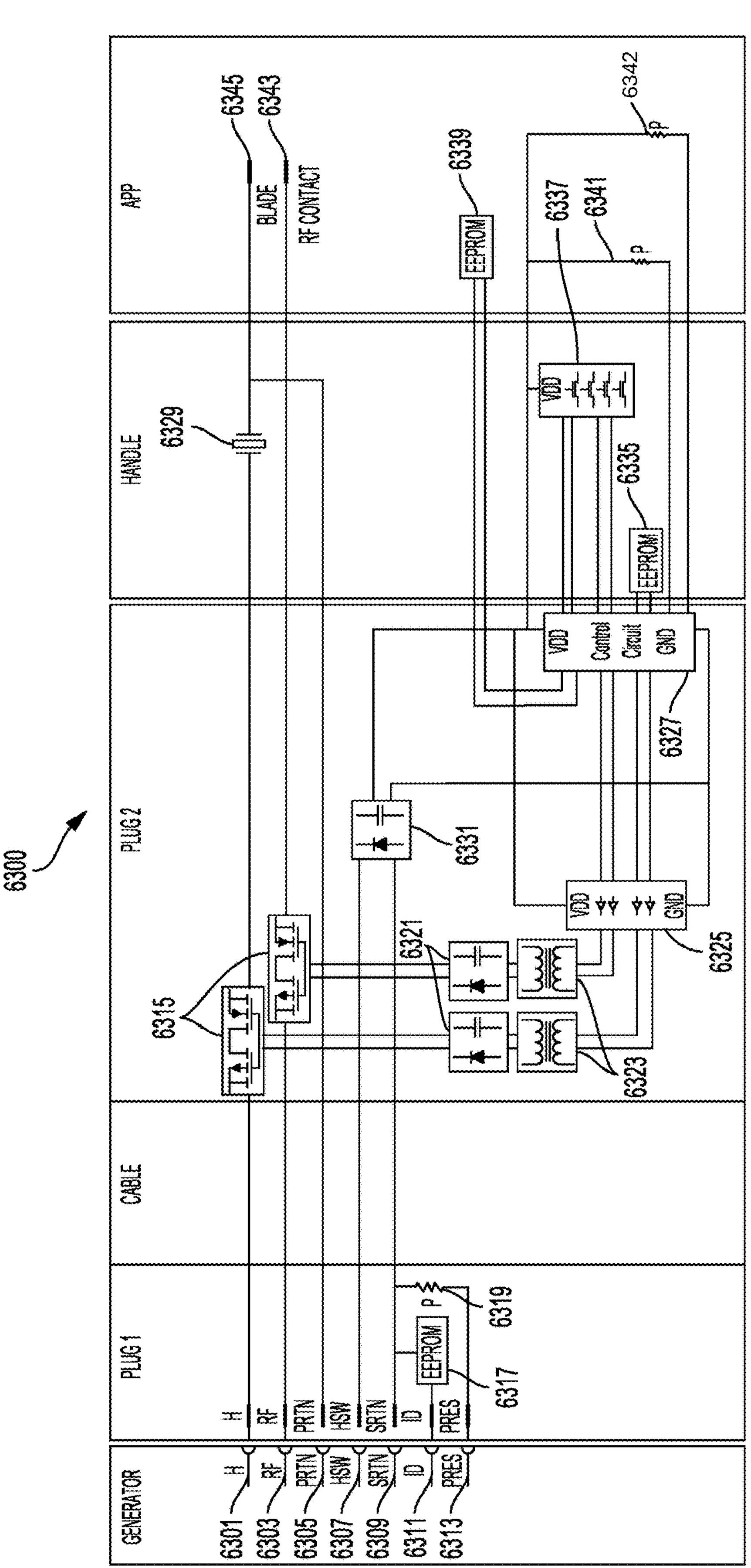
Figure 64:
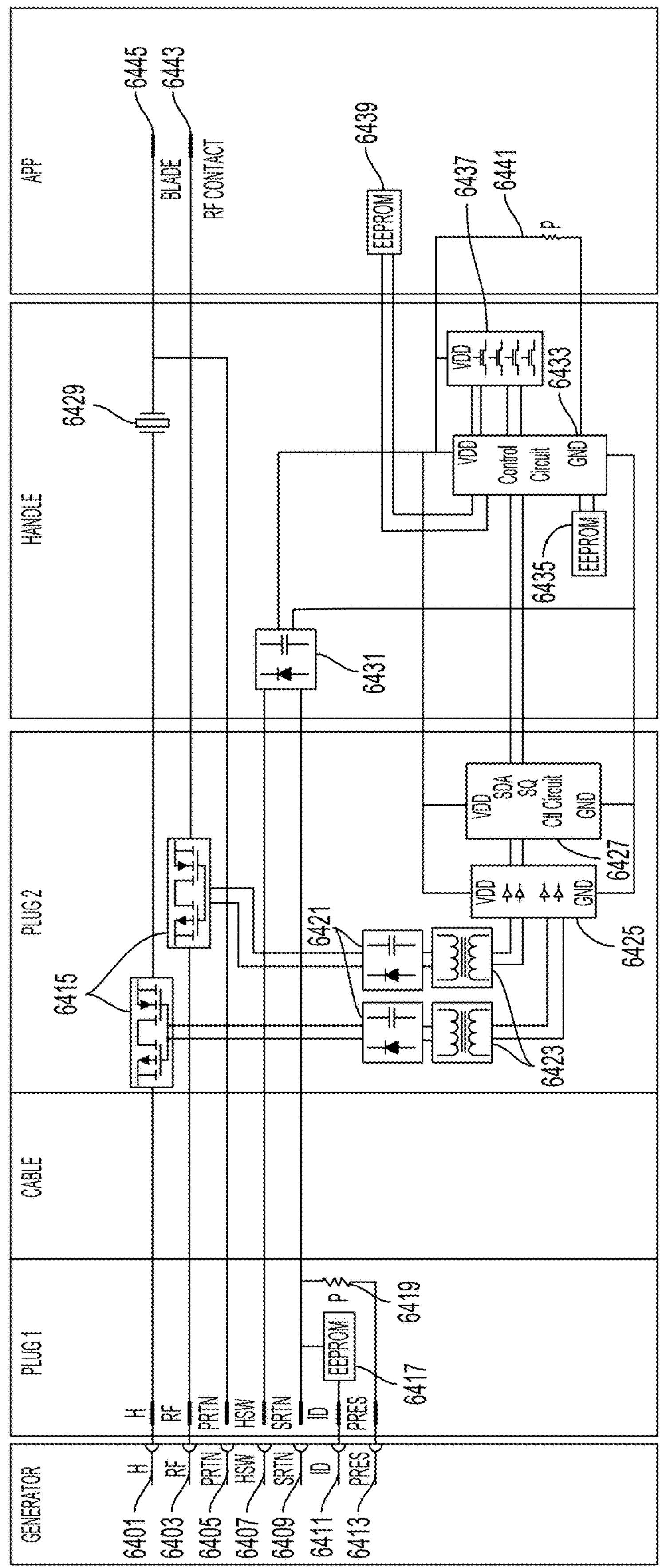
Figure 65:
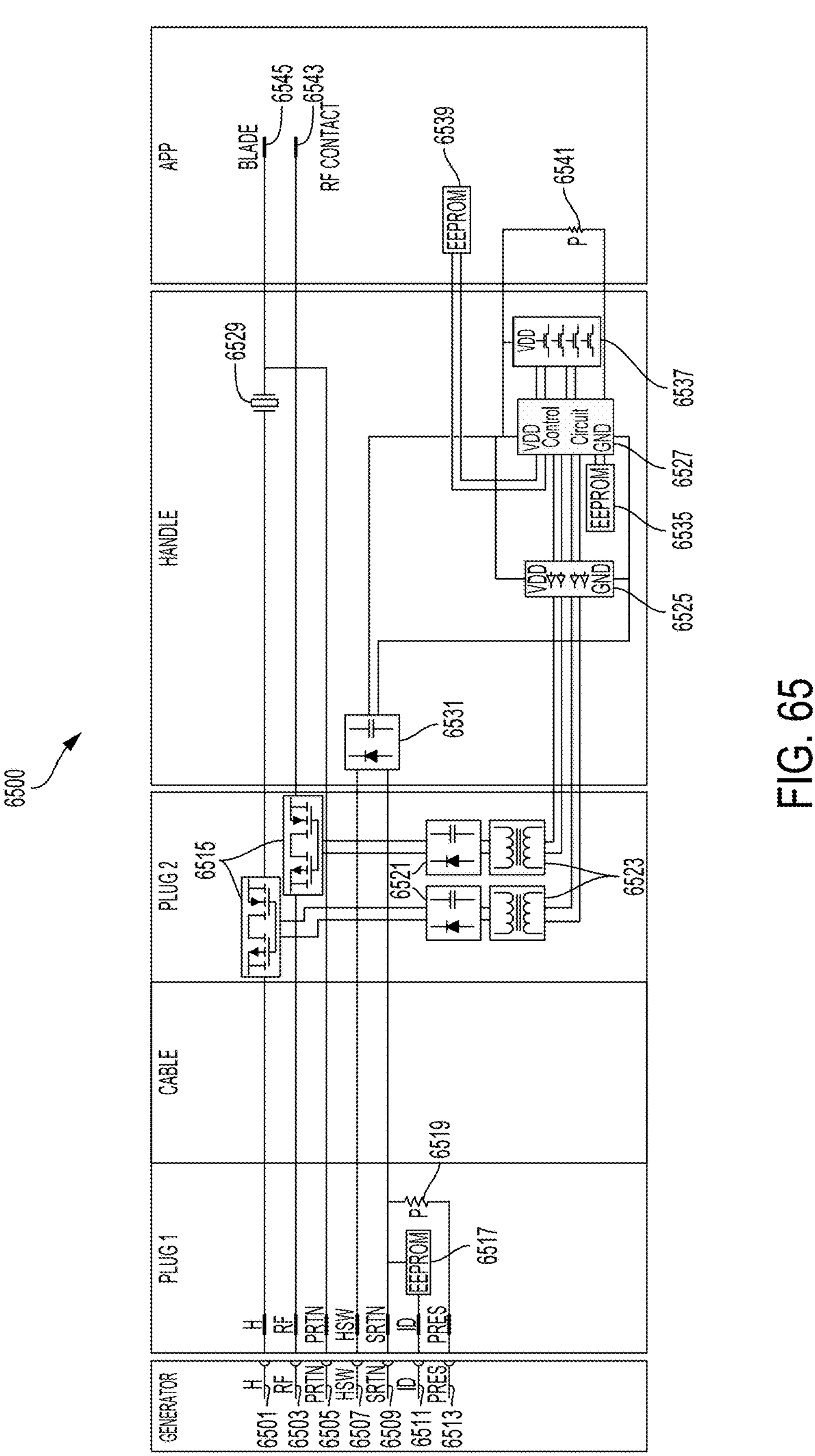
Figure 66:
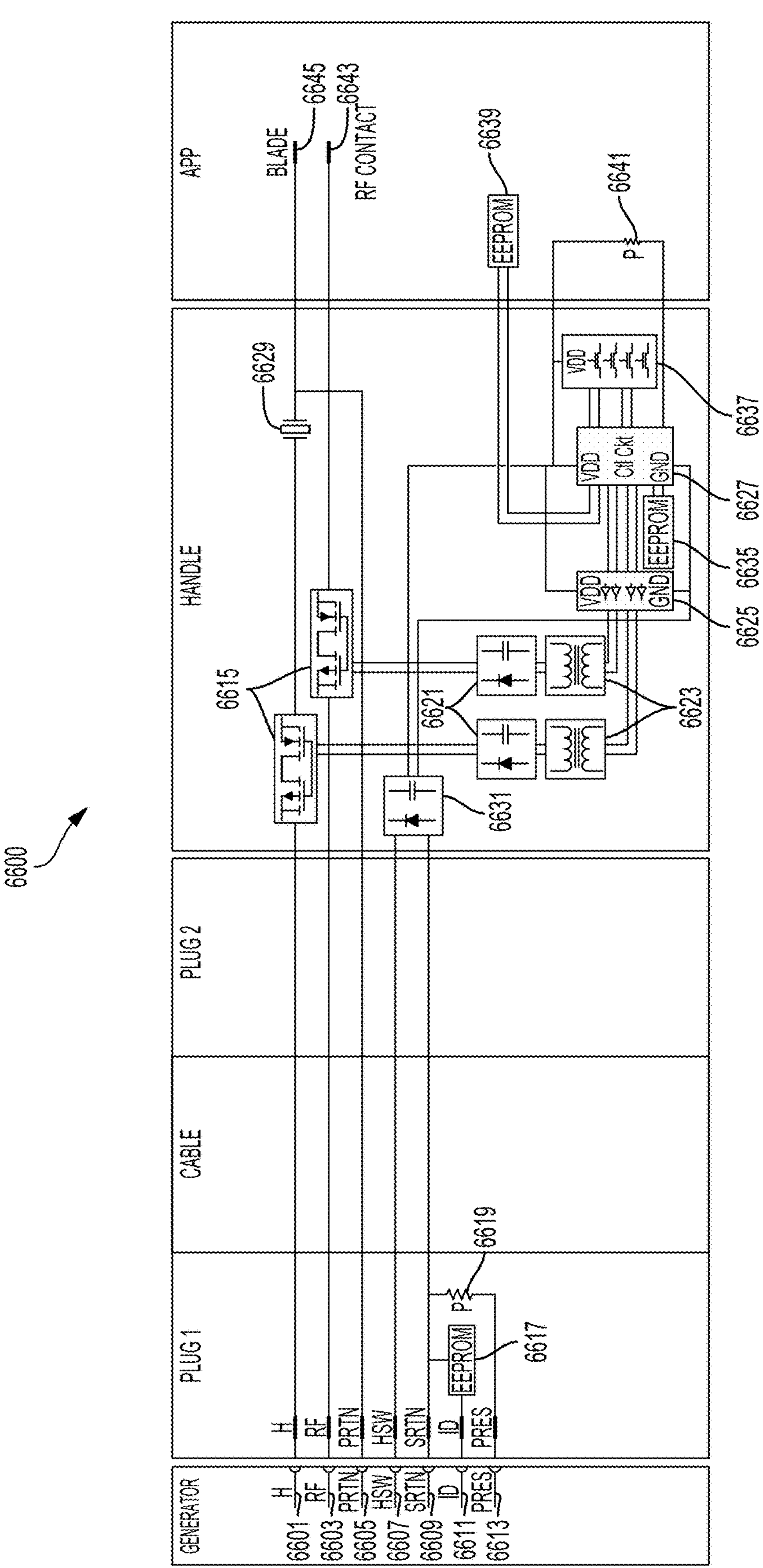
Figure 67:
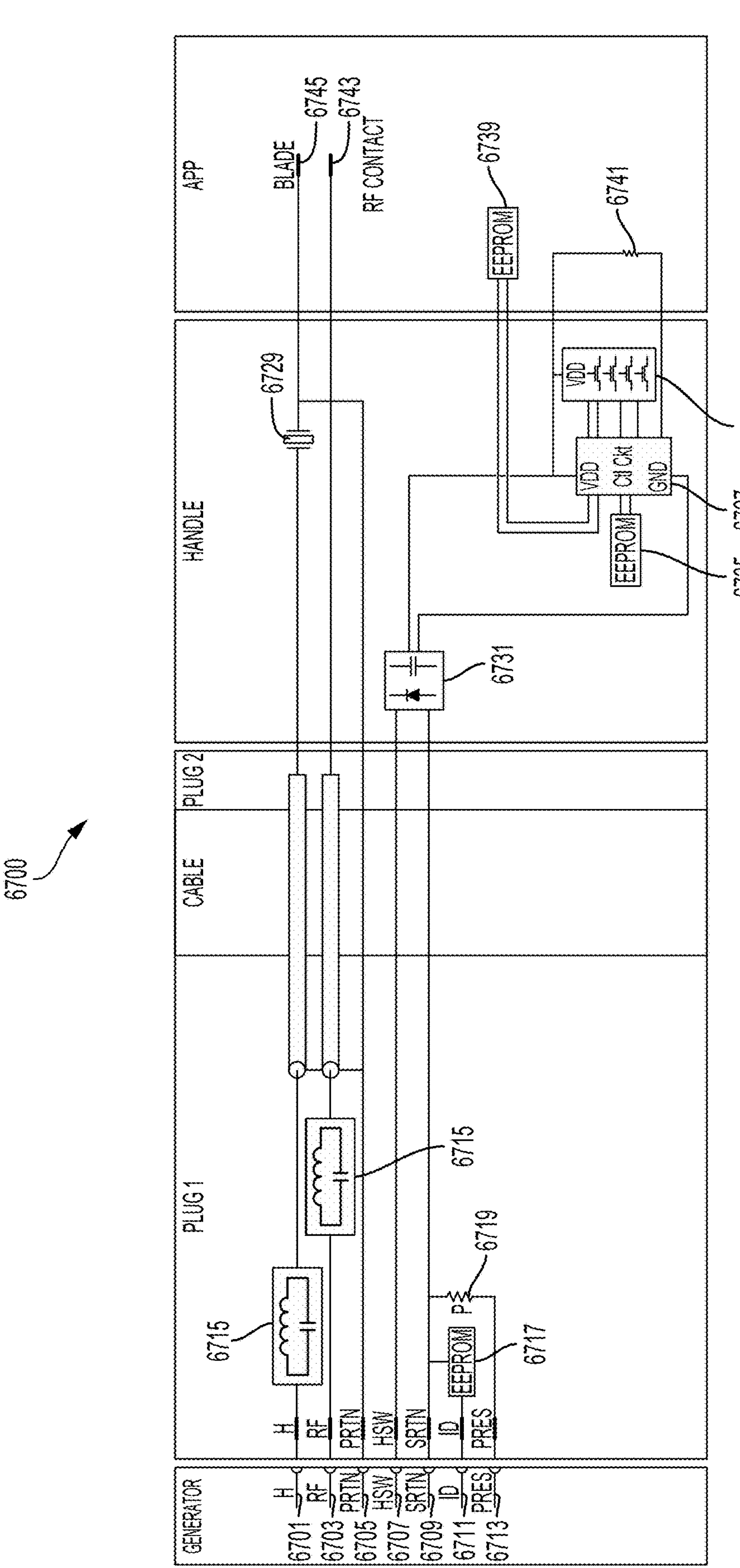
Figure 68:
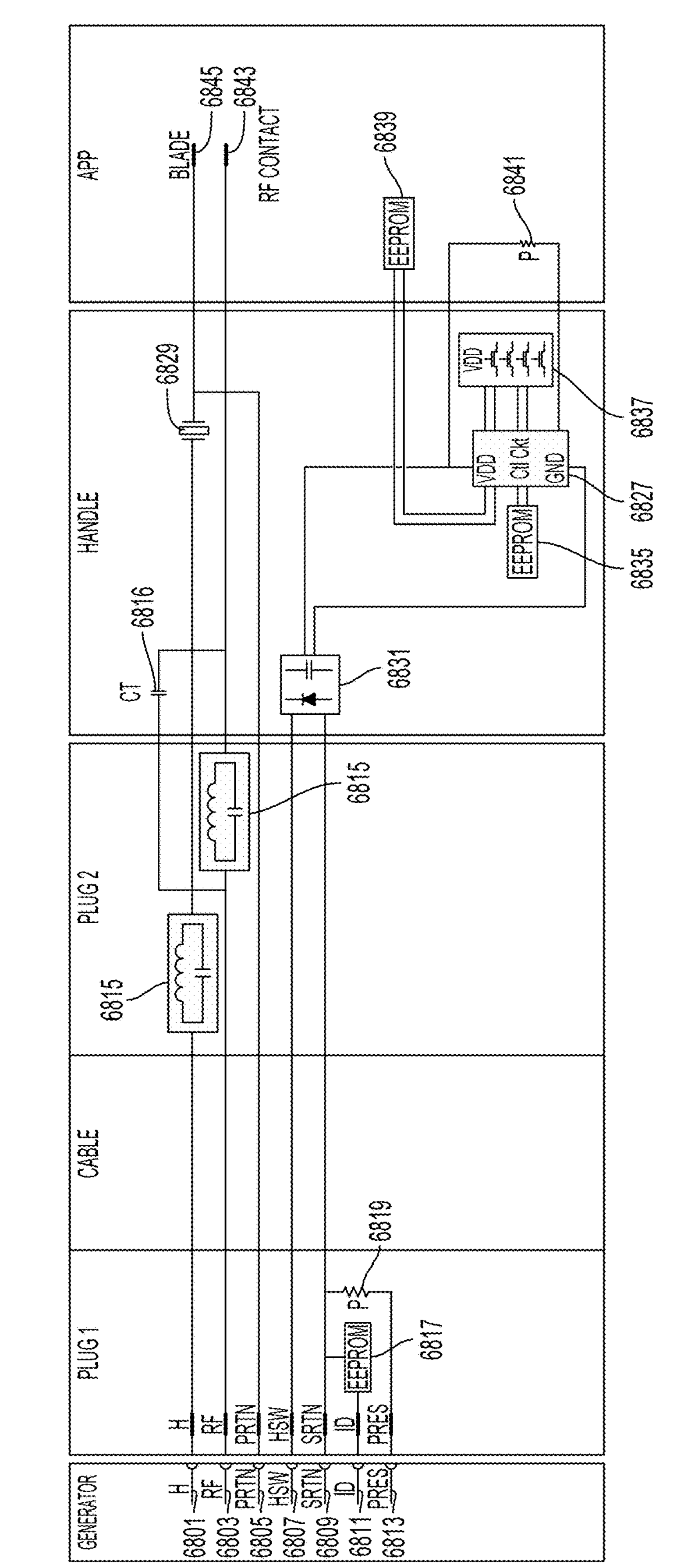
Figure 69:
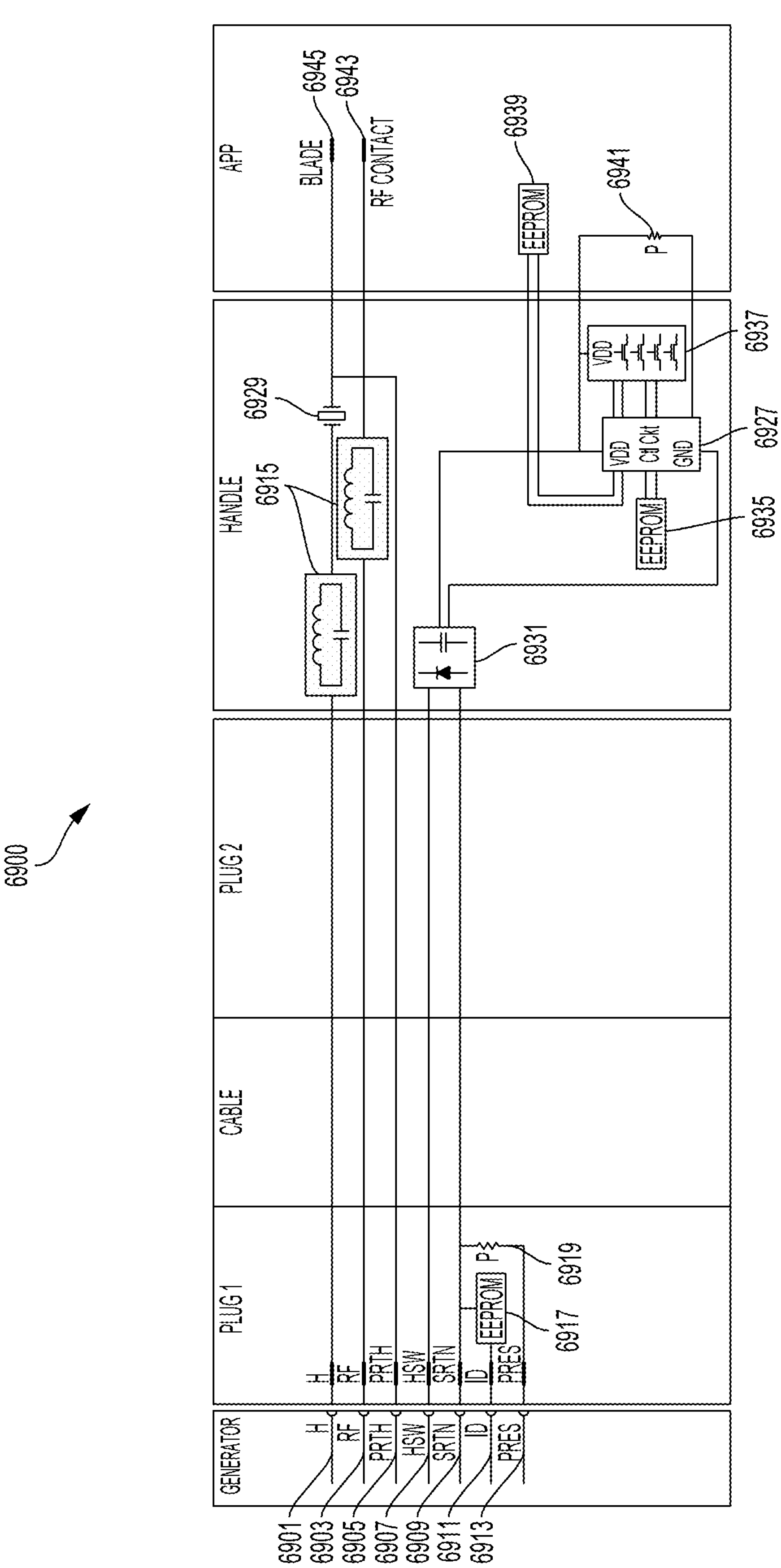
Figure 70:
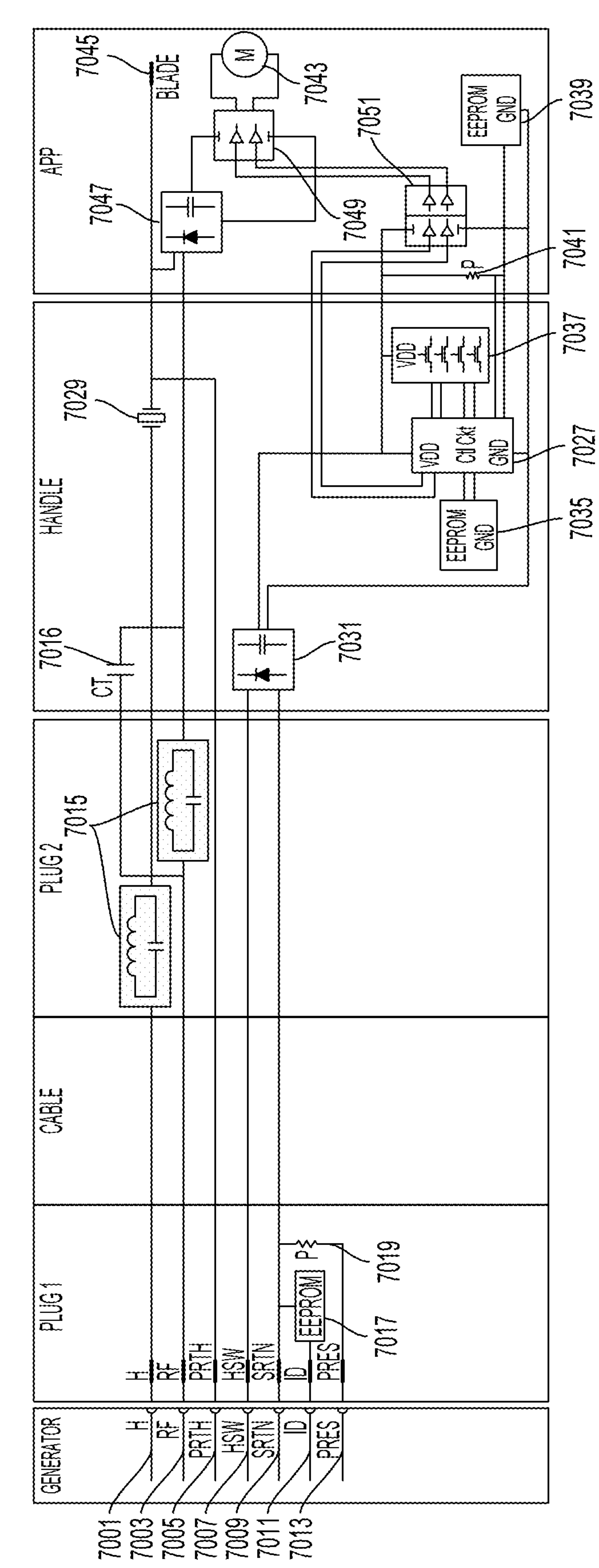
Figure 71:
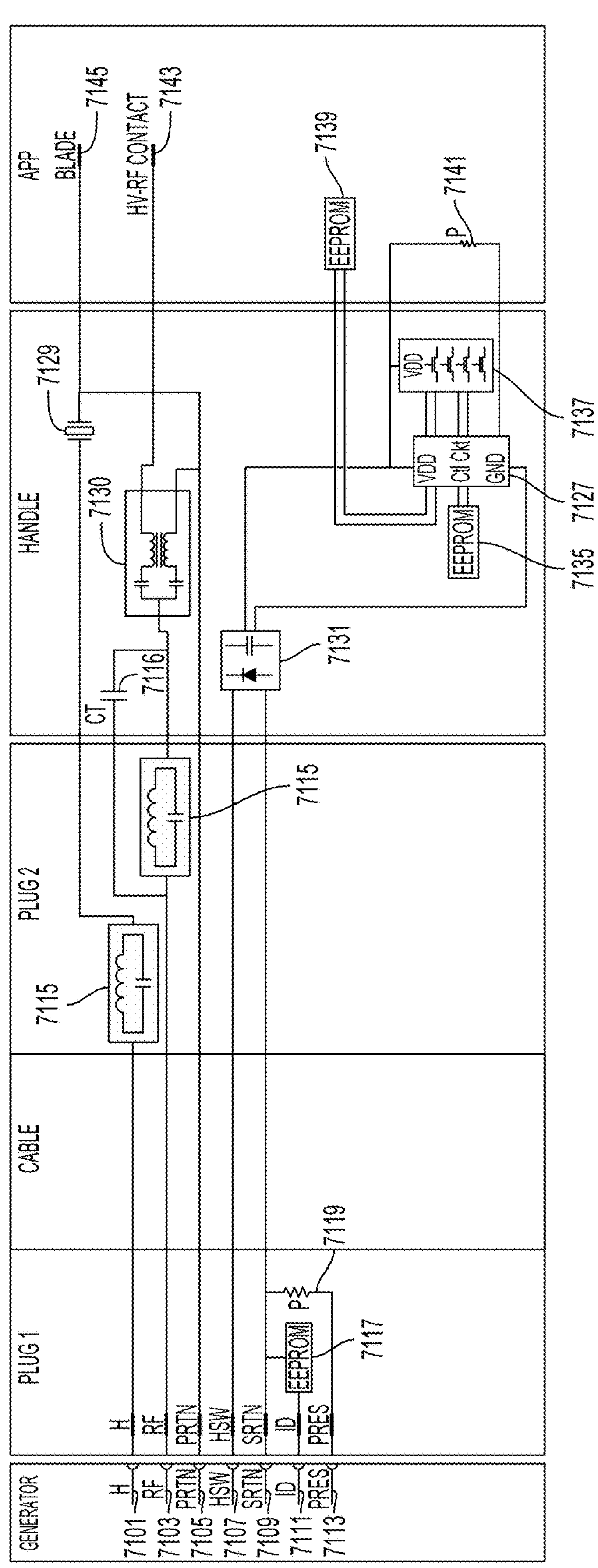
Figure 72:
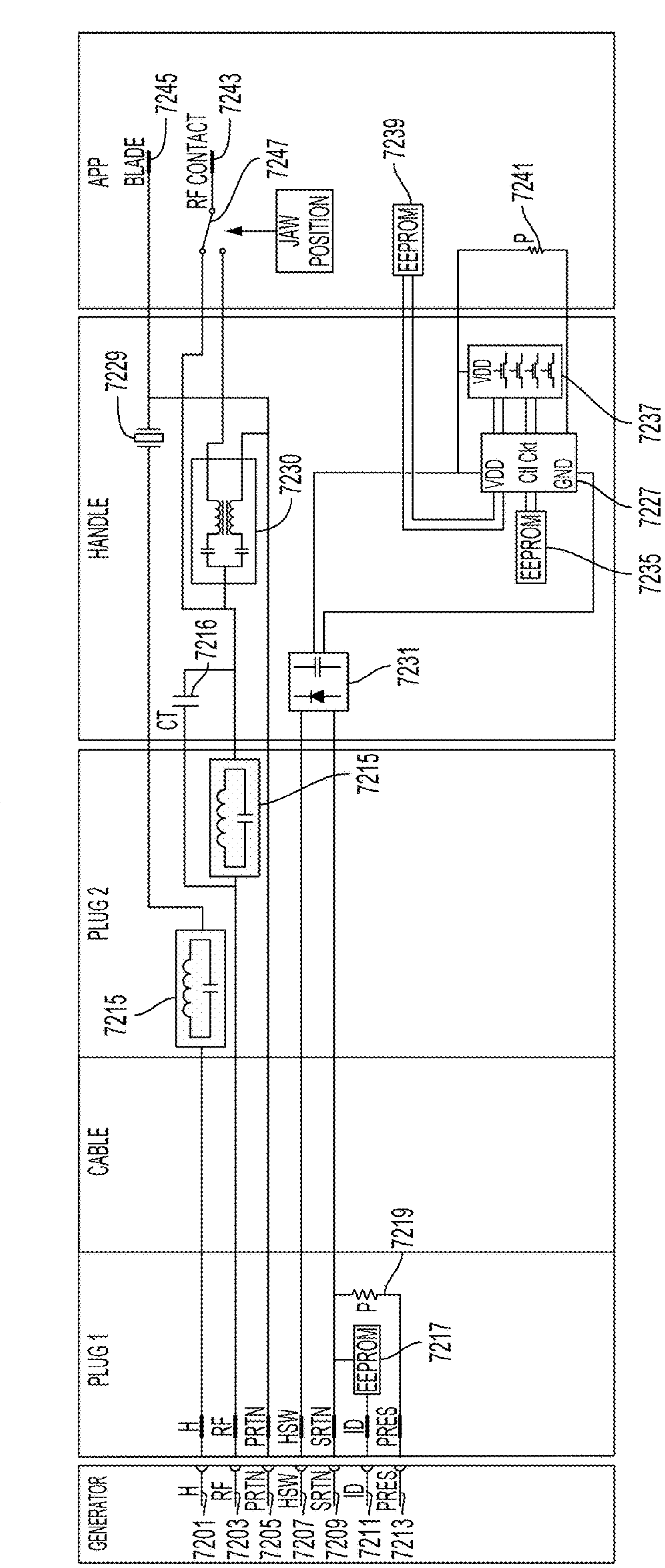
Figure 73:
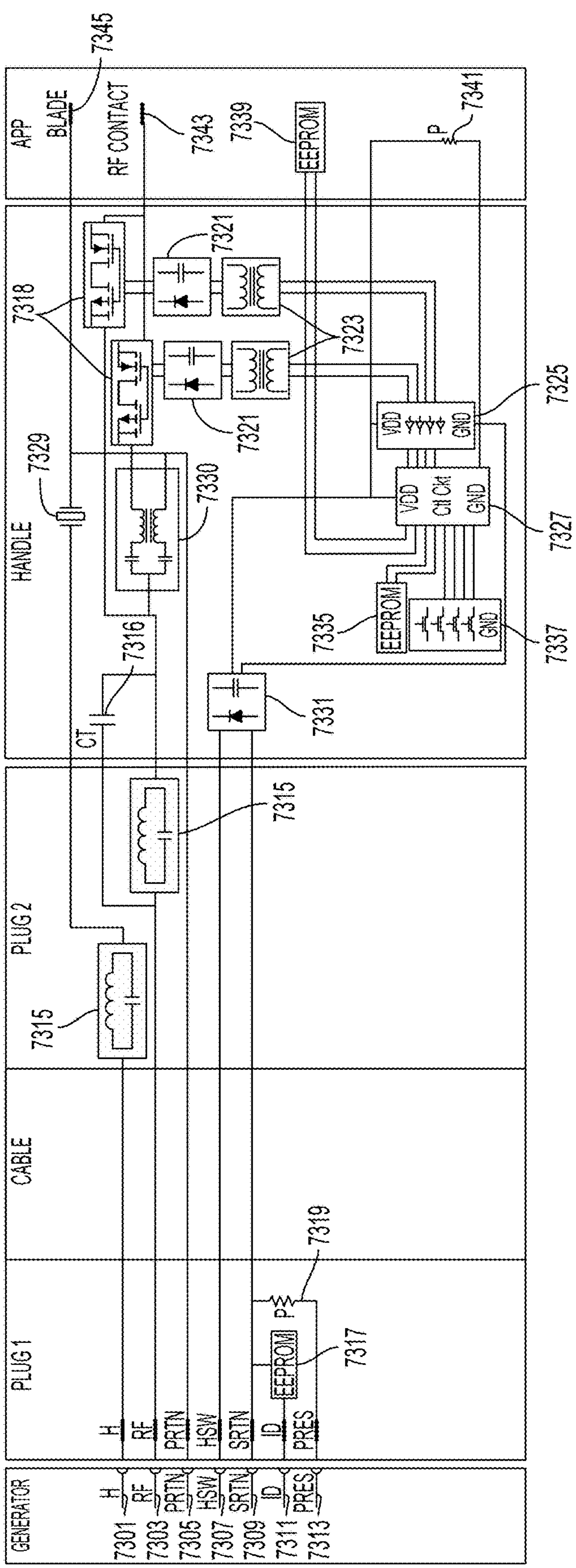
Figure 74:
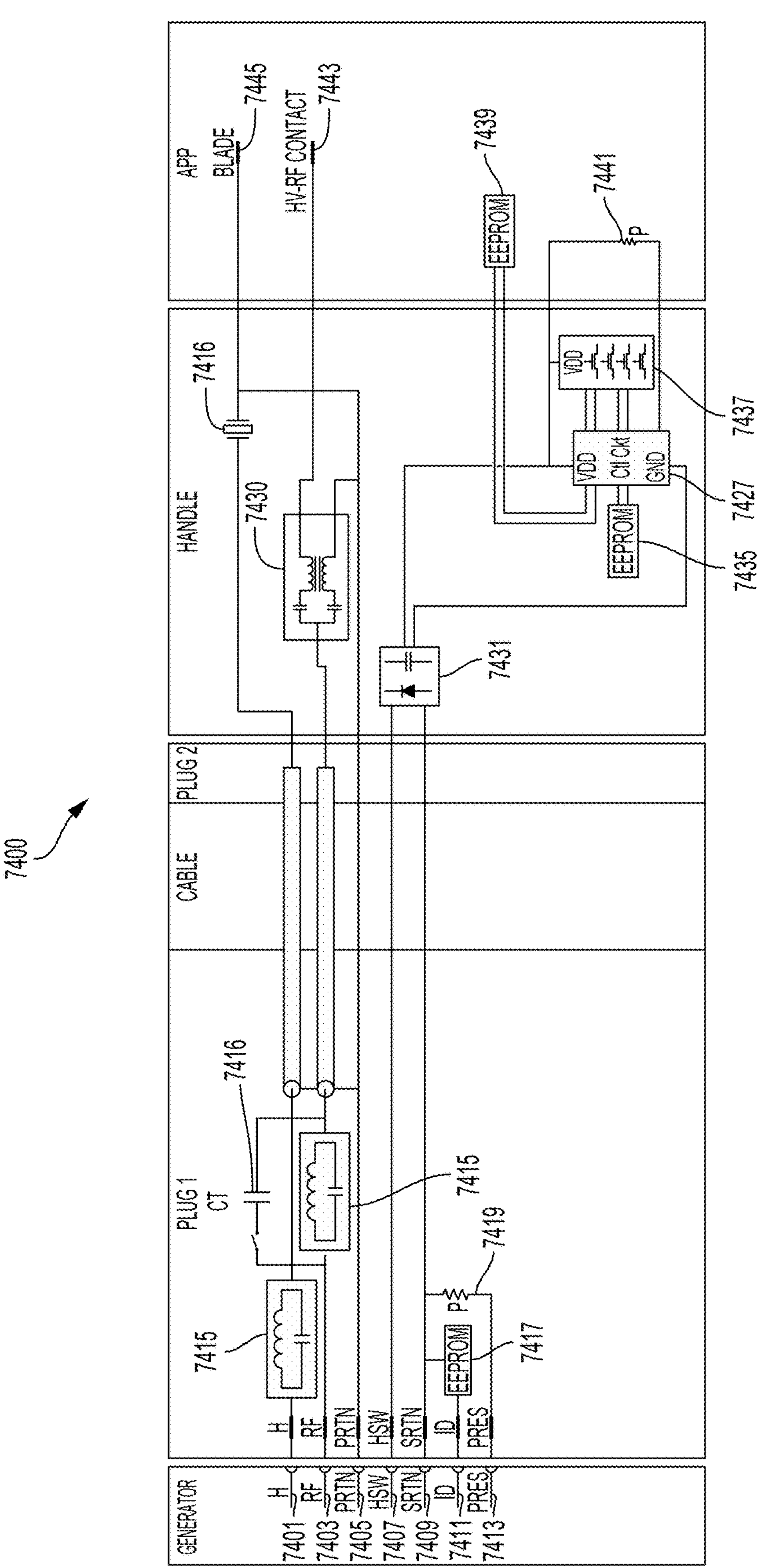
Figure 75:
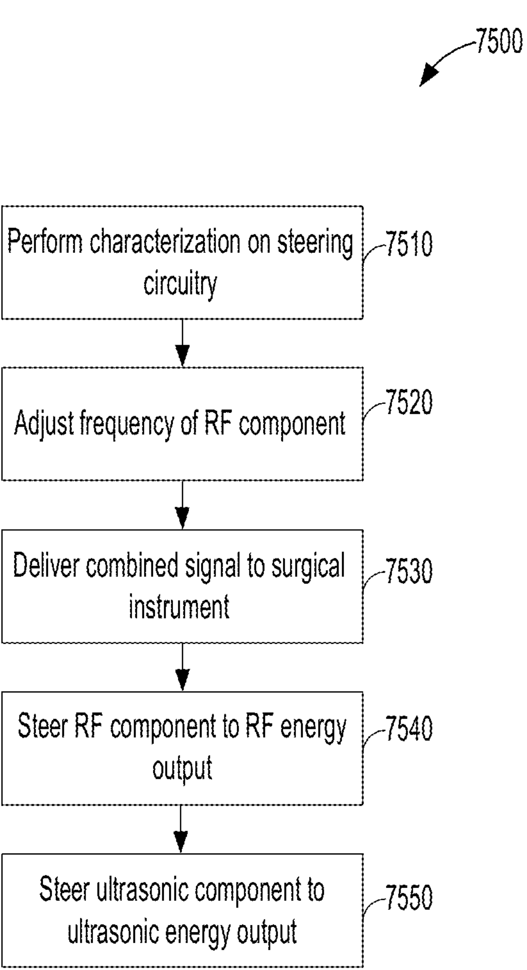
Figure 76:
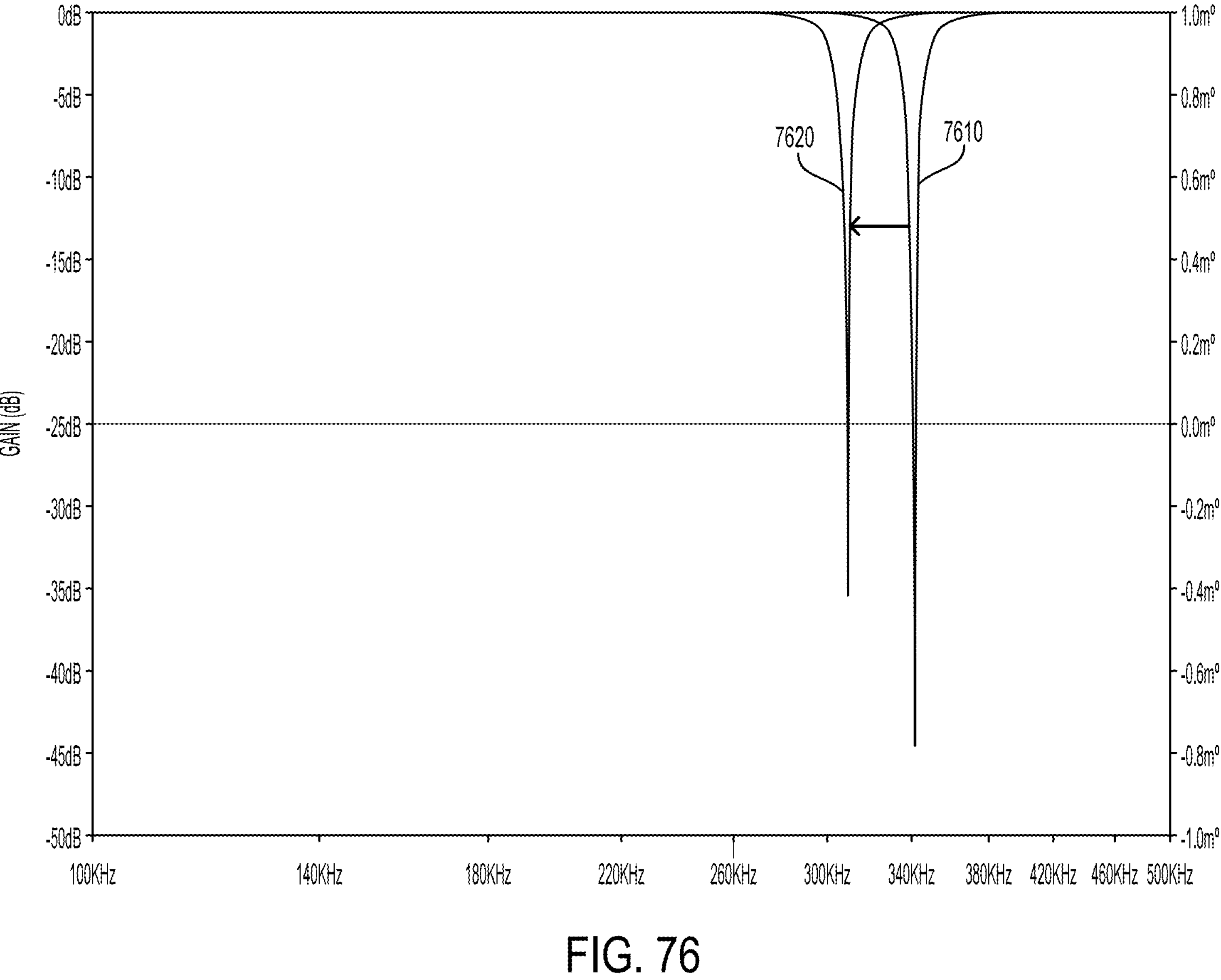
Figure 77:
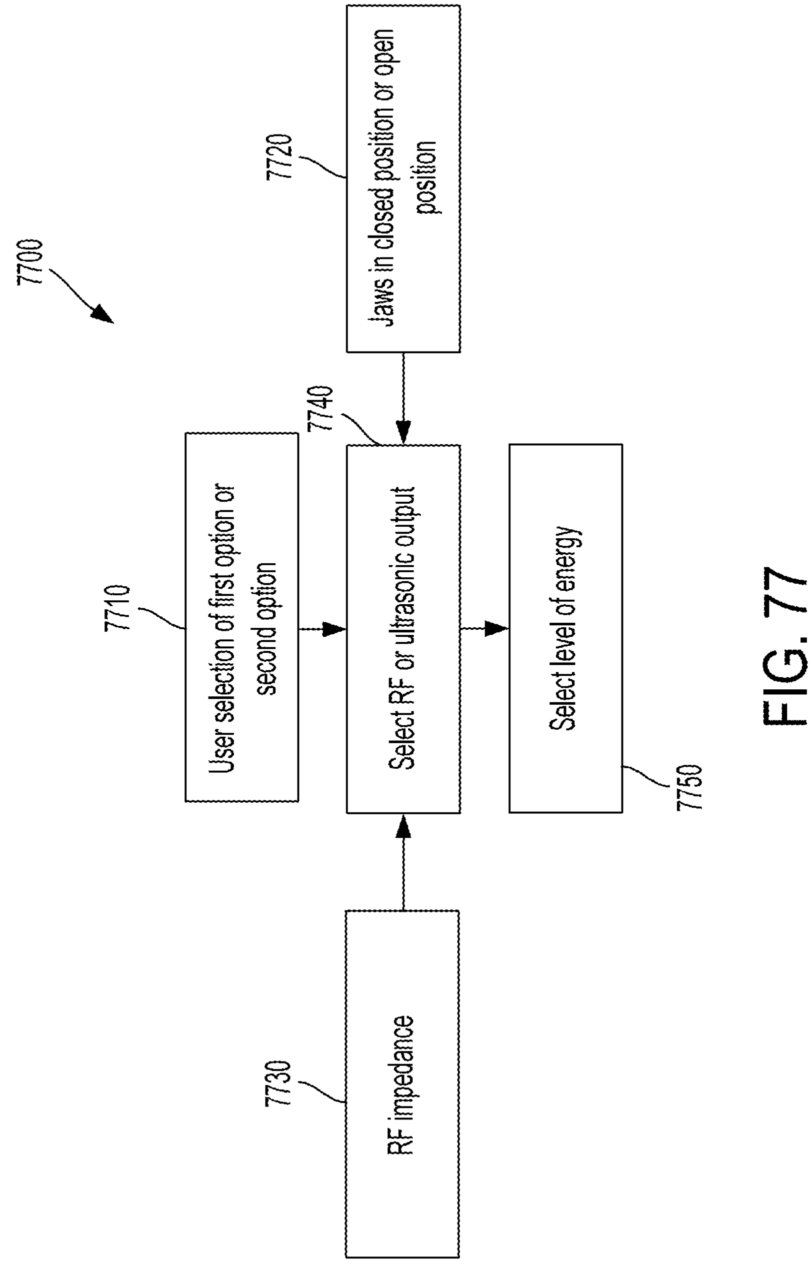
Figure 78:
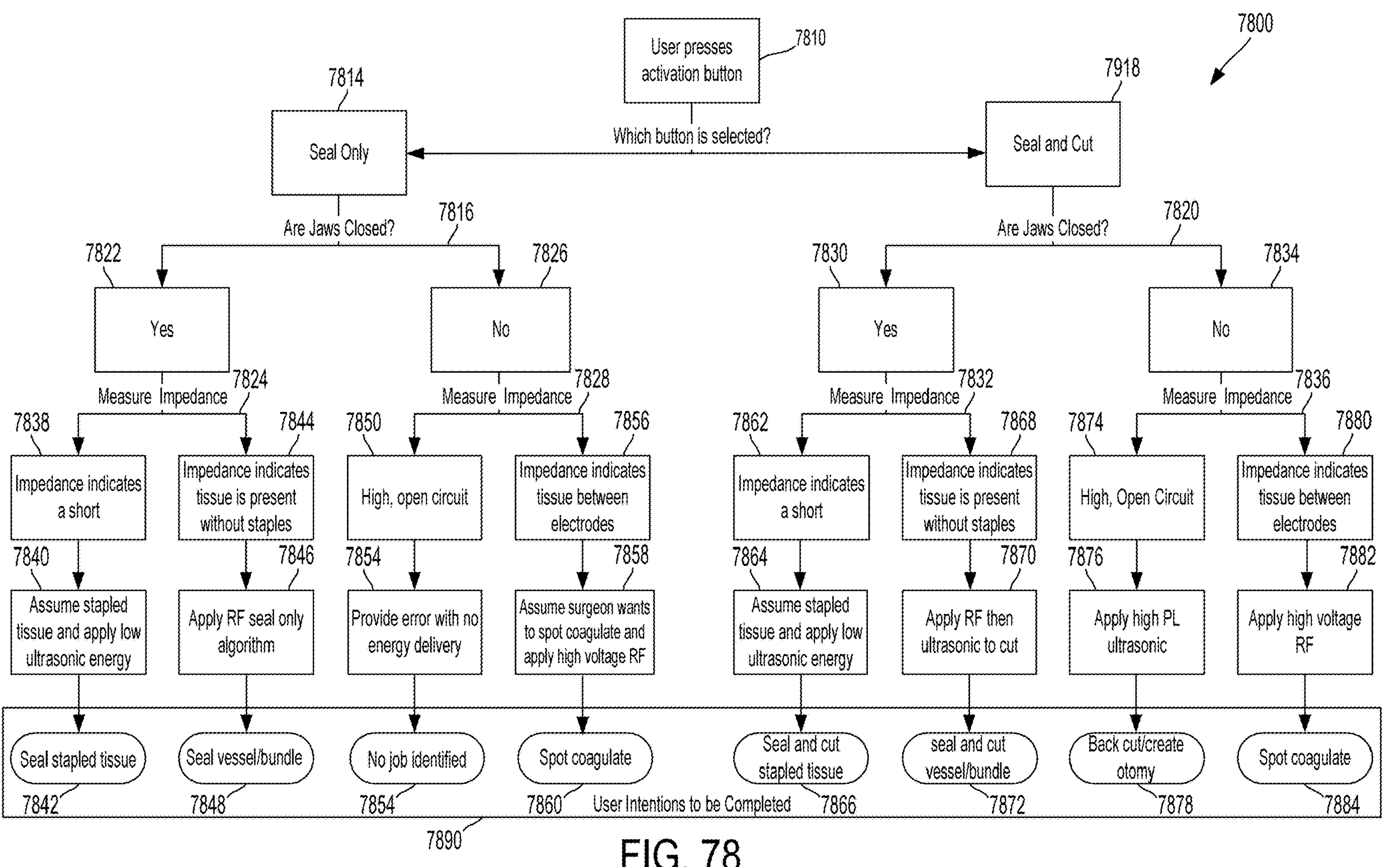
Figure 79:
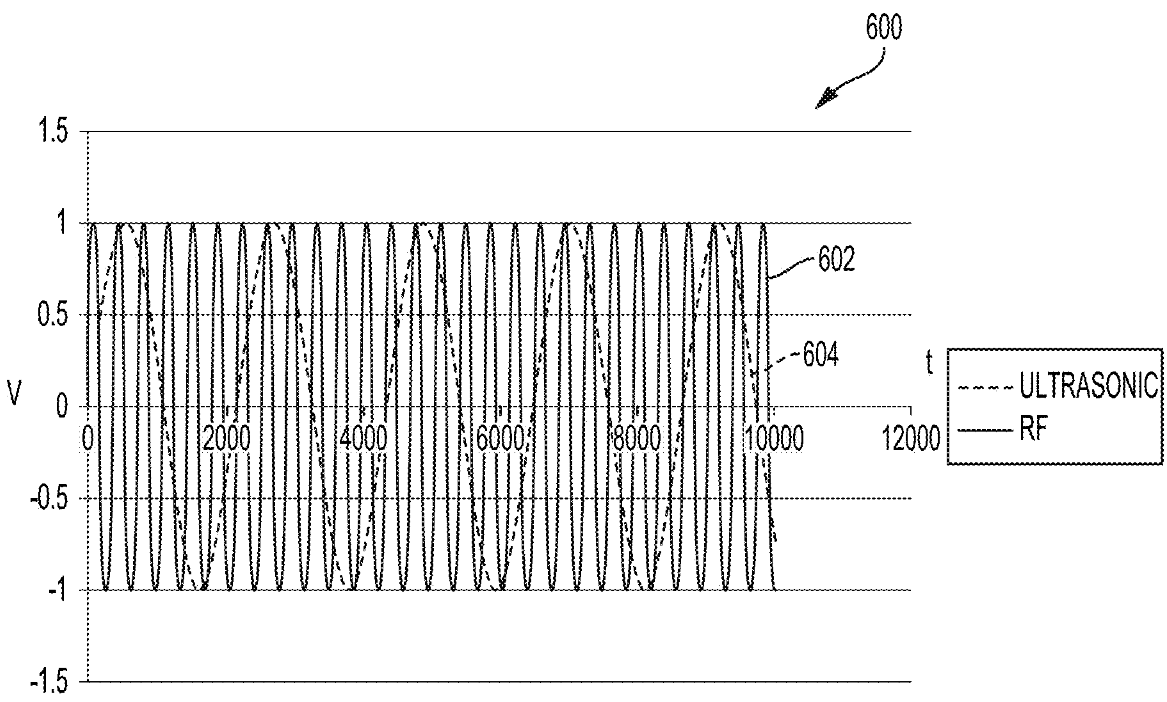
Figure 80:
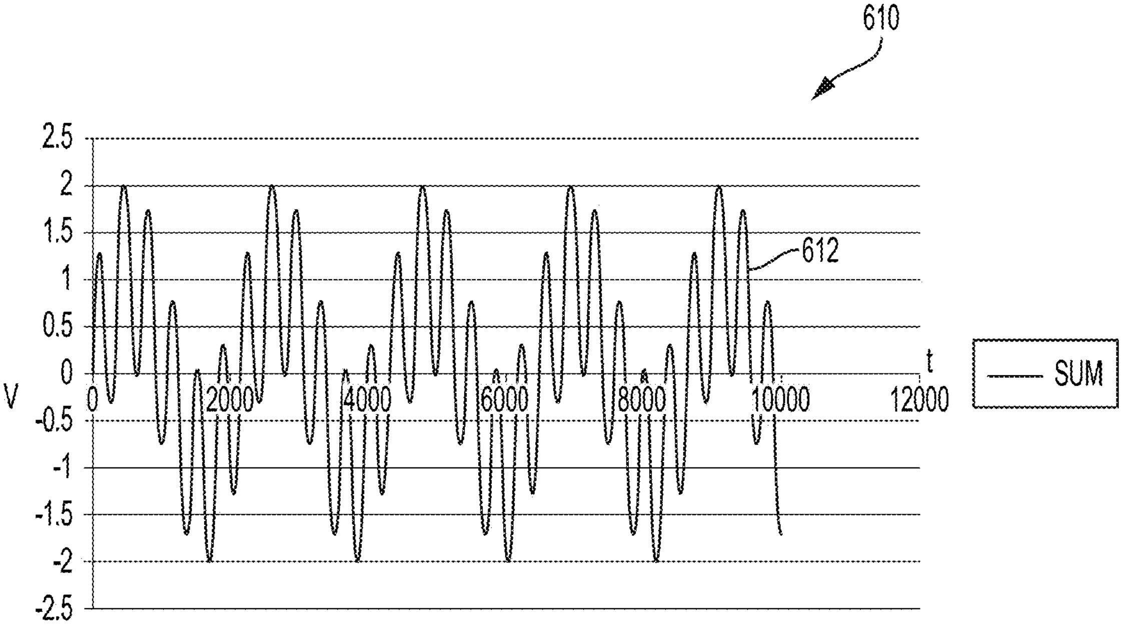
Figure 81:
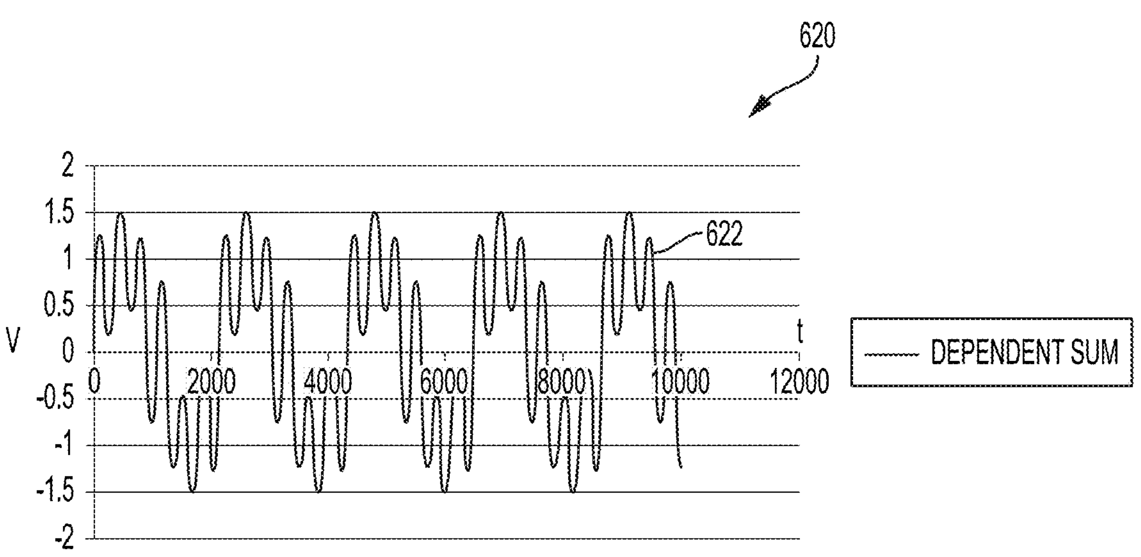
Figure 82:
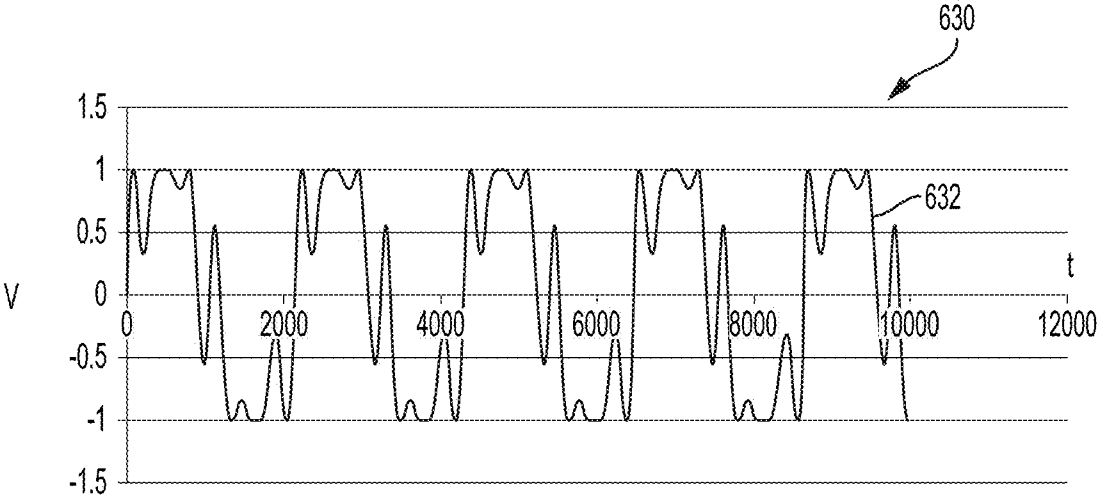
Figure 83:
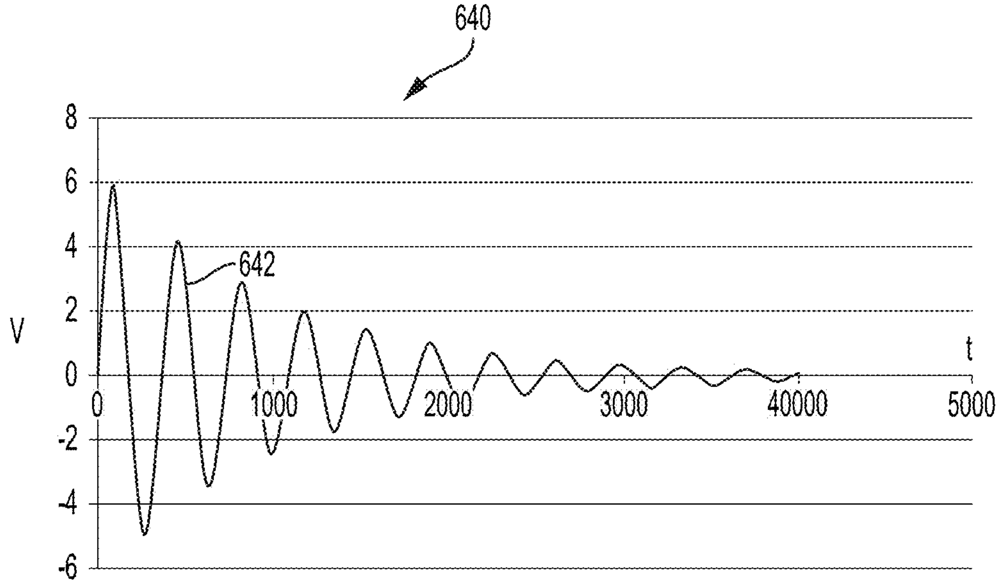

FIG. 15 displays a graph of simulation results of the circuit diagram shown in FIG. 14;

FIG. 16 displays graphs of simulation results of the circuit diagram shown in FIG. 14;

FIG. 17 displays graphs of simulation results of the circuit diagram shown in FIG. 14;

FIG. 18 displays graphs of simulation results of the circuit diagram shown in FIG. 14;

FIG. 19 displays graphs of simulation results of the circuit diagram shown in FIG. 14;

FIG. 20 displays graphs of simulation results of the circuit diagram shown in FIG. 14;

FIG. 21 displays graphs of simulation results of the circuit diagram shown in FIG. 14;

FIG. 22 is a circuit diagram, including a high frequency band stop filter, for a system that is configured to manage RF and ultrasonic currents output by a generator according to one aspect of the present disclosure;

FIG. 23 displays a graph of simulation results of the circuit diagram shown in FIG. 22;

FIG. 24 displays graphs of simulation results of the circuit diagram shown in FIG. 22;

FIG. 25 displays graphs of simulation results of the circuit diagram shown in FIG. 22;

FIG. 26 displays graphs of simulation results of the circuit diagram shown in FIG. 22;

FIG. 27 displays graphs of simulation results of the circuit diagram shown in FIG. 22;

FIG. 28 displays graphs of simulation results of the circuit diagram shown in FIG. 22;

FIG. 29 displays graphs of simulation results of the circuit diagram shown in FIG. 22;

FIG. 30 displays graphs of simulation results of the circuit diagram shown in FIG. 22;

FIG. 31 displays graphs of simulation results of the circuit diagram shown in FIG. 22;

FIG. 32 displays graphs of simulation results of the circuit diagram shown in FIG. 22;

FIG. 33 displays graphs of simulation results of the circuit diagram shown in FIG. 22;

FIG. 34 is a circuit diagram, including tuned LC circuits, for a system that is configured to manage RF and ultrasonic currents output by a generator according to one aspect of the present disclosure;

FIG. 35 is a circuit diagram, including series connected MOSFET transistors, for a system that is configured to manage RF and ultrasonic currents output by a generator according to one aspect of the present disclosure;

FIG. 36 displays a graph of simulation results of the circuit diagram shown in FIG. 35;

FIG. 37 displays graphs of simulation results of the circuit diagram shown in FIG. 35;

FIG. 38 displays graphs of simulation results of the circuit diagram shown in FIG. 35;

FIG. 39 displays graphs of simulation results of the circuit diagram shown in FIG. 35;

FIG. 40 displays graphs of simulation results of the circuit diagram shown in FIG. 35;

FIG. 41 displays a graph of simulation results of the circuit diagram shown in FIG. 35;

FIG. 42 is a circuit diagram, including a pair of MOSFET switches arranged source-source, for a system that is configured to manage RF and ultrasonic currents output by a generator according to one aspect of the present disclosure;

FIG. 43 is a circuit diagram, including series connected MOSFET transistors, for a system that is configured to manage RF and ultrasonic currents output by a generator according to one aspect of the present disclosure;

FIG. 44 displays graphs of simulation results of the circuit diagram shown in FIG. 43;

FIG. 45 displays graphs of simulation results of the circuit diagram shown in FIG. 43;

FIG. 46 displays a graph of simulation results of the circuit diagram shown in FIG. 43;

FIG. 47 displays graphs of simulation results of the circuit diagram shown in FIG. 43;

FIG. 48 displays graphs of simulation results of the circuit diagram shown in FIG. 43;

FIG. 49 displays a graph of simulation results of the circuit diagram shown in FIG. 43;

FIG. 50 is a circuit diagram, including a pair of electromechanical relays, for a system that is configured to manage RF and ultrasonic currents output by a generator according to one aspect of the present disclosure;

FIG. 51 is a circuit diagram, including a switch actuation, for a system that is configured to manage RF and ultrasonic currents output by a generator according to one aspect of the present disclosure;

FIG. 52 is a circuit diagram, including components from multiple configurations discussed in previous figures, for a system that is configured to manage RF and ultrasonic currents output by a generator according to one aspect of the present disclosure;

FIG. 53 is a circuit diagram for a system that is configured to manage RF and ultrasonic currents output by a generator according to one aspect of the present disclosure;

FIG. 54 displays graphs of simulation results of the circuit diagram shown in FIG. 53;

FIG. 55 displays graphs of simulation results of the circuit diagram shown in FIG. 53;

FIG. 56 displays graphs of simulation results of the circuit diagram shown in FIG. 53;

FIG. 57 displays graphs of simulation results of the circuit diagram shown in FIG. 53;

FIG. 58 displays graphs of simulation results of the circuit diagram shown in FIG. 53;

FIG. 59 displays graphs of simulation results of the circuit diagram shown in FIG. 53;

FIG. 60 is a circuit diagram of a notch filter for a system that is configured to manage RF and ultrasonic currents output by a generator according to one aspect of the present disclosure;

FIG. 61 is a graphical depiction of the frequency response of the circuit diagram shown in FIG. 60 according to one aspect of the present disclosure;

FIG. 62 is an illustration of a system configuration for a circuit topology, including MOSFET switches and a control circuit in the proximal plug, configured to manage RF and ultrasonic currents output by a generator according to one aspect of the present disclosure;

FIG. 63 is an illustration of a system configuration for a circuit topology, including MOSFET switches and a control circuit in the distal plug, configured to manage RF and ultrasonic currents output by a generator according to one aspect of the present disclosure;

FIG. 64 is an illustration of a system configuration for a circuit topology, including MOSFET switches and a control circuit in the distal plug and a control circuit in the handle, configured to manage RF and ultrasonic currents output by a generator according to one aspect of the present disclosure;

FIG. 65 is an illustration of a system configuration for a circuit topology, including MOSFET switches in the distal plug and a control circuit in the handle, configured to manage RF and ultrasonic currents output by a generator according to one aspect of the present disclosure;

FIG. 66 is an illustration of a system configuration for a circuit topology, including MOSFET switches and a control circuit in the handle, configured to manage RF and ultrasonic currents output by a generator according to one aspect of the present disclosure;

FIG. 67 is an illustration of a system configuration for a circuit topology, including bandstop filters in the proximal plug and a control circuit in the handle, configured to manage RF and ultrasonic currents output by a generator according to one aspect of the present disclosure;

FIG. 68 is an illustration of a system configuration for a circuit topology, including bandstop filters in the distal plug and a control circuit in the handle, configured to manage RF and ultrasonic currents output by a generator according to one aspect of the present disclosure;

FIG. 69 is an illustration of a system configuration for a circuit topology, including bandstop filters and a control circuit in the handle, configured to manage RF and ultrasonic currents output by a generator according to one aspect of the present disclosure;

FIG. 70 is an illustration of a system configuration for a circuit topology, including bandstop filters in the distal plug, a control circuit in the handle, and a DC motor in the application portion, configured to manage RF and ultrasonic currents output by a generator according to one aspect of the present disclosure;

FIG. 71 is an illustration of a system configuration for a circuit topology, including a fixed high voltage RF output in the application portion, bandstop filters in the distal plug, and a control circuit and transformer in handle, configured to manage RF and ultrasonic currents output by a generator according to one aspect of the present disclosure;

FIG. 72 is an illustration of a system configuration for a circuit topology, including a mechanically switched high voltage/low voltage RF output in the application portion, bandstop filters in distal plug, and a control circuit and transformer in the handle, configured to manage RF and ultrasonic currents output by a generator according to one aspect of the present disclosure;

FIG. 73 is an illustration of a system configuration for a circuit topology, including an electrically switched high voltage/low voltage RF output in the application portion, bandstop filters in distal plug, and a control circuit and transformer in the handle, configured to manage RF and ultrasonic currents output by a generator according to one aspect of the present disclosure;

FIG. 74 is an illustration of a system configuration for a circuit topology, including a fixed high voltage RF output in the application portion, bandstop filters in the proximal plug, and a control circuit and transformer in handle, configured to manage RF and ultrasonic currents output by a generator according to one aspect of the present disclosure;

FIG. 75 is a flow diagram illustrating a method for providing a combined signal by a generator to a surgical instrument;

FIG. 76 is a graphical depiction of the adjusted frequency response of the circuit diagram shown in FIG. 60 based on characterization of the steering circuitry according to one aspect of the present disclosure;

FIG. 77 is a block diagram illustrating the selection of operations of a surgical instrument based on various inputs;

FIG. 78 is a logic diagram illustrating specific operations of a surgical instrument selected based on various inputs;

FIG. 79 is an example graph of two waveforms of energy from a generator;

FIG. 80 is an example graph of the sum of the waveforms of FIG. 79;

FIG. 81 is an example graph of sum of the waveforms of FIG. 79 with the RF waveform dependent on the ultrasonic waveform;

FIG. 82 is an example graph of the sum of the waveforms of FIG. 79 with the RF waveform being a function of the ultrasonic waveform; and FIG. 83 is an example graph of a complex RF waveform with a high crest factor.

DESCRIPTION

In the following detailed description, reference is made to the accompanying drawings, which form a part hereof. In the drawings, similar symbols and reference characters typically identify similar components throughout the several views, unless context dictates otherwise. The illustrative aspects described in the detailed description, drawings, and claims are not meant to be limiting. Other aspects may be utilized, and other changes may be made, without departing from the scope of the subject matter presented here.

Before explaining the various aspects of the present disclosure in detail, it should be noted that the various aspects disclosed herein are not limited in their application or use to the details of construction and arrangement of parts illustrated in the accompanying drawings and description. Rather, the disclosed aspects may be positioned or incorporated in other aspects, variations and modifications thereof, and may be practiced or carried out in various ways. Accordingly, aspects disclosed herein are illustrative in nature and are not meant to limit the scope or application thereof. Furthermore, unless otherwise indicated, the terms and expressions employed herein have been chosen for the purpose of describing the aspects for the convenience of the reader and are not to limit the scope thereof. In addition, it should be understood that any one or more of the disclosed aspects, expressions of aspects, and/or examples thereof, can be combined with any one or more of the other disclosed aspects, expressions of aspects, and/or examples thereof, without limitation.

Also, in the following description, it is to be understood that terms such as front, back, inside, outside, top, bottom and the like are words of convenience and are not to be construed as limiting terms. Terminology used herein is not meant to be limiting insofar as devices described herein, or portions thereof, may be attached or utilized in other orientations. The various aspects will be described in more detail with reference to the drawings.

This application is related to the following commonly owned patent application filed on Sep. 14, 2016:

U.S. patent application Ser. No. 15/265,279, titled TECHNIQUES FOR OPERATING GENERATOR FOR DIGITALLY GENERATING ELECTRICAL SIGNAL WAVEFORMS AND SURGICAL INSTRUMENTS, by Wiener et al., now U.S. Patent Application Publication No. 2017/0086914.

This application is related to the following commonly owned patent applications filed on Sep. 7, 2016:

U.S. patent application Ser. No. 15/258,570, titled CIRCUIT TOPOLOGIES FOR COMBINED GENERATOR, by Wiener et al., now U.S. Patent Application Publication No. 2017/0086908;

U.S. patent application Ser. No. 15/258,578, titled CIRCUITS FOR SUPPLYING ISOLATED DIRECT CURRENT (DC) VOLTAGE TO SURGICAL INSTRUMENTS, by Wiener et al., now U.S. Patent Application Publication No. 2017/0086911;

U.S. patent application Ser. No. 15/258,586, titled FREQUENCY AGILE GENERATOR FOR A SURGICAL INSTRUMENT, by Yates et al., now U.S. Patent Application Publication No. 2017/0086909;

U.S. patent application Ser. No. 15/258,598, titled METHOD AND APPARATUS FOR SELECTING OPERATIONS OF A SURGICAL INSTRUMENT BASED ON USER INTENTION, by Asher et al., now U.S. Patent Application Publication No. 2017/0086876;

U.S. patent application Ser. No. 15/258,569, titled GENERATOR FOR DIGITALLY GENERATING ELECTRICAL SIGNAL WAVEFORMS FOR ELECTROSURGICAL AND ULTRASONIC SURGICAL INSTRUMENTS, by Wiener et al., now U.S. Pat. No. 10,194,973;

U.S. patent application Ser. No. 15/258,611, titled GENERATOR FOR DIGITALLY GENERATING COMBINED ELECTRICAL SIGNAL WAVEFORMS FOR ULTRASONIC SURGICAL INSTRUMENTS, by Wiener et al., now U.S. Patent Application Publication No. 2017/0086912;

U.S. patent application Ser. No. 15/258,650, titled PROTECTION TECHNIQUES FOR GENERATOR FOR DIGITALLY GENERATING ELECTROSURGICAL AND ULTRASONIC DIGITAL ELECTRICAL SIGNAL WAVEFORMS, by Yates et al., now U.S. Patent Application Publication No. 2017/0086913;

each of which is incorporated herein by reference in its entirety.

This application also is related to the following commonly owned patent applications filed on Jun. 9, 2016:

U.S. patent application Ser. No. 15/177,430, titled SURGICAL INSTRUMENT WITH USER ADAPTABLE TECHNIQUES, now U.S. Patent Application Publication No. 2017/0000541;

U.S. patent application Ser. No. 15/177,439, titled SURGICAL INSTRUMENT WITH USER ADAPTABLE TECHNIQUES BASED ON TISSUE TYPE, now U.S. Patent Application Publication No. 2017/0000516, now U.S. Patent Application Publication No. 2017/0000553;

U.S. patent application Ser. No. 15/177,449, titled SURGICAL SYSTEM WITH USER ADAPTABLE TECHNIQUES EMPLOYING MULTIPLE ENERGY MODALITIES BASED ON TISSUE;

U.S. patent application Ser. No. 15/177,456, titled SURGICAL SYSTEM WITH USER ADAPTABLE TECHNIQUES BASED ON TISSUE IMPEDANCE, now U.S. Patent Application Publication No. 2017/0000542;

U.S. patent application Ser. No. 15/177,466, titled SURGICAL SYSTEM WITH USER ADAPTABLE TECHNIQUES EMPLOYING SIMULTANEOUS ENERGY MODALITIES BASED ON TISSUE PARAMETERS, now U.S. Patent Application Publication No. 2017/0000554;

each of which is incorporated herein by reference in its entirety.

Figure 1:
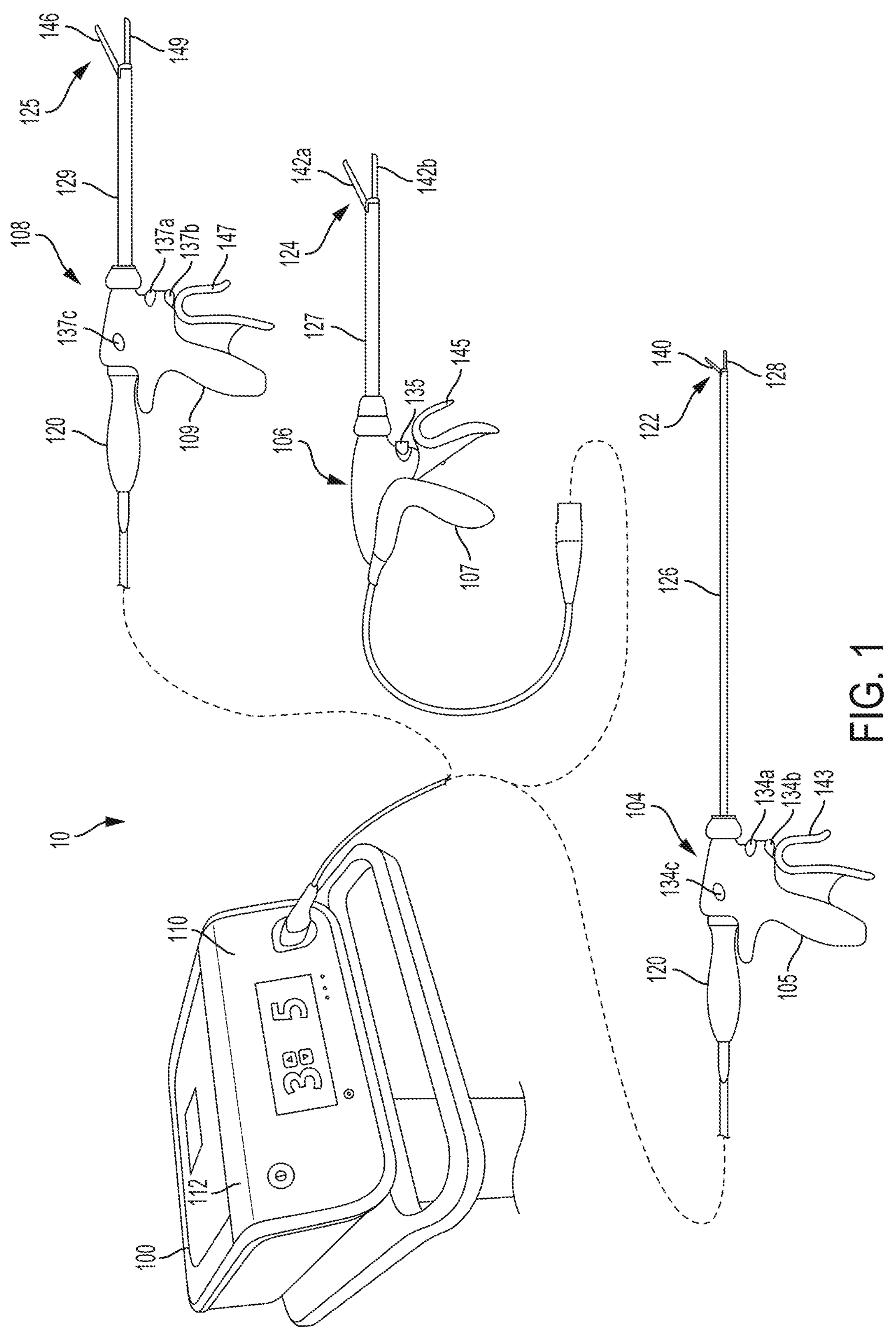
FIG. 1 illustrates one form of a surgical system comprising a generator and various surgical instruments usable therewith.
Figure 2:
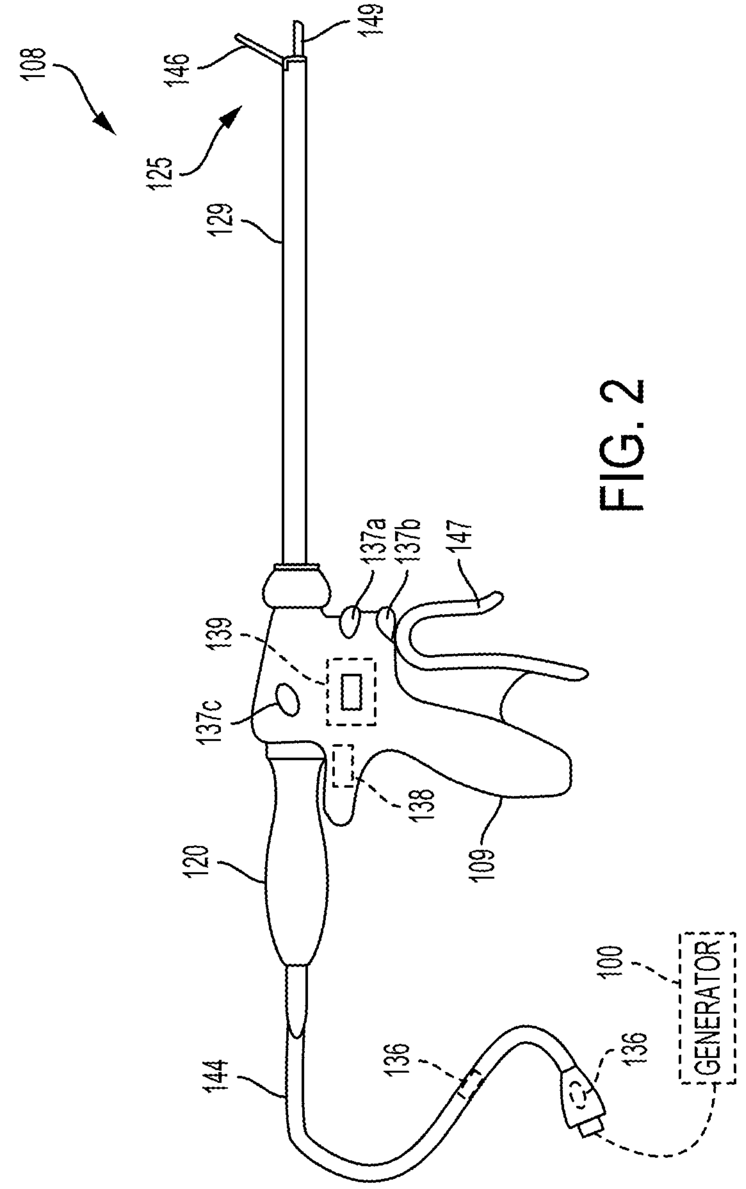
FIG. 2 is a diagram of the combination electrosurgical and ultrasonic instrument shown in FIG. 1.

With reference to FIGS. 1-5, one form of a surgical system 10 including a surgical instrument is illustrated. FIG. 1 illustrates one form of a surgical system 10 comprising a generator 100 and various surgical instruments 104, 106, 108 usable therewith, where the surgical instrument 104 is an ultrasonic surgical instrument, the surgical instrument 106 is an RF electrosurgical instrument 106, and the multifunction surgical instrument 108 is a combination ultrasonic/RF electrosurgical instrument. FIG. 2 is a diagram of the multifunction surgical instrument 108 shown in FIG. 1. With reference to both FIGS. 1 and 2, the generator 100 is configurable for use with a variety of surgical instruments.

According to various forms, the generator 100 may be configurable for use with different surgical instruments of different types including, for example, ultrasonic surgical instruments 104, RF electrosurgical instruments 106, and multifunction surgical instruments 108 that integrate RF and ultrasonic energies delivered simultaneously from the generator 100. Although in the form of FIG. 1, the generator 100 is shown separate from the surgical instruments 104, 106, 108 in one form, the generator 100 may be formed integrally with any of the surgical instruments 104, 106, 108 to form a unitary surgical system. The generator 100 comprises an input device 110 located on a front panel of the generator 100 console. The input device 110 may comprise any suitable device that generates signals suitable for programming the operation of the generator 100.

FIG. 1 illustrates a generator 100 configured to drive multiple surgical instruments 104, 106, 108. The first surgical instrument 104 is an ultrasonic surgical instrument 104 and comprises a handpiece 105 (HP), an ultrasonic transducer 120, a shaft 126, and an end effector 122. The end effector 122 comprises an ultrasonic blade 128 acoustically coupled to the ultrasonic transducer 120 and a clamp arm 140. The handpiece 105 comprises a trigger 143 to operate the clamp arm 140 and a combination of the toggle buttons 134*a*, 134*b*, 134*c* to energize and drive the ultrasonic blade 128 or other function. The toggle buttons 134*a*, 134*b*, 134*c* can be configured to energize the ultrasonic transducer 120 with the generator 100.

Still with reference to FIG. 1, the generator 100 also is configured to drive a second surgical instrument 106. The second surgical instrument 106 is an RF electrosurgical instrument and comprises a handpiece 107 (HP), a shaft 127, and an end effector 124. The end effector 124 comprises electrodes in the clamp arms 142*a*, 142*b* and return through an electrical conductor portion of the shaft 127. The electrodes are coupled to and energized by a bipolar energy source within the generator 100. The handpiece 107 comprises a trigger 145 to operate the clamp arms 142*a*, 142*b* and an energy button 135 to actuate an energy switch to energize the electrodes in the end effector 124.

Still with reference to FIG. 1, the generator 100 also is configured to drive a multifunction surgical instrument 108. The multifunction surgical instrument 108 comprises a handpiece 109 (HP), a shaft 129, and an end effector 125. The end effector comprises an ultrasonic blade 149 and a clamp arm 146. The ultrasonic blade 149 is acoustically coupled to the ultrasonic transducer 120. The handpiece 109 comprises a trigger 147 to operate the clamp arm 146 and a combination of the toggle buttons 137*a*, 137*b*, 137*c* to energize and drive the ultrasonic blade 149 or other function. The toggle buttons 137*a*, 137*b*, 137*c* can be configured to energize the ultrasonic transducer 120 with the generator 100 and energize the ultrasonic blade 149 with a bipolar energy source also contained within the generator 100.

With reference to both FIGS. 1 and 2, the generator 100 is configurable for use with a variety of surgical instruments. According to various forms, the generator 100 may be configurable for use with different surgical instruments of different types including, for example, the ultrasonic surgical instrument 104, the RF electrosurgical instrument 106, and the multifunction surgical instrument 108 that integrate RF and ultrasonic energies delivered simultaneously from the generator 100. Although in the form of FIG. 1, the generator 100 is shown separate from the surgical instruments 104, 106, 108, in one form, the generator 100 may be formed integrally with any one of the surgical instruments 104, 106, 108 to form a unitary surgical system. The generator 100 comprises an input device 110 located on a front panel of the generator 100 console. The input device 110 may comprise any suitable device that generates signals suitable for programming the operation of the generator 100. The generator 100 also may comprise one or more output devices 112.

With reference now to FIG. 2, the generator 100 is coupled to the multifunction surgical instrument 108. The generator 100 is coupled to the ultrasonic transducer 120 and electrodes located in the clamp arm 146 via a cable 144. The ultrasonic transducer 120 and a waveguide extending through a shaft 129 (waveguide not shown in FIG. 2) may collectively form an ultrasonic drive system driving an ultrasonic blade 149 of an end effector 125. The end effector 125 further may comprise a clamp arm 146 to clamp tissue located between the clamp arm 146 and the ultrasonic blade 149. The clamp arm 146 comprises one or more than one an electrode coupled to the a pole of the generator 100 (e.g., a positive pole). The ultrasonic blade 149 forms the second pole (e.g., the negative pole) and is also coupled to the generator 100. RF energy is applied to the electrode(s) in the clamp arm 146, through the tissue located between the clamp arm 146 and the ultrasonic blade 149, and through the ultrasonic blade 149 back to the generator 100 via the cable 144. In one form, the generator 100 may be configured to produce a drive signal of a particular voltage, current, and/or frequency output signal that can be varied or otherwise modified with high resolution, accuracy, and repeatability suitable for driving an ultrasonic transducer 120 and applying RF energy to tissue.

Still with reference to FIG. 2, It will be appreciated that the multifunction surgical instrument 108 may comprise any combination of the toggle buttons 137*a*, 137*b*, 134*c*. For example, the multifunction surgical instrument 108 could be configured to have only two toggle buttons: a toggle button 137*a* for producing maximum ultrasonic energy output and a toggle button 137*b* for producing a pulsed output at either the maximum or less than maximum power level. In this way, the drive signal output configuration of the generator 100 could be 5 continuous signals and 5 or 4 or 3 or 2 or 1 pulsed signals. In certain forms, the specific drive signal configuration may be controlled based upon, for example, nonvolatile memory such as an electrically erasable programmable read only memory (EEPROM) settings in the generator 100 and/or user power level selection(s).

In certain forms, a two-position switch may be provided as an alternative to a toggle button 137*c*. For example, the multifunction surgical instrument 108 may include a toggle button 137*a* for producing a continuous output at a maximum power level and a two-position toggle button 137*b*. In a first detented position, toggle button 137*b* may produce a continuous output at a less than maximum power level, and in a second detented position the toggle button 137*b* may produce a pulsed output (e.g., at either a maximum or less than maximum power level, depending upon the EEPROM settings). Any one of the buttons 137*a*, 137*b*, 137*c* may be configured to activate RF energy and apply the RF energy to the end effector 125.

Still with reference to FIG. 2, forms of the generator 100 may enable communication with instrument-based data circuits. For example, the generator 100 may be configured to communicate with a first data circuit 136 and/or a second data circuit 138. For example, the first data circuit 136 may indicate a burn-in frequency slope, as described herein. Additionally or alternatively, any type of information may be communicated to second data circuit for storage therein via a data circuit interface (e.g., using a logic device). Such information may comprise, for example, an updated number of operations in which the instrument has been used and/or dates and/or times of its usage. In certain forms, the second data circuit may transmit data acquired by one or more sensors (e.g., an instrument-based temperature sensor). In certain forms, the second data circuit may receive data from the generator 100 and provide an indication to a user (e.g., a light emitting diode (LED) indication or other visible indication) based on the received data. The second data circuit 138 contained in the multifunction surgical instrument 108. In some forms, the second data circuit 138 may be implemented in a many similar to that of the first data circuit 136 described herein. An instrument interface circuit may comprise a second data circuit interface to enable this communication. In one form, the second data circuit interface may comprise a tri-state digital interface, although other interfaces also may be used. In certain forms, the second data circuit may generally be any circuit for transmitting and/or receiving data. In one form, for example, the second data circuit may store information pertaining to the particular surgical instrument 104, 106, 108 with which it is associated. Such information may include, for example, a model number, a serial number, a number of operations in which the surgical instrument 104, 106, 108 has been used, and/or any other type of information. In the example of FIG. 2, the second data circuit 138 may store information about the electrical and/or ultrasonic properties of an associated ultrasonic transducer 120, end effector 125, ultrasonic energy drive system, or RF electrosurgical energy drive system. Various processes and techniques described herein may be executed by a generator. It will be appreciated, however, that in certain example forms, all or a part of these processes and techniques may be performed by internal logic 139 located in the multifunction surgical instrument 108.

Figure 3:
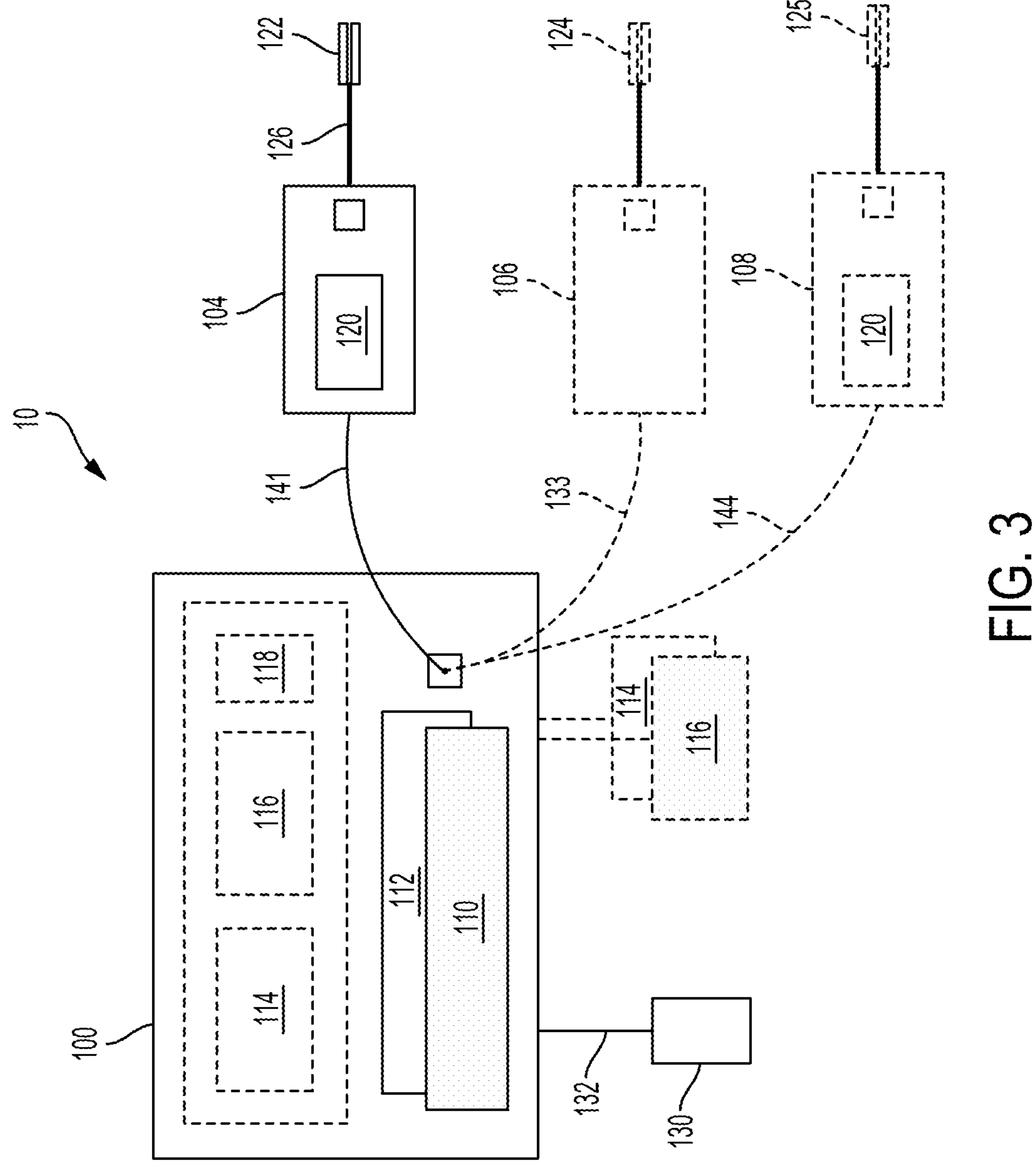
FIG. 3 is a diagram of the surgical system shown in FIG. 1.

FIG. 3 is a diagram of the surgical system 10 of FIG. 1. In various forms, the generator 100 may comprise several separate functional elements, such as modules and/or blocks. Different functional elements or modules may be configured for driving the different kinds of surgical instruments 104, 106, 108. For example, an ultrasonic drive circuit 114 may drive ultrasonic devices such as the surgical instrument 104 via a cable 141. An electrosurgery/RF drive circuit 116 may drive the RF electrosurgical instrument 106 via a cable 133. The respective drive circuits 114, 116, 118 may be combined as a combined RF/ultrasonic drive circuit 118 to generate both respective drive signals for driving multifunction surgical instruments 108 via a cable 144. In various forms, the ultrasonic drive circuit 114 and/or the electrosurgery/RF drive circuit 116 each may be formed integrally or externally with the generator 100. Alternatively, one or more of the drive circuits 114, 116, 118 may be provided as a separate circuit module electrically coupled to the generator 100. (The drive circuits 114, 116, 118 are shown in phantom to illustrate this option.) Also, in some forms, the electrosurgery/RF drive circuit 116 may be formed integrally with the ultrasonic drive circuit 114, or vice versa. Also, in some forms, the generator 100 may be omitted entirely and the drive circuits 114, 116, 118 may be executed by processors or other hardware within the respective surgical instruments 104, 106, 108.

In other forms, the electrical outputs of the ultrasonic drive circuit 114 and the electrosurgery/RF drive circuit 116 may be combined into a single electrical signal capable of driving the multifunction surgical instrument 108 simultaneously with electrosurgical RF and ultrasonic energies. This single electrical drive signal may be produced by the combination drive circuit 118. The multifunction surgical instrument 108 comprises an ultrasonic transducer 120 coupled to an ultrasonic blade and one or more electrodes in the end effector 125 to receive ultrasonic and electrosurgical RF energy. The multifunction surgical instrument 108 comprises signal processing components to split the combined RF/ultrasonic energy signal such that the RF signal can be delivered to the electrodes in the end effector 125 and the ultrasonic signal can be delivered to the ultrasonic transducer 120.

In accordance with the described forms, the ultrasonic drive circuit 114 may produce a drive signal or signals of particular voltages, currents, and frequencies, e.g., 55,500 cycles per second (Hz). The drive signal or signals may be provided to the ultrasonic surgical instrument 104, and specifically to the ultrasonic transducer 120, which may operate, for example, as described above. The ultrasonic transducer 120 and a waveguide extending through the shaft 126 (waveguide not shown) may collectively form an ultrasonic drive system driving an ultrasonic blade 128 of an end effector 122. In one form, the generator 100 may be configured to produce a drive signal of a particular voltage, current, and/or frequency output signal that can be stepped or otherwise modified with high resolution, accuracy, and repeatability.

The generator 100 may be activated to provide the drive signal to the ultrasonic transducer 120 in any suitable manner. For example, the generator 100 may comprise a foot switch 130 coupled to the generator 100 via a foot switch cable 132. A clinician may activate the ultrasonic transducer 120 by depressing the foot switch 130. In addition, or instead of the foot switch 130 some forms of the ultrasonic surgical instrument 104 may utilize one or more switches positioned on the handpiece that, when activated, may cause the generator 100 to activate the ultrasonic transducer 120. In one form, for example, the one or more switches may comprise a pair of toggle buttons 137*a*, 137*b* (FIG. 2), for example, to determine an operating mode of the ultrasonic surgical instrument 104. When the toggle button 137*a* is depressed, for example, the generator 100 may provide a maximum drive signal to the ultrasonic transducer 120, causing it to produce maximum ultrasonic energy output. Depressing toggle button 137*b* may cause the generator 100 to provide a user-selectable drive signal to the ultrasonic transducer 120, causing it to produce less than the maximum ultrasonic energy output.

Additionally or alternatively, the one or more switches may comprise a toggle button 137*c* that, when depressed, causes the generator 100 to provide a pulsed output. The pulses may be provided at any suitable frequency and grouping, for example. In certain forms, the power level of the pulses may be the power levels associated with toggle buttons 137*a*, 137*b* (maximum, less than maximum), for example.

It will be appreciated that the ultrasonic surgical instrument 104 and/or the multifunction surgical instrument 108 may comprise any combination of the toggle buttons 137*a*, 137*b*, 137*c*. For example, the multifunction surgical instrument 108 could be configured to have only two toggle buttons: a toggle button 137*a* for producing maximum ultrasonic energy output and a toggle button 137*c* for producing a pulsed output at either the maximum or less than maximum power level. In this way, the drive signal output configuration of the generator 100 could be 5 continuous signals and 5 or 4 or 3 or 2 or 1 pulsed signals. In certain forms, the specific drive signal configuration may be controlled based upon, for example, EEPROM settings in the generator 100 and/or user power level selection(s).

In certain forms, a two-position switch may be provided as an alternative to a toggle button 137*c*. For example, the ultrasonic surgical instrument 104 may include a toggle button 137*a* for producing a continuous output at a maximum power level and a two-position toggle button 137*b*. In a first detented position, toggle button 137*b* may produce a continuous output at a less than maximum power level, and in a second detented position the toggle button 137*b* may produce a pulsed output (e.g., at either a maximum or less than maximum power level, depending upon the EEPROM settings).

In accordance with the described forms, the electrosurgery/RF drive circuit 116 may generate a drive signal or signals with output power sufficient to perform bipolar electrosurgery using RF energy. In bipolar electrosurgery applications, the drive signal may be provided, for example, to electrodes located in the end effector 124 of the RF electrosurgical instrument 106, for example. Accordingly, the generator 100 may be configured for therapeutic purposes by applying electrical energy to the tissue sufficient for treating the tissue (e.g., coagulation, cauterization, tissue welding). The generator 100 may be configured for sub-therapeutic purposes by applying electrical energy to the tissue for monitoring parameters of the tissue during a procedure.

As previously discussed, the combination drive circuit 118 may be configured to drive both ultrasonic and RF electrosurgical energies. The ultrasonic and RF electrosurgical energies may be delivered though separate output ports of the generator 100 as separate signals or though a single port of the generator 100 as a single signal that is a combination of the ultrasonic and RF electrosurgical energies. In the latter case, the single signal can be separated by circuits located in the surgical instruments 104, 106, 108.

The surgical instruments 104, 106, 108 additionally or alternatively may comprise a switch to indicate a position of a jaw closure trigger for operating jaws of the end effector 122, 124, 125. Also, in some forms, the generator 100 may be activated based on the position of the jaw closure trigger, (e.g., as the clinician depresses the jaw closure trigger to close the jaws, ultrasonic energy may be applied).

The generator 100 may comprise an input device 110 (FIG. 1) located, for example, on a front panel of the generator 100 console. The input device 110 may comprise any suitable device that generates signals suitable for programming the operation of the generator 100. In operation, the user can program or otherwise control operation of the generator 100 using the input device 110. The input device 110 may comprise any suitable device that generates signals that can be used by the generator (e.g., by one or more processors contained in the generator) to control the operation of the generator 100 (e.g., operation of the ultrasonic drive circuit 114, electrosurgery/RF drive circuit 116, combined RF/ultrasonic drive circuit 118). In various forms, the input device 110 includes one or more of buttons, switches, thumbwheels, keyboard, keypad, touch screen monitor, pointing device, remote connection to a general purpose or dedicated computer. In other forms, the input device 110 may comprise a suitable user interface, such as one or more user interface screens displayed on a touch screen monitor, for example. Accordingly, by way of the input device 110, the user can set or program various operating parameters of the generator, such as, for example, current (I), voltage (V), frequency (f), and/or period (T) of a drive signal or signals generated by the ultrasonic drive circuit 114 and/or electrosurgery/RF drive circuit 116.

The generator 100 also may comprise an output device 112 (FIG. 1), such as an output indicator, located, for example, on a front panel of the generator 100 console. The output device 112 includes one or more devices for providing a sensory feedback to a user. Such devices may comprise, for example, visual feedback devices (e.g., a visual feedback device may comprise incandescent lamps, LEDs, graphical user interface, display, analog indicator, digital indicator, bar graph display, digital alphanumeric display, liquid crystal display (LCD) screen, light emitting diode (LED) indicators), audio feedback devices (e.g., an audio feedback device may comprise speaker, buzzer, audible, computer generated tone, computerized speech, voice user interface (VUI) to interact with computers through a voice/speech platform), or tactile feedback devices (e.g., a tactile feedback device comprises any type of vibratory feedback, haptic actuator).

Although certain modules and/or blocks of the generator 100 may be described by way of example, it can be appreciated that a greater or lesser number of modules and/or blocks may be used and still fall within the scope of the forms. Further, although various forms may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components. Also, in some forms, the various modules described herein may be implemented utilizing similar hardware positioned within the surgical instruments 104, 106, 108 (i.e., the external generator 100 may be omitted).

In one form, the ultrasonic drive circuit 114, electrosurgery/RF drive circuit 116, and/or the combination drive circuit 118 may comprise one or more embedded applications implemented as firmware, software, hardware, or any combination thereof. The drive circuits 114, 116, 118 may comprise various executable modules such as software, programs, data, drivers, application program interfaces (APIs), and so forth. The firmware may be stored in nonvolatile memory (NVM), such as in bit masked read-only memory (ROM) or flash memory. In various implementations, storing the firmware in ROM may preserve flash memory. The NVM may comprise other types of memory including, for example, programmable ROM (PROM), erasable programmable ROM (EPROM), electrically erasable programmable read only memory (EEPROM), or battery backed random-access memory (RAM) such as dynamic RAM (DRAM), Double-Data-Rate DRAM (DDRAM), and/or synchronous DRAM (SDRAM).

In one form, the drive circuits 114, 116, 118 comprise a hardware component implemented as a processor for executing program instructions for monitoring various measurable characteristics of the surgical instruments 104, 106, 108 and generating a corresponding output control signals for operating the surgical instruments 104, 106, 108. In forms in which the generator 100 is used in conjunction with the multifunction surgical instrument 108, the output control signal may drive the ultrasonic transducer 120 in cutting and/or coagulation operating modes. Electrical characteristics of the multifunction surgical instrument 108 and/or tissue may be measured and used to control operational aspects of the generator 100 and/or provided as feedback to the user. In forms in which the generator 100 is used in conjunction with the multifunction surgical instrument 108, the output control signal may supply electrical energy (e.g., RF energy) to the end effector 125 in cutting, coagulation and/or desiccation modes. Electrical characteristics of the multifunction surgical instrument 108 and/or tissue may be measured and used to control operational aspects of the generator 100 and/or provide feedback to the user. In various forms, as previously discussed, the hardware component may be implemented as a DSP, PLD, ASIC, circuits, and/or registers. In one form, the processor may be configured to store and execute computer software program instructions to generate the output signals for driving various components of the surgical instruments 104, 106, 108, such as the ultrasonic transducer 120 and the end effectors 122, 124, 125.

Figure 4:
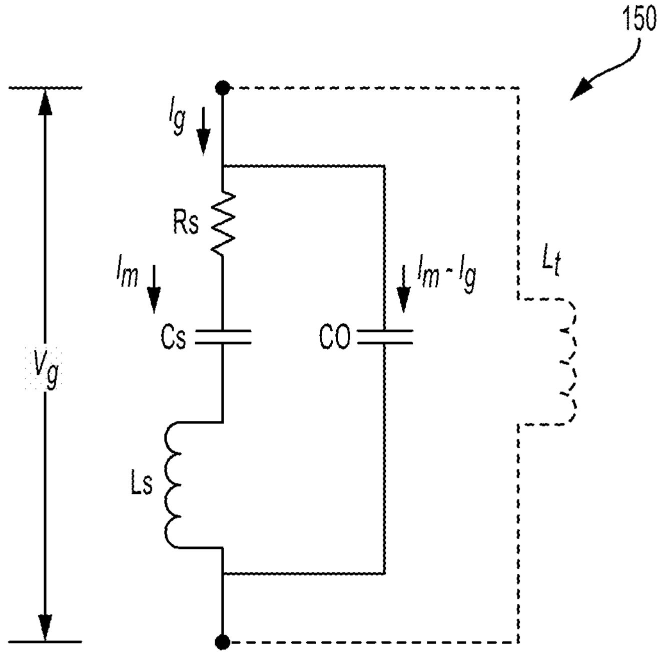
FIG. 4 is a model illustrating motional branch current in one form.

FIG. 4 illustrates an equivalent circuit 150 of an ultrasonic transducer, such as the ultrasonic transducer 120, according to one form. The equivalent circuit 150 comprises a first "motional" branch having a serially connected inductance $L_s$, resistance $R_s$ and capacitance $C_s$ that define the electromechanical properties of the resonator, and a second capacitive branch having a static capacitance $C_o$. Drive current $I_g$ may be received from a generator at a drive voltage $V_g$, with motional current $I_m$ flowing through the first branch and current $I_g$-$I_m$ flowing through the capacitive branch. Control of the electromechanical properties of the ultrasonic transducer may be achieved by suitably controlling $I_g$ and $V_g$. As explained above, conventional generator architectures may include a tuning inductor $L_t$ (shown in phantom in FIG. 4) for tuning out in a parallel resonance circuit the static capacitance Co at a resonant frequency so that substantially all of generator's current output $I_g$ flows through the motional branch. In this way, control of the motional branch current $I_m$ is achieved by controlling the generator current output $I_g$. The tuning inductor $L_t$ is specific to the static capacitance $C_o$ of an ultrasonic transducer, however, and a different ultrasonic transducer having a different static capacitance requires a different tuning inductor $L_t$. Moreover, because the tuning inductor $L_t$ is matched to the nominal value of the static capacitance Co at a single resonant frequency, accurate control of the motional branch current $I_m$ is assured only at that frequency, and as frequency shifts down with transducer temperature, accurate control of the motional branch current is compromised.

Forms of the generator 100 do not rely on a tuning inductor $L_t$ to monitor the motional branch current $I_m$. Instead, the generator 100 may use the measured value of the static capacitance $C_o$ in between applications of power for a specific ultrasonic surgical instrument 104 (along with drive signal voltage and current feedback data) to determine values of the motional branch current $I_m$ on a dynamic and ongoing basis (e.g., in real-time). Such forms of the generator 100 are therefore able to provide virtual tuning to simulate a system that is tuned or resonant with any value of static capacitance $C_o$ at any frequency, and not just at single resonant frequency dictated by a nominal value of the static capacitance $C_o$.

Figure 5:
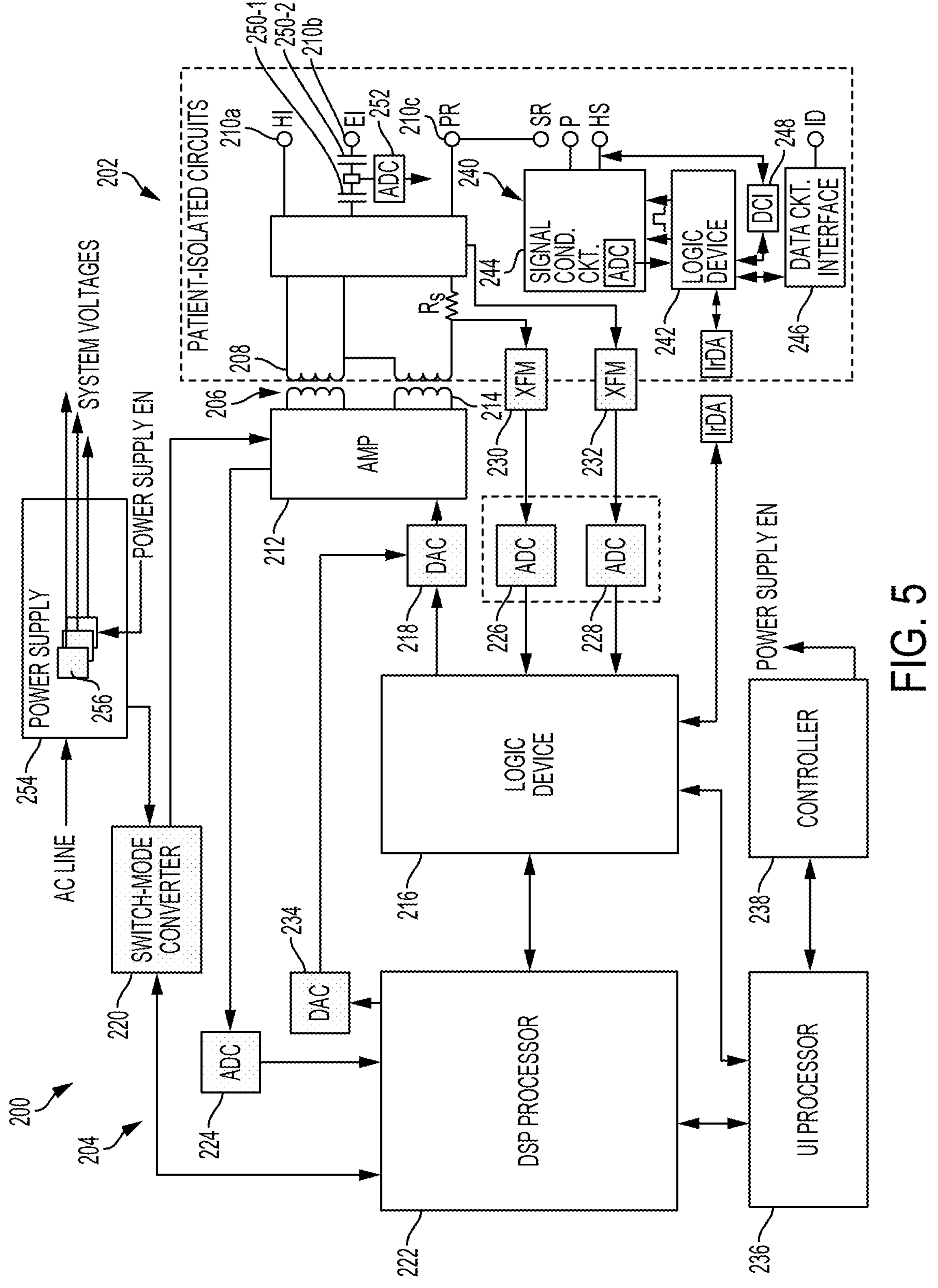
FIG. 5 is a structural view of a generator architecture in one form.

FIG. 5 is a simplified block diagram of a generator 200, which is one form of the generator 100 (FIGS. 1-3). The generator 200 is configured to provide inductorless tuning as described above, among other benefits. Additional details of the generator 200 are described in commonly assigned and contemporaneously filed U.S. Pat. No. 9,060,775, titled SURGICAL GENERATOR FOR ULTRASONIC AND ELECTROSURGICAL DEVICES, the disclosure of which is incorporated herein by reference in its entirety. With reference to FIG. 5, the generator 200 may comprise a patient isolated stage 202 in communication with a non-isolated stage 204 via a power transformer 206. A secondary winding 208 of the power transformer 206 is contained in the isolated stage 202 and may comprise a tapped configuration (e.g., a center-tapped or a non-center-tapped configuration) to define drive signal outputs 210*a*, 210*b*, 210*c* for delivering drive signals to different surgical instruments, such as, for example, an ultrasonic surgical instrument 104, an RF electrosurgical instrument 106, and a multifunction surgical instrument 108. In particular, drive signal outputs 210*a*, 210*c* may output an ultrasonic drive signal (e.g., a 420V root-mean-square [RMS] drive signal) to an ultrasonic surgical instrument 104, and drive signal outputs 210*b*, 210*c* may output an electrosurgical drive signal (e.g., a 100V RMS drive signal) to an RF electrosurgical instrument 106, with the drive signal output 2160*b* corresponding to the center tap of the power transformer 206.

In certain forms, the ultrasonic and electrosurgical drive signals may be provided simultaneously to distinct surgical instruments and/or to a single surgical instrument having the capability to deliver both ultrasonic and electrosurgical energy to tissue, such as the multifunction surgical instrument 108 (FIGS. 1-3). It will be appreciated that the electrosurgical signal, provided either to a dedicated electrosurgical instrument and/or to a combined multifunction ultrasonic/electrosurgical instrument may be either a therapeutic or sub-therapeutic level signal where the sub-therapeutic signal can be used, for example, to monitor tissue or instrument conditions and provide feedback to the generator. For example, the ultrasonic and RF signals can be delivered separately or simultaneously from a generator with a single output port in order to provide the desired output signal to the surgical instrument, as will be discussed in more detail below. Accordingly, the generator can combine the ultrasonic and electrosurgical RF energies and deliver the combined energies to the multifunction ultrasonic/electrosurgical instrument. Bipolar electrodes can be placed on one or both jaws of the end effector. One jaw may be driven by ultrasonic energy in addition to electrosurgical RF energy, working simultaneously. The ultrasonic energy may be employed to dissect tissue while the electrosurgical RF energy may be employed for vessel sealing.

The non-isolated stage 204 may comprise a power amplifier 212 having an output connected to a primary winding 214 of the power transformer 206. In certain forms the power amplifier 212 may be comprise a push-pull amplifier. For example, the non-isolated stage 204 may further comprise a logic device 216 for supplying a digital output to a digital-to-analog converter (DAC) circuit 218, which in turn supplies a corresponding analog signal to an input of the power amplifier 212. In certain forms the logic device 216 may comprise a programmable gate array (PGA), a field programmable gate array (FPGA), programmable logic device (PLD), among other logic circuits, for example. The logic device 216, by virtue of controlling the input of the power amplifier 212 via the DAC circuit 218, may therefore control any of a number of parameters (e.g., frequency, waveform shape, waveform amplitude) of drive signals appearing at the drive signal outputs 210*a*, 210*b*, 210*c*. In certain forms and as discussed below, the logic device 216, in conjunction with a processor (e.g., a digital signal processor discussed below), may implement a number of digital signal processing (DSP)-based and/or other control algorithms to control parameters of the drive signals output by the generator 200.

Power may be supplied to a power rail of the power amplifier 212 by a switch-mode regulator 220, e.g., power converter. In certain forms the switch-mode regulator 220 may comprise an adjustable buck regulator, for example. The non-isolated stage 204 may further comprise a first processor 222, which in one form may comprise a DSP processor such as an Analog Devices ADSP-21469 SHARC DSP, available from Analog Devices, Norwood, MA, for example, although in various forms any suitable processor may be employed. In certain forms the DSP processor 222 may control operation of the switch-mode regulator 220 responsive to voltage feedback data received from the power amplifier 212 by the DSP processor 222 via an analog-to-digital converter (ADC) circuit 224. In one form, for example, the DSP processor 222 may receive as input, via the ADC circuit 224, the waveform envelope of a signal (e.g., an RF signal) being amplified by the power amplifier 212. The DSP processor 222 may then control the switch-mode regulator 220 (e.g., via a pulse-width modulated (PWM) output) such that the rail voltage supplied to the power amplifier 212 tracks the waveform envelope of the amplified signal. By dynamically modulating the rail voltage of the power amplifier 212 based on the waveform envelope, the efficiency of the power amplifier 212 may be significantly improved relative to a fixed rail voltage amplifier schemes.

In certain forms, the logic device 216, in conjunction with the DSP processor 222, may implement a digital synthesis circuit such as a DDS (see e.g., FIGS. 13, 14) control scheme to control the waveform shape, frequency and/or amplitude of drive signals output by the generator 200. In one form, for example, the logic device 216 may implement a DDS control algorithm by recalling waveform samples stored in a dynamically-updated lookup table (LUT), such as a RAM LUT, which may be embedded in an FPGA. This control algorithm is particularly useful for ultrasonic applications in which an ultrasonic transducer, such as the ultrasonic transducer 120, may be driven by a clean sinusoidal current at its resonant frequency. Because other frequencies may excite parasitic resonances, minimizing or reducing the total distortion of the motional branch current may correspondingly minimize or reduce undesirable resonance effects. Because the waveform shape of a drive signal output by the generator 200 is impacted by various sources of distortion present in the output drive circuit (e.g., the power transformer 206, the power amplifier 212), voltage and current feedback data based on the drive signal may be input into an algorithm, such as an error control algorithm implemented by the DSP processor 222, which compensates for distortion by suitably pre-distorting or modifying the waveform samples stored in the LUT on a dynamic, ongoing basis (e.g., in real-time). In one form, the amount or degree of pre-distortion applied to the LUT samples may be based on the error between a computed motional branch current and a desired current waveform shape, with the error being determined on a sample-by-sample basis. In this way, the pre-distorted LUT samples, when processed through the drive circuit, may result in a motional branch drive signal having the desired waveform shape (e.g., sinusoidal) for optimally driving the ultrasonic transducer. In such forms, the LUT waveform samples will therefore not represent the desired waveform shape of the drive signal, but rather the waveform shape that is required to ultimately produce the desired waveform shape of the motional branch drive signal when distortion effects are taken into account.

The non-isolated stage 204 may further comprise a first ADC circuit 226 and a second ADC circuit 228 coupled to the output of the power transformer 206 via respective isolation transformers 230, 232 for respectively sampling the voltage and current of drive signals output by the generator 200. In certain forms, the ADC circuits 226, 228 may be configured to sample at high speeds (e.g., 80 mega samples per second [MSPS]) to enable oversampling of the drive signals. In one form, for example, the sampling speed of the ADC circuits 226, 228 may enable approximately 200× (depending on frequency) oversampling of the drive signals. In certain forms, the sampling operations of the ADC circuit 226, 228 may be performed by a single ADC circuit receiving input voltage and current signals via a two-way multiplexer. The use of high-speed sampling in forms of the generator 200 may enable, among other things, calculation of the complex current flowing through the motional branch (which may be used in certain forms to implement direct digital synthesis (DDS) based waveform shape control described above), accurate digital filtering of the sampled signals, and calculation of real power consumption with a high degree of precision. Voltage and current feedback data output by the ADC circuits 226, 228 may be received and processed (e.g., first-in-first-out [FIFO] buffer, multiplexer, etc.) by the logic device 216 and stored in data memory for subsequent retrieval by, for example, the DSP processor 222. As noted above, voltage and current feedback data may be used as input to an algorithm for pre-distorting or modifying LUT waveform samples on a dynamic and ongoing basis. In certain forms, this may require each stored voltage and current feedback data pair to be indexed based on, or otherwise associated with, a corresponding LUT sample that was output by the logic device 216 when the voltage and current feedback data pair was acquired. Synchronization of the LUT samples and the voltage and current feedback data in this manner contributes to the correct timing and stability of the pre-distortion algorithm.

In certain forms, the voltage and current feedback data may be used to control the frequency and/or amplitude (e.g., current amplitude) of the drive signals. In one form, for example, voltage and current feedback data may be used to determine impedance phase. The frequency of the drive signal may then be controlled to minimize or reduce the difference between the determined impedance phase and an impedance phase setpoint (e.g., 0°), thereby minimizing or reducing the effects of ultrasonic distortion and correspondingly enhancing impedance phase measurement accuracy. The determination of phase impedance and a frequency control signal may be implemented in the DSP processor 222, for example, with the frequency control signal being supplied as input to a DDS control algorithm implemented by the logic device 216.

In another form, for example, the current feedback data may be monitored in order to maintain the current amplitude of the drive signal at a current amplitude setpoint. The current amplitude setpoint may be specified directly or determined indirectly based on specified voltage amplitude and power setpoints. In certain forms, control of the current amplitude may be implemented by control algorithm, such as, for example, a proportional-integral-derivative (PID) control algorithm, in the DSP processor 222. Variables controlled by the control algorithm to suitably control the current amplitude of the drive signal may include, for example, the scaling of the LUT waveform samples stored in the logic device 216 and/or the full-scale output voltage of the DAC circuit 218 (which supplies the input to the power amplifier 212) via a DAC circuit 234.

The non-isolated stage 204 may further comprise a second processor 236 for providing, among other things user interface (UI) functionality. In one form, the UI processor 236 may comprise an Atmel AT91SAM9263 processor having an ARM 926EJ-S core, available from Atmel Corporation, San Jose, CA, for example. Examples of UI functionality supported by the UI processor 236 may include audible and visual user feedback, communication with peripheral devices (e.g., via a Universal Serial Bus [USB] interface), communication with the foot switch 130, communication with an input device 110 (e.g., a touch screen display) and communication with an output device 112 (e.g., a speaker), as shown in FIGS. 1 and 3. The UI processor 236 may communicate with the DSP processor 222 and the logic device 216 (e.g., via serial peripheral interface [SPI] buses). Although the UI processor 236 may primarily support UI functionality, it may also coordinate with the DSP processor 222 to implement hazard mitigation in certain forms. For example, the UI processor 236 may be programmed to monitor various aspects of user input and/or other inputs (e.g., touch screen inputs, foot switch 130 inputs as shown in FIG. 3, temperature sensor inputs) and may disable the drive output of the generator 200 when an erroneous condition is detected.

In certain forms, both the DSP processor 222 and the UI processor 236, for example, may determine and monitor the operating state of the generator 200. For the DSP processor 222, the operating state of the generator 200 may dictate, for example, which control and/or diagnostic processes are implemented by the DSP processor 222. For the UI processor 236, the operating state of the generator 200 may dictate, for example, which elements of a user interface (e.g., display screens, sounds) are presented to a user. The respective DSP and UI processors 222, 236 may independently maintain the current operating state of the generator 200 and recognize and evaluate possible transitions out of the current operating state. The DSP processor 222 may function as the master in this relationship and determine when transitions between operating states are to occur. The UI processor 236 may be aware of valid transitions between operating states and may confirm if a particular transition is appropriate. For example, when the DSP processor 222 instructs the UI processor 236 to transition to a specific state, the UI processor 236 may verify that requested transition is valid. In the event that a requested transition between states is determined to be invalid by the UI processor 236, the UI processor 236 may cause the generator 200 to enter a failure mode.

The non-isolated stage 204 may further comprise a controller 238 for monitoring input devices 110 (e.g., a capacitive touch sensor used for turning the generator 200 on and off, a capacitive touch screen). In certain forms, the controller 238 may comprise at least one processor and/or other controller device in communication with the UI processor 236. In one form, for example, the controller 238 may comprise a processor (e.g., a Mega168 8-bit controller available from Atmel) configured to monitor user input provided via one or more capacitive touch sensors. In one form, the controller 238 may comprise a touch screen controller (e.g., a QT5480 touch screen controller available from Atmel) to control and manage the acquisition of touch data from a capacitive touch screen.

In certain forms, when the generator 200 is in a "power off" state, the controller 238 may continue to receive operating power (e.g., via a line from a power supply of the generator 200, such as the power supply 254 discussed below). In this way, the controller 196 may continue to monitor an input device 110 (e.g., a capacitive touch sensor located on a front panel of the generator 200) for turning the generator 200 on and off. When the generator 200 is in the power off state, the controller 238 may wake the power supply (e.g., enable operation of one or more DC/DC voltage converters 256 of the power supply 254) if activation of the "on/off" input device 110 by a user is detected. The controller 238 may therefore initiate a sequence for transitioning the generator 200 to a "power on" state. Conversely, the controller 238 may initiate a sequence for transitioning the generator 200 to the power off state if activation of the "on/off" input device 110 is detected when the generator 200 is in the power on state. In certain forms, for example, the controller 238 may report activation of the "on/off" input device 110 to the UI processor 236, which in turn implements the necessary process sequence for transitioning the generator 200 to the power off state. In such forms, the controller 196 may have no independent ability for causing the removal of power from the generator 200 after its power on state has been established.

In certain forms, the controller 238 may cause the generator 200 to provide audible or other sensory feedback for alerting the user that a power on or power off sequence has been initiated. Such an alert may be provided at the beginning of a power on or power off sequence and prior to the commencement of other processes associated with the sequence.

In certain forms, the isolated stage 202 may comprise an instrument interface circuit 240 to, for example, provide a communication interface between a control circuit of a surgical instrument (e.g., a control circuit comprising handpiece switches) and components of the non-isolated stage 204, such as, for example, the logic device 216, the DSP processor 222 and/or the UI processor 236. The instrument interface circuit 240 may exchange information with components of the non-isolated stage 204 via a communication link that maintains a suitable degree of electrical isolation between the isolated and non-isolated stages 202, 204, such as, for example, an infrared (IR)-based communication link. Power may be supplied to the instrument interface circuit 240 using, for example, a low-dropout voltage regulator powered by an isolation transformer driven from the non-isolated stage 204.

In one form, the instrument interface circuit 240 may comprise a logic circuit 242 (e.g., logic circuit, programmable logic circuit, PGA, FPGA, PLD) in communication with a signal conditioning circuit 244. The signal conditioning circuit 244 may be configured to receive a periodic signal from the logic circuit 242 (e.g., a 2 kHz square wave) to generate a bipolar interrogation signal having an identical frequency. The interrogation signal may be generated, for example, using a bipolar current source fed by a differential amplifier. The interrogation signal may be communicated to a surgical instrument control circuit (e.g., by using a conductive pair in a cable that connects the generator 200 to the surgical instrument) and monitored to determine a state or configuration of the control circuit. The control circuit may comprise a number of switches, resistors and/or diodes to modify one or more characteristics (e.g., amplitude, rectification) of the interrogation signal such that a state or configuration of the control circuit is uniquely discernable based on the one or more characteristics. In one form, for example, the signal conditioning circuit 244 may comprise an ADC circuit for generating samples of a voltage signal appearing across inputs of the control circuit resulting from passage of interrogation signal therethrough. The logic circuit 242 (or a component of the non-isolated stage 204) may then determine the state or configuration of the control circuit based on the ADC circuit samples.

In one form, the instrument interface circuit 240 may comprise a first data circuit interface 246 to enable information exchange between the logic circuit 242 (or other element of the instrument interface circuit 240) and a first data circuit disposed in or otherwise associated with a surgical instrument. In certain forms, for example, a first data circuit 136 (FIG. 2) may be disposed in a cable integrally attached to a surgical instrument handpiece, or in an adaptor for interfacing a specific surgical instrument type or model with the generator 200. The first data circuit 136 may be implemented in any suitable manner and may communicate with the generator according to any suitable protocol including, for example, as described herein with respect to the first data circuit 136. In certain forms, the first data circuit may comprise a non-volatile storage device, such as an EEPROM device. In certain forms and referring again to FIG. 5, the first data circuit interface 246 may be implemented separately from the logic circuit 242 and comprise suitable circuitry (e.g., discrete logic devices, a processor) to enable communication between the logic circuit 242 and the first data circuit. In other forms, the first data circuit interface 246 may be integral with the logic circuit 242.

In certain forms, the first data circuit 136*FIG. 2) may store information pertaining to the particular surgical instrument with which it is associated. Such information may include, for example, a model number, a serial number, a number of operations in which the surgical instrument has been used, and/or any other type of information. This information may be read by the instrument interface circuit 240 (e.g., by the logic circuit 242), transferred to a component of the non-isolated stage 204 (e.g., to logic device 216, DSP processor 222 and/or UI processor 236) for presentation to a user via an output device 112 (FIGS. 1 and 3) and/or for controlling a function or operation of the generator 200. Additionally, any type of information may be communicated to first data circuit 136 for storage therein via the first data circuit interface 246 (e.g., using the logic circuit 242). Such information may comprise, for example, an updated number of operations in which the surgical instrument has been used and/or dates and/or times of its usage.

As discussed previously, a surgical instrument may be detachable from a handpiece (e.g., the multifunction surgical instrument 108 may be detachable from the handpiece 109) to promote instrument interchangeability and/or disposability. In such cases, conventional generators may be limited in their ability to recognize particular instrument configurations being used and to optimize control and diagnostic processes accordingly. The addition of readable data circuits to surgical instruments to address this issue is problematic from a compatibility standpoint, however. For example, designing a surgical instrument to remain backwardly compatible with generators that lack the requisite data reading functionality may be impractical due to, for example, differing signal schemes, configuration complexity, and cost. Forms of instruments discussed herein address these concerns by using data circuits that may be implemented in existing surgical instruments economically and with minimal configuration changes to preserve compatibility of the surgical instruments with current generator platforms.

Additionally, forms of the generator 200 may enable communication with instrument-based data circuits. For example, the generator 200 may be configured to communicate with a second data circuit 138 (FIG. 2) contained in an instrument (e.g., the multifunction surgical instrument 108 shown in FIG. 2). In some forms, the second data circuit 138 may be implemented in a many similar to that of the first data circuit 136 (FIG. 2) described herein. The instrument interface circuit 240 may comprise a second data circuit interface 248 to enable this communication. In one form, the second data circuit interface 248 may comprise a tri-state digital interface, although other interfaces may also be used. In certain forms, the second data circuit may generally be any circuit for transmitting and/or receiving data. In one form, for example, the second data circuit may store information pertaining to the particular surgical instrument with which it is associated. Such information may include, for example, a model number, a serial number, a number of operations in which the surgical instrument has been used, and/or any other type of information.

In some forms, the second data circuit 138 (FIG. 2) may store information about the electrical and/or ultrasonic properties of an associated ultrasonic transducer 120, end effector 125, or ultrasonic drive system. For example, the first data circuit 136 (FIG. 2) may indicate a burn-in frequency slope, as described herein. Additionally or alternatively, any type of information may be communicated to second data circuit for storage therein via the second data circuit interface 248 (e.g., using the logic circuit 242). Such information may comprise, for example, an updated number of operations in which the instrument has been used and/or dates and/or times of its usage. In certain forms, the second data circuit may transmit data acquired by one or more sensors (e.g., an instrument-based temperature sensor). In certain forms, the second data circuit may receive data from the generator 200 and provide an indication to a user (e.g., an LED indication or other visible indication) based on the received data.

In certain forms, the second data circuit and the second data circuit interface 248 may be configured such that communication between the logic circuit 242 and the second data circuit can be effected without the need to provide additional conductors for this purpose (e.g., dedicated conductors of a cable connecting a handpiece to the generator 200). In one form, for example, information may be communicated to and from the second data circuit using a 1-wire bus communication scheme implemented on existing cabling, such as one of the conductors used transmit interrogation signals from the signal conditioning circuit 244 to a control circuit in a handpiece. In this way, configuration changes or modifications to the surgical instrument that might otherwise be necessary are minimized or reduced. Moreover, because different types of communications implemented over a common physical channel can be frequency-band separated, the presence of a second data circuit may be "invisible" to generators that do not have the requisite data reading functionality, thus enabling backward compatibility of the surgical instrument.

In certain forms, the isolated stage 202 may comprise at least one blocking capacitor 250-1 connected to the drive signal output 210*b* to prevent passage of DC current to a patient. A single blocking capacitor may be required to comply with medical regulations or standards, for example. While failure in single-capacitor configurations is relatively uncommon, such failure may nonetheless have negative consequences. In one form, a second blocking capacitor 250-2 may be provided in series with the blocking capacitor 250-1, with current leakage from a point between the blocking capacitors 250-1, 250-2 being monitored by, for example, an ADC circuit 252 for sampling a voltage induced by leakage current. The samples may be received by the logic circuit 242, for example. Based changes in the leakage current (as indicated by the voltage samples in the form of FIG. 5), the generator 200 may determine when at least one of the blocking capacitors 250-1, 250-2 has failed. Accordingly, the form of FIG. 5 provides a benefit over single-capacitor configurations having a single point of failure.

In certain forms, the non-isolated stage 204 may comprise a power supply 254 for delivering DC power at a suitable voltage and current. The power supply may comprise, for example, a 400 W power supply for delivering a 48 VDC system voltage. The power supply 254 may further comprise one or more DC/DC voltage converters 256 for receiving the output of the power supply to generate DC outputs at the voltages and currents required by the various components of the generator 200. As discussed above in connection with the controller 238, one or more of the DC/DC voltage converters 256 may receive an input from the controller 238 when activation of the "on/off" input device 110 by a user is detected by the controller 238 to enable operation of, or wake, the DC/DC voltage converters 256.

Figure 6:
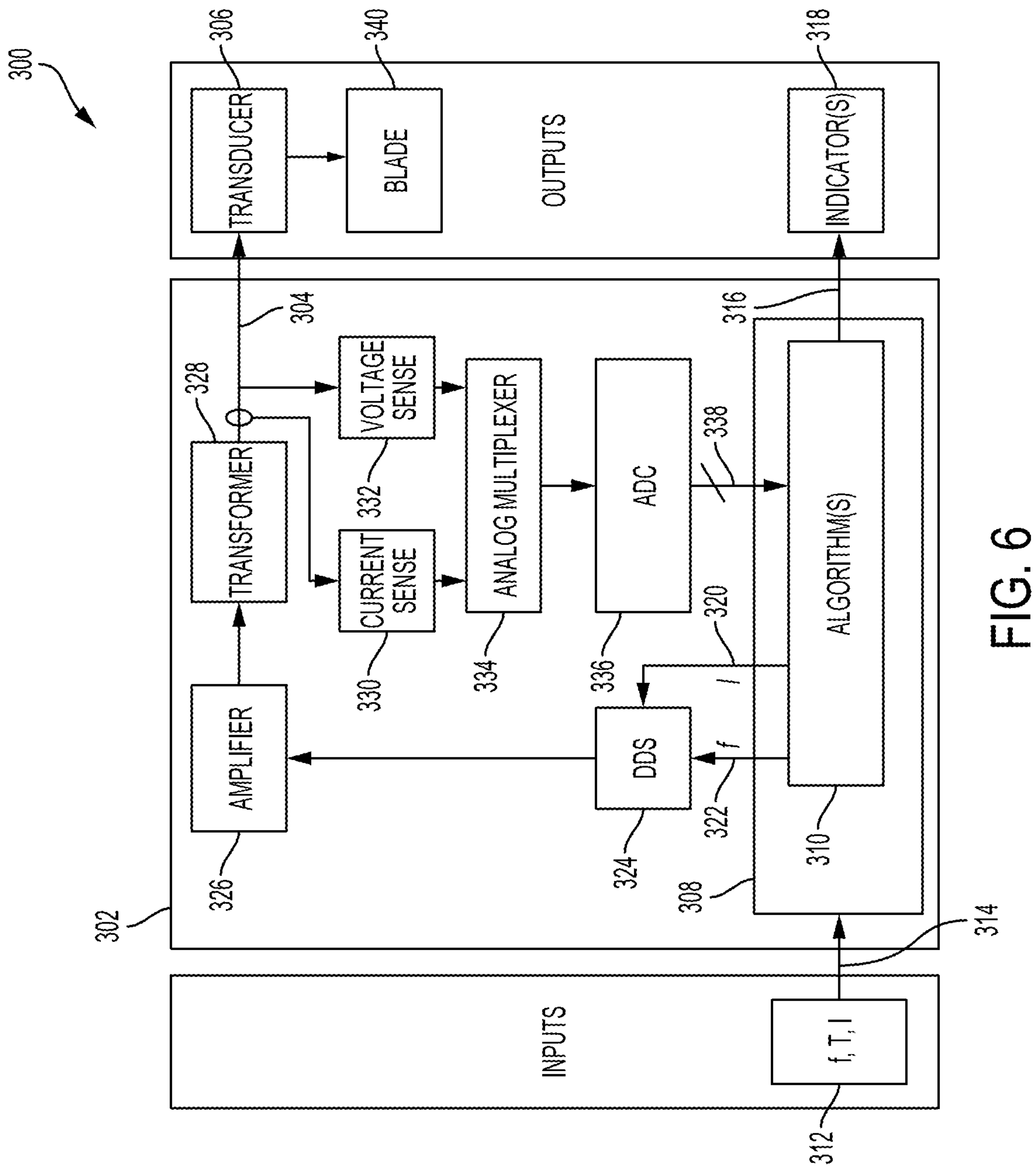
FIG. 6 illustrates one form of a drive system of a generator, which creates the ultrasonic electrical signal for driving an ultrasonic transducer.

FIG. 6 illustrates one form of a drive system 302 of a generator 300, which is one form of the generator 100 (FIGS. 1-3). The generator 300 is configured to provide an ultrasonic electrical signal for driving an ultrasonic transducer (e.g., ultrasonic transducer 120 FIGS. 1-3), also referred to as a drive signal. The generator 300 is similar to and may be interchangeable with the generators 100, 200 (FIGS. 1-3 and 5). The drive system 302 is flexible and can create an ultrasonic electrical drive signal 304 at a desired frequency and power level setting for driving the ultrasonic transducer 306. In various forms, the generator 300 may comprise several separate functional elements, such as modules and/or blocks. Although certain modules and/or blocks may be described by way of example, it can be appreciated that a greater or lesser number of modules and/or blocks may be used and still fall within the scope of the forms. Further, although various forms may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components.

In one form, the generator 300 drive system 302 may comprise one or more embedded applications implemented as firmware, software, hardware, or any combination thereof. The generator 300 drive system 302 may comprise various executable modules such as software, programs, data, drivers, application program interfaces (APIs), and so forth. The firmware may be stored in nonvolatile memory (NVM), such as in bit-masked read-only memory (ROM) or flash memory. In various implementations, storing the firmware in ROM may preserve flash memory. The NVM may comprise other types of memory including, for example, programmable ROM (PROM), erasable programmable ROM (EPROM), EEPROM, or battery backed random-access memory (RAM) such as dynamic RAM (DRAM), Double-Data-Rate DRAM (DDRAM), and/or synchronous DRAM (SDRAM).

In one form, the generator 300 drive system 302 comprises a hardware component implemented as a processor 308 for executing program instructions for monitoring various measurable characteristics of the ultrasonic surgical instrument 104 (FIG. 1) and generating an output signal for driving the ultrasonic transducer in cutting and/or coagulation operating modes. It will be appreciated by those skilled in the art that the generator 300 and the drive system 302 may comprise additional or fewer components and only a simplified version of the generator 300 and the drive system 302 are described herein for conciseness and clarity. In various forms, as previously discussed, the hardware component may be implemented as a DSP, PLD, ASIC, circuits, and/or registers. In one form, the processor 308 may be configured to store and execute computer software program instructions to generate the output signals for driving various components of the ultrasonic surgical instrument 104, such as a transducer, an end effector, and/or a blade.

In one form, under control of one or more software program routines, the processor 308 executes the methods in accordance with the described forms to generate an electrical signal output waveform comprising current (I), voltage (V), and/or frequency (f) for various time intervals or periods (T). The stepwise waveforms of the drive signals may be generated by forming a piecewise linear combination of constant functions over a plurality of time intervals created by stepping the generator 300 drive signals, e.g., output drive current (I), voltage (V), and/or frequency (f). The time intervals or periods (T) may be predetermined (e.g., fixed and/or programmed by the user) or may be variable. Variable time intervals may be defined by setting the drive signal to a first value and maintaining the drive signal at that value until a change is detected in a monitored characteristic. Examples of monitored characteristics may comprise, for example, transducer impedance, tissue impedance, tissue heating, tissue transection, tissue coagulation, and the like. The ultrasonic drive signals generated by the generator 300 include, without limitation, ultrasonic drive signals capable of exciting the ultrasonic transducer 306 in various vibratory modes such as, for example, the primary longitudinal mode and ultrasonics thereof as well flexural and torsional vibratory modes.

In one form, the executable modules comprise one or more algorithm(s) 310 stored in memory that when executed causes the processor 308 to generate an electrical signal output waveform comprising current (I), voltage (V), and/or frequency (f) for various time intervals or periods (T). The stepwise waveforms of the drive signals may be generated by forming a piecewise linear combination of constant functions over two or more time intervals created by stepping the output drive current (I), voltage (V), and/or frequency (f) of the generator 300. The drive signals may be generated either for predetermined fixed time intervals or periods (T) of time or variable time intervals or periods of time in accordance with the one or more algorithm(s) 310. Under control of the processor 308, the generator 100 outputs (e.g., increases or decreases) the current (I), voltage (V), and/or frequency (f) up or down at a particular resolution for a predetermined period (T) or until a predetermined condition is detected, such as a change in a monitored characteristic (e.g., transducer impedance, tissue impedance). The steps can change in programmed increments or decrements. If other steps are desired, the generator 300 can increase or decrease the step adaptively based on measured system characteristics.

In operation, the user can program the operation of the generator 300 using the input device 312 located on the front panel of the generator 300 console. The input device 312 may comprise any suitable device that generates signals 314 that can be applied to the processor 308 to control the operation of the generator 300. In various forms, the input device 312 includes buttons, switches, thumbwheels, keyboard, keypad, touch screen monitor, pointing device, remote connection to a general purpose or dedicated computer. In other forms, the input device 312 may comprise a suitable user interface. Accordingly, by way of the input device 312, the user can set or program the current (I), voltage (V), frequency (f), and/or period (T) for programming the output of the generator 300. The processor 308 then displays the selected power level by sending a signal on line 316 to an output indicator 318.

In various forms, the output indicator 318 may provide visual, audible, and/or tactile feedback to the surgeon to indicate the status of a surgical procedure, such as, for example, when tissue cutting and coagulating is complete based on a measured characteristic of the ultrasonic surgical instrument 104, e.g., transducer impedance, tissue impedance, or other measurements as subsequently described. By way of example, and not limitation, visual feedback comprises any type of visual indication device including incandescent lamps or LEDs, graphical user interface, display, analog indicator, digital indicator, bar graph display, digital alphanumeric display. By way of example, and not limitation, audible feedback comprises any type of buzzer, computer generated tone, computerized speech, voice user interface (VUI) to interact with computers through a voice/speech platform. By way of example, and not limitation, tactile feedback comprises any type of vibratory feedback provided through an instrument housing handle assembly.

In one form, the processor 308 may be configured or programmed to generate a digital current signal 320 and a digital frequency signal 322. These digital signals 320, 322 are applied to a digital synthesis circuit such as the DDS circuit 324 (see e.g., FIGS. 13, 14) to adjust the amplitude and the frequency (f) of the ultrasonic electrical drive signal 304 to the transducer. The output of the DDS circuit 324 is applied to a power amplifier 326 whose output is applied to a transformer 328. The output of the transformer 328 is the ultrasonic electrical drive signal 304 applied to the ultrasonic transducer 306, which is coupled to a blade by way of a waveguide. The output of the DDS circuit 324 may be stored in one more memory circuits including volatile (RAM) and non-volatile (ROM) memory circuits.

In one form, the generator 300 comprises one or more measurement modules or components that may be configured to monitor measurable characteristics of the ultrasonic instrument 104 (FIGS. 1, 2) or the multifunction electrosurgical/ultrasonic instrument 108 (FIGS. 1-3). In the illustrated form, the processor 308 may be employed to monitor and calculate system characteristics. As shown, the processor 308 measures the impedance Z of the transducer by monitoring the current supplied to the ultrasonic transducer 306 and the voltage applied to the transducer. In one form, a current sense circuit 330 is employed to sense the current flowing through the transducer and a voltage sense circuit 332 is employed to sense the output voltage applied to the ultrasonic transducer 306. These signals may be applied to the ADC circuit 336 via an analog multiplexer 334 circuit or switching circuit arrangement. The analog multiplexer 334 routes the appropriate analog signal to the ADC circuit 336 for conversion. In other forms, multiple ADC circuits 336 may be employed for each measured characteristic instead of the analog multiplexer 334 circuit. The processor 308 receives the digital output 338 of the ADC circuit 336 and calculates the transducer impedance Z based on the measured values of current and voltage. The processor 308 adjusts the ultrasonic electrical drive signal 304 such that it can generate a desired power versus load curve. In accordance with programmed algorithm(s) 310, the processor 308 can step the ultrasonic electrical drive signal 304, e.g., the current or frequency, in any suitable increment or decrement in response to the transducer impedance Z.

Figure 7:
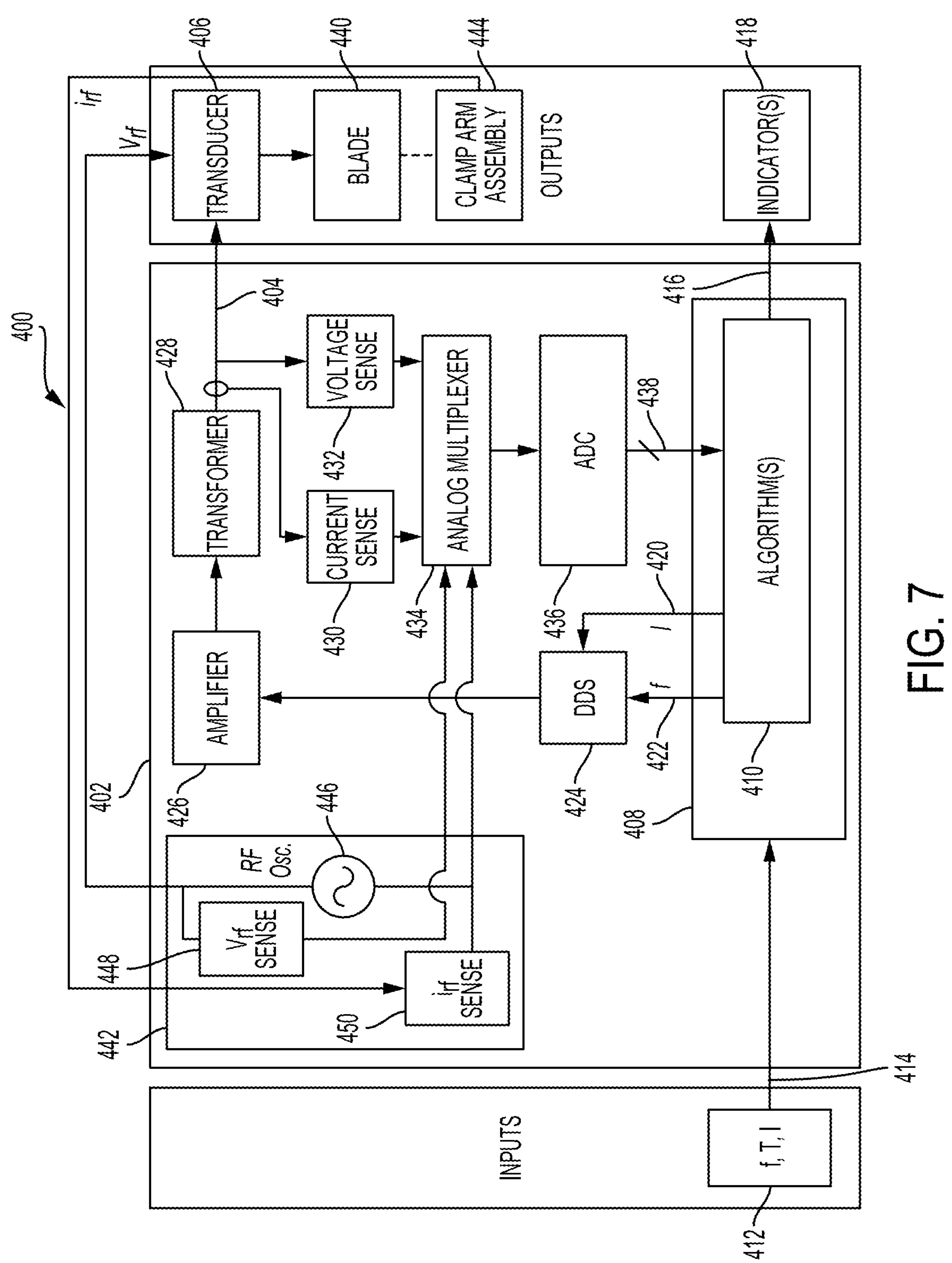
FIG. 7 illustrates one form of a drive system of a generator comprising a tissue impedance module.

FIG. 7 illustrates one aspect of a drive system 402 of the generator 400, which is one form of the generator 100 (FIGS. 1-3). In operation, the user can program the operation of the generator 400 using the input device 412 located on the front panel of the generator 400 console. The input device 412 may comprise any suitable device that generates signals 414 that can be applied to the processor 408 to control the operation of the generator 400. In various forms, the input device 412 includes buttons, switches, thumbwheels, keyboard, keypad, touch screen monitor, pointing device, remote connection to a general purpose or dedicated computer. In other forms, the input device 412 may comprise a suitable user interface. Accordingly, by way of the input device 412, the user can set or program the current (I), voltage (V), frequency (f), and/or period (T) for programming the output of the generator 400. The processor 408 then displays the selected power level by sending a signal on line 416 to an output indicator 418.

The generator 400 comprises a tissue impedance module 442. The drive system 402 is configured to generate electrical drive signal 404 to drive the ultrasonic transducer 406. In one aspect, the tissue impedance module 442 may be configured to measure the impedance Zt of tissue grasped between the blade 440 and the clamp arm assembly 444. The tissue impedance module 442 comprises an RF oscillator 446, an RF voltage sensing circuit 448, and an RF current sensing circuit 450. The RF voltage and RF current sensing circuits 448, 450 respond to the RF voltage Vrf applied to the blade 440 electrode and the RF current irf flowing through the blade 440 electrode, the tissue, and the conductive portion of the clamp arm assembly 444. The sensed voltage Vrf and current Irf are converted to digital form by the ADC circuit 436 via the analog multiplexer 434. The processor 408 receives the digital output 438 of the ADC circuit 436 and determines the tissue impedance Zt by calculating the ratio of the RF voltage Vrf to current Irf measured by the RF voltage sense circuit 448 and the RF current sense circuit 450. In one aspect, the transection of the inner muscle layer and the tissue may be detected by sensing the tissue impedance Zt. Accordingly, detection of the tissue impedance Zt may be integrated with an automated process for separating the inner muscle layer from the outer adventitia layer prior to transecting the tissue without causing a significant amount of heating, which normally occurs at resonance.

In one form, the RF voltage Vrf applied to the blade 440 electrode and the RF current Irf flowing through the blade 440 electrode, the tissue, and the conductive portion of the clamp arm assembly 451 are suitable for vessel sealing and/or dissecting. Thus, the RF power output of the generator 400 can be selected for non-therapeutic functions such as tissue impedance measurements as well as therapeutic functions such as vessel sealing and/or dissection. It will be appreciated, that in the context of the present disclosure, the ultrasonic and the RF electrosurgical energies can be supplied by the generator either individually or simultaneously.

In various forms, feedback is provided by the output indicator 418 shown in FIGS. 6 and 7. The output indicator 418 is particularly useful in applications where the tissue being manipulated by the end effector is out of the user's field of view and the user cannot see when a change of state occurs in the tissue. The output indicator 418 communicates to the user that a change in tissue state has occurred. As previously discussed, the output indicator 418 may be configured to provide various types of feedback to the user including, without limitation, visual, audible, and/or tactile feedback to indicate to the user (e.g., surgeon, clinician) that the tissue has undergone a change of state or condition of the tissue. By way of example, and not limitation, as previously discussed, visual feedback comprises any type of visual indication device including incandescent lamps or LEDs, graphical user interface, display, analog indicator, digital indicator, bar graph display, digital alphanumeric display. By way of example, and not limitation, audible feedback comprises any type of buzzer, computer generated tone, computerized speech, VUI to interact with computers through a voice/speech platform. By way of example, and not limitation, tactile feedback comprises any type of vibratory feedback provided through the instrument housing handle assembly. The change of state of the tissue may be determined based on transducer and tissue impedance measurements as previously described, or based on voltage, current, and frequency measurements.

In one form, the processor 408 may be configured or programmed to generate a digital current signal 420 and a digital frequency signal 422. These digital signals 420, 422 are applied to a digital synthesis circuit such as the DDS circuit 424 (see e.g., FIGS. 13, 14) to adjust the amplitude and the frequency (f) of the electrical drive signal 404 to the transducer 406. The output of the DDS circuit 424 is applied to a power amplifier 426 whose output is applied to a transformer 428. The output of the transformer 428 is the electrical drive signal 404 applied to the ultrasonic transducer 406, which is coupled to a blade by way of a waveguide. The output of the DDS circuit 424 may be stored in one more memory circuits including volatile (RAM) and non-volatile (ROM) memory circuits.

In one form, the generator 400 comprises one or more measurement modules or components that may be configured to monitor measurable characteristics of the ultrasonic instrument 104 (FIGS. 1, 3) or the multifunction electrosurgical/ultrasonic instrument 108 (FIGS. 1-3). In the illustrated form, the processor 408 may be employed to monitor and calculate system characteristics. As shown, the processor 408 measures the impedance Z of the transducer by monitoring the current supplied to the ultrasonic transducer 406 and the voltage applied to the transducer. In one form, a current sense circuit 430 is employed to sense the current flowing through the transducer and a voltage sense circuit 432 is employed to sense the output voltage applied to the ultrasonic transducer 406. These signals may be applied to the ADC circuit 436 via an analog multiplexer 434 circuit or switching circuit arrangement. The analog multiplexer 434 routes the appropriate analog signal to the ADC circuit 436 for conversion. In other forms, multiple ADC circuits 436 may be employed for each measured characteristic instead of the analog multiplexer 434 circuit. The processor 408 receives the digital output 438 of the ADC circuit 436 and calculates the transducer impedance Z based on the measured values of current and voltage. The processor 308 adjusts the electrical drive signal 404 such that it can generate a desired power versus load curve. In accordance with programmed algorithm(s) 410, the processor 408 can step the ultrasonic electrical drive signal 404, e.g., the current or frequency, in any suitable increment or decrement in response to the transducer impedance Z.

With reference to FIGS. 6 and 7, in various forms, the various executable instructions or modules (e.g., algorithms 310, 410) comprising computer readable instructions can be executed by the processor 308, 408 portion of the generator 300, 400. In various forms, the operations described with respect to the algorithms may be implemented as one or more software components, e.g., programs, subroutines, logic; one or more hardware components, e.g., processors, DSPs, PLDs, ASICs, circuits, registers; and/or combinations of software and hardware. In one form, the executable instructions to perform the algorithms may be stored in memory. When executed, the instructions cause the processor 308, 408 to determine a change in tissue state provide feedback to the user by way of the output indicator 318, 418. In accordance with such executable instructions, the processor 308, 408 monitors and evaluates the voltage, current, and/or frequency signal samples available from the generator 300, 400 and according to the evaluation of such signal samples determines whether a change in tissue state has occurred. As further described below, a change in tissue state may be determined based on the type of ultrasonic instrument and the power level that the instrument is energized at. In response to the feedback, the operational mode of the surgical instruments 104, 106, 108 (FIGS. 1-3) may be controlled by the user or may be automatically or semi-automatically controlled.

Figure 8:
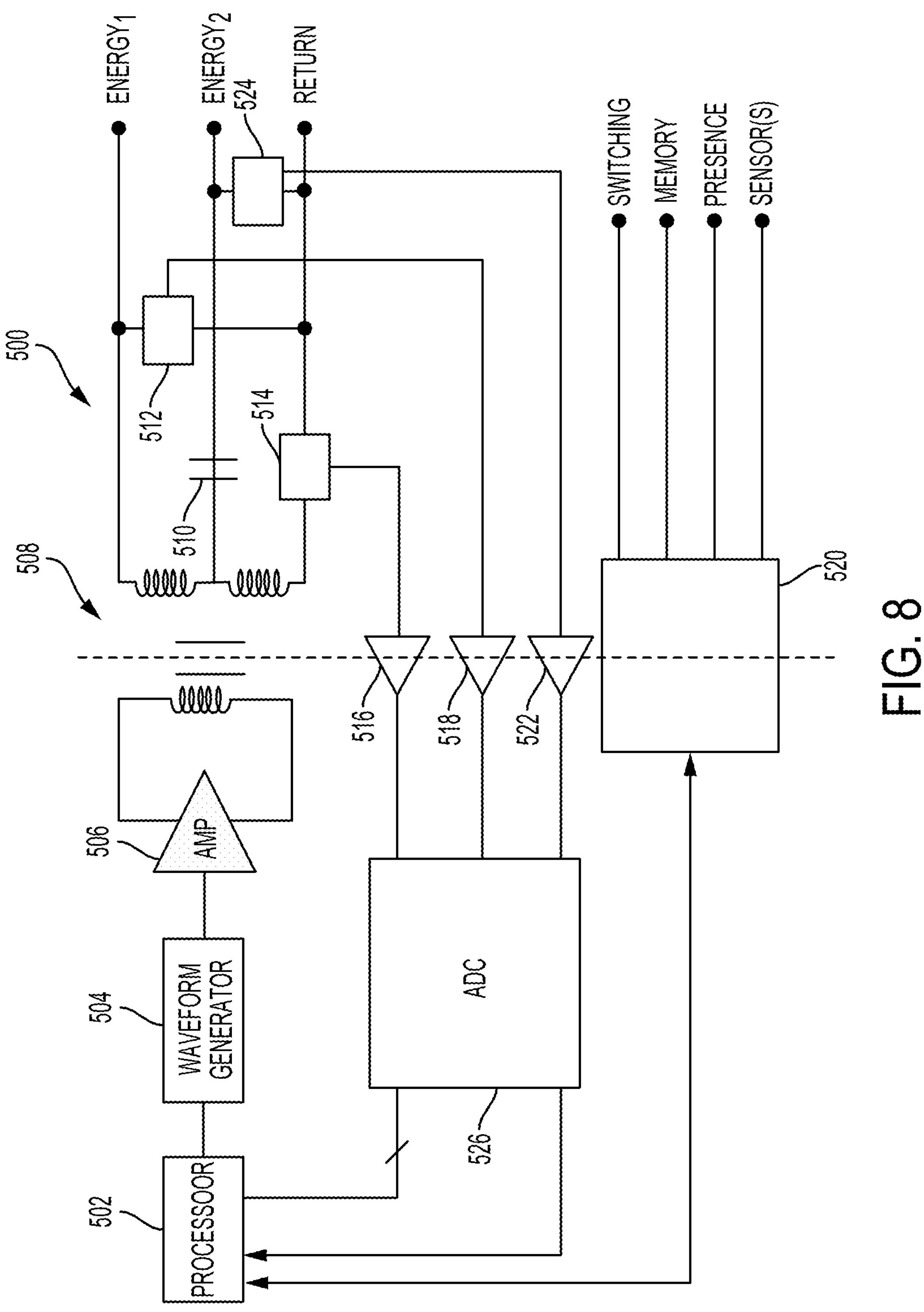
FIG. 8 illustrates an example of a combined radio frequency and ultrasonic energy generator for delivering energy to a surgical instrument.

FIG. 8 illustrates an example of a generator 500, which is one form of the generator 100 (FIGS. 1-3). The generator 500 is configured to deliver multiple energy modalities to a surgical instrument. The generator 500 includes functionalities of the generators 200, 300, 400 shown in FIGS. 5-7. The generator 500 provides RF and ultrasonic signals for delivering energy to a surgical instrument. The RF and ultrasonic signals may be provided alone or in combination and may be provided simultaneously. As noted above, at least one generator output can deliver multiple energy modalities (e.g., ultrasonic, bipolar or monopolar RF, irreversible and/or reversible electroporation, and/or microwave energy, among others) through a single port and these signals can be delivered separately or simultaneously to the end effector to treat tissue. The generator 500 comprises a processor 502 coupled to a waveform generator 504. The processor 502 and waveform generator 504 are configured to generate a variety of signal waveforms based on information stored in a memory coupled to the processor 502, not shown for clarity of disclosure. The digital information associated with a waveform is provided to the waveform generator 504 which includes one or more DAC circuits to convert the digital input into an analog output. The analog output is fed to an amplifier 1106 for signal conditioning and amplification. The conditioned and amplified output of the amplifier 506 is coupled to a power transformer 508. The signals are coupled across the power transformer 508 to the secondary side, which is in the patient isolation side. A first signal of a first energy modality is provided to the surgical instrument between the terminals labeled ENERGY1 and RETURN. A second signal of a second energy modality is coupled across a capacitor 510 and is provided to the surgical instrument between the terminals labeled ENERGY2 and RETURN. It will be appreciated that more than two energy modalities may be output and thus the subscript "n" may be used to designate that up to n ENERGYn terminals may be provided, where n is a positive integer greater than 1. It also will be appreciated that up to "n" return paths RETURNn may be provided without departing from the scope of the present disclosure.

A first voltage sensing circuit 512 is coupled across the terminals labeled ENERGY1 and the RETURN path to measure the output voltage therebetween. A second voltage sensing circuit 524 is coupled across the terminals labeled ENERGY2 and the RETURN path to measure the output voltage therebetween. A current sensing circuit 514 is disposed in series with the RETURN leg of the secondary side of the power transformer 508 as shown to measure the output current for either energy modality. If different return paths are provided for each energy modality, then a separate current sensing circuit should be provided in each return leg. The outputs of the first and second voltage sensing circuits 512, 524 are provided to respective isolation transformers 516, 522 and the output of the current sensing circuit 514 is provided to another isolation transformer 518. The outputs of the isolation transformers 516, 518, 522 in the on the primary side of the power transformer 508 (non-patient-isolated side) are provided to a one or more ADC circuit 526. The digitized output of the ADC circuit 526 is provided to the processor 502 for further processing and computation. The output voltages and output current feedback information can be employed to adjust the output voltage and current provided to the surgical instrument and to compute output impedance, among other parameters. Input/output communications between the processor 502 and patient isolated circuits is provided through an interface circuit 520. Sensors also may be in electrical communication with the processor 502 by way of the interface circuit 520.

In one aspect, the impedance may be determined by the processor 502 by dividing the output of either the first voltage sensing circuit 512 coupled across the terminals labeled ENERGY1/RETURN or the second voltage sensing circuit 524 coupled across the terminals labeled ENERGY2/RETURN by the output of the current sensing circuit 514 disposed in series with the RETURN leg of the secondary side of the power transformer 508. The outputs of the first and second voltage sensing circuits 512, 524 are provided to separate isolations transformers 516, 522 and the output of the current sensing circuit 514 is provided to another isolation transformer 516. The digitized voltage and current sensing measurements from the ADC circuit 526 are provided the processor 502 for computing impedance. As an example, the first energy modality ENERGY1 may be ultrasonic energy and the second energy modality ENERGY2 may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 8 shows a single return path RETURN may be provided for two or more energy modalities, in other aspects multiple return paths RETURNn may be provided for each energy modality ENERGYn. Thus, as described herein, the ultrasonic transducer impedance may be measured by dividing the output of the first voltage sensing circuit 512 by the current sensing circuit 514 and the tissue impedance may be measured by dividing the output of the second voltage sensing circuit 524 by the current sensing circuit 514.

As shown in FIG. 8, the generator 500 comprising at least one output port can include a power transformer 508 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 500 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 500 can be steered, switched, or filtered to provide the frequency to the end effector of the surgical instrument. The connection of an ultrasonic transducer to the generator 500 output would be preferably located between the output labeled ENERGY1 and RETURN as shown in FIG. 8. An In one example, a connection of RF bipolar electrodes to the generator 500 output would be preferably located between the output labeled ENERGY2 and RETURN. In the case of monopolar output, the preferred connections would be active electrode (e.g., pencil or other probe) to the ENERGY2 output and a suitable return pad connected to the RETURN output.

In other aspects, the generators 100, 200, 300, 400, 500 described in connection with FIGS. 1-3 and 5-8, the ultrasonic drive circuit 114, and/or electrosurgery/RF drive circuit 116 as described in connection with FIG. 3 may be formed integrally with any one of the surgical instruments 104, 106, 108 described in connection with FIGS. 1 and 2. Accordingly, any of the processors, digital signal processors, circuits, controllers, logic devices, ADCs, DACs, amplifiers, converters, transformers, signal conditioners, data interface circuits, current and voltage sensing circuits, direct digital synthesis circuits, multiplexer (analog or digital), waveform generators, RF generators, memory, and the like, described in connection with any one of the generators 100, 200, 300, 400, 500 can be located within the surgical instruments 104, 106, 108 or may be located remotely from the surgical instruments 104, 106, 108 and coupled to the surgical instruments via wired and/or wireless electrical connections.

Figure 9:
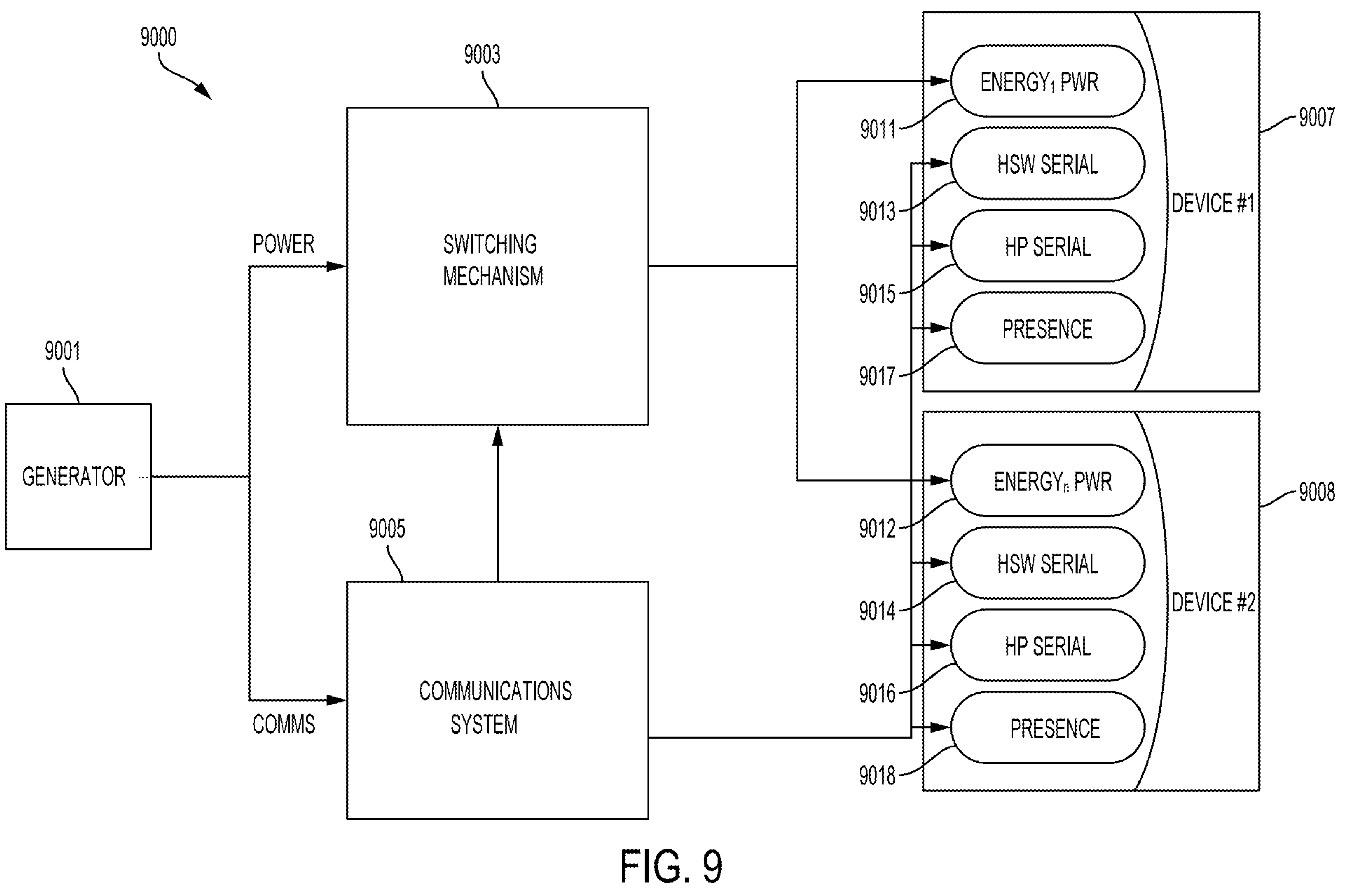
FIG. 9 is a diagram of a system for delivering combined radio frequency and ultrasonic energy to a plurality of surgical instruments.

FIG. 9 shows a diagram of an electrosurgical system 9000 that allows for two ports on a generator 9001 and accounts for electrical isolation between two surgical instruments 9007, 9008. A scheme is provided for electrical isolation between the two instruments 9007, 9008 as they are located on the same patient isolation circuit. According to the configuration shown in FIG. 9, unintended electrical power feedback is prevented through the electrosurgical system 9000. In various aspects, power field effect transistors (FETs) or relays are used to electrically isolate all power lines for each of the two surgical instruments 9007, 9008. According to one aspect, the power FETs or relays are controlled by a 1-wire communication protocol.

As shown in FIG. 9, a generator 9001, which is one form of the generator 100 (FIGS. 1-3), is coupled to a power switching mechanism 9003 and a communications system 9005. In one aspect, the power switching mechanism 9003 comprises power solid state switches such as, for example, FET or MOSFET transistors, and/or relays, such as electromechanical relays. In one aspect, the communications system 9005 comprises components for D1 emulation, FPGA expansion, and time slicing functionalities. The power switching mechanism 9003 is coupled to the communications system 9005. Each of the power switching mechanism 9003 and the communications system 9005 are coupled to surgical instruments 9007, 9009 (labeled device 1 and device 2). Each of surgical instruments 9007, 9009 comprise components for a combined RF and ultrasonic energy input 9011, handswitch (HSW) 1-wire serial protocol interface 9013, HP 1-wire serial protocol interface 9015, and a presence resistor interface 9017. The power switching mechanism 9003 is coupled to the RF and Ultrasonic energy input 9011 for each of surgical instruments 9007, 9008. The communications system 9005 is coupled to the HSW 1-wire serial interface 9013, 9014, the HP 1-wire serial protocol interface 9015, 9016, and presence interface 9017, 9018 for each of surgical instruments 9007, 9008. While two surgical instruments are shown in FIG. 9, there may be more than two devices according to various aspects.

Figure 10:
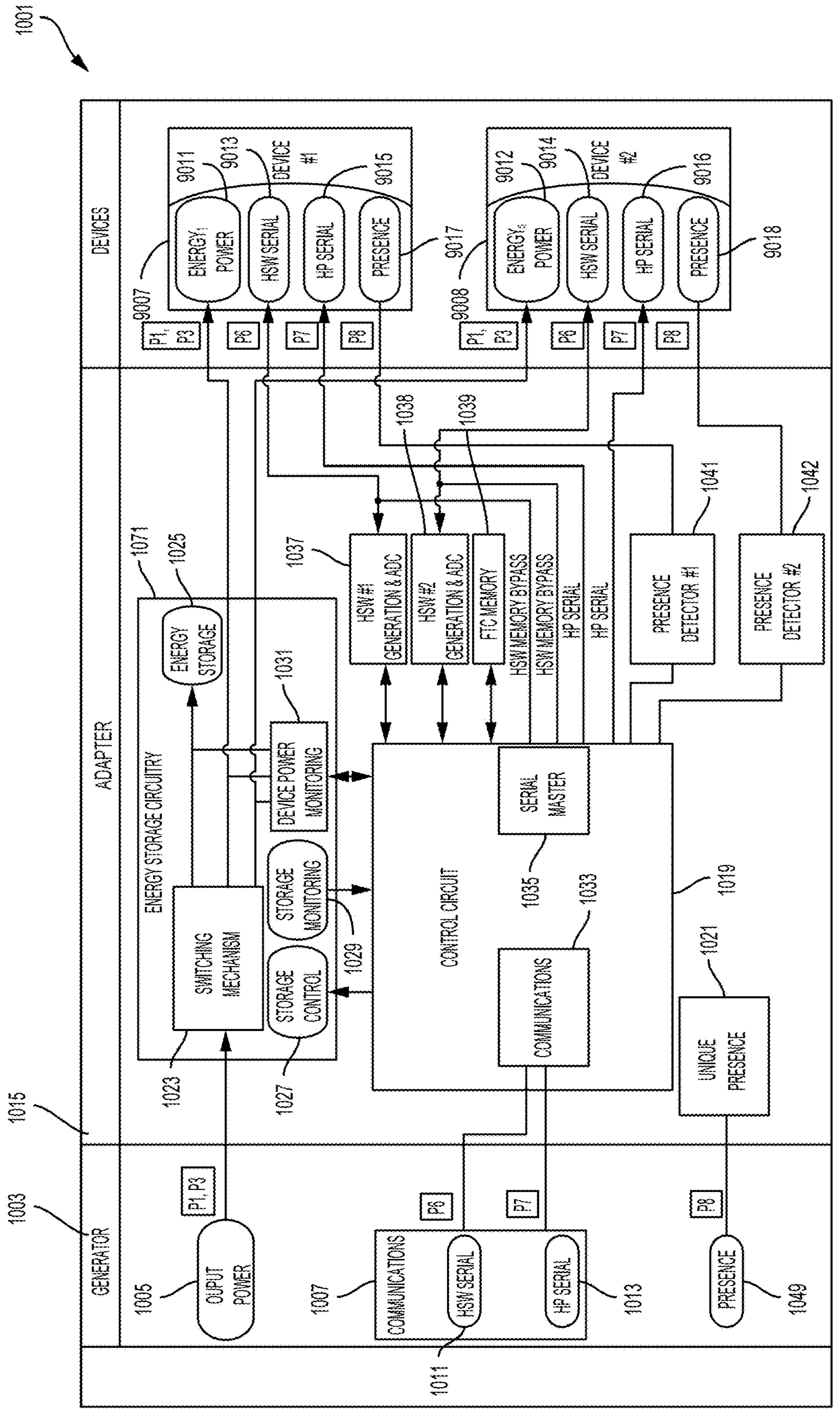
FIG. 10 illustrates a communications architecture of a system for delivering combined radio frequency and ultrasonic energy to a plurality of surgical instruments.
Figure 11:
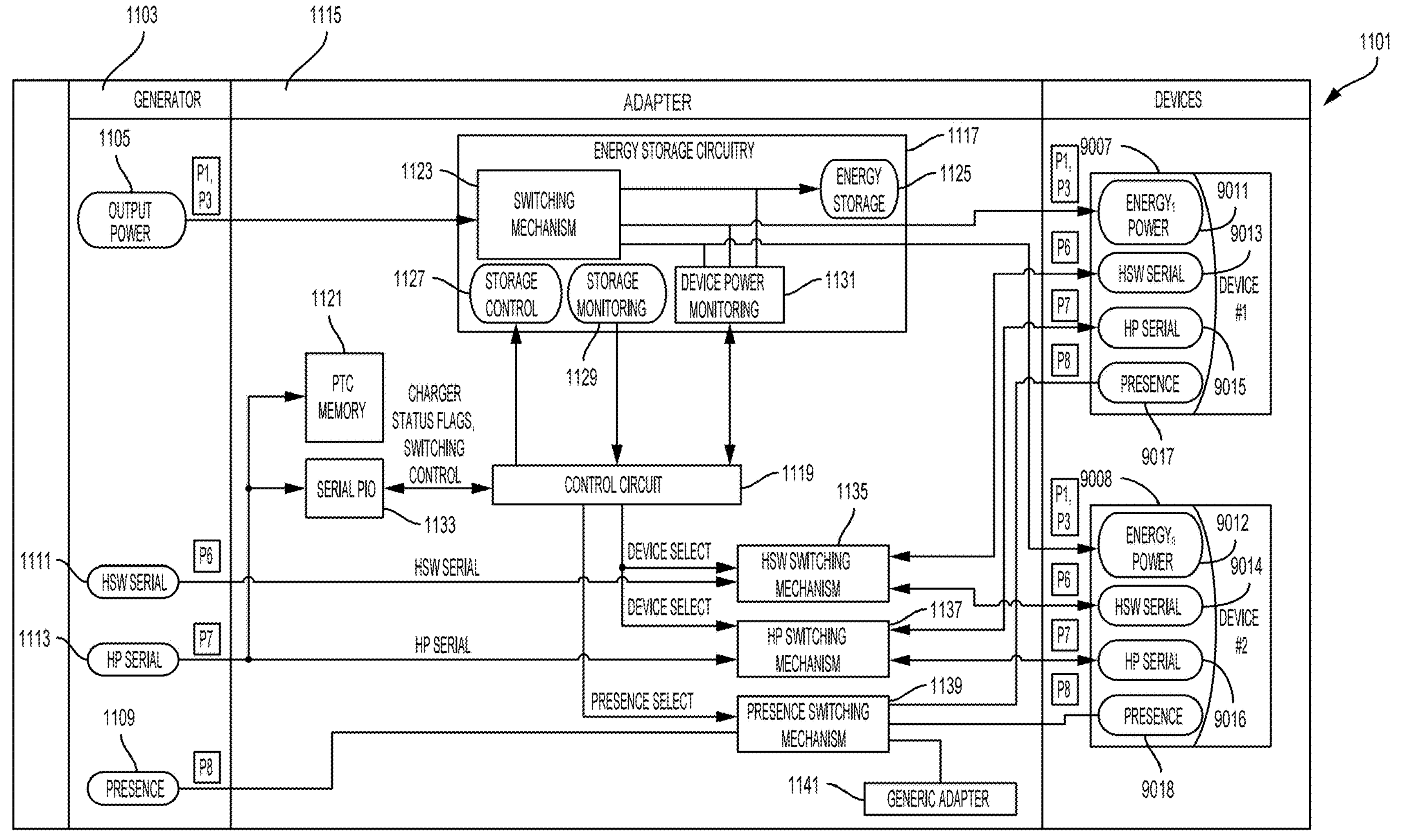
FIG. 11 illustrates a communications architecture of a system for delivering combined radio frequency and ultrasonic energy to a plurality of surgical instruments.
Figure 12:
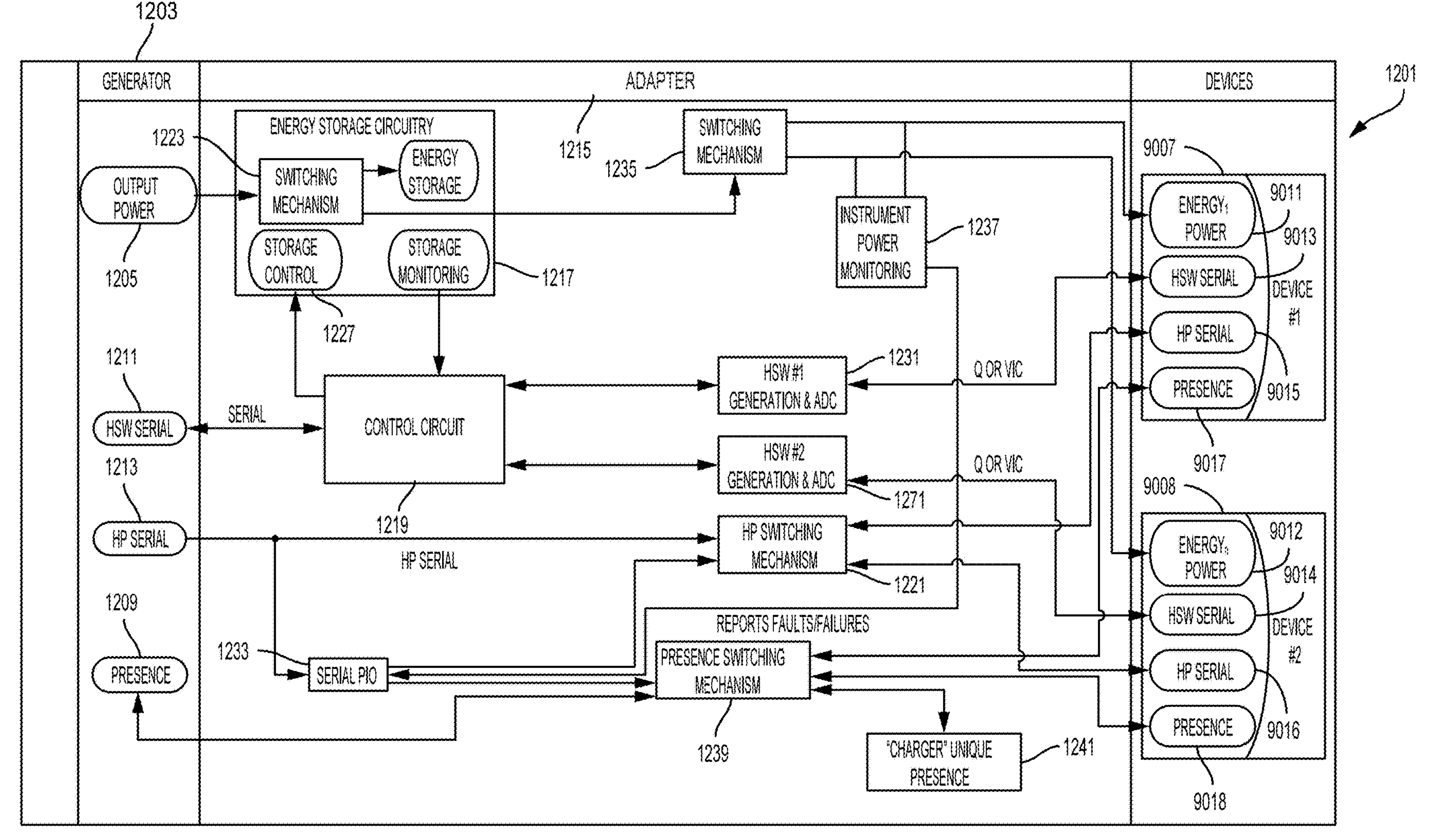
FIG. 12 illustrates a communications architecture of a system for delivering combined radio frequency and ultrasonic energy to a plurality of surgical instruments.

FIGS. 10-12 illustrate aspects of an interface with a generator to support two instruments simultaneously that allows the instruments to quickly switch between active/inactive by a user in a sterile field. FIGS. 10-12 describe multiple communication schemes which would allow for a super cap/battery charger and dual surgical instruments. The aspects of FIGS. 10-12 allow for communications to two surgical instruments in the surgical field from a generator with at least one communications port and allow for an operator in sterile field to switch between devices, for example, without modifying the surgical instruments.

FIG. 10 is a diagram of a communications architecture of system 1001 comprising a generator 1003, which is one form of the generator 100 (FIGS. 1-3), and surgical instruments 9007, 9008, which are shown in FIG. 9. According to FIG. 10, the generator 9001 is configured for delivering multiple energy modalities to a plurality of surgical instruments. As discussed herein the various energy modalities include, without limitation, ultrasonic, bipolar or monopolar RF, reversible and/or irreversible electroporation, and/or microwave energy modalities. The generator 9001 comprises a combined energy modality power output 1005, a communications interface 1007, and a presence interface 1049. According to the aspect of FIG. 10, the communications interface 1007 comprises an handswitch (HSW) serial interface 1011 and an handpiece (HP) serial interface 1013. The serial interfaces 1011, 1013 may comprise inter-integrated circuit ($I^2C$), half duplex SPI, and/or Universal Asynchronous Receiver Transmitter (UART) components and/or functionalities. The generator 1003 provides the combined energy modalities power output 1005 to an adapter 1015, for example, a pass-through charger (PTC). The adapter 1015 comprises energy storage circuit 1071, control circuit 1019, a unique presence element 1021, and associated circuit discussed below. In one aspect, the presence element 1021 is a resistor. In another aspect, the presence element 1021 may be a bar code, Quick Response (QR) code, or similar code, or a value stored in memory such as, for example, a value stored in NVM. The presence element 1021 may be unique to the adapter 1015 so that, in the event that another adapter that did not use the same wire interfaces could not be used with the unique presence element 1021. In one aspect, the unique presence element 1021 is a resistor. The energy storage circuit 1071 comprises a switching mechanism 1023, energy storage device 1025, storage control 1027, storage monitoring component 1029, and a device power monitoring component 1031. The control circuit 1019 may comprise a processor, FPGA, PLD, complex programmable logic device (CPLD), microcontroller, DSP, and/or ASIC, for example. According to the aspect shown in FIG. 10, an FPGA or microcontroller would act as an extension of an existing, similar computing hardware and allows for information to be relayed from on entity to another entity.

The switching mechanism 1023 is configured to receive the combined energy power output 1005 from the generator 1003 and it may be provided to the energy storage device 1025, surgical instrument 9007, and/or surgical instrument 9008. The device power monitoring component 1031 is coupled to the channels for the energy storage device 1025, surgical instrument 9007, surgical instrument 9008, and may monitor where power is flowing. The control circuit 1019 comprises communication interface 1033 coupled to the handswitch serial interface 1011 and an handpiece serial interface 1013 of the generator 1003. The control circuit 1019 is also coupled to the storage control 1027, storage monitoring component 1029, and device power monitoring component 1031 of the energy storage circuit 1071.

The control circuit 1019 further comprises a serial master interface 1035 that is coupled to handswitch (HSW) #1 circuit 1037 and handswitch (HSW) #2 circuit 1038, includes generation and ADC, a form of memory (non volatile or flash) 1039, along with a method for detecting the presence of an attached instrument (Presence) #1 circuit 1041 and Presence #2 circuit 1042, which includes a voltage or current source and ADC. The serial master interface 1035 also includes handswitch NVM bypass channels, which couple the serial master interface 1035 to the outputs of the handswitch #1 circuit 1037 and the handswitch #2 circuit 1038, respectively. The handswitch #1 circuit 1037 and handswitch #2 circuit 1038 are coupled to the HSW 1-wire serial protocol interfaces 9013, 9014 of the surgical instruments 9007, 9008, respectively. The serial master interface 1035 further includes handpiece serial channels that are coupled to the HP 1-wire serial protocol interfaces 9015, 9016 of the surgical instruments 9007, 9008, respectively. Further, Presence #1 and Presence #2 circuits 1041, 1042 are coupled to the presence interfaces 9017, 9018 of the surgical instruments 9007, 9008, respectively.

The system 1001 allows the control circuit 1019, such as an FPGA, to communicate with more surgical instruments using adapter 1015, which acts as an expansion adapter device. According to various aspects, the adapter 1015 expands the Input/Output (I/O) capability of the generator 1003 control. The adapter 1015 may function as an extension of the central processing unit that allows commands to be transmitted over a bus between the adapter 1015 and the generator 1003 and unpacks the commands and use them to bit-bang over interfaces or to control connected analog circuit. The adapter 1015 also allows for reading in ADC values from connected surgical instruments 9007, 9008 and relay this information to the generator control and the generator control would then control the two surgical instruments 9007, 9008. According to various aspects, the generator 1003 may control the surgical instruments 9007, 9008 as two separate state machines and may store the data.

Existing interfaces (the handswitch serial interface 1011 and the handpiece serial interface 1013 lines from generator 1003) may be used in a two-wire communication protocol that enables the generator 1003 control to communicate with multiple surgical instruments connected to a dual port interface, similar to the topology of a universal serial bus (USB) hub. This allows interfacing with two separate surgical instruments simultaneously. The system 1001 may be able to generate and read hand switch waveforms and be able to handle incoming handpiece serial buses. It would also monitor two separate presence elements in the surgical instruments 9007, 9008. In one aspect, the system 1001 may include a unique presence element and may have its own NVM.

Further, according to various aspects, the control circuit 1019 may be controlled by the generator 1003. The communication between the adapter 1015 and connected surgical instruments 9007, 9008 may be relayed to generator control. The generator 1003 would control the waveform generation circuit connected to the adapter 1015 to simultaneously generate handswitch signals for surgical instruments 9007, 9008.

The system 1001 may allow surgical instrument activity that can be simultaneously detected/monitored for two surgical instruments, even during activation. If upgradeable, the adapter 1015 would be capable of handling new surgical instrument communications protocols. Further, fast switching between surgical instruments may be accomplished.

FIG. 11 illustrates a communication architecture of system 1101 of a generator 1103, which is one form of the generator 100 (FIGS. 1-3), and surgical instruments 9007, 9008 shown in FIG. 9. According to FIG. 11, the generator 1103 is configured for delivering multiple energy modalities to a plurality of surgical instruments. As discussed herein the various energy modalities include, without limitation, ultrasonic, bipolar or monopolar RF, reversible and/or irreversible electroporation, and/or microwave energy modalities. As shown in FIG. 11, the generator 1103 comprises a combined energy modality power output 1105, an handswitch (HSW) serial interface 1111, a handpiece (HP) serial interface 1113, and a presence interface 1109. The generator 1103 provides the power output 1105 to an adapter 1115. According to the aspect shown in FIG. 11, communications between the adapter 1115 and the generator 1103 may be done solely through serial interfaces, such as the handswitch serial and handpiece serial interfaces 1111, 1113. The generator 1103 may use these handswitch and handpiece serial interfaces 1111, 1113 to control which instrument the generator 1103 is communicating with. Further, switching between instruments could occur between handswitch frames or at a much slower rate.

The adapter 1115 comprises energy storage circuit 1117, control circuit 1119, an adapter memory 1121 (e.g., a NVM such as an EEPROM), a serial programmable input/output (PIO) integrated circuit 1133, an handswitch Switching Mechanism 1135, an handpiece Switching Mechanism 1137, a Presence Switching Mechanism 1139, and a Generic Adapter 1141. In one aspect, the serial PIO integrated circuit 1133 may be an addressable switch. The energy storage circuitry 1117 comprises a switching mechanism 1123, energy storage device 1125, storage control component 1127, storage monitoring component 1129, and a device power monitoring component 1131. The control circuit 1119 may comprise a processor, FPGA, CPLD, PLD, microcontroller, DSP, and/or an ASIC, for example. According to the aspect of FIG. 11, an FPGA or microcontroller may have limited functionality and may solely comprise functionality for monitoring and communicating energy storage.

The switching mechanism 1123 is configured to receive the combined energy power output 1105 from the generator 1103 and it may be provided to the energy storage device 1125, surgical instrument 9007, and/or surgical instrument 9008. The device power monitoring component 1131 is coupled to the channels for the energy storage device 1125, surgical instrument 9007, surgical instrument 9008, and may monitor where power is flowing.

The control circuit 1119 is coupled to the serial PIO integrated circuit 1133 and the serial PIO integrated circuit 1133 is coupled to the handpiece serial interface 1113 of the generator 1103. The control circuit 1119 may receive information regarding charger status flags and switching controls from the serial PIO integrated circuit 1133. Further, the control circuit 1119 is coupled to the handswitch switching mechanism 1135, the handpiece switching mechanism 1137, and the presence switching mechanism 1139. According to the aspect of FIG. 11, the control circuit 1119 may be coupled to the handswitch (HSW) switching mechanism 1135 and the handpiece switching mechanism 1137 for device selection and the control circuit 1119 may be coupled to the presence switching Mechanism 1139 for presence selection.

The handswitch switching mechanism 1135, the handpiece switching mechanism 1137, and the presence switching mechanism 1139 are coupled to the handswitch serial interface 1111, the handpiece serial interface 1113, and the presence interface 1109 of generator 1103, respectively. Further, the handswitch switching mechanism 1135, the handpiece switching mechanism 1137, and the presence switching mechanism 1139 are coupled to the HSW 1-wire serial protocol interfaces 9013, 9014, the HP 1-wire serial protocol interfaces 9015, 9016, and the presence interfaces 9017, 9018 of the surgical instruments 9007, 9008, respectively. Further, the presence switching mechanism 1139 is coupled to the generic adapter 1141.

The generator 1103 switches between monitoring the surgical instruments 9007, 9008. According to various aspects, this switching may require the generator 1103 control to keep track of surgical instruments 9007, 9008 and run two separate state machines. The control circuit 1119 will need to remember which surgical instruments are connected, so that it can output an appropriate waveform to the ports where appropriate. The generator 1103 may generate/monitor hand switch signals, as well as communicating with serial NVM devices, such adapter memory 1121. The generator 1103 may maintain constant communication with the activating surgical instrument for the duration of the activation.

System 1101 also allows for a generic adapter presence element. When first plugged in or powered on, the adapter 1115 would present this adapter resistance to the generator 1103. The generator 1103 may then relay commands to the adapter 1115 to switch between the different presence elements corresponding to the different surgical instruments 9007, 9008 connected to it. Accordingly, the generator 1103 is able to use its existing presence resistance circuit. The NVM memory 1121 exists on the adapter 1115 for additional identification of the adapter and to provide a level of security. In addition, the adapter 1115 has a serial I/O device, i.e. serial PIO integrated circuit 1133. The serial PIO integrated circuit 1133 provides a communication link between the generator 1103 and the adapter 1115.

It may be possible to communicate over the handpiece serial bus using serial communications to handpiece NVMs and UART style communication to the control circuit 1119. According to one aspect, if SLOW serial communication is used (i.e. not overdrive) and a high speed serial protocol is used, system 1101 may need to ensure that the communications protocol does not generate a signal that looked like a serial reset pulse. This would allow better generator 1103 to adapter 1115 communications and faster switching times between surgical instruments 9007, 9008.

The system 1101 uses generator communications protocol and analog circuit and allows the generator to accomplish decision making. It is a simple and efficient solution that uses a small number of circuit devices.

FIG. 12 illustrates a communications architecture of system 1201 of a generator 1203, which is one form of the generator 100 (FIGS. 1-3), and surgical instruments 9007, 9008 shown in FIG. 9. According to FIG. 12, the generator 1203 is configured for delivering multiple energy modalities to a plurality of surgical instruments. As discussed herein the various energy modalities include, without limitation, ultrasonic, bipolar or monopolar RF, reversible and/or irreversible electroporation, and/or microwave energy modalities. As shown in FIG. 12, the generator 1203 comprises a combined energy modality power output 1205, an handswitch serial interface 1211, an handpiece serial interface 1213, and a presence interface 1209. In one aspect, the handpiece serial interface 1213 allows for communication with the handpiece lines of the surgical instruments 9007, 9008 and also allows for control of the adapter 1215. The generator 1203 provides the combined energy modality power output 1205 to an adapter 1215. The adapter 1215 comprises energy storage circuit 1217, control circuit 1219, a serial PIO integrated circuit 1233, handswitch (HSW) #1 circuit 1231, handswitch (HSW) #2 circuit 1271, handpiece switching mechanism 1221, presence switching mechanism 1239, switching mechanism 1235, instrument power monitoring 1237, and unique presence 1241. As shown in FIG. 12, the handswitch #1 circuit 1231 and the handswitch #2 circuit 1271 may comprise generation and ADC circuits. In one aspect, handswitch #1 circuit 1231 and/or handswitch #2 circuit 1271 comprise generation circuit with the ability to generate handswitch waveforms.

The control circuit 1219 is coupled to the handswitch serial interface 1211 of the generator 1203 while the serial PIO integrated circuit 1233 is coupled to the handpiece serial interface 1213 as is the handpiece switching mechanism 1221. Further, the control circuit 1119 is coupled to the handswitch #1 circuit 1231 and the handswitch #2 circuit 1271. The control circuit 1119 may comprise a processor, FPGA, CPLD, PLD, microcontroller, and/or ASIC, for example. In the example shown in FIG. 12, the control circuit 1219 modulates two devices into at least one digital waveform, which enable the generator 1203 to perform the button monitoring and decision making. The control circuit 1219 also may allow for communication to two independent surgical instruments could receive either waveform. The serial PIO integrated circuit 1233 is further coupled to the handpiece switching mechanism 1221, the instrument power monitoring 1237, and the presence switching mechanism 1239. The instrument power monitoring 1237 and the serial PIO integrated circuit 1233 may communicate results and failures to the generator 1203.

The switching mechanism 1223 is configured to receive the combined RF/ultrasonic power output 1205 from the generator 1203 and it may be provided to the energy storage circuit 1225 or the switching mechanism 1235. The control circuit 1219 is also coupled to the storage control 1227 and storage monitoring 1229 of the energy storage circuit 1217. The switching mechanism 1235 may provide the power output received from the switching mechanism 1223 to surgical instrument 9007, and/or surgical instrument 9008. The instrument power monitoring 1237 is coupled to the channels for the power output to the surgical instrument 9007 and surgical instrument 9008. The instrument power monitoring 1237 also may ensure that the switching mechanism 1235 is outputting power to correct location.

The handswitch #1 circuit 1231 and the handswitch #2 circuit 1271 are coupled to the HSW 1-wire serial protocol interfaces 9013, 9014 of the surgical instruments 9007, 9008, respectively. The handpiece switching mechanism 1221 is coupled to the handpiece serial interface 1213 of the generator 1203 and to the HP 1-wire serial protocol interfaces 9015, 9016 of the surgical instruments 9007, 9008, respectively. Further, the presence switching mechanism 1239 is coupled to the presence interface 1209 of the generator 1203 and to the presence Interfaces 9017, 9018 of the surgical instruments 9007, 9008, respectively. Further, Presence Switching mechanism is coupled to the unique presence 1241. In one aspect, different instrument presence elements may be switched on an on-demand basis using serial I/O or an adapter micro protocol.

A first communications protocol will be used to communicate to the control circuit 1219 on the adapter 1215. The generator 1203 also may have the ability to monitor surgical instruments 9007, 9008 at once. The adapter 1215 may comprise circuit to provide handswitch signal generation (e.g., in handswitch #1 circuit 1231 and handswitch #2 circuit 1271) along with ADCs to interpret this data. The adapter 1215 may modulate two surgical instrument signals into at least a first waveform and may have the ability to read in the first and second waveforms. In various aspects, the second waveforms may be interpreted and translated into the format of the first waveforms. Further, the first protocol has the ability to send 12 bits at 615 bits/sec.

The control circuit 1219 may take the handswitch data from surgical instruments 9007, 9008 and modulate it into a first protocol. There are a few ways of doing this, but it may mean that surgical instruments 9007, 9008 may comprise a first protocol functionality. The system 1201 could communicate 4-6 buttons from the surgical instrument 9007 and 4-6 buttons from the surgical instrument 9008 in the first protocol frame. Alternatively, the system 1201 could use some form of addressing to access the surgical instruments 9007, 9008. The control circuit 1219 may have the ability to address separate devices by having the generator 1203 send the control circuit 1219 different addresses split into two different address spaces, one for surgical instrument 9007 and one for surgical instrument 9008.

The handpiece communications may involve some form of switch that could either be controlled via a serial I/O device or through the control circuit 1219 via a first protocol style communication interface from the generator 1203. In one aspect, energy storage monitoring 1229 and switching between surgical instruments 9007, 9008 and charging states could be handled in this manner as well. Certain first protocol addresses could be assigned to the data from the energy storage circuit 1225 and to the surgical instruments 9007, 9008 themselves. Presence elements could also be switched in with this format. Further, in one aspect, the control circuit 1219 may translate frames into a separate format, which may mean that the control circuit 1219 might need to make some decisions on whether button presses on surgical instruments 9007, 9008 are valid or not. The system 1201 would, however, allow the generator 1203 to fully monitor the surgical instruments 9007, 9008 at the same time time-slicing or handling a new communications protocol on the handswitch serial interface 1211 of the generator 1203. The system 1201 uses generator communications to simultaneously detect the activity of two surgical instruments, even during activation.

As noted above, a single output generator can deliver both RF and ultrasonic energy through a single port and these signals can be delivered separately or simultaneously to the end effector to treat tissue. One aspect of a combined RF and ultrasonic generator is shown in FIG. 1. As shown in FIG. 1, a single output port generator can include a single output transformer with multiple taps to provide power, either RF or ultrasonic energy, to the end effector depending on the type of treatment of tissue being performed. For example, the generator can deliver energy with higher voltage and lower current to drive an ultrasonic transducer, with lower voltage and higher current as required to drive electrodes for sealing tissue, or with a coagulation waveform for spot coagulation using either monopolar or bipolar electrosurgical electrodes. The output waveform from the generator can be steered, switched, or filtered to provide the desired frequency to the end effector of the surgical instrument.

The surgical instruments described herein can also include features to allow the energy being delivered by the generator to be dynamically changed based on the type of tissue being treated by an end effector of a surgical instrument. An algorithm for controlling the power output from a generator, such as generator 100, that is delivered to the end effector of the surgical instrument can include an input that represents the tissue type to allow the energy profile from the generator to be dynamically changed during the procedure based on the type of tissue being effected by the end effector of the surgical instrument.

Various algorithms can be used to select a power profile to allow the energy being delivered from the generator to dynamically change based on the tissue type being treated by the surgical instrument.

In order to determine the type of tissue being treated by the end effector of the surgical instrument, a tissue coefficient of friction can be calculated. The calculated tissue coefficient of friction is compared to a database of tissue coefficients of friction that correlates each tissue coefficient with a tissue type, as will be discussed in more detail below. The calculated tissue coefficient of friction and its related tissue type are used by an algorithm to control the energy being delivered from the generator to the surgical instrument. In one form, the tissue coefficient of friction is described by:

$$\mu = \frac{Q}{\vartheta \cdot N}$$

Where Q is the rate of heat generation, $\vartheta$ is the velocity of the ultrasonic motion of the end effector, and N is the force applied to the tissue by the end effector. The velocity of the ultrasonic motion is a known value from the settings of the generator. Since the value $\vartheta$ is a known value, the tissue coefficient of friction can be calculated using the slope of a graph of heat generation versus force on the tissue.

The force applied to the tissue by the end effector can be measured in a variety of ways using different type of components to measure force. This force measurement can be used, for example in the equation above, to determine the tissue coefficient of friction of the tissue being treated to determine its tissue type.

FIGS. 13-42 describe various examples of circuit topologies of a system with a combined generator configured to provide a combined signal with RF and ultrasonic energy frequencies to one or more surgical instruments.

Figure 13:
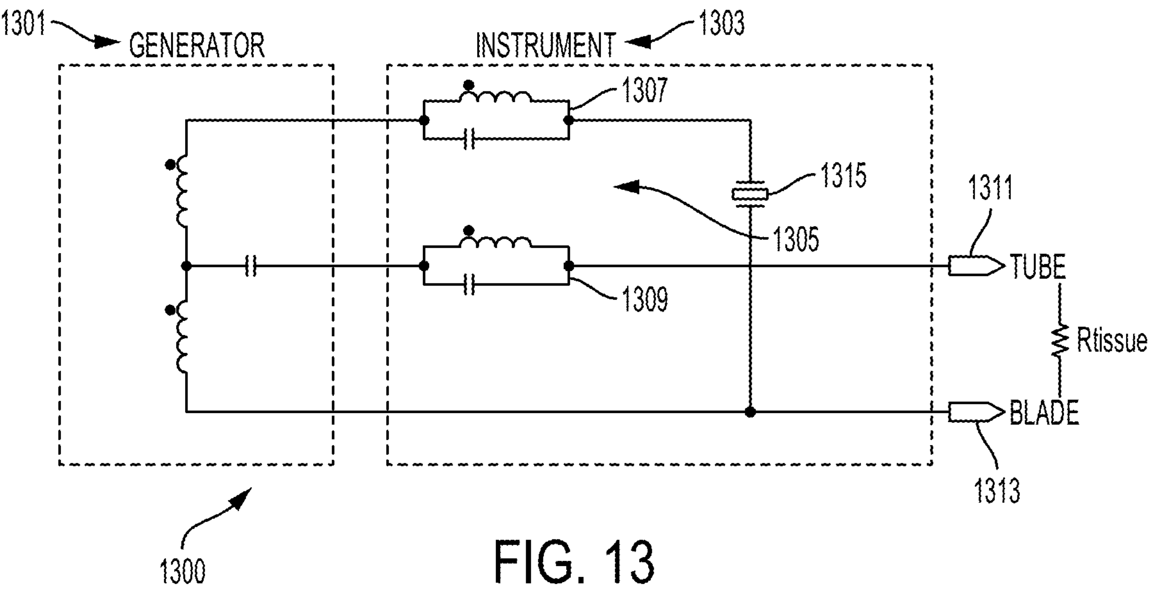
FIG. 13 is a circuit diagram for a system that is configured to manage RF and ultrasonic currents output by a generator according to one aspect of the present disclosure.

FIG. 13 displays a circuit diagram for a system 1300 including a band-stop filtering circuit 1305 for a combined ultrasonic and RF surgical instrument 1303 that is configured to manage RF and ultrasonic currents output by a generator 1301. The band-stop filter circuit 1305 leverages a variable output frequency of the generator 1301 and employs tuned LC filter circuits 1307, 1309 to block unwanted output current. The circuit band-stop filter 1305 does not disconnect either the ultrasonic transducer or the RF output galvanically. Instead, both outputs are connected to their respective output terminals 1311, 1313 through an LC parallel resonant network of the tuned LC filter circuits 1307, 1309, respectively. A resonator 1315 is coupled to LC filter circuit 1307 and ultrasonic output terminal 1313 (labeled blade). As shown in FIG. 13, the LC filter circuit 1307 forms a parallel resonant network in series with the ultrasonic output terminal 1313 is tuned to the RF output frequency and exhibits an extremely high impedance at ~300 kHz. The parallel resonant network of the LC filter circuit 1309 in series with the RF output terminal 1311 is tuned to the ultrasonic output frequency and exhibits an extremely high impedance at ~55 kHz.

Undesirable frequency content is blocked to each output terminal 1311, 113, thereby preventing unwanted excitation/dissipation in the transducer and unwanted low frequency current in the tissue. Depending on the attenuation required for each output terminal 1311, 1313, in aspects, the LC filter circuits 1307, 1309 can be further enhanced with additional resonant components. Since this concept does not rely on direct interaction with a control circuit in the surgical instrument, no changes or direct interface to the ASIC would be needed.

The band-stop filter circuit 1305 has the potential of allowing simultaneous RF and Ultrasonic therapy to the same surgical instrument. According to various aspects, a complex, multi-frequency output waveform may be applied and the resonant filters remain effective.

FIG. 14 displays a circuit diagram for a system 1400 for a combined ultrasonic and RF surgical instrument 1409 that is configured to manage RF and ultrasonic currents output by a generator 1401. System 1400 may be used for analyzing a high frequency band-stop filter. As shown in FIG. 14, system 1400 includes: an ultrasonic output of the generator 1401, with leakage inductance 1403 and sensing components 1405; 10' Cable model 1407 (which, according to the aspect of FIG. 14, has properties of 3.1 uH, 194 pF, 1 ohm); and a combined ultrasonic and RF surgical instrument 1409 that includes a parallel LC filter circuit 1411 for blocking RF content and an ultrasonic transducer 1413. FIGS. 15-21 are graphical depictions of simulation results for the system 1400 that illustrate the effect of the LC filter circuit 1411 that is intended to block high frequency RF content and prevent excessive RF current to the ultrasonic transducer 1413.

The system 1400 was simulated in both the stop-band, at 350 kHz, and the pass band, at 55 kHz, to shown that the parallel LC filter circuit 1411 is effective at blocking the unwanted current while still allowing normal operation in the pass-band. For the stop-band simulation, the generator 1401 is set to maximum RF amplitude of 100 $V_{rms}$ on the RF output which results in 365 $V_{pk}$ on the ultrasonic tap as shown below. For the pass-band simulation, the generator 1401 is set to maximum ultrasonic output voltage of 150 $V_{rms}$ or 212 $V_{pk}$ and the transducer is loaded to 400 ohms.

According to FIG. 15, the normalized transducer voltage versus frequency is shown in the plots 1501, 1503 with and without the LC filter circuit 1411, respectively. The voltage rise in the unfiltered plot 1503 is due to the un-damped series resonance of the transformer leakage inductance and C0. This resonance coincidently falls near the 350 kHz output frequency for the RF output of the generator 1401. The presence of the band-stop filter dominates the output impedance and results in significant attenuation at 350 kHz, however, it also results in some gain peaking at a lower frequency than is seen without the LC filter circuit 1411. Any gain peaks shown on these plots 1501, 1503 may amplify ultrasonic content at these frequencies, therefore, aspects of the present disclosure may maintain a low distortion output while in ultrasonic mode.

FIG. 16 shows the time domain waveforms of the system 1400 with the output frequency set to the stop-band, at 350 kHz. The plots 1603, 1601 illustrate the transducer current versus time with and without the band-stop LC filter circuit 1411, respectively. Plot 1601 demonstrates that without a filter or switch to disconnect the ultrasonic transducer 1413, the large value of C0 acts as a short circuit and results in large output currents. The currents shown may not be realized in some generator configurations and might result instead in a shutdown or service-oriented architecture (SOA) fault. Plot 1603 demonstrates that the LC filter circuit 1411 can effectively block the RF content at the resonant frequency, resulting in only milliamps of current in the transducer 1413. The LC filter circuit 1411 may block/cancel the full output voltage amplitude of 365 $V_{pk}$.

FIG. 17 shows the generator 1401 output power versus time at 350 kHz, where the plots 1701, 1703 are without and with the band-stop LC filter circuit 1411, respectively. FIG. 17 illustrates that the total dissipation in the system 1400 may be kept low; however, this aspect does not include core losses in the inductor (labeled Lf) and only reflects conduction losses from the circulating current in the LC tank of the LC filter circuit 1411. The circulating currents 1803, 1805, of the inductor (labeled Lf) and capacitor (labeled Cf), respectively, of the LC filter circuit 1411 are shown according to current versus time in FIG. 18. The voltage 1801 across the LC filter circuit 1411 is shown according to voltage versus time. The core losses in the inductor (labeled Lf) may be very significant under test conditions, depending on the specific material, size and configuration of the resonant inductor shown in FIG. 14.

FIG. 19 shows the current of the transducer 1413 where the output frequency of the generator 1401 is set to a pass-band of 55 kHz. Plots 1901, 1903 are in terms of current versus time, and show the current of the ultrasonic transducer 1413 without and with LC filter circuit 1411, respectively. The plots 1901, 1903 illustrate the time domain waveforms of the system 1400 and demonstrate that the normal operation of the ultrasonic transducer 1413 would be unaffected by the presence of the LC filter circuit 1411. According to the aspect of FIG. 14, the inductor (labeled Lf) in the LC filter circuit 1411 is dominant at the pass-band frequency (55 kHz) and represents a low enough impedance to allow normal load current to flow to the ultrasonic transducer 1413 with minimal phase shift or loss.

Additionally, FIG. 20 shows the generator 1401 output power in terms of real power versus time, where the output frequency of the generator 1401 is set to the pass-band of 55 kHz. Plots 2001, 2003 are without and with the LC filter circuit 1411, respectively. Further, FIG. 21 shows plots of the voltage 2101 across the LC filter circuit 1411 at 55 kHz and of the currents in the inductor (labeled 2103 and capacitor 2105 of the LC filter circuit 1411 at 55 kHz, where the inductor, L, is equal to 100 uH, and the capacitor, C, is equal to 2.07 nF. According to aspects, generator configuration software may need to be updated to compensate for the presence of the LC filter circuit 1411 and account for its effects in the control loop, but the plots of FIGS. 19-21 indicate that ultrasonic functionality of the ultrasonic transducer 1413 should remain unaffected by the LC filter circuit 1411.

FIG. 22 illustrates a circuit diagram for a system 2200 that includes a high frequency band-stop filter according to one aspect of the present disclosure. The system 2200 includes: the RF output of the generator 2201, with leakage inductance 2203 and series output capacitor 2207; cable model 2209 (which, according to the aspect of FIG. 22, has properties of 3.1 uH, 194 pF, 1 ohm); a surgical instrument 2211 including parallel LC filter circuit 2213 for blocking ultrasonic content; and tissue impedance 2215.

This system 2200 was simulated in both the stop-band, at 55 kHz, and the pass band, at 350 kHz. For the stop-band simulation, the generator 2301 is set to maximum amplitude of 150 $V_{rms}$ on the ultrasonic output which results in 82 $V_{pk}$ on the RF output. For the pass-band simulation, the generator 2301 is set to maximum RF output voltage of 100 Vrms or 141 Vpk and the tissue impedance is set to 50 ohms. FIGS. 23-33 provide simulation results that show that the system 2200 is effective at blocking unwanted current while still allowing normal operation in the pass-band.

FIG. 23 shows the normalized output (applied at the tissue impedance) in terms of voltage versus frequency. The plots 2301, 2303 are with and without the LC filter 2213, respectively. Plot 2303 (no LC filter) shows some attenuation at low frequency. This is due to the series capacitor 2205 that resides in the generator. According to the aspects shown in FIG. 23, the capacitor 2205 has a value of 47 nF. The series capacitance 2205 is resonant with the cable 2209 and transformer leakage inductance 2203 and the response can be seen gently peaking very near 300 kHz before the series inductance dominates the output impedance and begins to once again cause some attenuation.

Plot 2301 (with the LC filter) shows significant attenuation at 55 kHz. The attenuation is most effective in a very narrow band, but that is acceptable since the harmonic output operates in a well-defined operating frequency. As the output frequency increases past 300 kHz, the capacitance dominates the LC filter and a resonant peak is formed near 500 Khz. According to one aspect, the RF output can be tuned to this peak. There is a relatively small amount of attenuation in the 300-500 kHz range and operating points in this range would be acceptable depending on the application. The high frequency attenuation is largely lossless, and results from a reactive voltage drop across the LC tank.

FIG. 24 shows the time domain waveforms of the current through the tissue impedance 2215 where the output frequency of the generator 2201 is set to the stop-band, at 55 kHz. The plots 2401, 2403 are without and with the band-stop LC filter 2213, respectively. Plot 2403 shows that the tissue current can be kept low, even at a maximum harmonic output voltage of 150 $V_{rms}$ with the application of the band-stop LC filter 2213.

FIG. 25 illustrates real power versus time for the output power of the generator 2201 where the output frequency is set to the stop-band, at 55 kHz. Plots 2501, 2503 are without and with the band-stop LC filter 2213, respectively. FIG. 25 shows that the conduction losses from the circulating current in the LC tank of the band-stop LC filter 2213 may be kept very low.

FIG. 26 shows the voltage across the LC filter 2213 and the circulating currents of the inductor (labeled Lf2) and capacitor (labeled Cf2) shown FIG. 22. Plot 2601 is the voltage across the LC filter 2213 in terms of the voltage versus time and plots 2603 and 2605 are the circulating currents of the inductor (labeled Lf2) and capacitor (labeled Cf2) in terms of current versus time, respectively. The core losses in the inductor of the LC filter circuit 2213 are less in system 2200 than the core losses in the inductor of the LC filter circuit 1411 of system 1400, due to the lower frequency, voltage, and current in resonance, comparatively.

FIG. 27 shows time domain waveforms of the transducer current where the output frequency is set to the pass-band, at 350 kHz. The plots 2701, 2703 are without and with the LC filter 2213, respectively. The plots 2701, 2703 show that the normal operation RF output would be unaffected by the presence of the LC filter 2213. The capacitor (labeled Cf2 in FIG. 22) in the LC circuit 2213 is dominant at this frequency and the capacitor represents a low enough impedance to allow normal load current to flow with minimal phase shift or loss.

FIG. 28 displays the generator output power where the output frequency is set to the pass-band, at 350 kHz. Plots 2801 and 2803 are plots of real power versus time without and with LC filter 2213, respectively. It can be seen in FIG. 28 that the output power of the generator 2201 is reduced with the LC filter 2213 versus without. This is due to the capacitive reactance of the filter 2213 causing a voltage drop and effectively reducing the output voltage at the tissue 2215. Further, FIG. 29 shows plots of the voltage 2901 across the LC Filter 2213 at 55 kHz along with plots of the inductor current 2903 and capacitor current 2905 of the LC filter 2213 at 55 kHz, where the inductor, Lf2, is equal to 750 uH, and the capacitor, Cf2, is equal to 11 nF.

The system 2200 was also simulated for a high voltage transducer. The high voltage transducer simulation set the maximum harmonic voltage to $400V_{rms}$ and the transducer model 2211 was changed so that the high voltage transducer has a C0 capacitance of 1.1 nF and a maximum load (tissue) impedance of 1000 ohms. The high voltage transducer system was simulated in both the stop-band, at 350 kHz, and the pass band, at 55 kHz, to demonstrate that the high voltage transducer system is effective at blocking the unwanted current while still allowing normal operation in the pass-band. For the stop-band simulation, the generator 2201 was set to maximum RF amplitude of $100V_{rms}$ on the RF output which results in 365 Vpk on the harmonic output. For the pass-band simulation, the generator 2201 was set to maximum harmonic output voltage of $400V_{rms}$, or 566 Vpk, and the high voltage transducer was loaded to 1000 ohms. FIGS. 30-33 illustrate the results of the high voltage transducer simulation.

FIG. 30 provides the resonant filter current and generator output power, at 350 kHz. FIG. 30 shows plots of the inductor current 3001 and capacitor current 3003, in Current (Amps) versus time, and a plot of the output power 3005 of the generator 2201, in Power (Watts) versus time. Further, FIG. 31 provides plots of the voltage 3101 and current 3103 across the high voltage transducer at 350 kHz. Additionally, FIG. 32 provides plots of resonant filter current and output power of the generator, at 55 kHz. FIG. 32 shows plots of the inductor current 3201 and capacitor current 3203, in Current (Amps) versus time, and a plot of the output power 3205 of the generator, in Power (Watts) versus time. Lastly, FIG. 33 provides plots of the voltage 3301 and current 3303 across the high voltage transducer at 55 kHz.

The previous simulation results show that the configurations of the LC band-stop filter of the present disclosure are effective at blocking the RF output frequency. Additionally, the simulation results also show that circuit design configurations may be optimized for the inductor and capacitor components. According to various aspects, these components may be sized and configured to support the resonant current and high output voltage of a system, while doing so at relatively low loss.

According to one aspect, resonant capacitors of the LC band-stop filter are chosen so that the resonant capacitor offers a small size and a low dissipation factor at the frequency of use. A high frequency mica capacitor, such as the CD16 series shown below in TABLE 1, has exceptional performance at the RF output frequency and offers a high current carrying capacity. According to one aspect, a single component with these specifications meets the circuit requirements without the requirement that it be connected in parallel with another component to limit losses.

TABLE 1

| Manufacturer | Part Number | Length | Height | Thickness | Current @ 500 kHz | ESR |
|---|---|---|---|---|---|---|
| Cornell Dubilier | CD16FD222J03 | 11.9 mm | 13.2 mm | 6.4 mm | 2.1 Arms | 0.07 ohm |

According to various aspects, the inductor may be the primary source of loss in a LC band-stop filter circuit and may also drive the overall size of the circuit. There may be tradeoffs between these two factors, because smaller core geometries operate at high flux density and consequently, may have more loss. Although core loss is a consideration for both the high frequency and low frequency inductor components, core loss will be more critical for the high frequency component. According to one aspect, selection of a high efficiency core material that is optimized to operate at frequencies above 300 kHz is beneficial in order to keep losses at a particular level.

Configuration parameters for selection of an inductor include: the efficiency and performance of an optimized inductor configuration; the space available in the handle of a hand piece of the surgical instrument; the duty cycle of the application; the ability of the hand piece configuration to dissipate heat and remain acceptably cool.

As mentioned, losses may be driven predominantly by the inductor, assuming an appropriate capacitor is used that has a low dissipation factor. The mode of operation that will dissipate the most power may be when the LC circuit is operating at resonance (blocking) and not when it is passing the generator output to the respective load of the LC circuit. While at resonance, the full output voltage of the generator is seen by the LC circuit causing maximum core loss and the circulating current that is being exchanged between the capacitor and inductor may also cause copper losses.

The robustness and simplicity of the circuit components enhances safety parameters of the systems described above, for example, because the likelihood of component failure is diminished. According to various aspects, in the event of a damaged defective resonant component, systems of the present disclosure may rely on a generator to detect the presence of the defective component and correct the impedance vs frequency characteristic with a pre-run diagnostic. A pre-run diagnostic may offer direct confirmation that the LC circuit is tuned and undamaged.

According to various aspects, size and weight for the systems may be controlled by the inductor. The configuration considerations for the inductor configurations discussed above may push the inductor to be larger and heavier in order to keep the efficiency at an acceptable level. According to various aspects, given an identical set of output power requirements, the size and weight of LC band-stop filter circuit configuration may be greater than a solid state switch-based (e.g., MOSFET switch-based) configuration discussed below. According to one aspect, an LC circuit may potentially consist of a mere four passive components. According to another aspect, the LC circuit may not require the use of a printed circuit board. According to other aspects, the LC circuit may be implemented without any ASIC or hand switch electronics. Complexity of the LC circuit may increase depending on the needs of the specific application and on the possibility of implementing a hybrid concept that combines more than one of the circuits of the present disclosure. The prospect of very few components, no printed circuit board, or at least a minimalistic one, will serve to reduce both component and labor costs for the circuit configurations discussed above with regard to FIGS. 13-33. According to various aspects, some components may be custom engineered or high performance off-the-shelf items.

FIG. 34 is a circuit diagram of a system 3400 for a combined Ultrasonic and RF surgical instrument 3403 that is configured to manage RF and ultrasonic currents output by a generator 3401. The instrument circuit 3405 uses solid state switches such as MOSFET switches 3407, 3409 arranged in series to provide AC switching for each output 3411, 3413. Rather than the MOSFET switches 3407, 3409 being directly controlled by a control circuit, the instrument circuit 3405 employs tuned LC circuits 3421, 3423 to enhance the MOSFET switches 3407, 3409. Resonator 3419 is coupled to MOSFET switch 3407 is coupled to and ultrasonic output 3413 (labeled blade). This approach uses a pair of MOSFET switches 3407, 3409 that are arranged source-source, creating an AC switch. Rather than having the ASIC control the MOSFET enhancement, this approach leverages a coupled inductor 3415, 3417 that is capacitor tuned to enhance the gates of the MOSFET switches 3407, 3409 at the appropriate output frequency. When driving at the resonant frequency, the LC circuit 3421, 3423 generates a voltage on the primary of the coupled inductor 3415, 3417, which produces a gate enhancement potential. Since the MOSFET gate represents a minimal load, the inductor 3415, 3417 and gate drive circuitry can be relatively small and efficient.

FIG. 35 illustrates a circuit diagram for a system 3500 that includes: the Ultrasonic and RF output of the generator 3501; and an instrument 3503 that includes series connected solid state switches such as MOSFET switches 3505, 3507, a coupled inductor 3511, and an ultrasonic transducer model 3509 loaded to 400 ohms. The system 3500 was simulated at both 350 kHz and 55 kHz to verify correct functionality in both operating states: the blocking mode and the pass-through mode. For the blocking mode, the generator 3501 was set to maximum amplitude of $100V_{rms}$ on the RF output, which results in $365V_{pk}$ on the ultrasonic output. For the pass-through mode, the generator 3501 is set to maximum ultrasonic output voltage of $150V_{rms}$ or $212V_{pk}$ and the ultrasonic transducer model 3509 is loaded to 400 ohms.

FIGS. 36-41 provide simulation results for the system 3500. FIG. 36 displays the un-clipped MOSFET gate voltage v. frequency, when the RF output amplitude equals $100V_{rms}$. Plot 3600 shows the peak voltage at the secondary of the coupled inductor. The potential shown is unclipped, as the nonlinear transfer function of the Zener diode (labeled as D1 is FIG. 35) is not modeled in an AC sweep. According to one embodiment, BSP299 MOSFETs are used that have a minimum gate threshold of 2.1V, and accordingly the MOSFETs will be fully enhanced with a 55 kHz output signal but will remain off at 350 kHz, even at a maximum output amplitude of $100V_{rms}$.

As shown in FIG. 37, plots 3701 and 3703 illustrate the voltage of the coupled inductor 3511 and the MOSFET gate-source voltage, respectively, when the system 3500 is in the blocking mode. Further, as shown in FIG. 38, plots 3801 and 3803 illustrate the transducer 3509 current and voltage, respectively, when the system 3500 is in the blocking mode. The plots 3701, 3703, 3801, and 3803 show the time domain waveforms of the system 3500 with the output frequency set to 350 kHz and an RF amplitude of 100 Vrms. Further, the plots 3701, 3703, 3801, and 3803 show that the MOSFET S3505, 3507 are effectively off and the transducer 3509 is blocking excess current in the transducer 3509 when the system 3500 is in the blocking mode.

As shown in FIG. 39, plots 3901 and 3903 illustrate the voltage of the coupled inductor 3511 and the MOSFET gate-source voltage, respectively, when the system 3500 is in the pass-through mode.

Further, as shown in FIG. 40, plots 4001 and 4003 illustrate the transducer 3509 current and voltage, respectively, when the system 3500 is in the pass-through mode. The plots 3901, 3903, 4001, and 4003 show the time domain waveforms of the system 3500 with the output frequency set to 55.5 kHz and a harmonic amplitude of $150V_{rms}$. The plots 3901, 3903, 4001, and 4003 also show that the MOSFETs are effectively enhanced and the transducer is receiving full output voltage and current.

The plot 4101 shown in FIG. 41 displays the total MOSFET losses in 3505 and 3507 in system 3500, when the system 3500 is in the pass-through mode. The plot 4101 shows that the losses in the MOSFETs 3505, 3507 are less than 1 W total. Losses for the system 3500 are primarily based on the MOSFET switches 3505, 3507. The MOSFET switches 3505, 3507 may be optimized for each of the harmonic and RF outputs and since the switching time is in the millisecond scale and not nanoseconds, high efficiency parts may allow for low total losses. Overall power efficiency of the system 3500 may exceed other circuit designs.

The size and weight of the instrument 3503 with a resonant MOSFET circuit may be moderate. The MOSFETs used to interrupt the generator output may be smaller than an equivalent RF band stop filter implementation, but in some embodiments they may require some board level thermal management, which may consume board space. According to embodiments, components of the system 3500 may be substantially off-the shelf and require no custom engineered components. According to embodiments, a possible custom component may be a coupled inductor, which might include a special form factor or inductance. Overall, the cost of a resonant MOSFET switch is moderate.

FIG. 42 is a circuit diagram of a system 4200 for a combined ultrasonic and RF surgical instrument 4203 that is configured to manage RF and ultrasonic currents output by a generator 4201. The instrument circuit 4205 uses a pair of solid state switches such as MOSFET switches 4215, 4217 that are arranged source-source, creating an AC switch. The control circuit 4206 (e.g., ASIC) controls the MOSFET enhancement with control signals that are coupled via pulse transformers 4219, 4221. Since the MOSFET gate represents a minimal load and the switching rate is low, the power required to enhance the pair of MOSFET switches 4215, 4217 is very low. The control circuit 4206 outputs would be buffered by a small driver IC (not shown) that provides the pulse current needed to drive one or both of the pulse transformers 4219, 4221. One polarity of differential pulse applied to a pulse transformer 4219, 4221 will enhance the pair of MOSFET switches 4215, 4217, and the opposite polarity will turn the pair of MOSFET switches 4215, 4217 off. The pulse pattern will repeat at a maintenance interval to enforce the gate-source condition of the pair of MOSFET switches 4215, 4217. Discrete logic hardware can also be used to enforce mutually exclusive conditions in each AC switch and provide a partial mitigation to potential safety concerns.

FIG. 43 illustrates a circuit diagram for a system 4300 that includes: the Ultrasonic and RF output of the generator 4301; and an instrument 4303 including series connected pair of solid state switches such as MOSFET switches 4305, 4307, a transducer model 4309 loaded to 400 ohms; power/GND reference 4311 via a rectified hand switch; and pulse generators 4313, 4315 representing logic buffers or MOSFET driver ICs. This system 4300 was simulated at 55 kHz in both the 'On' state and the 'Off' state to verify correct functionality in both operating states. For the both operating states the generator 4301 is set to maximum amplitude of 150 Vrms on the ultrasonic output.

Losses for the system 4300 are driven primarily by the pair of MOSFET switches 4305, 4307. According to various aspects, these parts can be optimized for each output and since the switching time is in the millisecond scale and not nanoseconds, high efficiency parts may be available that contribute low total loss. The remaining components that enhance the MOSFET are not power components and should not be a significant contributor to losses. Overall power efficiency of the system 4300 is considered to be good. According to various aspects, a single fault tolerant architecture that employs redundant components may provide a solution to a component failure hazard. The size and weight of the ASIC controlled MOSFET switch circuit configuration of instrument 4303 is excellent. The MOSFETs used to interrupt the generator output may be smaller than equivalent RF filter implementations, but may also require some board level thermal management that consumes board space. According to various aspects, the pulse transformer and buffer that enhance the MOSFET switch may also be very small. Additionally, the components for the ASIC controlled MOSFET switch circuit configuration of instrument 4303 may off-the shelf and require no custom engineered components.

FIGS. 44-46 show the performance of the ASIC controlled MOSFET switch circuit design of instrument 4303 in the off-state. Although the MOSFET pairs 4305, 4307 are initially off at 0V, the gate source voltage is driven to a negative voltage in this state to improve transient immunity and ensure that the MOSFET pairs 4305, 4307 stay in the off state. Gate switching begins at t=10 ms to allow response times to be evaluated. FIG. 44 shows a plot 4403 of the output of pulse generator 4315 and a plot 4401 of the voltage across the gate-source of the MOSFET labeled M4. FIG. 45 shows a plot 4501 of the voltage of the transducer 4309 and a plot 4503 of the current through the transducer 4309, when the system 4300 is in the off-state. FIG. 46 shows a plot 4601 of the total MOSFET losses in the MOSFET pairs 4305 when the system 4300 is in the off-state.

FIGS. 47-49 show the performance of the ASIC controlled MOSFET switch circuit design of instrument 4303 in the on-state. Gate switching begins at t=10 ms to allow response times to be evaluated. FIG. 47 shows a plot 4703 of the output of pulse generator 4315 and a plot 4701 of the voltage across the gate-source of the MOSFET labeled M4. FIG. 48 shows a plot 4801 of the voltage of the transducer 4309 and a plot 4803 of the current through the transducer 4309, when the system 4300 is in the off-state. FIG. 49 shows a plot 4901 of the total MOSFET losses in the MOSFET pairs 4305 when the system 4300 is in the off-state.

Losses for the system 4300 are driven primarily by the MOSFET switches 4305, 4307. According to embodiments, these parts can be optimized for each output and since the switching time is in the millisecond scale and not nanoseconds, high efficiency parts may be available that contribute low total loss. The remaining components that enhance the MOSFET are not power components and should not be a significant contributor to losses. Overall power efficiency of the system 4300 is considered to be good. According to embodiments, a single fault tolerant architecture that employs redundant components may provide a solution to a component failure hazard. The size and weight of the ASIC controlled MOSFET switch circuit design of instrument 4303 is excellent. The MOSFETs used to interrupt the generator output may be smaller than equivalent RF filter implementations, but may also require some board level thermal management that consumes board space. According to embodiments, the pulse transformer and buffer that enhance the MOSFET switch may also be very small. Additionally, the components for the ASIC controlled MOSFET switch circuit design of instrument 4303 may off-the shelf and require no custom engineered components. Overall, the cost of the ASIC controlled MOSFET switch circuit design of instrument 4303 is good.

FIG. 50 is a circuit diagram of a system 5000 for a combined ultrasonic and RF surgical instrument 5003 that is configured to manage RF and ultrasonic currents output by a generator 5001. The system 5000 uses electromechanical relays 5015, 5017 for switching for each output 5011, 5013. The relays 5015, 5017 are driven by control signals from the control circuit 5019 (e.g., ASIC). Resonator 5021 is coupled to a relay 5017 and the ultrasonic output 5013 (labeled blade).

The system 5000 is similar to the ASIC controlled MOSFET switch configurations discussed with regard to FIGS. 25-26, but the MOSFET switching element(s) have been replaced with an electromechanical relay. Unlike the MOSFET which requires minimal power to enhance, a non-latching relay may require too much power to actuate continuously; therefore a latching type relay is a preferred option for the electromechanical relays 5015, 5017 of system 5000. According to various aspects, the isolation that was provided by a pulse transformer in the MOSFET configurations, discussed with regard to FIGS. 25-26, may be integrated in the relay which gives an intrinsic isolation between coil and contacts. Furthermore, in other aspects where a relay is chosen that employs force guided contacts, an auxiliary set of sensing contacts can be used to provide feedback signals to the control circuit 5019 that confirm the state of the contacts for safety mitigation.

FIG. 51 is a circuit diagram of a system 5100 for a combined ultrasonic and RF surgical instrument 5103 that is configured to manage RF and ultrasonic currents output by a generator 5101. The system 5100 includes electromechanical relays 5115, 5117 and system 5100 uses a switch actuation initiated by an operator of the combined ultrasonic and RF surgical instrument 5103 to connect the appropriate output 5111 or 5113 within the combined ultrasonic and RF surgical instrument 5103 via the electromechanical relays 5115, 5117. As shown in the aspect of FIG. 51, the switch actuation may be accomplished via buttons and a pivot or toggle that accomplishes the appropriate opening or closure of the electromechanical relays 5115 or 5117. Resonator 5121 is coupled to electromechanical relay 5117 and ultrasonic output 5113 (labeled blade).

Other configurations discussed herein may use a signal switch closure to command a secondary power switch actuation via a control circuit. The system 5100 eliminates circuitry that may be necessary for such a secondary electronic actuation and uses an input to a switch 5123 to both command the control circuit 5119 (e.g., ASIC) for activation and engage the appropriate output 5111 or 5113 to the combined ultrasonic and RF surgical instrument 5103. In one aspect, the switch that performs this may be a snap-action variety which requires very little throw to engage the contacts. In another aspect, a mechanical rocker style switch mechanism may be employed in the combined ultrasonic and RF surgical instrument 5103 which ensures that the two states are mutually exclusive.

FIG. 52 is a circuit diagram of a system 5200 for a combined ultrasonic and RF surgical instrument 5203 that is configured to manage RF and ultrasonic currents output by a generator 5201. The combined ultrasonic and RF surgical instrument 5203 employs a configuration that shares components from other circuit configurations discussed herein to form an optimized device. The combined ultrasonic and RF surgical instrument 5203 includes a parallel LC filter circuit 5223 coupled to a crystal 5221, which feeds the output of the generator 5201 to the ultrasonic output 5213 of the combined ultrasonic and RF surgical instrument 5203. Additionally, a control circuit 5219 is coupled to a pulse transformer 5215. The pulse transformer 5215 is coupled to a pair of solid state switches such as MOSFET switches 5217 that are arranged source-source, creating an AC switch, which feeds the output of the generator 5201 to the RF output 5211 of the combined ultrasonic and RF surgical instrument 5203.

FIG. 53 is a circuit diagram for a system 5300 that is configured to manage RF and ultrasonic currents output by a generator according to one aspect of the present disclosure. The system 5300 that applies a band-stop filter circuit design to generate a DC voltage within a surgical instrument. The DC voltage can be used to power components in the surgical instrument. For example, the DC voltage could be used to drive a small motor for articulation of an end effector, or other uses as appropriate. As shown in FIG. 53, the system 5300 includes: the ultrasonic and RF output of a generator 5301; and an instrument 5303 including tuned band-stop filter circuits 5305, 5307 for each output of the generator 5301, a transducer model 5309 loaded to 400 ohms, and a rectifier 5311 and motor load 5313 for the instrument 5303. In one aspect, the rectifier 5311 produces 12V DC and the power consumed by the motor load 5313 is 5 W.

FIGS. 54-59 provide simulation results for the system 5300 shown in FIG. 53. For the simulations, the ultrasonic output voltage was set to 150 Vrms and the RF voltage (350 kHz) is summed with the ultrasonic voltage that emulates the wave-shaping capability of a DDS within the generator. The RF content is initially off and then gated on at t=3 ms, in order to check for disturbances on the ultrasonic output. The RF amplitude was set to 20V, which results in a rectified DC bus voltage of $12V_{DC}$. The motor is represented as a 30 ohm resistor that loads the DC bus to approximately 5 W.

FIG. 54 displays graphs of simulation results of the circuit diagram for the system 5300 shown in FIG. 53. FIG. 54 displays the generator 5301 output at the ultrasonic terminal and the RF terminal in terms of voltage versus time. Plot 5401 is the ultrasonic terminal voltage (measured at a reference of the capacitor labeled Cf1) and Plot 5403 is the RF terminal voltage (measured at a reference of the resistor labeled Rvs).

FIG. 55 displays graphs of simulation results of the circuit diagram for the system 5300 shown in FIG. 53. FIG. 55 displays the generator 5301 output from time 2.9 ms to 3.1 ms from plots 5401 and 5403 in FIG. 14.

FIG. 56 displays graphs of simulation results of the circuit diagram shown in FIG. 53. FIG. 56 is a graph of the circuit model 5309 of the ultrasonic transducer voltage and DC bus voltage provided by the rectifier 5311 in terms of voltage versus time. Plot 5601 is the transducer circuit model 5309 voltage (measured at a reference of the resistor labeled Rp) and Plot 5603 is the DC bus voltage (measured at a reference of the diodes labeled D1 and D2).

FIG. 57 displays graphs of simulation results of the circuit diagram shown in FIG. 53. FIG. 57 displays the transducer circuit model 5309 voltage and the DC bus voltage provided by the rectifier 5311 from time 2.9 ms to 3.1 ms as shown in plots 5601 and 5603 in FIG. 56.

FIG. 58 displays graphs of simulation results of the circuit diagram shown in FIG. 53. FIG. 58 displays the power consumed by the load of the transducer circuit model 5309 and the power consumed by the motor load 5313 in terms of watts versus time. Plot 5801 is the power consumed by the load of the transducer circuit model 5309 (measured at a reference of the resistor labeled Rm) and Plot 5803 is the power consumed by the motor load 5313 (measured at a reference of the resistor labeled Rs1).

FIG. 59 displays graphs of simulation results of the circuit diagram shown in FIG. 53. FIG. 59 displays the power consumed by the load of the transducer circuit model 5309 and the power consumed by the motor load 5313 from time 2.8 ms to 3.2 ms as shown in plots 5801 and 5803 in FIG. 58.

The simulations indicates that by using band-stop output filters, a mixed frequency waveform produced by the generator can be split and diverted to separate output loads. The simulation also shows that a DC bus can readily be generated to power a variety of low energy loads within the instrument 5303. According to the aspect of FIG. 53, there is not an appreciable disturbance in the ultrasonic output when the DC bus is active; however there are some distortions that can be seen as the rectifier 5311 and capacitor (labeled Cf2) of filter circuit 5305 are charging the DC bus. This distortion effect may be reduced by controlling the ramp rate of the high frequency content rather than using a step function.

Turning now to FIG. 70, there is illustrated a system configuration for an example circuit topology shown and described with regard to FIGS. 53-59. The system configuration comprises a plurality sections, where the plurality of sections include a generator (labeled GENERATOR), a proximal plug (labeled PLUG 1), a cable, a distal plug (labeled PLUG 2), a handle of a surgical instrument, and an application portion (labeled APP) of a surgical instrument. According to various aspects, the proximal plug may be a component of the generator, it may be a component of cable, or it may be separate component. Similarly, the distal plug may be a component of the cable, it may be a component of handle, or it may be separate component.

FIG. 70 further illustrates a system 7000 that includes bandstop filters in the distal plug, an ASIC in the handle, and a DC motor in the application portion. The generator comprises interfaces for an ultrasonic signal 7001, an interface for an RF signal 7003, a primary return terminal interface 7005, an HSW interface 7007, a secondary return terminal interface 7009, an identification interface 7011, and a presence interface 7013. The proximal plug comprises matching interfaces to those of generator, an EEPROM 7017, and presence resistor 7019. The proximal plug outputs are carried through the cable without any component circuitry in the cable. The distal plug comprises a pair of bandstop filters 7015. The handle comprises rectifier circuit 7031, a non-volatile memory such as EEPROM 7035, control circuit 7027 (e.g., ASIC), switch array 7037, capacitor 7016, and resonator 7029. Rectifier circuit 7031 comprises at least one diode and at least one capacitor. Control circuit 7027 is coupled to EEPROM 7035, switch array 7037, and rectifier circuit 7031. The switch array 7037 may comprise electromechanical devices such as transistor devices. The transistor devices may include Field-effect transistors (FET), Bipolar Junction Transistors (BJT), or a combination thereof.

The application portion comprises EEPROM 7039, presence resistor 7041, and an output for ultrasonic energy 7045. The application portion further comprises rectifier circuit 7047, driver circuit 7049, driver circuit 7051, and DC motor 7043. Rectifier circuit 7047 comprises at least one diode and at least one capacitor. The rectifier circuit 7047 is coupled to the driver circuit 7049, which is coupled to the DC motor 7043. Driver circuit 7051 is coupled to control circuit 7027 and driver circuit 7049. EEPROM 7039 and presence resistor 7041 are also coupled to control circuit 7027. The system 7000 allows switching between an RF mode and an ultrasonic mode and supports mixed output frequencies, which allows tissues impedance sensing while the ultrasonic output is active. It also provides for a DC motor at the ultrasonic output that uses energy directed to the RF output terminal for generating a DC voltage.

Turning now to FIG. 62, there is illustrated a system 6200 that includes electro-mechanical or solid state switches comprising transistors such as MOSFET switches and a control circuit in the proximal plug and a control circuit in the handle. The generator comprises interfaces for an ultrasonic signal 6201, an interface for an RF signal 6203, a primary return terminal interface 6205, an HSW interface 6207, a secondary return terminal interface 6209, an identification interface 6211, and a presence interface 6213. The proximal plug comprises matching interfaces to those of generator, a pair of MOSFET switches 6215, an EEPROM 6217, and presence resistor 6219. The MOSFET switches 6215 are each coupled to rectifier circuits 6221 that are each coupled to a pair of coupling inductors 6223. Each rectifier circuit 6221 may comprise at least one diode and at least one capacitor. The control circuit 6227 (e.g., ASIC) is coupled to a driver circuit 6225 that feeds the coupling inductors 6223 and the rectifier circuits 6221 to control the state of the MOSFET switches 6215. The proximal plug outputs are carried through the cable and the distal plug to the handle without any component circuitry in either the cable or the distal plug. The handle comprises resonator 6229, rectifier circuit 6231, control circuit 6233 (e.g., ASIC), EEPROM 6235, and switch array 6237. The switch array 6237 may comprise electro-mechanical devices, transistor devices, and the like. The transistor devices may include BJTs, FETs, MOSFETs, or a combination thereof. Rectifier circuit 6231 may comprise at least one diode and at least one capacitor. Control circuit 6233 is coupled to EEPROM 6235 and receives outputs from control circuit 6227 in the proximal plug.

The application portion comprises EEPROM 6239, presence resistor 6241, and outputs for RF and ultrasonic energy 6243, 6245, respectively. EEPROM 6239 and presence resistor 6241 are coupled to control circuit 6233. The system 6200 allows switching between an RF mode and an ultrasonic, also called ultrasonic, mode and allows for a transfer of weight, volume, and heat away from the handle and application portion. The two control circuits 6227, 6233 (e.g., ASIC devices) may also add flexibility to features that are available in the handle and the proximal plug.

FIG. 63 illustrates a system 6300 that includes electro-mechanical or solid state switches such as MOSFET switches and a control circuit in the distal plug. The generator comprises interfaces for an ultrasonic signal 6301, an interface for an RF signal 6303, a primary return terminal interface 6305, an HSW interface 6307, a secondary return terminal interface 6309, an identification interface 6311, and a presence interface 6313. The proximal plug comprises matching interfaces to those of generator, an EEPROM 6317, and presence resistor 6319. The proximal plug outputs are carried through the cable without any component circuitry in the cable. The distal plug comprises MOSFET switches 6315 that are each coupled to rectifier circuits 6321 that are each coupled to a pair of coupling inductors 6323. Each of rectifier circuits 6321 comprises at least one diode and at least one capacitor. The control circuit 6327 (e.g., ASIC) is coupled to a driver circuit 6325 that feeds into the coupling inductors 6323 and the rectifier circuits 6321 to control the state of the MOSFET switches 6315. The distal plug also includes rectifier circuit 6331 coupled to the HSW interface 6307 and the secondary return terminal interface 6309 of the generator and feed into control circuit 6327. Rectifier circuit 6331 comprises at least one diode and at least one capacitor. The handle comprises resonator 6329, EEPROM 6335, switch array 6337, and presence resistor 6341. The switch array 6337 may comprise electro-mechanical devices, transistor devices, and the like. The transistor devices may include BJTs, FETs, MOSFETs, or a combination thereof. Control circuit 6327 is coupled to EEPROM 6335, switch array 6337, and presence resistor 6341 in the handle.

The application portion comprises EEPROM 6339, presence resistor 6342, and outputs for RF and ultrasonic energy 6343, 6345, respectively. EEPROM 6339 and presence resistor 6342 are coupled to control circuit 6327. The system 6300 allows switching between an RF mode and an ultrasonic mode and allows for minimal cost and complexity in the handle of the surgical instrument.

FIG. 64 illustrates a system 6400 that includes electro-mechanical or solid state switches such as MOSFET switches and a control circuit in the distal plug and a control circuit in the handle. The generator comprises interfaces for an ultrasonic signal 6401, an interface for an RF signal 6403, a primary return terminal interface 6405, an HSW interface 6407, a secondary return terminal interface 6409, an identification interface 6411, and a presence interface 6413. The proximal plug comprises matching interfaces to those of generator, an EEPROM 6417, and presence resistor 6419. The proximal plug outputs are carried through the cable without any component circuitry in the cable. Distal plug comprises a pair of MOSFET switches 6415, The MOSFET switches 6415 are each coupled to rectifier circuits 6421 that are each coupled to a pair of coupling inductors 6423, all located within the distal plug. The rectifier circuits 6421 each comprise at least one diode and at least one capacitor. The control circuit 6427 (e.g., ASIC) is coupled to a driver circuit 6425, which are also located in the distal plug, that feeds the coupling inductors 6423 and the rectifier circuits 6421 to control the state of the MOSFET switches 6415. The handle comprises resonator 6429, rectifier circuit 6431, control circuit 6433 (e.g., ASIC), EEPROM 6435, and switch array 6437. The switch array 6437 may comprise electro-mechanical devices, transistor devices, and the like. The transistor devices may include BJTs, FETs, MOSFETs, or a combination thereof. Rectifier circuit 6431 comprises at least one diode and at least one capacitor. Control circuit 6433 is coupled to EEPROM 6435 and receives outputs from control circuit 6427 in the distal plug.

The application portion comprises EEPROM 6439, presence resistor 6441, and outputs for RF and ultrasonic energy 6443, 6445, respectively. EEPROM 6439 and presence resistor 6441 are coupled to control circuit 6433. The system 6400 allows switching between an RF mode and an ultrasonic mode and the two control circuits 6427, 6433 (e.g., ASIC devices) may also add flexibility to features that are available in the handle and the distal plug.

FIG. 65 illustrates a system 6500 that includes electro-mechanical or solid state switches such as MOSFET switches in the distal plug and a control circuit in the handle. The generator comprises interfaces for an ultrasonic signal 6501, an interface for an RF signal 6503, a primary return terminal interface 6505, an HSW interface 6507, a secondary return terminal interface 6509, an identification interface 6511, and a presence interface 6513. The proximal plug comprises matching interfaces to those of generator, an EEPROM 6517, and presence resistor 6519. The proximal plug outputs are carried through the cable without any component circuitry in the cable. The distal plug comprises MOSFET switches 6515 that are each coupled to rectifier circuits 6521, which are each coupled to a pair of coupling inductors 6523. Each of rectifier circuits 6521 comprise at least one diode and at least one capacitor. The handle comprises rectifier circuit 6531, driver circuit 6525, control circuit 6327, EEPROM 6535, switch array 6537, and resonator 6529. The switch array 6537 may comprise electro-mechanical devices, transistor devices, and the like. The transistor devices may include BJTs, FETs, MOSFETs, or a combination thereof. The control circuit 6527 (e.g., ASIC) is coupled to a driver circuit 6525 that feeds into the coupling inductors 6523 and the rectifier circuits 6521 to control the state of the MOSFET switches 6515. Rectifier circuit 6531 is coupled to the HSW interface 6507 and the secondary return terminal interface 6509 of the generator and feed into control circuit 6527. As shown, rectifier circuit 6531 may comprise at least one diode and at least one capacitor. Control circuit 6527 is coupled to EEPROM 6535, switch array 6537.

The application portion comprises EEPROM 6539, presence resistor 6541, and outputs for RF and ultrasonic energy 6543, 6545, respectively. EEPROM 6539 and presence resistor 6541 are coupled to control circuit 6527. The system 6500 allows switching between an RF mode.

FIG. 66 illustrates a system 6600 that includes electro-mechanical or solid state switches such as MOSFET switches and a control circuit in the handle. The generator comprises interfaces for an ultrasonic signal 6601, an interface for an RF signal 6603, a primary return terminal interface 6605, an HSW interface 6607, a secondary return terminal interface 6609, an identification interface 6611, and a presence interface 6613. The proximal plug comprises matching interfaces to those of generator, an EEPROM 6617, and presence resistor 6619. The proximal plug outputs are carried through the cable and the distal plug to the handle without any component circuitry in either the cable or the distal plug. The handle comprises the MOSFET switches 6615 that are each coupled to rectifier circuits 6621, which are each coupled to a pair of coupling inductors 6623, also in the handle. The rectifier circuits 6621 each comprise at least one diode and at least one capacitor. The control circuit 6627 (e.g., ASIC) is coupled to a driver circuit that feeds into the coupling inductors 6623 and the rectifier circuits 6621 to control the state of the MOSFET switches 6615. The driver circuit 6625 and control circuit 6627 are located in the handle. The handle further comprises resonator 6629, rectifier circuits 6631 comprising a diode and a capacitor, EEPROM 6635, and switch array 6637. The switch array 6637 may comprise electro-mechanical devices, transistor devices, and the like. The transistor devices may include BJTs, FETs, MOSFETs, or a combination thereof. The rectifier portion of the diode and capacitor circuit 6631 is coupled to the HSW interface 6607 and the secondary return terminal interface 6609 of the generator and feed into control circuit 6627.

The application portion comprises EEPROM 6639, presence resistor 6641, and outputs for RF and ultrasonic energy 6643, 6645, respectively. EEPROM 6639 and presence resistor 6241 are coupled to control circuit 6627. The system 6600 allows switching between an RF mode and an ultrasonic mode and allows for a low cost cable configuration.

FIG. 67 illustrates a system 6700 that includes bandstop filters in the proximal plug and a control circuit in the handle. The generator comprises interfaces for an ultrasonic signal 6701, an interface for an RF signal 6703, a primary return terminal interface 6705, an HSW interface 6707, a secondary return terminal interface 6709, an identification interface 6711, and a presence interface 6713. The proximal plug comprises matching interfaces to those of generator, a pair of bandstop filters 6715, an EEPROM 6717, and presence resistor 6719. The proximal plug outputs are carried through the cable and the distal plug to the handle without any component circuitry in either the cable or the distal plug. The handle comprises resonator 6729, rectifier circuit 6731, control circuit 6727 (e.g., ASIC), EEPROM 6735, and switch array 6737. Rectifier circuit 6731 comprises at least one diode and at least one capacitor. The switch array 6737 may comprise electro-mechanical devices, transistor devices, and the like. The transistor devices may include BJTs, FETs, MOSFETs, or a combination thereof. Control circuit 6727 is coupled to EEPROM 6735 and rectifier circuit 6731 are coupled to the HSW interface 6707 and the secondary return terminal interface 6709 of the generator and feed into control circuit 6727.

The application portion comprises EEPROM 6739, presence resistor 6741, and outputs for RF and ultrasonic energy 6743, 6745, respectively. The pair of bandstop filters 6715 are coupled to the outputs for RF and ultrasonic energy 6743, 6745. EEPROM 6739 and presence resistor 6741 are coupled to control circuit 6727. The system 6700 allows switching between an RF mode and an ultrasonic mode and supports mixed output frequencies, which allows tissues impedance sensing while the ultrasonic output is active. It also allows for a transfer of weight, volume, and heat away from the handle and application portion.

FIG. 68 illustrates a system 6800 that includes bandstop filters in the distal plug and a control circuit in the handle. The generator comprises interfaces for an ultrasonic signal 6801, an interface for an RF signal 6803, a primary return terminal interface 6805, an HSW interface 6807, a secondary return terminal interface 6809, an identification interface 6811, and a presence interface 6813. The proximal plug comprises matching interfaces to those of generator, an EEPROM 6817, and presence resistor 6819. The proximal plug outputs are carried through the cable without any component circuitry in the cable. The distal plug comprises a pair of bandstop filters 6715. The handle comprises rectifier circuit 6831, EEPROM 6835, control circuit 6827, switch array 6837, capacitor 6816, and resonator 6829. Rectifier circuit 6831 comprises at least one diode and at least one capacitor. The control circuit 6827 is coupled to EEPROM 6835, switch array 6837, and rectifier circuit 6831. The switch array 6837 may comprise electro-mechanical devices, transistor devices, and the like. The transistor devices may include BJTs, FETs, MOSFETs, or a combination thereof.

The application portion comprises EEPROM 6839, presence resistor 6841, and outputs for RF and ultrasonic energy 6843, 6845, respectively. The pair of bandstop filters 6815 are coupled to the outputs for RF and ultrasonic energy 6843, 6845. EEPROM 6839 and presence resistor 6841 are coupled to control circuit 6827. The system 6800 allows switching between an RF mode and an ultrasonic mode and supports mixed output frequencies, which allows tissues impedance sensing while the ultrasonic output is active.

FIG. 69 illustrates a system 6900 that includes bandstop filters and a control circuit in the handle. The generator comprises interfaces for an ultrasonic signal 6901, an interface for an RF signal 6903, a primary return terminal interface 6905, an HSW interface 6907, a secondary return terminal interface 6909, an identification interface 6911, and a presence interface 6913. The proximal plug comprises matching interfaces to those of generator, an EEPROM 6917, and presence resistor 6919. The proximal plug outputs are carried through the cable and distal plug without any component circuitry in either the cable or the distal plug. The handle comprises a pair of bandstop filters 6915, rectifier circuit 6931, EEPROM 6935, control circuit 6927, switch array 6937, and resonator 6929. Rectifier circuit 6931 comprises at least one diode and at least one capacitor. Control circuit 6927 is coupled to EEPROM 6935, switch array 6937, and rectifier circuit 6931. The switch array 6937 may comprise electro-mechanical devices, transistor devices, and the like. The transistor devices may include BJTs, FETs, MOSFETs, or a combination thereof.

The application portion comprises EEPROM 6939, presence resistor 6941, and outputs for RF and ultrasonic energy 6943, 6945, respectively. The pair of bandstop filters 6915 are coupled to the outputs for RF and ultrasonic energy 6943, 6945. EEPROM 6939 and presence resistor 6941 are coupled to control circuit 6927. The system 6900 allows switching between an RF mode and an ultrasonic mode and supports mixed output frequencies, which allows tissues impedance sensing while the ultrasonic output is active. It also provides for a low cost cable configuration.

FIG. 70 illustrates a system 7000 that includes bandstop filters in the distal plug, a control circuit in the handle, and a DC motor in the application portion. The generator comprises interfaces for an ultrasonic signal 7001, an interface for an RF signal 7003, a primary return terminal interface 7005, an HSW interface 7007, a secondary return terminal interface 7009, an identification interface 7011, and a presence interface 7013. The proximal plug comprises matching interfaces to those of generator, an EEPROM 7017, and presence resistor 7019. The proximal plug outputs are carried through the cable without any component circuitry in the cable. The distal plug comprises a pair of bandstop filters 7015. The handle comprises rectifier circuit 7031, EEPROM 7035, control circuit 7027, switch array 7037, capacitor 7016, and resonator 7029. Rectifier circuit 7031 comprises at least one diode and at least one capacitor. Control circuit 7027 is coupled to EEPROM 7035, switch array 7037, and rectifier circuit 7031. The switch array 7037 may comprise electro-mechanical devices, transistor devices, and the like. The transistor devices may include BJTs, FETs, MOSFETs, or a combination thereof.

The application portion comprises EEPROM 7039, presence resistor 7041, and an output for ultrasonic energy 7045. The application portion further comprises rectifier circuit 7047, driver circuit 7049, driver circuit 7051, and DC motor 7043. Rectifier circuit 7047 comprises at least one diode and at least one capacitor. The rectifier circuit 7047 is coupled to the driver circuit 7049, which is coupled to the DC motor 7043. Driver circuit 7051 is coupled to control circuit 7027 and driver circuit 7049. EEPROM 7039 and presence resistor 7041 are also coupled to control circuit 7027. The system 7000 allows switching between an RF mode and an ultrasonic mode and supports mixed output frequencies, which allows tissues impedance sensing while the ultrasonic output is active. It also provides for a DC motor at the ultrasonic output that uses energy directed to the RF output terminal for generating a DC voltage.

FIG. 71 illustrates a system 7100 that includes a fixed high voltage RF output in the application portion, bandstop filters in the distal plug, and a control circuit and transformer in handle. The generator comprises interfaces for an ultrasonic signal 7101, an interface for an RF signal 7103, a primary return terminal interface 7105, an HSW interface 7107, a secondary return terminal interface 7109, an identification interface 7111, and a presence interface 7113. The proximal plug comprises matching interfaces to those of generator, an EEPROM 7117, and presence resistor 7119. The proximal plug outputs are carried through the cable without any component circuitry in the cable. The distal plug comprises a pair of bandstop filters 7115. The handle comprises rectifier circuits 7131 comprising a diode and a capacitor, EEPROM 7135, control circuit 7127, transformer 7130, capacitor 7116, switch array 7137, and resonator 7129. The control circuit 7127 is coupled to EEPROM 7135, switch array 7137, and rectifier circuits 7131 comprising a diode and a capacitor. The switch array 7137 may comprise electro-mechanical devices, transistor devices, and the like. The transistor devices may include BJTs, FETs, MOSFETs, or a combination thereof.

The application portion comprises EEPROM 7139, presence resistor 7141, and high voltage RF and ultrasonic energy outputs 7143, 7145, respectively. Transformer 7130 is coupled to one of the bandstop filters 7115 and the secondary side of transformer 7130 is coupled to the high voltage RF and ultrasonic energy outputs 7143, 7145. EEPROM 7139 and presence resistor 7141 are coupled to control circuit 7127. The system 7100 allows switching between an RF mode and an ultrasonic mode and supports mixed output frequencies, which allows tissues impedance sensing while the ultrasonic output is active. It also supports high RF output voltage for surface coagulation.

FIG. 72 illustrates a system 7200 that includes a mechanically switched high voltage/low voltage RF output in the application portion, bandstop filters in distal plug, and a control circuit and transformer in the handle. The generator comprises interfaces for an ultrasonic signal 7201, an interface for an RF signal 7203, a primary return terminal interface 7205, an HSW interface 7207, a secondary return terminal interface 7209, an identification interface 7211, and a presence interface 7213. The proximal plug comprises matching interfaces to those of generator, an EEPROM 7217, and presence resistor 7219. The proximal plug outputs are carried through the cable without any component circuitry in the cable. The distal plug comprises a pair of bandstop filters 7215. The handle comprises rectifier circuit 7231, EEPROM 7235, control circuit 7227, transformer 7230, capacitor 7216, switch array 7237, and resonator 7229. The control circuit 7227 is coupled to EEPROM 7235, switch array 7237, and rectifier circuit 7231. Rectifier circuit 7231 comprises at least one diode and at least one capacitor. The switch array 7237 may comprise electro-mechanical devices, transistor devices, and the like. The transistor devices may include BJTs, FETs, MOSFETs, or a combination thereof.

The application portion comprises EEPROM 7239, presence resistor 7241, end effector jaw position switch 7247, and RF and ultrasonic energy outputs 7243, 7245, respectively. Transformer 7230 is coupled to one of the bandstop filters 7215. The secondary side of transformer 7230 is coupled to the ultrasonic energy output 7245 and one position of the end effector jaw position switch 7247, while the other position of the end effector jaw position switch 7247 is coupled to the primary side of transformer 7230. EEPROM 7239 and presence resistor 7241 are coupled to control circuit 7227. The system 7200 allows switching between an RF mode and an ultrasonic mode and supports mixed output frequencies, which allows tissues impedance sensing while the ultrasonic output is active. It also supports high RF output voltage for surface coagulation when end effector jaws are open and supports standard RF voltages for sealing and cutting when the jaws are closed.

FIG. 73 illustrates a system 7300 that includes an electrically switched high voltage/low voltage RF output in the application portion, bandstop filters in distal plug, and a control circuit and transformer in the handle. The generator comprises interfaces for an ultrasonic signal 7301, an interface for an RF signal 7303, a primary return terminal interface 7305, an HSW interface 7307, a secondary return terminal interface 7309, an identification interface 7311, and a presence interface 7313. The proximal plug comprises matching interfaces to those of generator, an EEPROM 7317, and presence resistor 7319. The proximal plug outputs are carried through the cable without any component circuitry in the cable. The distal plug comprises a pair of bandstop filters 7315. The handle comprises rectifier circuit 7331, EEPROM 7335, control circuit 7327, transformer 7330, capacitor 7316, switch array 7337, and resonator 7329, driver circuit 7325, a pair of MOSFET switches 7318, rectifier circuits 7321, and a pair of coupling inductors 7323. The switch array 7337 may comprise electro-mechanical devices, transistor devices, and the like. The transistor devices may include BJTs, FETs, MOSFETs, or a combination thereof. The pair of MOSFET switches 7318 are coupled to the rectifier circuits 7321 are coupled to coupling inductors 6223. Rectifier circuits 7321 each comprise at least one diode and at least one capacitor. The coupling inductors are coupled to driver circuit 6225, which is coupled to control circuit 7327. The coupling inductors are also coupled to driver circuit 7325. The control circuit 7227 is coupled to EEPROM 7335, switch array 7337, and rectifier circuit 7331.

The application portion comprises EEPROM 7339, presence resistor 7341, and outputs for RF and ultrasonic energy 7343, 7345, respectively. Transformer 7230 is coupled to one of the bandstop filters 7315 and one of the MOSFET switches 7318 on the primary side. The secondary side of transformer 7230 is coupled to the other MOSFET switches 7318. EEPROM 7339 and presence resistor 7341 are coupled to control circuit 7327. The system 7300 allows switching between an RF mode and an ultrasonic mode and supports mixed output frequencies, which allows tissues impedance sensing while the ultrasonic output is active. It also supports high RF output voltage for surface coagulation when end effector jaws are open and supports standard RF voltages for sealing and cutting when the jaws are closed.

FIG. 74 illustrates a system 7400 that includes a fixed high voltage RF output in the application portion, bandstop filters in the proximal plug, and a control circuit and transformer in handle. The generator comprises interfaces for an ultrasonic signal 7401, an interface for an RF signal 7403, a primary return terminal interface 7405, an HSW interface 7407, a secondary return terminal interface 7409, an identification interface 7411, and a presence interface 7413. The proximal plug comprises matching interfaces to those of generator, an EEPROM 7417, presence resistor 7419, a pair of bandstop filters 7415, and switched capacitor 7416 (which include a switch circuit element and a capacitor circuit element). The proximal plug outputs are carried through the cable and distal plug without any component circuitry in either the cable or the distal plug. The handle comprises rectifier circuit 7431, EEPROM 7435, control circuit 7427, transformer 7430, switch array 7437, and resonator 7429. The control circuit 7427 is coupled to EEPROM 7435, switch array 7437, and rectifier circuit 7431. Rectifier circuit comprises at least one diode and at least one capacitor. The switch array 7437 may comprise electro-mechanical devices, transistor devices, and the like. The transistor devices may include BJTs, FETs, MOSFETs, or a combination thereof.

The application portion comprises EEPROM 7439, presence resistor 7441, and high voltage RF and ultrasonic energy outputs 7443, 7445, respectively. Transformer 7430 is coupled to one of the bandstop filters 7115 and the secondary side of transformer 7130 is coupled to the high voltage RF and ultrasonic energy outputs 7443, 7445. EEPROM 7439 and presence resistor 7441 are coupled to control circuit 7427. The system 7400 allows switching between an RF mode and an ultrasonic mode and supports mixed output frequencies, which allows tissues impedance sensing while the ultrasonic output is active. It also supports high RF output voltage for surface coagulation and transfers weight, volume, and heat away from the handle and application portion.

FIG. 75 shows a flow diagram illustrating a method 7500 for providing a combined signal by a generator to a surgical instrument. The combined signal may comprise a radio frequency (RF) component and an ultrasonic component. The surgical instrument may comprise an RF energy output, an ultrasonic energy output, and a circuit. The circuit may be a steering circuitry.

Characterization is performed 7510 on at least one component of the circuit. A frequency of the RF component is adjusted 7520 based on a result of the characterization. The generator delivers 7530 the combined signal to the surgical instrument. The circuit steers 7540 the RF component to the RF energy output, and steers 7550 the ultrasonic component to the ultrasonic energy output.

Turning now back to FIG. 60, there is illustrated an example of a notch filter 1400 and FIG. 61 is a graphical depiction of the frequency response 6100 of the circuit diagram shown in FIG. 60 according to one aspect of the present disclosure. FIG. 61 provides an analysis of the transfer function frequency response 6100 of the notch filter 1400. A Monte Carlo analysis of the notch filter 1400 was run with the tolerances of the capacitor 1401 and inductor 1402 set to 5%. According to the plot shown in FIG. 61, variations in the transfer function frequency response is described by the three frequency responses 6102, 6104, 6106 of the filter 1400 showing three separate notch frequencies. According to aspects of the present disclosure, the frequency of the output of a generator can be adjusted to fit the response of the filter 1400.

Turning now to FIG. 76, there is shown a plot illustrating adjustment of the RF frequency response of the circuit diagram shown in FIG. 60 based on characterization of the steering circuitry. The notch filter 1400 of FIG. 60 in the steering circuitry may have a frequency response 7610 at the time of manufacturing. But when conditions such as temperature and aging change, the frequency response of the notch filter 1400 may change to look like the other frequency response 7620. In the latter case, the generator 100 may change the notch frequency set by the RF components from about 340 KHz to about 310 KHz. Therefore, the unwanted RF component can be filtered out for the ultrasonic output.

Turning now to FIGS. 66 and 69, there are illustrated system configurations of example circuit topologies shown and described with regard to FIGS. 60, 61, 75, and 76. The system configurations comprise a plurality sections, where the plurality of sections include a generator (labeled GENERATOR), a proximal plug (labeled PLUG 1), a cable, a distal plug (labeled PLUG 2), a handle of a surgical instrument, and an application portion (labeled APP) of a surgical instrument. According to various aspects, the proximal plug may be a component of the generator, it may be a component of cable, or it may be separate component. Similarly, the distal plug may be a component of the cable, it may be a component of handle, or it may be separate component.

FIG. 77 is a block diagram 7700 illustrating the selection of operations of a surgical instrument based on various inputs. The surgical instrument may comprise an RF energy output and an ultrasonic energy output. The surgical instrument may further comprise a first jaw and a second jaw configured for pivotal movement between a closed position and an open position.

A first input 7710 indicating a user selection of one of a first option and a second option may be received. For example, the first option may a seal only option, and the second option may be a seal and cut option. The user selection may be received as a button selection. For example, the button may be a switch or trigger located at a handle of the surgical instrument. Signal from a trigger aperture sensor may be fed via ASIC (application specific integration circuit) in the surgical instrument to a generator of RF and/or ultrasonic signals.

A second input 7720 indicating whether the first jaw and the second jaw are in the closed position or in the open position 7720 may be received. For example, a jaw aperture sensor in the surgical instrument may be used to sense the open or closed position, and a corresponding signal may be fed via ASIC in the surgical instrument to the generator of RF and/or ultrasonic signals.

A third input 7730 indicating electrical impedance at the RF energy output may be received. Low electrical impedance may indicate a short condition, which may be caused by a stapled tissue. Medium electrical impedance may indicate that a tissue is present without staples. High electrical impedance may indicate an open circuit condition.

Based at least in part on the first input 7710, the second input 7720 and the third input 7730, a mode of operation for treating a tissue may be selected 7740 from a plurality of modes of operation, which may comprise a first mode wherein the RF energy output applies RF energy to the tissue, and a second mode wherein the ultrasonic energy output applies ultrasonic energy to the tissue. The plurality of modes of operation may further comprise a third mode wherein the RF energy output applies RF energy to the tissue and the ultrasonic energy output applies ultrasonic energy to the tissue; and a fourth mode wherein no RF energy or ultrasonic energy is applied to the tissue.

A level of energy applied by the RF energy output or ultrasonic energy output may also be selected 7750 based at least in part on the first input, the second input and the third input. For example, an EEPROM (Electrically Erasable Programmable Read-Only Memory) located at the surgical instrument or a non-volatile memory located at the generator may be accessed to load a wave-shape table and other RF and/or ultrasonic parameters such as voltage, current, power, and algorithm in order to performed the desired operation in the most optimal way.

According to some aspects of the present disclosure, the first input 7710, the second input 7720 and the third input 7730 may be received at a generator for providing RF energy and ultrasonic energy to the surgical instrument, and the selections are performed at the generator.

FIG. 78 shows a logic diagram 7800 illustrating specific operations of a surgical instrument selected based on various inputs. In particular, the logic diagram 7800 may be executed by multifunction surgical instrument 108 coupled to the generator 100 as shown in FIGS. 1 and 2 to complete a variety of user intentions 7890. As described herein, the system may be contained in the generator 100, the plug or adapter, and/or the surgical instrument 108 or device. The logic described by the logic diagram 7800 can be executed by any of the processing circuits described in connection with FIGS. 5-12 (e.g., processor, controller, digital signal processor, control circuit, and/or logic device collectively referred to as "system").

Accordingly, with reference now to FIGS. 1, 2, and 14, the surgical instrument 108 includes a mode selection button to select one of a seal only mode 7814 or a seal and cut mode 7818. When the user presses 7810 the mode selection button on the surgical instrument 108, the system determines whether the user intended to employ the seal only mode 7814 or the seal and cut mode 7818. The user election of the seal only mode 7814 will be described first.

Accordingly, upon selecting the seal only mode 7814, the system determines 7816 whether the clamp arm 146 of the surgical instrument 108 is in an open position or a closed position and then measures the impedance between the clamp arm 146 and the ultrasonic blade 149. When the clamp arm 146 is in a closed position 7822 the measured electrical impedance 7824 between the electrode in the clamp arm 146 and the ultrasonic blade 149 is low 7938 or indicates a short circuit, the system assumes that stapled tissue is present between the jaws 125 and applies 7840 low ultrasonic energy to the tissue located between the clamp arm 146 and the ultrasonic blade 149. Accordingly, the surgical instrument 108 completes the user intention of sealing 7842 stapled tissue located between the clamp arm 146 and the ultrasonic blade 149.

Still with reference to the seal only mode 7814 sequence, when the he clamp arm 146 is in a closed position 7822 and the measured electrical impedance 7824 is within a range that indicates 7844 the presence of tissue without staples between the clamp arm 146 and the ultrasonic blade 149, the system applies 7846 RF energy according to a predetermined seal only algorithm. Accordingly, the surgical instrument 108 completes the user intention 7948 of sealing a vessel or tissue bundle located between the clamp arm 146 and the ultrasonic blade 149.

Still with reference to the seal only mode 7814, when the seal only mode 7814 is selected and the clamp arm 146 is in an open 7826 position, and the measured electrical impedance 7828 is high 7850 or indicates an open circuit, the system determines that an error has occurred and provides 7854 an error indication but does not deliver either RF or ultrasonic energy. Accordingly, the surgical instrument 108 completes the user intention 7854 of no job identified.

Still with reference to the seal only mode 7814 sequence, when the clamp arm 146 is in an open position 7926 and the electrical impedance 7828 is medium 7856 or indicates the presence of tissue located between the clamp arm 146 and the ultrasonic blade 149, the system determines that the user intends to perform spot coagulation and applies 7858 high voltage RF energy to the tissue. Accordingly, the surgical instrument 108 completes the user intention 7860 of spot coagulating the tissue. The RF energy provided for spot coagulation also may have a high crest factor as shown and described in connection with FIG. 21.

Having described the seal only mode 7814 sequence, the description now turns to the seal and cut mode 7818 sequence. When the seal and cut mode 7818 option is selected, the system determines 7820 whether the clamp arm 146 is in an open position or a closed position. When the clamp arm 146 is in a closed position 7830 and the measured electrical impedance 7832 is low 7862 or indicates the presence of a short circuit, the system determines that stapled tissue is located between the clamp arm 146 and the ultrasonic blade 149 and applies 7864 low ultrasonic energy to the stapled tissue. Accordingly, the surgical instrument 108 completes the user intention 7866 of sealing and cutting stapled tissue located between the clamp arm 146 and the ultrasonic blade 149.

Still with reference to the seal and cut mode 7818, when the clamp arm 146 is in a closed 7830 and the measured electrical impedance 7832 is medium 7868 or indicates that tissue without staples is present between the clamp arm 146 and the ultrasonic blade 149, the system firstly applies 7870 RF energy to seal the tissue and secondly applies 7870 ultrasonic energy to cut the tissue. Accordingly, the surgical instrument 108 completes the user intention 7872 of sealing and cutting a vessel or tissue bundle located between the clamp arm 146 and the ultrasonic blade 149.

Still with reference to the seal and cut mode 7818, when the clamp arm 146 is in an open position 7834 and the measured electrical impedance 7836 is high 7874 or indicates an open circuit, the system applies 7876 high ultrasonic energy to the tissue. Accordingly, the surgical instrument 108 completes the user intention 7878 of back cutting or creating an otomy.

Still with reference to the seal and cut mode 7818, when the clamp arm 146 is in an open position 7834 and the measured electrical impedance 7836 is medium 7880 or indicates that tissue is present between the clamp arm 146 and the ultrasonic blade 149, the system determines that the user intends to perform spot coagulation and applies 7882 high voltage RF to the to the tissue. Accordingly, the surgical instrument 108 completes the user intention 7884 of spot coagulation. The RF energy provided for spot coagulation may have a high crest factor as shown and described in connection with FIG. 21.

Therefore, according to aspects of the present disclosure, various tissue effects can be provided in an automatic fashion. Therefore, a user does not need to access a complicated set of buttons or other inputs to perform the desired operation.

Turning now to FIGS. 66 and 69, there are illustrated system configurations of example circuit topologies shown and described with regard to FIGS. 77 and 78. The system configurations comprise a plurality sections, where the plurality of sections include a generator (labeled GENERATOR), a proximal plug (labeled PLUG 1), a cable, a distal plug (labeled PLUG 2), a handle of a surgical instrument, and an application portion (labeled APP) of a surgical instrument. According to various aspects, the proximal plug may be a component of the generator, it may be a component of cable, or it may be separate component. Similarly, the distal plug may be a component of the cable, it may be a component of handle, or it may be separate component.

Examples of waveforms representing energy for delivery from a generator are illustrated in FIGS. 79-83. FIG. 79 illustrates an example graph 600 showing first and second individual waveforms representing an RF output signal 602 and an ultrasonic output signal 604 superimposed on the same time and voltage scale for comparison purposes. These output signals 602, 604 are provided at the ENERGY output of the generator 100. Time (t) is shown along the horizontal axis and voltage (V) is shown along the vertical axis. The RF output signal 602 has a frequency of about 330 kHz RF and a peak-to-peak voltage of ±1V. The ultrasonic output signal 604 has a frequency of about 55 kHz and a peak-to-peak voltage of ±1V. It will be appreciated that the time (t) scale along the horizontal axis and the voltage (V) scale along the vertical axis are normalized for comparison purposes and may be different actual implementations, or represent other electrical parameters such as current.

FIG. 80 illustrates an example graph 610 showing the sum of the two output signals 602, 604 shown in FIG. 79. Time (t) is shown along the horizontal axis and voltage (V) is shown along the vertical axis. The sum of the RF output signal 602 and the ultrasonic output signal 604 shown in FIG. 79 produces a combined output signal 612 having a 2V peak-to-peak voltage, which is twice the amplitude of the original RF and ultrasonic signals shown (1V peak-to-peak) shown in FIG. 79. An amplitude of twice the original amplitude can cause problems with the output section of the generator, such as distortion, saturation, clipping of the output, or stresses on the output components. Thus, the management of a single combined output signal 612 that has multiple treatment components is an important aspect of the generator 500 shown in FIG. 8. There are a variety of ways to achieve this management. In one form, one of the two RF or ultrasonic output signals 602, 604 can be dependent on the peaks of the other output signal. In one aspect, the RF output signal 602 may depend on the peaks of the ultrasonic signal 604, such that the output is reduced when a peak is anticipated. Such a function and resulting waveform is shown in FIG. 81.

For example, FIG. 81 illustrates an example graph 620 showing a combined output signal 622 representative of a dependent sum of the output signals 602, 604 shown in FIG. 79. Time (t) is shown along the horizontal axis and voltage (V) is shown along the vertical axis. As shown in FIG. 79, the RF output signal 602 component of FIG. 79 depends on the peaks of the ultrasonic output signal 604 component of FIG. 79 such that the amplitude of the RF output signal component of the dependent sum combined output signal 622 is reduced when an ultrasonic peak is anticipated. As shown in the example graph 620 in FIG. 79, the peaks have been reduced from 2 to 1.5. In another form, one of the output signals is a function of the other output signal.

For example, FIG. 83 illustrates an example graph of an analog waveform 630 showing an output signal 632 representative of a dependent sum of the output signals 602, 604 shown in FIG. 79. Time (t) is shown along the horizontal axis and voltage (V) is shown along the vertical axis. As shown in FIG. 83, the RF output signal 602 is a function of the ultrasonic output signal 604. This provides a hard limit on the amplitude of the output. As shown in FIG. 83, the ultrasonic output signal 604 is extractable as a sine wave while the RF output signal 602 has distortion but not in a way to affect the coagulation performance of the RF output signal 602.

A variety of other techniques can be used for compressing and/or limiting the waveforms of the output signals. It should be noted that the integrity of the ultrasonic output signal 604 (FIG. 79) can be more important than the integrity of the RF output signal 602 (FIG. 79) as long as the RF output signal 602 has low frequency components for safe patient levels so as to avoid neuro-muscular stimulation. In another form, the frequency of an RF waveform can be changed on a continuous basis in order to manage the peaks of the waveform. Waveform control is important as more complex RF waveforms, such as a coagulation-type waveform 642, as illustrated in the graph 640 shown in FIG. 83, are implemented with the system. Again, time (t) is shown along the horizontal axis and voltage (V) is shown along the vertical axis. The coagulation-type waveform 642 illustrated in FIG. 83 has a crest factor of 5.8, for example.

While the examples herein are described mainly in the context of electrosurgical instruments, it should be understood that the teachings herein may be readily applied to a variety of other types of medical instruments. By way of example only, the teachings herein may be readily applied to tissue graspers, tissue retrieval pouch deploying instruments, surgical staplers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Aspects of the present disclosure have application in conventional endoscopic and open surgical instrumentation as well as application in robotic-assisted surgery. For instance, those of ordinary skill in the art will recognize that various teaching herein may be readily combined with various teachings of U.S. Pat. No. 6,783,524, titled ROBOTIC SURGICAL TOOL WITH ULTRASOUND CAUTERIZING AND CUTTING INSTRUMENT, published Aug. 31, 2004, the disclosure of which is incorporated by reference herein.

Aspects of the devices disclosed herein can be designed to be disposed of after a single use, or they can be designed to be used multiple times. Various aspects may, in either or both cases, be reconditioned for reuse after at least one use. Reconditioning may include any combination of the steps of disassembly of the device, followed by cleaning or replacement of particular pieces, and subsequent reassembly. In particular, aspects of the device may be disassembled, and any number of the particular pieces or parts of the device may be selectively replaced or removed in any combination. Upon cleaning and/or replacement of particular parts, aspects of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, aspects described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various aspects of the present disclosure, further adaptations of the methods and systems described herein may be accomplished by appropriate modifications by one of ordinary skill in the art without departing from the scope of the present disclosure. Several of such potential modifications have been mentioned, and others will be apparent to those skilled in the art. For instance, the examples, aspects, geometrics, materials, dimensions, ratios, steps, and the like discussed above are illustrative and are not required. Accordingly, the scope of the present disclosure should be considered in terms of the following claims and is understood not to be limited to the details of structure and operation shown and described in the specification and drawings.

While various details have been set forth in the foregoing description, it will be appreciated that the various aspects of the techniques for circuit topologies for combined generator may be practiced without these specific details. One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Further, while several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

For conciseness and clarity of disclosure, selected aspects of the foregoing disclosure have been shown in block diagram form rather than in detail. Some portions of the detailed descriptions provided herein may be presented in terms of instructions that operate on data that is stored in a computer memory. Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities.

Unless specifically stated otherwise as apparent from the foregoing disclosure, it is appreciated that, throughout the foregoing disclosure, discussions using terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one form, several portions of the subject matter described herein may be implemented via an application specific integrated circuits (ASIC), a field programmable gate array (FPGA), a digital signal processor (DSP), or other integrated formats. However, those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative form of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In some instances, one or more elements may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other. It is to be understood that depicted architectures of different components contained within, or connected with, different other components are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated also can be viewed as being "operably connected," or "operably coupled," to each other to achieve the desired functionality, and any two components capable of being so associated also can be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In other instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present disclosure have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "one form," or "a form" means that a particular feature, structure, or characteristic described in connection with the aspect is included in at least one aspect. Thus, appearances of the phrases "in one aspect," "in an aspect," "in one form," or "in an form" in various places throughout the specification are not necessarily all referring to the same aspect. Furthermore, the particular features, structures or characteristics may be combined in any suitable manner in one or more aspects.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

All of the above-mentioned U.S. patents, U.S. patent application publications, U.S. patent applications, foreign patents, foreign patent applications, non-patent publications referred to in this specification and/or listed in any Application Data Sheet, or any other disclosure material are incorporated herein by reference, to the extent not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

Various aspects of the subject matter described herein are set out in the following numbered clauses:

1. A system for managing RF and ultrasonic signals output by a generator, comprising: a surgical instrument comprising an RF energy output, an ultrasonic energy output, and a circuit configured to receive a combined Radio Frequency (RF) and ultrasonic signal from the generator; wherein the circuit is configured to filter frequency content of the combined signal and is configured to provide a first filtered signal to the RF energy output and a second filtered signal to the ultrasonic energy output.

2. The system of clause 1, wherein the circuit comprises a resonator.

3. The system of clause 1 or 2, wherein the circuit comprises a high frequency band-stop filter.

4. The system of any one of clauses 1-3, wherein the high frequency band-stop filter comprises a first LC filter circuit and a second LC filter circuit.

5. The system of any one of clauses 1-4, wherein the combined signal comprises a 350 kHz component.

6. The system of any one of clauses 1-5, wherein the combined signal comprises a 55 kHz component.

7. The system of any one of clauses 1-6, wherein the surgical instrument is configured to apply a therapy from the RF energy output and the ultrasonic energy output simultaneously.

8. A system for managing RF and ultrasonic signals output by a generator, comprising: a surgical instrument comprising an RF energy output, an ultrasonic energy output, and a circuit configured to receive a combined Radio Frequency (RF) and ultrasonic signal from the generator; wherein the circuit is configured to switch between the RF energy output and the ultrasonic energy output according to the combined signal received from the generator.

9. The system of clause 8, wherein the circuit comprises two pairs of MOSFET switches.

10. The system of clause 9, wherein each of the two pairs of MOSFET switches is connected source to source.

11. The system of clause 9 or 10, further comprising a first coupled inductor and a second coupled inductor.

12. The system of clause 11, wherein the gate of each MOSFET of a first pair of MOSFET switches is coupled together and is coupled to the first coupled inductor.

13. The system of clause 11 or 12, wherein the gate of each MOSFET of a second pair of MOSFET switches is coupled together and is coupled to the second coupled inductor.

14. The system of any one of clauses 11-13, further comprising a first capacitor and a second capacitor, wherein the first capacitor is coupled to the primary side of the first coupled inductor and the second capacitor is coupled to the primary side of the second coupled inductor.

15. The system of any one of clauses 9-14, further comprising a control circuit, a first pulse transformer, and a second pulse transformer, wherein the control circuit is coupled to the first and second pulse transformers, and wherein the first pulse transformer is coupled to a first pair of the two pairs of MOSFET switches and the second pulse transformer is coupled to a second pair of the two pairs of MOSFET switches.

16. The system of clause 15, wherein each of the two pairs of MOSFET switches are connected source to source.

17. The system of clause 16, wherein the gate of each MOSFET of the first pair of MOSFET switches is coupled together and is coupled to the first pulse transformer.

18. The system of clause 16 or 17, wherein the gate of each MOSFET of a second pair of MOSFET switches is coupled together and is coupled to the second pulse transformer.

19. The system of clause 18, wherein the circuit comprises a first switching element coupled to the RF energy output and a second switching element coupled to the ultrasonic energy output.

20. The system of clause 19, wherein the first switching element and the second switching element are each electromechanical relays.

21. The system of clause 19 or 20, wherein the first switching element and the second switching element are coupled to a control circuit.

22. The system of any one of clauses 19-21, further comprising a switch mechanism to actuate the first switching element and the second switching element.

23. The system of clause 22, wherein the switch mechanism is a mechanical rocker style switch mechanism.

24. A system for managing RF and ultrasonic signals output by a generator, comprising: a surgical instrument comprising an RF energy output, an ultrasonic energy output, and a circuit configured to receive a combined Radio Frequency (RF) and ultrasonic signal from the generator; wherein the circuit comprises: a filter circuit configured to filter frequency content of the combined signal; and a switching element configured to switch between an on-state and an off-state to one of the RF energy output or the ultrasonic energy output according to the combined signal received from the generator.

25. The system of clause 24, wherein the filter circuit is coupled to the ultrasonic energy output and the switching element is coupled to the RF energy output.

26. A system for managing radio frequency (RF) and ultrasonic signals output by a generator, comprising: a surgical instrument comprising an RF energy output, an ultrasonic energy output, and a circuit; wherein the circuit is configured to: receive a combined RF and ultrasonic signal from the generator; generate an RF filtered signal by filtering RF frequency content from the combined signal; generate an ultrasonic filtered signal by filtering ultrasonic frequency content from the combined signal; provide the RF filtered signal to the RF energy output; and provide the ultrasonic filtered signal to the ultrasonic energy output.

27. The system of clause 26, wherein the circuit comprises: a first resonator tuned to a frequency of the RF output; and a second resonator tuned to a frequency of the ultrasonic output.

28. The system of clause 26 or 27, wherein the circuit comprises a high frequency band-stop filter.

29. The system of any one of clauses 26-28, wherein the high frequency band-stop filter comprises a first inductor-capacitor (LC) filter circuit configured to block the RF frequency content of the combined signal and a second LC filter circuit configured to block the ultrasonic frequency content of the combined signal.

30. The system of any one of clauses 26-29, wherein the circuit comprises a high frequency pass band filter.

31. The system of any one of clauses 26-30, wherein the high frequency pass band filter comprises a first resistor-inductor-capacitor (RLC) filter circuit configured to allow passage of the RF frequency content of the combined signal while blocking all other frequency content and a second RLC filter circuit configured to allow passage of the ultrasonic frequency content of the combined signal while blocking all other frequency content.

32. The system of any one of clauses 26-31, wherein the surgical instrument is configured to apply a therapy from the RF energy output and the ultrasonic energy output simultaneously.

33. A system for managing radio frequency (RF) and ultrasonic signals output by a generator, comprising: a surgical instrument comprising an RF energy output, an ultrasonic energy output, and a circuit; wherein the circuit is configured to: receive a combined RF and ultrasonic signal from the generator; and switch between the RF energy output and the ultrasonic energy output according to the combined signal received from the generator.

34. The system of clause 33, wherein the circuit comprises two pairs of metal oxide semiconductor field effect transistor (MOSFET) switches.

35. The system of clause 33 or 34, wherein each of the two pairs of MOSFET switches is connected source to source.

36. The system of any one of clauses 34-35, wherein the circuit further comprises a first coupled inductor and a second coupled inductor.

37. The system of any one of clauses 33-36, wherein the two pairs of MOSFET switches comprises a first pair of MOSFET switches and a second pair of MOSFET switches; and a gate of each MOSFET of the first pair of MOSFET switches is coupled together and is coupled to the first coupled inductor.

38. The system of any one of clauses 33-37, wherein the gate of each MOSFET of the second pair of MOSFET switches is coupled together and is coupled to the second coupled inductor.

39. The system of any one of clauses 33-38, wherein: the circuit further comprises a first capacitor and a second capacitor; the first capacitor is coupled to a primary side of the first coupled inductor; and the second capacitor is coupled to a primary side of the second coupled inductor.

40. The system of any one of clauses 33-39, wherein the circuit further comprises: an application-specific integrated circuit (ASIC); a first pulse transformer coupled to the ASIC on a first side of the first pulse transformer and coupled to a first pair of the two pairs of MOSFET switches on a second side of the first pulse transformer; and a second pulse transformer coupled to the ASIC on a first side of the second pulse transformer and coupled to a second pair of the two pairs of MOSFET switches on a second side of the second pulse transformer.

41. The system of any one of clauses 33-40, wherein one polarity of a differential pulse applied to the first pulse transformer is configured to enhance the first pair of MOSFET pairs, and an opposite polarity of the differential pulse applied to the first pulse transformer is configured to turn off the first pair of MOSFET pairs.

42. The system of any one of clauses 33-41, wherein the circuit comprises: an application-specific integrated circuit (ASIC); a first electromechanical relay coupled to the ASIC and the RF energy output and is configured to switch to the RF energy output; and a second electromechanical relay coupled to the ASIC and the ultrasonic energy output and is configured to switch to the ultrasonic energy output.

43. The system of any one of clauses 33-42, wherein the circuit further comprises a switch mechanism configured to actuate the first electromechanical relay and the second electromechanical relay.

44. The system of any one of clauses 33-44, wherein the switch mechanism comprises a mechanical rocker style switch mechanism.

45. A system for managing radio frequency (RF) and ultrasonic signals output by a generator, comprising: a surgical instrument comprising an RF energy output, an ultrasonic energy output, and a circuit; wherein the circuit is configured to receive a combined RF and ultrasonic signal from the generator; and the circuit comprises: a filter circuit configured to filter frequency content of the combined signal; and a switching element configured to switch between an on-state and an off-state to one of the RF energy output or the ultrasonic energy output according to the combined signal received from the generator.

46. A system for managing radio frequency (RF) and ultrasonic signals output by a generator, comprising: a surgical instrument comprising a direct current (DC) motor load, an ultrasonic energy output, and a circuit; wherein the circuit is configured to: receive a combined RF and ultrasonic signal from the generator; generate an ultrasonic filtered signal by filtering ultrasonic frequency content from the combined RF and ultrasonic signal; generate DC voltage by filtering RF frequency content from the combined RF and ultrasonic signal; provide the DC voltage to the DC motor load; and provide the ultrasonic filtered signal to the ultrasonic energy output.

47. The system of clause 46, wherein the surgical instrument further comprises at least one electrical component, and the DC motor load is configured to power the at least one electrical component using the generated DC voltage.

48. The system of clause 46 or 47, wherein the at least one electrical component comprises an end effector.

49. The system of any one of clauses 46-48, wherein the at least one electrical component comprises one or more light emitting diodes (LEDs).

50. The system of any one of clauses 46-49, wherein the at least one electrical component comprises one or more sensors configured to detect a physiological condition of tissue at a surgical site.

51. The system of any one of clauses 46-50, wherein the circuit comprises a high frequency band-stop filter.

52. The system of any one of clauses 46-51, wherein filtering the ultrasonic frequency content comprises filtering the ultrasonic frequency content through the high frequency band-stop filter.

53. The system of any one of clauses 46-52, wherein generating the DC voltage by filtering comprises filtering the RF frequency content through the high frequency band-stop filter.

54. The system of any one of clauses 46-53, wherein the circuit comprises a rectifier configured to produce the DC voltage.

55. The system of any one of clauses 46-54, wherein the surgical instrument is configured to apply a therapy of RF energy through the DC motor load and the ultrasonic energy output simultaneously.

56. The system of any one of clauses 46-55, wherein the surgical instrument is configured to switch between applying RF energy through the DC motor load and applying ultrasonic energy through the ultrasonic energy output.

57. The system of any one of clauses 46-56, wherein the circuit further comprises: an application specific integrated circuit (ASIC); a memory coupled to the ASIC; a switch array coupled to the ASIC; and a rectifier coupled to the ASIC; wherein the ASIC is configured to control switching between the DC motor load and the ultrasonic energy output through the switch array.

58. A surgical instrument comprising: a direct current (DC) motor load; an ultrasonic energy output, and a circuit; wherein the circuit is configured to: receive a combined radio frequency (RF) and ultrasonic signal from a generator electrically coupled to the surgical instrument; generate an ultrasonic filtered signal by filtering ultrasonic frequency content from the combined RF and ultrasonic signal; generate DC voltage by filtering RF frequency content from the combined RF and ultrasonic signal; provide the DC voltage to the DC motor load; and provide the ultrasonic filtered signal to the ultrasonic energy output.

59. The surgical instrument of clause 58, further comprising an end effector, and wherein the DC motor load is configured to power the end effector using the generated DC voltage.

60. The surgical instrument of clause 58 or 59, wherein the circuit comprises a high frequency band-stop filter.

61. The surgical instrument of any one of clauses 58-60, wherein filtering the ultrasonic frequency content comprises filtering the ultrasonic frequency content through the high frequency band-stop filter.

62. The surgical instrument of any one of clauses 58-61, wherein generating the DC voltage by filtering comprises filtering the RF frequency content through the high frequency band-stop filter.

63. The surgical instrument of any one of clauses 58-62, wherein the surgical instrument is configured to apply a therapy of RF energy through the DC motor load and the ultrasonic energy output simultaneously.

64. The surgical instrument of any one of clauses 58-63, wherein the circuit is further configured to switch between applying RF energy through the DC motor load and applying ultrasonic energy through the ultrasonic energy output.

65. A surgical instrument comprising: a direct current (DC) motor load; an ultrasonic energy output; and a circuit, the circuit comprising: an application specific integrated circuit (ASIC); a memory coupled to the ASIC; a switch array coupled to the ASIC; and a rectifier coupled to the ASIC; wherein the circuit is configured to: receive a combined radio frequency (RF) and ultrasonic signal from a generator electrically coupled to the surgical instrument; generate an ultrasonic filtered signal by filtering ultrasonic frequency content from the combined RF and ultrasonic signal; generate DC voltage by filtering RF frequency content from the combined RF and ultrasonic signal; provide the DC voltage to the DC motor load; and provide the ultrasonic filtered signal to the ultrasonic energy output; wherein the ASIC is configured to control switching between applying RF energy through the DC motor load and applying ultrasonic energy through the ultrasonic energy output.

66. A system comprising a generator and a surgical instrument, wherein the generator is configured to deliver a combined signal comprising a radio frequency (RF) component and an ultrasonic component to the surgical instrument; and the surgical instrument comprises: an RF energy output, an ultrasonic energy output, a circuit configured to steer the RF component to the RF energy output and steer the ultrasonic component to the ultrasonic energy output, wherein the generator is configured to adjust a frequency of the RF component based on a characterization of a circuit component of the circuit.

67. The system of clause 66, wherein the circuit component comprises a band-stop filter.

68. The system of clause 66 or 67, wherein the circuit further comprises a variable component.

69. The system of any one of clauses 66-68, wherein the characterization of the circuit component comprises sending a ping signal to the circuit component.

70. The system of any one of clauses 66-69, wherein a result of the characterization is stored in the surgical instrument.

71. The system of any one of clauses 66-70, wherein the characterization is performed when the surgical instrument is manufactured.

72. The system of any one of clauses 66-71, wherein the characterization is performed when the surgical instrument is connected to the generator.

73. The system of any one of clauses 66-72, wherein the characterization is performed after the surgical instrument delivers energy to a tissue.

74. The system of any one of clauses 66-73, wherein the characterization is performed while the surgical instrument is delivering energy to a tissue.

75. The system of any one of clauses 66-74, wherein the characterization is performed periodically.

76. A method for providing a combined signal comprising a radio frequency (RF) component and an ultrasonic component by a generator to a surgical instrument, the surgical instrument comprising an RF energy output, an ultrasonic energy output and a circuit, the method comprising: performing characterization on a circuit component of the circuit; adjusting a frequency of the RF component based on a result of the characterization; delivering, by the generator, the combined signal to the surgical instrument; steering, by the circuit, the RF component to the RF energy output; and steering, by the circuit, the ultrasonic component to the ultrasonic energy output.

77. The method of clause 76, wherein the circuit component comprises a band-stop filter.

78. The method of clause 76 or 77, wherein the circuit further comprises a variable component.

79. The method of any one of clauses 76-78, wherein performing characterization on the circuit component comprises sending a ping signal to the circuit component.

80. The method of any one of clauses 76-79, further comprising storing a result of the characterization in the surgical instrument.

81. The method of any one of clauses 76-80, wherein the characterization is performed when the surgical instrument is manufactured.

82. The method of any one of clauses 76-81, wherein the characterization is performed when the surgical instrument is connected to the generator.

83. The method of any one of clauses 76-82, wherein the characterization is performed after the surgical instrument delivers energy to a tissue.

84. The method of any one of clauses 76-83, wherein the characterization is performed while the surgical instrument is delivering energy to a tissue.

85. A generator for providing a combined signal comprising a radio frequency (RF) component and an ultrasonic component to a surgical instrument, the generator being configured to: perform characterization on a circuit component of a circuit of the surgical instrument for steering the RF component to an RF output and steering the ultrasonic component to an ultrasonic output; adjust a frequency of the RF component based on a result of the characterization; and deliver the combined signal to the surgical instrument.

86. A method for operating a surgical instrument, the surgical instrument comprising a radio frequency (RF) energy output, an ultrasonic energy output, and a first jaw and a second jaw configured for pivotal movement between a closed position and an open position, the method comprising: receiving a first input indicating a user selection of one of a first option and a second option; receiving a second input indicating whether the first jaw and the second jaw are in the closed position or in the open position; receiving a third input indicating electrical impedance at the RF energy output; and selecting a mode of operation for treating a tissue from a plurality of modes of operation based at least in part on the first input, the second input and the third input, wherein the plurality of modes of operation comprises: a first mode wherein the RF energy output applies RF energy to the tissue; and a second mode wherein the ultrasonic energy output applies ultrasonic energy to the tissue.

87. The method of clause 86, wherein the first option is a seal only option, and the second option is a seal and cut option.

88. The method of clause 86 or 87, wherein the user selection is a button selection.

89. The method of any one of clauses 86-88, wherein the plurality of modes of operation further comprises: a third mode wherein the RF energy output applies RF energy to the tissue and the ultrasonic energy output applies ultrasonic energy to the tissue; and a fourth mode wherein no RF energy or ultrasonic energy is applied to the tissue.

90. The method of clause 89, wherein the third mode is selected when the first input indicates the second option, the second input indicates the closed position, and the third input indicates medium electrical impedance, wherein RF energy is applied before ultrasonic energy is applied.

91. The method of clause 89, wherein the fourth mode is selected when the first input indicates the first option, the second input indicates the open position, and the third input indicates high electrical impedance.

92. The method of any one of clauses 86-91, further comprising selecting a level of energy applied by the RF energy output based at least in part on the first input, the second input and the third input.

93. The method of any one of clauses 86-92, wherein the first mode is selected and the level of energy applied by the RF energy output is selected as high, when the second input indicates the open position, and the third input indicates medium electrical impedance.

94. The method of any one of clauses 86-93, further comprising selecting a level of energy applied by the ultrasonic energy output based at least in part on the first input, the second input and the third input.

95. The method of any one of clauses 86-94, wherein the second mode is selected and the level of energy applied by the ultrasonic energy output is selected as low, when the second input indicates the closed position, and the third input indicates low electrical impedance.

96. The method of any one of clauses 86-94, wherein the second mode is selected and the level of energy applied by the ultrasonic energy output is selected as high, when the first input indicates the second option, the second input indicates the open position, and the third input indicates high electrical impedance.

97. The method of any one of clauses 86-96, wherein the first mode is selected when the first input indicates the first option, the second input indicates the closed position, and the third input indicates medium electrical impedance.

98. The method of any one of clauses 86-97, further comprising selecting a waveform of energy applied by the RF energy output or the ultrasonic energy output based at least in part on the first input, the second input and the third input.

99. A generator for delivering radio frequency (RF) energy and ultrasonic energy to a surgical instrument, the surgical instrument comprising a first jaw and a second jaw configured for pivotal movement between a closed position and an open position, the generator being configured to: receive a first input indicating a user selection of one of a first option and a second option; receive a second input indicating whether the first jaw and the second jaw are in the closed position or in the open position; receive a third input indicating electrical impedance at a RF energy output of the surgical instrument; and select a mode of operation for treating a tissue from a plurality of modes of operation based at least in part on the first input, the second input and the third input, wherein the plurality of modes of operation comprises: a first mode wherein the generator delivers RF energy to the surgical instrument; and a second mode wherein the generator delivers ultrasonic energy to the surgical instrument.

100. The generator of clause 99, wherein the plurality of modes of operation further comprises: a third mode wherein the generator delivers RF energy and ultrasonic energy to the surgical instrument; and a fourth mode wherein the generator delivers no RF energy or ultrasonic energy to the surgical instrument.

101. The generator of clause 99 or 100, wherein the generator is further configured to deliver RF energy to the surgical instrument at a level determined based at least in part on the first input, the second input and the third input.

102. The generator of anyone of clauses 99-101, wherein the generator is configured to select the first mode and the level of RF energy is determined as high, when the second input indicates the open position, and the third input indicates medium electrical impedance.

103. The generator of any one of clauses 99-102, wherein the generator is further configured to deliver ultrasonic energy to the surgical instrument at a level determined based at least in part on the first input, the second input and the third input.

104. The generator of any one of clauses 99-103, wherein the generator is configured to select the second mode and the level of ultrasonic energy is determined as low, when the second input indicates the closed position, and the third input indicates low electrical impedance.

105. A surgical instrument comprising: a first jaw and a second jaw configured for pivotal movement between a closed position and an open position; a radio frequency (RF) energy output configured to apply RF energy to a tissue at least when a first mode of operation is selected; and an ultrasonic energy output configured to apply ultrasonic energy to the tissue at least when a second mode of operation is selected, wherein a mode of operation is selected from a plurality of modes of operation comprising the first mode and the second mode based at least in part on a first input, a second input and a third input, wherein: the first input indicates a user selection of one of a first option and a second option; the second input indicates whether the first jaw and the second jaw are in the closed position or in the open position; and the third input indicates electrical impedance at the RF energy output.

106. A method, comprising receiving, by a surgical instrument a combined radio frequency (RF) and ultrasonic signal from a generator, the surgical instrument comprising an RF energy output, an ultrasonic energy output, and a circuit; generating, by the circuit, a RF filtered signal by filtering RF frequency content from the combined signal; filtering, by the circuit, ultrasonic frequency content from the combined signal; generating, by the circuit, an ultrasonic filtered signal; providing, by the circuit, the RF filtered signal to the RF energy output; and providing, by the circuit, the ultrasonic filtered signal to the ultrasonic energy output.

107. The method of clause 106, comprising tuning, by the circuit, a first resonator to a frequency of the RF output; and tuning, by the circuit, a second resonator to a frequency of the ultrasonic output.

108. The method of clause 106 or 107, wherein the circuit comprises a high frequency band-stop filter, the method comprising blocking, by a first inductor-capacitor (LC) filter circuit of the high frequency band-stop filter, the RF frequency content of the combined signal; and blocking, by a second LC filter circuit of the high frequency band-stop filter, the ultrasonic frequency content of the combined signal.

109. The method of any one of clauses 106-108, wherein the circuit comprises a high frequency pass band filter, the method comprising passing, by a first resistor-inductor-capacitor (RLC) filter circuit of the high frequency pass band filter, the RF frequency content of the combined signal; blocking, by the first RLC filter, all other frequency content; passing, by a second RLC filter circuit of the high frequency pass band filter, the ultrasonic frequency content of the combined signal; and blocking, by the second RLC filter circuit, all other frequency content.

110. The method of any one of clauses 106-109, simultaneously applying, by the surgical instrument, a therapy from the RF energy output and the ultrasonic energy output.

111. The method of any one of clauses 106-110, comprising switching between the RF energy output and the ultrasonic energy output according to the combined signal received from the generator.

112. The method of any one of clauses 106-111, wherein the surgical instrument comprises a direct current (DC) motor load, the method comprising generating, by the circuit, a DC voltage by filtering the RF frequency content from the combined RF and ultrasonic signal; and providing, by the circuit, the DC voltage to the DC motor load.

113. A method, comprising receiving, by a surgical instrument, a combined signal comprising a radio frequency (RF) component and an ultrasonic component, from a generator, the surgical instrument comprising an RF energy output, an ultrasonic energy output, and a circuit configured to steer the RF component to the RF energy output and steer the ultrasonic component to the ultrasonic energy output; characterizing a circuit component of the circuit; and adjusting a frequency of the RF component based on the characterization of the circuit component.

114. The method of clause 113, wherein the characterization of the circuit component comprises receiving, by the circuit, a ping signal to the circuit component.

115. The method of clause 113 or 114, comprising storing a result of the characterization in a memory component of the surgical instrument.

116. The method of any one of clauses 113-115, comprising performing the characterization when the surgical instrument is manufactured; when the surgical instrument is connected to the generator; after the surgical instrument delivers energy to a tissue; while the surgical instrument is delivering energy to a tissue; or periodically.

117. The method of any one of clauses 113-116, comprising steering, by the circuit, the RF component to the RF energy output; and steering, by the circuit, the ultrasonic component to the ultrasonic energy output.

118. A method, comprising receiving, by a surgical instrument, a first input indicating a user selection of a first option or a second option, the surgical instrument comprising a radio frequency (RF) energy output, an ultrasonic energy output, and a first jaw and a second jaw configured for pivotal movement between a closed position and an open position; receiving, by the surgical instrument, a second input indicating whether the first jaw and the second jaw are in the closed position or in the open position; and selecting, by the surgical instrument, a first mode or a second mode of treating a tissue based on the first input and the second input, wherein the first mode comprises applying RF energy to the tissue; and the second mode comprises applying ultrasonic energy to the tissue.

119. The method of clause 118, comprising selecting, by the surgical instrument, a third mode or a fourth mode of treating a tissue based on the first input and the second input, wherein the third mode comprises applying the RF energy and the ultrasonic energy to the tissue; and the fourth mode comprising applying no RF energy or ultrasonic energy to the tissue.

120. The method of clause 118 or 119, comprising selecting the third mode when the first input indicates the second option, the second input indicates the closed position, and the third input indicates medium electrical impedance; and applying the RF energy to the tissue before applying the ultrasonic energy.

121. The method of any one of clauses 119 or 120, comprising selecting the fourth mode when the first input indicates the first option, the second input indicates the open position, and the third input indicates high electrical impedance.

122. The method of any one of clauses 118-121, further comprising selecting a level of energy applied by the RF energy output based on the first input and second input.

123. The method of any one of clauses 118-122, further comprising selecting a level of energy applied by the ultrasonic energy output based on the first input and second input.

124. The method of any one of clauses 118-123, comprising selecting the first mode when the first input indicates the first option, the second input indicates the closed position, and a third input indicates medium electrical impedance.

125. The method of any one of clauses 118-124, comprising selecting a waveform of energy applied by the RF energy output or the ultrasonic energy output based on the first input and the second input.

The invention claimed is:

1. A control circuit, to:

receive a first input corresponding to a user selection;

receive a second input corresponding to an impedance measurement;

receive a combined signal from a generator, wherein the combined signal comprises an RF component and an ultrasonic component; and select between a first mode and a second mode of treating tissue based on the first input and the second input, wherein:

the first mode comprises providing the RF component of the combined signal to an electrode of a surgical instrument; and the second mode comprises providing the ultrasonic component of the combined signal to an ultrasonic blade of the surgical instrument.

2. The control circuit of claim 1, further to receive a third input corresponding a position of a clamp arm of the surgical instrument.

3. The control circuit of claim 2, wherein selecting between the first mode and the second mode is further based on the third input.

4. The control circuit of claim 1, further to select a third mode of treating tissue based on the first input and the second input, wherein the third mode comprises providing the RF component of the combined signal to the electrode and providing the ultrasonic component of the combined signal to the ultrasonic blade.

5. The control circuit of claim 1, further to select a third mode of treating tissue based on the first input and the second input, wherein the third mode comprises abstaining from providing the RF component or the ultrasonic component to the surgical instrument.

6. The control circuit of claim 1, further to determine a short circuit condition or an open circuit condition based on the received second input.

7. The control circuit of claim 1, further to control an energy level of the RF component and the ultrasonic component based on the first input and the second input.

8. A control circuit, to:

receive a first input corresponding to a position of a clamp arm of a surgical instrument;

receive a second input corresponding to an impedance measurement;

receive a combined signal from a generator, wherein the combined signal comprises an RF component and an ultrasonic component; and select between a first mode and a second mode of treating tissue based on the first input and the second input, wherein:

the first mode comprises providing the RF component of the combined signal to an electrode of a surgical instrument; and the second mode comprises providing the ultrasonic component of the combined signal to an ultrasonic blade of the surgical instrument.

9. The control circuit of claim 8, further to receive a third input corresponding a user selection.

10. The control circuit of claim 9, wherein selecting between the first mode and the second mode is further based on the third input.

11. The control circuit of claim 8, further to select a third mode of treating tissue based on the first input and the second input, wherein the third mode comprises providing the RF component of the combined signal to the electrode and providing the ultrasonic component of the combined signal to the ultrasonic blade.

12. The control circuit of claim 8, further to select a third mode of treating tissue based on the first input and the second input, wherein the third mode comprises abstaining from providing the RF component or the ultrasonic component to the surgical instrument.

13. The control circuit of claim 8, further to determine a short circuit condition or an open circuit condition based on the received second input.

14. The control circuit of claim 8, further to control an energy level of the RF component and the ultrasonic component based on the first input and the second input.

15. A control circuit, configured to:

receive a first input corresponding to a user selection;

receive a second input corresponding to an impedance measurement;

receive a combined signal from a generator, wherein the combined signal comprises an RF component and an ultrasonic component;

determine if the RF component of the combined signal is to be provided to a surgical instrument based on the first input and the second input; and determine if the ultrasonic component of the combined signal is to be provided to the surgical instrument based on the first input and the second input.

16. The control circuit of claim 15, further to receive a third input corresponding to a position of a clamp arm of a surgical instrument.

17. The control circuit of claim 16, wherein:

determining if the RF component of the combined signal is to be provided to the surgical instrument is further based on the third input; and determining if the ultrasonic component of the combined signal is to be provided to the surgical instrument is further based on the third input.

18. The control circuit of claim 16, further to determine a short circuit condition or an open circuit condition based on the received second input.

19. The control circuit of claim 16, further to control an energy level of the RF component and the ultrasonic component based on the first input and the second input.

* * * * *